US007740623B2

(12) United States Patent
Nayak et al.

(10) Patent No.: US 7,740,623 B2
(45) Date of Patent: Jun. 22, 2010

(54) DEVICES AND METHODS FOR INTERSTITIAL INJECTION OF BIOLOGIC AGENTS INTO TISSUE

(75) Inventors: Asha S. Nayak, Menlo Park, CA (US); Matthew D. Bonner, Plymouth, MN (US); Paul T. Rothstein, Elk River, MN (US); Prasanga D. Hiniduma-Lokuge, Minneapolis, MN (US); James R. Keogh, Brooklyn Park, MN (US); Raymond W. Usher, Coon Rapids, MN (US); Scott E. Jahns, Brooklyn Park, MN (US); Victor T. Chen, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1102 days.

(21) Appl. No.: 11/159,752

(22) Filed: Jun. 23, 2005

(65) Prior Publication Data

US 2006/0041243 A1   Feb. 23, 2006

Related U.S. Application Data

(63) Continuation-in-part of application No. 11/000,798, filed on Nov. 30, 2004, which is a continuation-in-part of application No. 10/341,743, filed on Jan. 14, 2003, and a continuation-in-part of application No. 10/622,147, filed on Jul. 17, 2003, now Pat. No. 6,918,908, which is a continuation-in-part of application No. 10/342,932, filed on Jan. 15, 2003, now Pat. No. 6,837,848, said application No. 11/000,798 is a continuation-in-part of application No. 10/156,315, filed on May 28, 2002, now Pat. No. 7,507,235, which is a continuation of application No. 09/879,294, filed on Jun. 12, 2001, now Pat. No. 6,447,443.

(60) Provisional application No. 60/261,343, filed on Jan. 13, 2001, provisional application No. 60/263,739, filed on Jan. 24, 2001, provisional application No. 60/282,029, filed on Apr. 6, 2001, provisional application No. 60/286,952, filed on Apr. 26, 2001.

(51) Int. Cl.
*A61M 31/00* (2006.01)
*A61M 37/00* (2006.01)

(52) U.S. Cl. .......................... 604/500; 604/82; 604/506

(58) Field of Classification Search ................. 604/506, 604/173; 600/37
See application file for complete search history.

(56) References Cited

U.S. PATENT DOCUMENTS 1,127,948 A    2/1915   Wappler (Continued)

FOREIGN PATENT DOCUMENTS

DE    43 13 903    9/1994

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Nicholas D Lucchesi
*Assistant Examiner*—Ian K Holloway
(74) *Attorney, Agent, or Firm*—Mike Jaro; Jeffrey J. Hohenshell

(57) ABSTRACT

The current invention discloses a method for treating infracted/ischemic injury to a myocardium by injecting a substance into the myocardium. The injected substance helps to prevent negative adaptive remodeling by providing mechanical reinforcement or mechanical reinforcement combined with biological therapy. A number of substances for injection are disclosed, including multi component substances such as platelet gel, and other substances. The substances disclosed may contain additives to augment/enhance the desired effects of the injection. The invention also discloses devices used to inject the substances. The devices can include means for ensuring needles do not penetrate beyond a desired depth into the myocardium. The devices can also include needles having multiple lumens such that the components of the platelet gel will be combined at the injection site and begin polymerization in the myocardium.

24 Claims, 64 Drawing Sheets

U.S. PATENT DOCUMENTS

| | | |
|---|---|---|
| 2,004,559 A | 6/1935 | Wappler et al. |
| 3,470,875 A | 10/1969 | Johnson et al. |
| 3,630,207 A | 12/1971 | Kahn et al. |
| 3,664,330 A | 5/1972 | Deutsch |
| 3,736,936 A | 6/1973 | Basiulis et al. |
| 3,741,211 A | 6/1973 | Vreeland |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,901,242 A | 8/1975 | Storz |
| 3,902,501 A | 9/1975 | Citron et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,043,342 A | 8/1977 | Morrison, Jr. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,270,549 A | 6/1981 | Heilman |
| 4,275,734 A | 6/1981 | Mitchiner |
| 4,278,090 A | 7/1981 | van Gerven |
| 4,291,707 A | 9/1981 | Heilman et al. |
| 4,312,337 A | 1/1982 | Donohue et al. |
| 4,353,371 A | 10/1982 | Cosman |
| 4,377,168 A | 3/1983 | Rzasa et al. |
| 4,492,231 A | 1/1985 | Auth |
| 4,519,389 A | 5/1985 | Gudkin et al. |
| 4,590,934 A | 5/1986 | Malis et al. |
| 4,598,698 A | 7/1986 | Siegmund |
| 4,601,290 A | 7/1986 | Effron et al. |
| 4,662,376 A | 5/1987 | Belanger |
| 4,664,110 A | 5/1987 | Schanzlin |
| 4,706,667 A | 11/1987 | Roos |
| 4,723,940 A | 2/1988 | Wiegerinck |
| 4,726,358 A | 2/1988 | Brady |
| 4,732,149 A | 3/1988 | Sutter |
| 4,735,206 A | 4/1988 | Hewson |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,815,478 A | 3/1989 | Buchbinder et al. |
| 4,832,048 A | 5/1989 | Cohen |
| 4,872,346 A | 10/1989 | Kelly-Fry et al. |
| 4,898,577 A | 2/1990 | Badger et al. |
| 4,916,922 A | 4/1990 | Mullens |
| 4,917,095 A | 4/1990 | Fry et al. |
| 4,928,688 A | 5/1990 | Mower |
| 4,936,281 A | 6/1990 | Stasz |
| 4,940,062 A | 7/1990 | Hampton et al. |
| 4,940,064 A | 7/1990 | Desai |
| 4,946,460 A | 8/1990 | Merry et al. |
| 4,991,578 A | 2/1991 | Cohen |
| 5,009,661 A | 4/1991 | Michelson |
| 5,013,312 A | 5/1991 | Parins et al. |
| 5,026,779 A | 6/1991 | Musch et al. |
| 5,029,574 A | 7/1991 | Shimamura et al. |
| 5,033,477 A | 7/1991 | Chin et al. |
| 5,044,165 A | 9/1991 | Linner et al. |
| 5,044,947 A | 9/1991 | Sachdeva et al. |
| 5,071,428 A | 12/1991 | Chin et al. |
| 5,076,285 A | 12/1991 | Hess et al. |
| 5,078,713 A | 1/1992 | Varney |
| 5,080,102 A | 1/1992 | Dory |
| 5,080,660 A | 1/1992 | Buelina |
| 5,083,565 A | 1/1992 | Parins et al. |
| 5,085,657 A | 2/1992 | Ben-Simhon |
| 5,087,243 A | 2/1992 | Avitall |
| 5,100,388 A | 3/1992 | Behl et al. |
| 5,108,390 A | 4/1992 | Potocky et al. |
| 5,116,332 A | 5/1992 | Lottick |
| 5,125,928 A | 6/1992 | Parins et al. |
| 5,147,355 A | 9/1992 | Friedman et al. |
| 5,156,149 A | 10/1992 | Hudrlik |
| 5,178,133 A | 1/1993 | Pena |
| 5,190,541 A | 3/1993 | Abele et al. |
| 5,207,674 A | 5/1993 | Hamilton |
| 5,207,691 A | 5/1993 | Nardella |
| 5,217,460 A | 6/1993 | Knoepfler |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,242,441 A | 9/1993 | Avitall |
| 5,242,458 A | 9/1993 | Bendel et al. |
| 5,250,047 A | 10/1993 | Rydell |
| 5,250,075 A | 10/1993 | Badie |
| 5,254,116 A | 10/1993 | Baust et al. |
| 5,254,130 A | 10/1993 | Johnson |
| 5,254,600 A | 10/1993 | Blanpied et al. |
| 5,263,493 A | 11/1993 | Avitall |
| 5,269,291 A | 12/1993 | Carter |
| 5,269,326 A | 12/1993 | Verrier |
| 5,269,780 A | 12/1993 | Roos |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,281,216 A | 1/1994 | Klicek |
| 5,293,869 A | 3/1994 | Edwards et al. |
| 5,295,484 A | 3/1994 | Marcus et al. |
| 5,306,234 A | 4/1994 | Johnson |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,318,589 A | 6/1994 | Lichtman |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,327,905 A | 7/1994 | Avitall |
| 5,334,181 A | 8/1994 | Rubinsky et al. |
| 5,334,193 A | 8/1994 | Nardella |
| 5,336,252 A | 8/1994 | Cohen |
| 5,348,554 A | 9/1994 | Imran et al. |
| 5,353,783 A | 10/1994 | Nakao et al. |
| 5,354,258 A | 10/1994 | Dory |
| 5,354,297 A | 10/1994 | Avitall |
| 5,357,956 A | 10/1994 | Nardella |
| 5,361,752 A | 11/1994 | Moll et al. |
| 5,385,148 A | 1/1995 | Lesh et al. |
| 5,387,234 A | 2/1995 | Hirschberg |
| 5,396,887 A | 3/1995 | Imran |
| 5,397,304 A | 3/1995 | Truckai |
| 5,397,339 A | 3/1995 | Desai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |

| | | | | | | |
|---|---|---|---|---|---|---|
| 5,403,312 A | 4/1995 | Yates et al. | | 5,578,007 A | 11/1996 | Imran |
| 5,405,376 A | 4/1995 | Mulier et al. | | 5,582,609 A | 12/1996 | Swanson et al. |
| 5,409,483 A | 4/1995 | Campbell et al. | | 5,587,723 A | 12/1996 | Otake et al. |
| 5,411,529 A | 5/1995 | Hudrlik | | 5,588,432 A | 12/1996 | Crowley |
| 5,423,807 A | 6/1995 | Milder | | 5,590,657 A | 1/1997 | Cain et al. |
| 5,423,811 A | 6/1995 | Imran et al. | | 5,591,192 A | 1/1997 | Privitera et al. |
| 5,423,878 A | 6/1995 | Franz | | 5,595,183 A | 1/1997 | Swanson et al. |
| 5,427,119 A | 6/1995 | Swartz et al. | | 5,599,350 A | 2/1997 | Schulze et al. |
| 5,429,131 A | 7/1995 | Scheinman et al. | | 5,607,462 A | 3/1997 | Imran |
| 5,429,636 A | 7/1995 | Shikhman et al. | | 5,611,813 A | 3/1997 | Lichtman |
| 5,431,649 A | 7/1995 | Mulier et al. | | 5,617,854 A | 4/1997 | Munsif |
| 5,433,708 A | 7/1995 | Nichols et al. | | 5,620,459 A | 4/1997 | Lichtman |
| 5,435,308 A | 7/1995 | Gallup et al. | | 5,630,837 A | 5/1997 | Crowley |
| 5,437,651 A | 8/1995 | Todd et al. | | 5,632,717 A | 5/1997 | Yoon |
| 5,438,302 A | 8/1995 | Goble | | 5,637,090 A | 6/1997 | McGee et al. |
| 5,441,483 A | 8/1995 | Avitall | | 5,642,736 A | 7/1997 | Avitall |
| 5,443,463 A | 8/1995 | Stern et al. | | 5,643,197 A | 7/1997 | Brucker et al. |
| 5,443,470 A | 8/1995 | Stern et al. | | 5,649,957 A | 7/1997 | Levin et al. |
| 5,445,638 A | 8/1995 | Rydell et al. | | 5,651,378 A | 7/1997 | Matheny et al. |
| 5,449,355 A | 9/1995 | Rhum et al. | | 5,655,219 A | 8/1997 | Jusa et al. |
| 5,450,843 A | 9/1995 | Moll et al. | | 5,656,029 A | 8/1997 | Imran et al. |
| 5,451,223 A | 9/1995 | Ben-Simhon | | 5,658,278 A | 8/1997 | Imran et al. |
| 5,452,582 A | 9/1995 | Longsworth | | 5,671,747 A | 9/1997 | Connor |
| 5,452,733 A | 9/1995 | Sterman et al. | | 5,672,174 A | 9/1997 | Gough et al. |
| 5,454,370 A | 10/1995 | Avitall | | 5,673,695 A | 10/1997 | McGee et al. |
| 5,462,545 A | 10/1995 | Wang et al. | | 5,674,220 A | 10/1997 | Fox et al. |
| 5,464,447 A | 11/1995 | Fogarty et al. | | 5,676,662 A | 10/1997 | Fleischhacker et al. |
| 5,465,716 A | 11/1995 | Avitall | | 5,676,692 A | 10/1997 | Sanghvi et al. |
| 5,465,717 A | 11/1995 | Imran et al. | | 5,676,693 A | 10/1997 | Lafontaine |
| 5,469,853 A | 11/1995 | Law et al. | | 5,678,550 A | 10/1997 | Bassen et al. |
| 5,472,441 A | 12/1995 | Edwards et al. | | 5,680,860 A | 10/1997 | Imran |
| 5,472,876 A | 12/1995 | Fahy | | 5,681,278 A | 10/1997 | Igo et al. |
| 5,478,309 A | 12/1995 | Sweezer et al. | | 5,681,308 A | 10/1997 | Edwards et al. |
| 5,478,330 A | 12/1995 | Imran et al. | | 5,683,384 A | 11/1997 | Gough et al. |
| 5,480,409 A | 1/1996 | Riza | | 5,687,723 A | 11/1997 | Avitall |
| 5,486,193 A | 1/1996 | Bourne et al. | | 5,687,737 A | 11/1997 | Branham et al. |
| 5,487,385 A | 1/1996 | Avitall | | 5,688,267 A | 11/1997 | Panescu et al. |
| 5,487,757 A | 1/1996 | Truckai et al. | | 5,688,270 A | 11/1997 | Yates et al. |
| 5,496,312 A | 3/1996 | Klicek | | 5,690,611 A | 11/1997 | Swartz et al. |
| 5,497,774 A | 3/1996 | Swartz et al. | | 5,693,051 A | 12/1997 | Schulze et al. |
| 5,498,248 A | 3/1996 | Milder | | 5,697,536 A | 12/1997 | Eggers et al. |
| 5,500,011 A | 3/1996 | Desai | | 5,697,882 A | 12/1997 | Eggers et al. |
| 5,500,012 A | 3/1996 | Brucker et al. | | 5,697,925 A | 12/1997 | Taylor |
| 5,505,730 A | 4/1996 | Edwards | | 5,697,927 A | 12/1997 | Imran et al. |
| 5,516,505 A | 5/1996 | McDow | | 5,697,928 A | 12/1997 | Walcott et al. |
| 5,520,682 A | 5/1996 | Baust et al. | | 5,700,282 A * | 12/1997 | Zabara .......................... 607/9 |
| 5,522,788 A | 6/1996 | Kuzmak et al. | | 5,702,359 A | 12/1997 | Hofmann et al. |
| 5,522,870 A | 6/1996 | Ben-Zion | | 5,702,390 A | 12/1997 | Austin et al. |
| 5,531,744 A | 7/1996 | Nardella et al. | | 5,702,438 A | 12/1997 | Avitall |
| 5,536,267 A | 7/1996 | Edwards et al. | | 5,709,680 A | 1/1998 | Yates et al. |
| 5,545,195 A | 8/1996 | Lennox et al. | | 5,713,942 A | 2/1998 | Stern |
| 5,545,200 A | 8/1996 | West et al. | | 5,716,389 A | 2/1998 | Walinsky et al. |
| 5,549,636 A | 8/1996 | Li | | 5,716,392 A | 2/1998 | Bourgeois et al. |
| 5,549,661 A | 8/1996 | Kordis et al. | | 5,718,241 A | 2/1998 | Ben-Haim et al. |
| 5,553,612 A | 9/1996 | Lundback | | 5,718,701 A | 2/1998 | Shai et al. |
| 5,555,883 A | 9/1996 | Avitall | | 5,718,703 A | 2/1998 | Chin |
| 5,558,671 A | 9/1996 | Yates | | 5,720,775 A | 2/1998 | Lanard |
| 5,560,362 A | 10/1996 | Silwa, Jr. et al. | | 5,722,402 A | 3/1998 | Swanson et al. |
| 5,562,699 A | 10/1996 | Heimberger et al. | | 5,722,403 A | 3/1998 | McGee et al. |
| 5,562,700 A | 10/1996 | Huitema et al. | | 5,725,512 A | 3/1998 | Swartz et al. |
| 5,562,720 A | 10/1996 | Stern et al. | | 5,728,143 A | 3/1998 | Gough et al. |
| 5,562,721 A | 10/1996 | Marchlinski et al. | | 5,730,074 A | 3/1998 | Peter |
| 5,564,440 A | 10/1996 | Swartz et al. | | 5,730,127 A | 3/1998 | Avitall |
| 5,569,241 A | 10/1996 | Edwards | | 5,730,704 A | 3/1998 | Avitall |
| 5,571,088 A | 11/1996 | Lennox et al. | | 5,730,757 A | 3/1998 | Benetti et al. |
| 5,571,119 A | 11/1996 | Atala et al. | | 5,733,280 A | 3/1998 | Avitall |
| 5,571,215 A | 11/1996 | Sterman et al. | | 5,735,280 A | 4/1998 | Sherman et al. |
| 5,573,532 A | 11/1996 | Chang et al. | | 5,735,290 A | 4/1998 | Sterman et al. |
| 5,575,766 A | 11/1996 | Swartz et al. | | 5,735,847 A | 4/1998 | Gough et al. |
| 5,575,772 A | 11/1996 | Lennox | | 5,735,849 A | 4/1998 | Baden et al. |
| 5,575,788 A | 11/1996 | Baker et al. | | 5,738,628 A | 4/1998 | Sierocuk et al. |
| 5,575,805 A | 11/1996 | Li | | 5,740,808 A | 4/1998 | Panescu et al. |
| 5,575,810 A | 11/1996 | Swanson et al. | | 5,755,664 A | 5/1998 | Rubenstein |

| | | | | | | |
|---|---|---|---|---|---|---|
| 5,755,717 A | 5/1998 | Yates et al. | | 5,891,138 A | 4/1999 | Tu et al. |
| 5,755,760 A | 5/1998 | Maguire et al. | | 5,893,848 A | 4/1999 | Negus et al. |
| 5,759,158 A | 6/1998 | Swanson | | 5,893,863 A | 4/1999 | Yoon |
| 5,769,846 A | 6/1998 | Edwards et al. | | 5,895,417 A | 4/1999 | Pomeranz et al. |
| 5,773,033 A | 6/1998 | Cochrum et al. | | 5,897,529 A * | 4/1999 | Ponzi ..................... 604/95.04 |
| 5,776,130 A | 7/1998 | Buysse et al. | | 5,897,553 A | 4/1999 | Mulier |
| 5,782,827 A | 7/1998 | Gough et al. | | 5,897,554 A | 4/1999 | Chia et al. |
| 5,782,828 A | 7/1998 | Chen et al. | | 5,899,898 A | 5/1999 | Arless et al. |
| 5,785,706 A | 7/1998 | Bednarek | | 5,899,899 A | 5/1999 | Arless et al. |
| H1745 H | 8/1998 | Paraschac | | 5,902,289 A | 5/1999 | Swartz et al. |
| 5,788,636 A | 8/1998 | Curley | | 5,904,711 A | 5/1999 | Flom et al. |
| 5,792,140 A | 8/1998 | Tu et al. | | 5,906,580 A | 5/1999 | Kline-Schoder et al. |
| 5,797,906 A | 8/1998 | Rhum et al. | | 5,906,587 A | 5/1999 | Zimmon |
| 5,797,959 A | 8/1998 | Castro et al. | | 5,906,606 A | 5/1999 | Chee et al. |
| 5,797,960 A | 8/1998 | Stevens et al. | | 5,908,029 A | 6/1999 | Knudson et al. |
| 5,800,428 A | 9/1998 | Nelson et al. | | 5,910,129 A | 6/1999 | Koblish et al. |
| 5,800,482 A | 9/1998 | Pomeranz et al. | | 5,913,855 A | 6/1999 | Gough et al. |
| 5,800,484 A | 9/1998 | Gough et al. | | 5,913,876 A | 6/1999 | Taylor et al. |
| 5,803,911 A | 9/1998 | Inukai et al. | | 5,916,213 A | 6/1999 | Haissaguerre et al. |
| 5,807,393 A | 9/1998 | Williamson et al. | | 5,916,214 A | 6/1999 | Cosio et al. |
| 5,807,395 A | 9/1998 | Mulier et al. | | 5,921,924 A | 7/1999 | Avitall |
| 5,810,802 A | 9/1998 | Panescu et al. | | 5,921,982 A | 7/1999 | Lesh et al. |
| 5,810,804 A | 9/1998 | Gough et al. | | 5,925,038 A | 7/1999 | Panescu et al. |
| 5,810,805 A | 9/1998 | Sutcu et al. | | 5,925,042 A | 7/1999 | Gough et al. |
| 5,810,811 A | 9/1998 | Yates et al. | | 5,925,424 A | 7/1999 | Stevens et al. |
| 5,814,028 A | 9/1998 | Swartz et al. | | 5,927,284 A | 7/1999 | Borst et al. |
| 5,817,005 A | 10/1998 | Cohen | | 5,928,138 A | 7/1999 | Knight et al. |
| 5,817,091 A | 10/1998 | Nardella et al. | | 5,928,191 A | 7/1999 | Houser et al. |
| 5,823,955 A | 10/1998 | Kuck et al. | | 5,928,229 A | 7/1999 | Gough et al. |
| 5,823,956 A | 10/1998 | Roth et al. | | 5,931,810 A | 8/1999 | Grabek |
| 5,827,216 A | 10/1998 | Igo et al. | | 5,931,836 A | 8/1999 | Hatta et al. |
| 5,829,447 A | 11/1998 | Stevens et al. | | 5,931,848 A | 8/1999 | Saadat |
| 5,836,311 A | 11/1998 | Borst et al. | | 5,935,126 A | 8/1999 | Riza |
| 5,836,947 A | 11/1998 | Fleischman et al. | | 5,938,660 A | 8/1999 | Swartz et al. |
| 5,840,030 A | 11/1998 | Ferek-Petric et al. | | 5,941,251 A | 8/1999 | Panescu et al. |
| 5,842,984 A | 12/1998 | Avitall | | 5,941,845 A | 8/1999 | Tu et al. |
| 5,843,075 A | 12/1998 | Taylor | | 5,944,718 A | 8/1999 | Austin et al. |
| 5,843,122 A | 12/1998 | Riza | | 5,947,938 A | 9/1999 | Swartz et al. |
| 5,844,349 A | 12/1998 | Oakley et al. | | 5,951,547 A | 9/1999 | Gough et al. |
| 5,846,187 A | 12/1998 | Wells et al. | | 5,951,552 A | 9/1999 | Long et al. |
| 5,846,191 A | 12/1998 | Wells et al. | | 5,954,661 A | 9/1999 | Greenspon et al. |
| 5,846,238 A | 12/1998 | Jackson et al. | | 5,954,665 A | 9/1999 | Ben-Haim |
| 5,849,011 A | 12/1998 | Jones et al. | | 5,954,757 A | 9/1999 | Gray |
| 5,849,020 A | 12/1998 | Long et al. | | 5,961,514 A | 10/1999 | Long et al. |
| 5,849,028 A | 12/1998 | Chen | | 5,967,976 A | 10/1999 | Larsen |
| 5,853,411 A | 12/1998 | Whayne et al. | | 5,971,980 A | 10/1999 | Sherman |
| 5,855,590 A | 1/1999 | Malecki et al. | | 5,971,983 A | 10/1999 | Lesh |
| 5,855,614 A | 1/1999 | Stevens et al. | | 5,972,013 A | 10/1999 | Schmidt |
| 5,860,975 A | 1/1999 | Goble et al. | | 5,972,026 A | 10/1999 | Laufer et al. |
| 5,863,290 A | 1/1999 | Gough et al. | | 5,978,714 A | 11/1999 | Zadini et al. |
| 5,863,291 A | 1/1999 | Schaer | | 5,980,516 A | 11/1999 | Mulier et al. |
| 5,868,737 A | 2/1999 | Taylor et al. | | 5,980,517 A | 11/1999 | Gough |
| 5,868,770 A | 2/1999 | Rygaard | | 5,984,281 A | 11/1999 | Hacker et al. |
| 5,871,483 A | 2/1999 | Jackson et al. | | 5,993,447 A | 11/1999 | Blewett et al. |
| 5,871,523 A | 2/1999 | Fleischman et al. | | 5,997,533 A | 12/1999 | Kuhns |
| 5,871,525 A | 2/1999 | Edwards et al. | | 6,004,269 A | 12/1999 | Crowley et al. |
| 5,873,845 A | 2/1999 | Cline et al. | | 6,006,138 A | 12/1999 | Don Michael |
| 5,873,896 A | 2/1999 | Ideker | | 6,007,499 A | 12/1999 | Martin et al. |
| 5,875,782 A | 3/1999 | Ferrari et al. | | 6,010,476 A | 1/2000 | Saadat |
| 5,876,398 A | 3/1999 | Mulier et al. | | 6,010,516 A | 1/2000 | Hulka |
| 5,876,399 A | 3/1999 | Chia et al. | | 6,010,531 A | 1/2000 | Donlon et al. |
| 5,876,400 A | 3/1999 | Songer | | 6,012,457 A | 1/2000 | Lesh |
| 5,876,401 A | 3/1999 | Schulze et al. | | 6,013,074 A | 1/2000 | Taylor |
| 5,879,295 A | 3/1999 | Li et al. | | 6,015,378 A | 1/2000 | Borst et al. |
| 5,879,296 A | 3/1999 | Ockuly et al. | | 6,016,809 A | 1/2000 | Mulier et al. |
| 5,881,732 A | 3/1999 | Sung et al. | | 6,016,811 A | 1/2000 | Knopp et al. |
| 5,882,346 A | 3/1999 | Pomeranz et al. | | 6,017,358 A | 1/2000 | Yoon et al. |
| 5,883,690 A | 3/1999 | Meyers et al. | | 6,023,638 A | 2/2000 | Swanson |
| 5,883,703 A | 3/1999 | Knirck et al. | | 6,024,740 A | 2/2000 | Lesh et al. |
| 5,885,278 A | 3/1999 | Fleischman | | 6,024,741 A | 2/2000 | Williamson et al. |
| 5,891,028 A | 4/1999 | Lundbäck | | 6,030,403 A | 2/2000 | Long et al. |
| 5,891,135 A | 4/1999 | Jackson et al. | | 6,033,402 A | 3/2000 | Tu et al. |
| 5,891,136 A | 4/1999 | McGee et al. | | 6,036,641 A | 3/2000 | Taylor et al. |

| | | | |
|---|---|---|---|
| 6,036,670 A | 3/2000 | Wijeratne et al. |
| 6,039,731 A | 3/2000 | Taylor et al. |
| 6,039,733 A | 3/2000 | Buysse et al. |
| 6,039,748 A | 3/2000 | Savage et al. |
| 6,042,556 A | 3/2000 | Beach et al. |
| 6,047,218 A | 4/2000 | Whayne et al. |
| 6,048,329 A | 4/2000 | Thompson et al. |
| 6,050,996 A | 4/2000 | Schmaltz et al. |
| 6,059,719 A | 5/2000 | Yamamoto et al. |
| 6,060,454 A | 5/2000 | Duhaylongsod |
| 6,063,081 A | 5/2000 | Mulier |
| 6,064,901 A | 5/2000 | Cartmell et al. |
| 6,064,902 A | 5/2000 | Haissaguerre et al. |
| 6,068,653 A | 5/2000 | LaFontaine |
| 6,071,279 A | 6/2000 | Whayne et al. |
| 6,071,281 A | 6/2000 | Burnside et al. |
| 6,080,175 A | 6/2000 | Hogendijk |
| 6,083,150 A | 7/2000 | Aznoian et al. |
| 6,083,222 A | 7/2000 | Klein et al. |
| 6,088,894 A | 7/2000 | Oakley |
| 6,096,037 A | 8/2000 | Mulier |
| 6,102,853 A | 8/2000 | Scirica et al. |
| 6,110,098 A | 8/2000 | Renirie et al. |
| 6,113,592 A | 9/2000 | Taylor |
| 6,113,595 A | 9/2000 | Muntermann |
| 6,113,598 A | 9/2000 | Baker |
| 6,117,101 A | 9/2000 | Diederich et al. |
| 6,120,496 A | 9/2000 | Whayne et al. |
| 6,123,703 A | 9/2000 | Tu et al. |
| 6,126,658 A | 10/2000 | Baker |
| 6,129,662 A | 10/2000 | Li et al. |
| 6,142,993 A | 11/2000 | Whayne et al. |
| 6,142,994 A | 11/2000 | Swanson et al. |
| 6,152,920 A | 11/2000 | Thompson et al. |
| 6,156,009 A | 12/2000 | Grabek |
| 6,156,033 A | 12/2000 | Tu et al. |
| 6,161,543 A | 12/2000 | Cox et al. |
| 6,162,195 A | 12/2000 | Igo et al. |
| 6,162,220 A | 12/2000 | Nezhat |
| 6,165,174 A | 12/2000 | Jacobs et al. |
| 6,185,356 B1 | 2/2001 | Parker et al. |
| 6,193,713 B1 | 2/2001 | Geistert et al. |
| 6,199,556 B1 | 3/2001 | Benetti et al. |
| 6,203,557 B1 | 3/2001 | Chin |
| 6,206,823 B1 | 3/2001 | Kolata et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,334 B1 | 5/2001 | Easterbrook, III et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,254,525 B1 | 7/2001 | Reinhardt et al. |
| 6,264,087 B1 | 7/2001 | Whitman |
| 6,264,670 B1 | 7/2001 | Chin |
| 6,267,761 B1 | 7/2001 | Ryan |
| 6,270,471 B1 | 8/2001 | Hechel et al. |
| 6,273,887 B1 | 8/2001 | Yamauchi et al. |
| 6,277,117 B1 | 8/2001 | Tetzlaff et al. |
| 6,292,678 B1 | 9/2001 | Hall et al. |
| 6,293,943 B1 | 9/2001 | Panescu et al. |
| 6,296,619 B1 | 10/2001 | Brisken et al. |
| 6,296,640 B1 | 10/2001 | Wampler et al. |
| 6,302,880 B1 | 10/2001 | Schaer |
| 6,304,712 B1 | 10/2001 | Davis |
| 6,308,091 B1 | 10/2001 | Avitall |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,319,230 B1 | 11/2001 | Palasis et al. |
| 6,319,231 B1 | 11/2001 | Palasis et al. |
| 6,325,797 B1 | 12/2001 | Stewart et al. |
| 6,328,736 B1 | 12/2001 | Mulier |
| 6,332,089 B1 | 12/2001 | Acker et al. |
| 6,332,468 B1 | 12/2001 | Benetti |
| 6,332,881 B1 | 12/2001 | Carner et al. |
| 6,334,860 B1 | 1/2002 | Dorn |
| 6,356,790 B1 | 3/2002 | Maguire et al. |
| 6,358,248 B1 | 3/2002 | Mulier |
| 6,358,249 B1 | 3/2002 | Chen et al. |
| 6,361,531 B1 | 3/2002 | Hissong |
| 6,363,279 B1 | 3/2002 | Ben-Haim et al. |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,381,499 B1 | 4/2002 | Taylor et al. |
| 6,383,151 B1 | 5/2002 | Diederich et al. |
| 6,385,472 B1 | 5/2002 | Hall et al. |
| 6,391,024 B1 | 5/2002 | Sun et al. |
| 6,394,948 B1 | 5/2002 | Borst et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,423,051 B1 | 7/2002 | Kaplan et al. |
| 6,425,867 B1 | 7/2002 | Vaezy et al. |
| 6,428,180 B1 | 8/2002 | Karram et al. |
| 6,429,217 B1 | 8/2002 | Puskas |
| 6,430,426 B2 | 8/2002 | Avitall |
| 6,440,130 B1 | 8/2002 | Mulier |
| 6,443,952 B1 | 9/2002 | Mulier |
| 6,443,970 B1 | 9/2002 | Schulze et al. |
| 6,447,443 B1 | 9/2002 | Keogh et al. |
| 6,447,507 B1 | 9/2002 | Bednarek et al. |
| 6,461,314 B1 | 10/2002 | Pant et al. |
| 6,461,356 B1 | 10/2002 | Patterson |
| 6,464,630 B1 | 10/2002 | Borst et al. |
| 6,464,700 B1 | 10/2002 | Koblish et al. |
| 6,464,707 B1 | 10/2002 | Bjerken |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,728 B1 | 11/2002 | Wright |
| 6,484,727 B1 | 11/2002 | Vaska et al. |
| 6,487,441 B1 | 11/2002 | Swanson et al. |
| 6,488,678 B2 | 12/2002 | Sherman |
| 6,488,680 B1 | 12/2002 | Francischelli |
| 6,502,575 B1 | 1/2003 | Jacobs et al. |
| 6,504,985 B2 | 1/2003 | Parker et al. |
| 6,506,189 B1 | 1/2003 | Rittman, III et al. |
| 6,506,200 B1 | 1/2003 | Chin |
| 6,514,250 B1 | 2/2003 | Jahns |
| 6,517,536 B2 | 2/2003 | Hooven |
| 6,527,767 B2 | 3/2003 | Wang et al. |
| 6,532,338 B1 | 3/2003 | Nemoto |
| 6,537,248 B2 | 3/2003 | Mulier |
| 6,537,272 B2 | 3/2003 | Christopherson |
| 6,540,740 B2 | 4/2003 | Lehmann et al. |
| 6,546,935 B2 | 4/2003 | Hooven |
| 6,549,812 B1 | 4/2003 | Smits |
| 6,551,338 B1 | 4/2003 | Chiu et al. |
| 6,554,768 B1 | 4/2003 | Leonard |
| 6,558,314 B1 | 5/2003 | Adelman et al. |
| 6,558,382 B2 | 5/2003 | Jahns |
| 6,575,969 B1 | 6/2003 | Rittman, III et al. |
| 6,584,360 B2 | 6/2003 | Francischelli |

| Patent/Pub No. | Date | Inventor |
|---|---|---|
| 6,585,732 B2 | 7/2003 | Mulier |
| 6,591,049 B2 | 7/2003 | Williams et al. |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,632,222 B1 | 10/2003 | Edwards et al. |
| 6,641,604 B1* | 11/2003 | Adelman et al. ............... 600/37 |
| 6,645,199 B1 | 11/2003 | Jenkins et al. |
| 6,648,883 B2 | 11/2003 | Francischelli |
| 6,651,672 B2 | 11/2003 | Roth |
| 6,656,175 B2 | 12/2003 | Francischelli |
| 6,663,627 B2 | 12/2003 | Francischelli |
| 6,666,844 B1 | 12/2003 | Igo et al. |
| 6,679,882 B1 | 1/2004 | Kornerup |
| 6,689,103 B1 | 2/2004 | Palasis |
| 6,692,450 B1 | 2/2004 | Coleman |
| 6,692,491 B1 | 2/2004 | Phan |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,709,413 B1* | 3/2004 | Chance et al. ............. 604/6.04 |
| 6,716,211 B2 | 4/2004 | Mulier |
| 6,736,810 B2 | 5/2004 | Hoey |
| 6,743,211 B1* | 6/2004 | Prausnitz et al. ............ 604/239 |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,837,848 B2 | 1/2005 | Bonner et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,918,908 B2 | 7/2005 | Bonner |
| 6,936,046 B2 | 8/2005 | Hissong |
| 6,942,639 B2* | 9/2005 | Baugh et al. ................. 604/82 |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 6,969,373 B2 | 11/2005 | Schwartz et al. |
| 2001/0031961 A1 | 10/2001 | Hooven |
| 2001/0039419 A1 | 11/2001 | Francischelli et al. |
| 2002/0002329 A1 | 1/2002 | Avitall |
| 2002/0002372 A1 | 1/2002 | Jahns et al. |
| 2002/0009275 A1 | 1/2002 | Williams et al. |
| 2002/0019629 A1 | 2/2002 | Dietz et al. |
| 2002/0032440 A1 | 3/2002 | Hooven |
| 2002/0052602 A1 | 5/2002 | Wang et al. |
| 2002/0082595 A1 | 6/2002 | Langberg et al. |
| 2002/0091382 A1 | 7/2002 | Hooven |
| 2002/0091383 A1 | 7/2002 | Hooven |
| 2002/0091384 A1 | 7/2002 | Hooven |
| 2002/0095139 A1 | 7/2002 | Keogh et al. |
| 2002/0099364 A1 | 7/2002 | Lalonde |
| 2002/0103484 A1 | 8/2002 | Hooven |
| 2002/0107513 A1 | 8/2002 | Hooven |
| 2002/0107514 A1 | 8/2002 | Hooven |
| 2002/0115990 A1 | 8/2002 | Acker |
| 2002/0115993 A1 | 8/2002 | Hooven |
| 2002/0120263 A1 | 8/2002 | Brown et al. |
| 2002/0120316 A1 | 8/2002 | Hooven |
| 2002/0128643 A1 | 9/2002 | Simpson et al. |
| 2002/0138109 A1 | 9/2002 | Jahns et al. |
| 2002/0183738 A1 | 12/2002 | Chee et al. |
| 2003/0004507 A1 | 1/2003 | Francischelli et al. |
| 2003/0009094 A1 | 1/2003 | Segner et al. |
| 2003/0018252 A1 | 1/2003 | Duchon et al. |
| 2003/0018329 A1 | 1/2003 | Hooven |
| 2003/0028187 A1 | 2/2003 | Vaska et al. |
| 2003/0032952 A1 | 2/2003 | Hooven |
| 2003/0045871 A1 | 3/2003 | Jain et al. |
| 2003/0045872 A1 | 3/2003 | Jacobs |
| 2003/0050557 A1 | 3/2003 | Susil et al. |
| 2003/0060822 A1 | 3/2003 | Schaer et al. |
| 2003/0069572 A1 | 4/2003 | Wellman et al. |
| 2003/0069577 A1 | 4/2003 | Vaska et al. |
| 2003/0073991 A1 | 4/2003 | Francischelli et al. |
| 2003/0078570 A1 | 4/2003 | Heiner et al. |
| 2003/0078574 A1 | 4/2003 | Hall et al. |
| 2003/0091547 A1 | 5/2003 | Edelberg et al. |
| 2003/0093104 A1 | 5/2003 | Bonner et al. |
| 2003/0097124 A1 | 5/2003 | Lehmann et al. |
| 2003/0100895 A1 | 5/2003 | Simpson et al. |
| 2003/0114844 A1 | 6/2003 | Ormsby et al. |
| 2003/0120268 A1 | 6/2003 | Bertolero et al. |
| 2003/0125726 A1 | 7/2003 | Maguire et al. |
| 2003/0125729 A1 | 7/2003 | Hooven |
| 2003/0125730 A1 | 7/2003 | Berube et al. |
| 2003/0130598 A1 | 7/2003 | Manning et al. |
| 2003/0135207 A1 | 7/2003 | Langberg et al. |
| 2003/0144656 A1 | 7/2003 | Ocel |
| 2003/0144657 A1 | 7/2003 | Bowe et al. |
| 2003/0158548 A1 | 8/2003 | Phan et al. |
| 2003/0171745 A1 | 9/2003 | Francischelli et al. |
| 2003/0178032 A1 | 9/2003 | Ingle et al. |
| 2003/0187460 A1 | 10/2003 | Chin et al. |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0102804 A1* | 5/2004 | Chin .......................... 606/190 |
| 2004/0138621 A1 | 7/2004 | Jahns |
| 2004/0138656 A1 | 7/2004 | Francischelli |
| 2004/0143260 A1 | 7/2004 | Francischelli |
| 2004/0167558 A1* | 8/2004 | Igo et al. .................... 606/185 |
| 2004/0186465 A1 | 9/2004 | Francischelli |
| 2004/0186531 A1 | 9/2004 | Jahns et al. |
| 2004/0215183 A1 | 10/2004 | Hoey |
| 2004/0216748 A1 | 11/2004 | Chin |
| 2004/0220560 A1 | 11/2004 | Briscoe |
| 2004/0236322 A1 | 11/2004 | Mulier |
| 2004/0249368 A1 | 12/2004 | Hooven |
| 2004/0267326 A1 | 12/2004 | Ocel |
| 2005/0010095 A1 | 1/2005 | Stewart et al. |
| 2005/0020901 A1 | 1/2005 | Belson et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0203561 A1 | 9/2005 | Palmer et al. |
| 2005/0203562 A1 | 9/2005 | Palmer et al. |
| 2005/0209564 A1 | 9/2005 | Bonner |
| 2005/0236325 A1* | 10/2005 | Dolecek et al. .......... 210/512.1 |
| 2005/0256522 A1 | 11/2005 | Francischelli et al. |
| 2005/0261673 A1 | 11/2005 | Bonner et al. |
| 2005/0267454 A1 | 12/2005 | Hissong |
| 2006/0009756 A1 | 1/2006 | Francischelli |
| 2006/0009759 A1 | 1/2006 | Christian |
| 2006/0041243 A1 | 2/2006 | Nayak |

2007/0049863 A1  3/2007  Jahns

FOREIGN PATENT DOCUMENTS

| | | |
|---|---|---|
| EP | 0 450 608 | 10/1991 |
| EP | 0 765 639 | 4/1997 |
| EP | 1585446 | 10/2005 |
| EP | 1589879 | 11/2005 |
| WO | 92/05828 | 4/1992 |
| WO | 93/25267 | 12/1993 |
| WO | 97/10764 | 3/1997 |
| WO | 97/32525 | 9/1997 |
| WO | 98/17187 | 4/1998 |
| WO | 98/53750 | 12/1998 |
| WO | 99/02096 | 1/1999 |
| WO | 99/04696 | 2/1999 |
| WO | 99/12487 | 3/1999 |
| WO | 99/44519 | 9/1999 |
| WO | 99/56486 | 11/1999 |
| WO | 99/56644 | 11/1999 |
| WO | 99/56648 | 11/1999 |
| WO | 99/59486 | 11/1999 |
| WO | 00/21449 | 4/2000 |
| WO | 00/27310 | 5/2000 |
| WO | 00/27311 | 5/2000 |
| WO | 00/27312 | 5/2000 |
| WO | 00/27313 | 5/2000 |
| WO | 00/42931 | 7/2000 |
| WO | 00/42932 | 7/2000 |
| WO | 00/42933 | 7/2000 |
| WO | 00/42934 | 7/2000 |
| WO | 00/67647 | 11/2000 |
| WO | 00/72912 | 12/2000 |
| WO | 00/74574 | 12/2000 |
| WO | 01/82812 | 11/2001 |
| WO | 01/82813 | 11/2001 |
| WO | 02/00278 | 1/2002 |
| WO | 02/087454 | 11/2002 |
| WO | 02/102252 | 12/2002 |
| WO | 03/105706 | 12/2003 |
| WO | 2004/064647 | 8/2004 |
| WO | 2007/002227 | 1/2007 |
| WO | 2007/005297 | 1/2007 |

OTHER PUBLICATIONS

Gallagher et al., "Cryosurgical Ablation of Accessory Atrioventricular Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 ½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

ISR from PCT/US2005/043200 (dated Mar. 29, 2006) (4 pages).

Berjano, et al., "Bipolar Electrosurgery with Long Electrodes for RF Coagulation of Atrial Tissue," Proceedings 19th International Conference IEEE/EMBS Oct. 30 —Nov. 2, 1997, Chicago, IL, USA, PP. 2528-2530.

Chen, et al., "Radiofrequency and Cryoablation of Atrial Fibrillation in Patients Undergoing Valvular Operations," Annals of Thoracic Surety, 1998:65:1666-1672.

Elvan, et al., Abstract, "Radiofrequency Catheter Ablation of the Atria Reduces Inducibility and Duration of ATrial Fibrillation in Dogs," Circulation, 1995:91:2235-2244.

Inoue, et al., "Video Assisted Thoracoscopic and Cardioscopic Radiofrequency Maze Ablation," ASAIO Journal, 1997, pp. 334-337.

Kawaguchi, et al., "Factors Affecting Rhythm After the Maze Procedure for Atrial Fibrillation," Circulation, 1996 94(9 Supp):II139-42.

Kim, et al., Abstract "The Cox-Maze III Procedure for Atrial Fibrillation Associated with Rheumatic Mitral Valve Disease," The Annals of Thoracic Surgery, 2000; pp. 1-5.

Kosakai, et al., "Cox Maze Procedure for Chronic Atrial Fibrillation Associated with Mitral Valve Disease," the Journal of Thoracic and Cardiovascular Surgery, 1994; vol. 108, No. 6, pp. 1049-1055.

Robbins, et al., "Pulmonary Vein Stenosis After Catheter Ablation of Atrial Fibrillation,"Circulation, 1998; 98:1769-1775.

Sueda, et al., "Efficacy of a Simple Left Atrial Procedure for Chronic Atrial Fibrillation in Mitral Valve Operations," The Annals of Thoracic Surgery, 1997, vol. 63, pp. 1070-1073.

Sueda, et al., "Simple Left Atrial Procedure for Chronic Atrial Fibrillation Associated with Mitral Valve Disease," The Annals of Thoracic Surgery, 1996; 62:1796-1800.

Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiology, 2000, vol. 35, No. 2, pp. 442-450.

Non-final office action from U.S. Appl. No. 10/156,315, dated Dec. 14, 2007 (11 pages).

Written opinion from International application No. PCT/US2004/000597 dated May 8, 2004 (7 pages).

Written opinion from International application No. PCT/US2006/024189 dated Apr. 1, 2007 (4 pages).

Written opinion from International application No. PCT/US2006/024191 dated Nov. 1, 2007 (6 pages).

Randall et al., "Local epicardial chemical ablation of vagal input to sino-atrial and atrioventricular recions of the canine heart." Journal of the Autonomic nervous system. 1984, pp. 145-159.

Guidraudon et al., "Surgical ablation of posterior septal accessory pathways in the Wolff-Parkison-White syndrome by a closed heart technique." Journal of Thoracic Cardiovascular Surgery. 1986, p. 406-413.

* cited by examiner

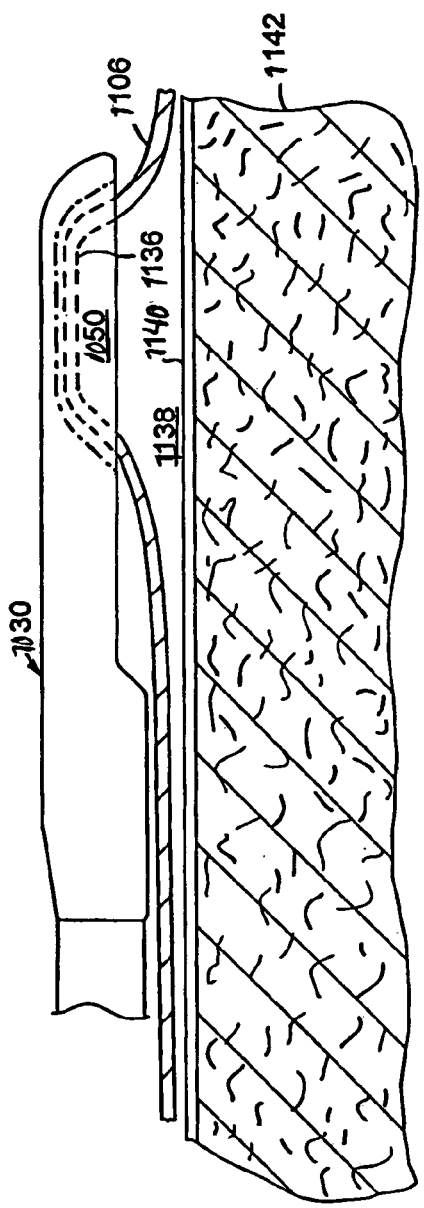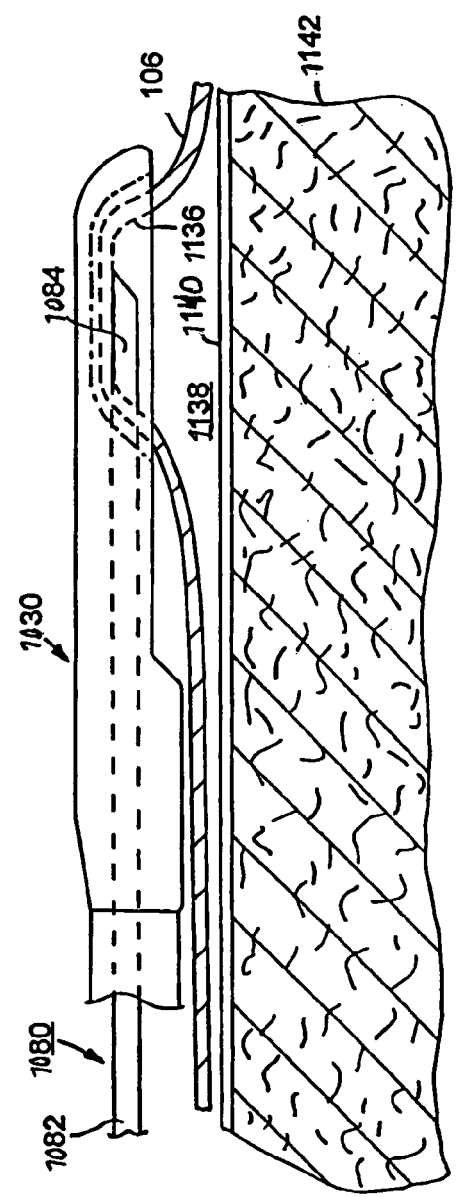
FIG. 2a
FIG. 2b

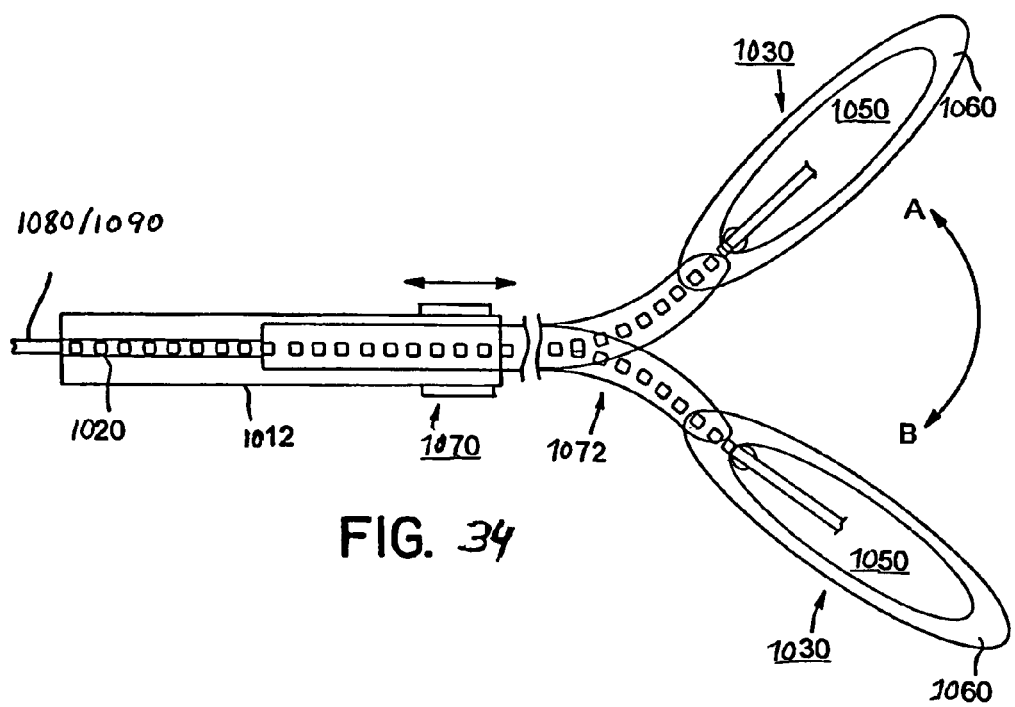
FIG. 34
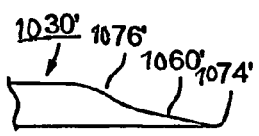
FIG. 35A
FIG. 36A
FIG. 37A
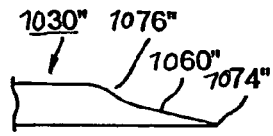
FIG. 35B
FIG. 36B
FIG. 37B

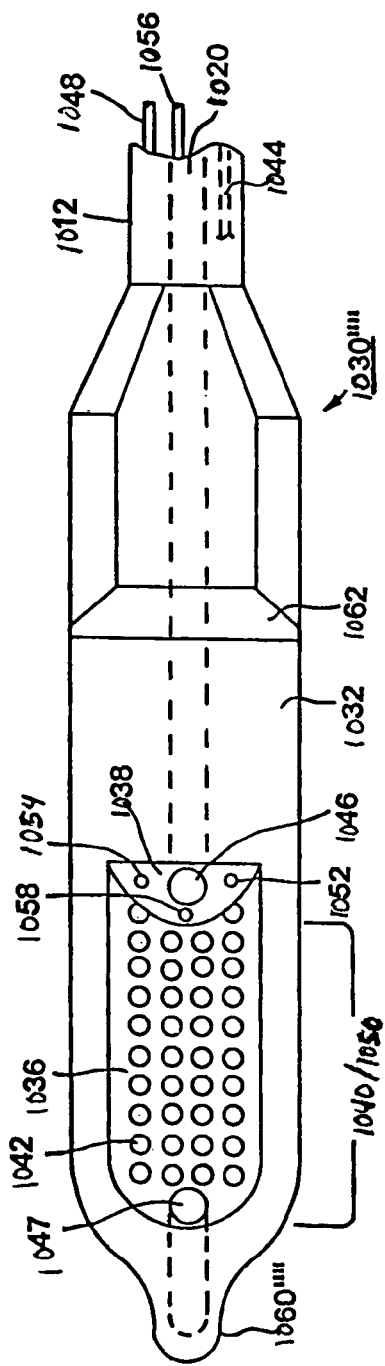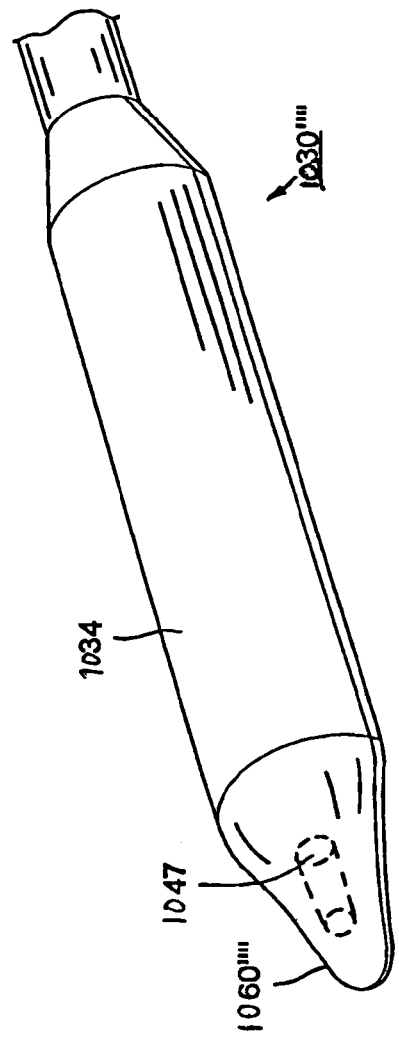
FIG. 41
FIG. 42

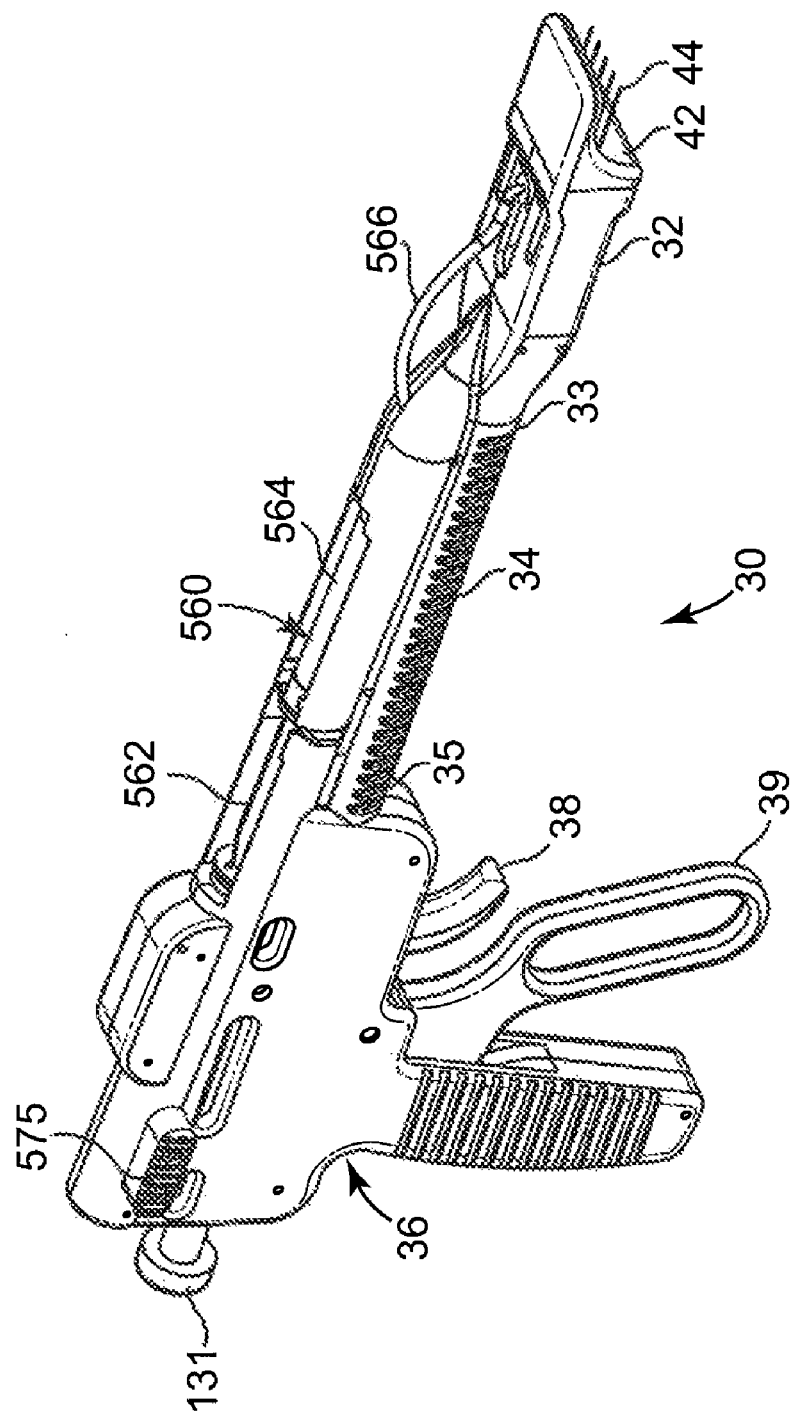

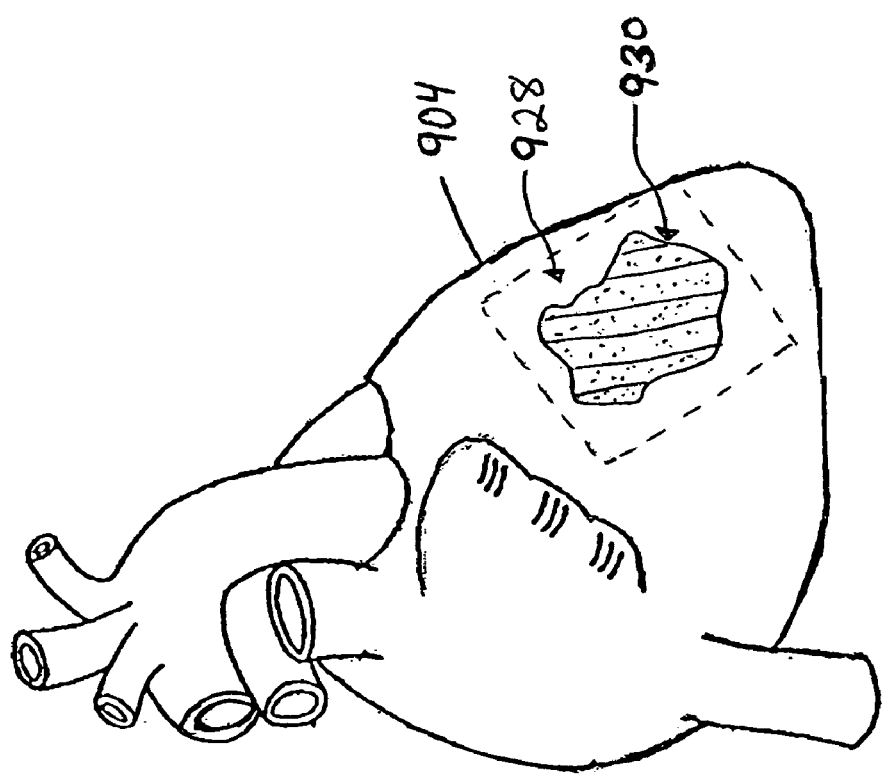

DEVICES AND METHODS FOR INTERSTITIAL INJECTION OF BIOLOGIC AGENTS INTO TISSUE

CROSS-REFERENCE TO RELATED APPLICATIONS

This application is a continuation-in-part of U.S. patent application Ser. No. 11/000,798, filed Nov. 30, 2004, which is a continuation-in-part of U.S. patent application Ser. No. 10/341,743, filed Jan. 14, 2003, the disclosures of which are incorporated herein by reference.

U.S. patent application Ser. No. 11/000,798, filed Nov. 30, 2004, is also a continuation-in-part of U.S. patent application Ser. No. 10/622,147, filed Jul. 17, 2003, now U.S. Pat. No. 6,918,908 which is a continuation-in-part of U.S. patent application Ser. No. 10/342,932, filed Jan. 15, 2003, now U.S. Pat No. 6,837,848 which is related to commonly assigned U.S. patent application Ser. No. 10/283,794, filed Oct. 30, 2002, for METHODS AND APPARATUS FOR ACCESSING AND STABILIZING AN AREA OF THE HEART in the names of Gary W. Guenst et al., U.S. patent application Ser. No. 10/342,960 filed Jan. 15, 2003, for METHODS AND TOOLS FOR ACCESSING AN ANATOMIC SPACE in the name of Gary W. Guenst, and U.S. patent application Ser. No. 10/284,771 filed Oct. 31, 2002, for ANATOMIC SPACE ACCESS SUCTION TOOLS AND METHODS in the names of Koen Michels et al., the disclosures of which are incorporated herein by reference.

U.S. patent application Ser. No. 11/000,798, filed Nov. 30, 2004, is also a continuation-in-part of U.S. patent application Ser. No. 10/156,315, filed May 28, 2002, now U.S. Pat. No. 7,507,235 which is a continuation of U.S. patent application Ser. No. 09/879,294, filed Jun. 12, 2001, now U.S. Pat. No. 6,447,443, which claims priority to co-owned U.S. Provisional Patent Application Ser. No. 60/261,343 filed Jan. 13, 2001, Ser. No. 60/263,739 filed Jan. 24, 2001, Ser. No. 60/282,029 filed Apr. 6, 2001 and Ser. No. 60/286,952 filed Apr. 26, 2001, the disclosures of which are incorporated herein by reference.

FIELD OF THE INVENTION

The present invention is related generally to medical devices and methods. More specifically, the present invention relates to methods and devices for injecting medical and biological agents into tissue. The present invention includes medical devices and therapeutic methods for use in treating injuries in injured, ischemic, or infarcted tissue. Methods of the present invention include driving injection needles into tissue that find one, non-limiting use in a minimally invasive procedure for injecting cells and/or agents into an infarct zone to repair myocardial tissue.

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, covers the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

It is frequently medically necessary to access the pericardial space to treat an injury, infection, disease or defect of the heart, e.g., an occluded coronary artery, an infarct zone, a defective heart valve, aberrant electrical pathways causing tachyarrhythmias, bacterial infections, to provide cardiac resynchronization therapy, or to place epicardial pacing or cardioversion/defibrillation electrodes against the epicardium or into the myocardium at selected sites. It is necessary in these procedures to surgically expose and cut through the pericardium to obtain access to the pericardial space.

Highly invasive surgical techniques, referred to as a median sternotomy (open-chest surgical exposure) or a thoracotomy, have been typically employed to provide the surgeon access to the pericardial space and the heart. A median sternotomy incision begins just below the sternal notch and extends slightly below the xyphoid process. A sternal retractor is used to separate the sternal edges for optimal exposure of the heart. Hemostasis of the sternal edges is typically obtained using electrocautery with a ball-tip electrode and a thin layer of bone wax.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced In order to reduce the risk of morbidity, expense, trauma, patient mortality, infection, and other complications associated with open-chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing coronary artery bypass graft (CABG) procedures using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through ports inserted in the incisions, and a thoracoscope to view the accessed cardiac site while the procedure is performed as shown, for example, in U.S. Pat. Nos. 6,332,468, 5,464,447, and 5,716,392. Surgical trocars having a diameter of about 3 mm to 15 mm are fitted into lumens of tubular trocar sleeves, cannulae or ports, and the assemblies are inserted into skin incisions. The trocar tip is advanced to puncture the abdomen or chest to reach the pericardium, and the trocar is then withdrawn leaving the sleeve or port in place. Surgical instruments and other devices such as fiber optic thoracoscopes can be inserted into the body cavity through the sleeve or port lumens. As stated in the '468 patent, instruments advanced through trocars can include electrosurgical tools, graspers, forceps, scalpels, electrocauteries, clip appliers, scissors, etc.

In such procedures, the surgeon can stop the heart by utilizing a series of internal catheters to stop blood flow through the aorta and to administer cardioplegia solution. The endoscopic approach utilizes groin cannulation to establish cardio-pulmonary bypass (CPB) and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

Problems may develop during CPB due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from CPB include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during CPB, some surgeons have attempted to perform cardiac-related medical procedures without cardiac arrest and CPB. For example, Trapp and Bisarya in "Placement of Coronary Artery Bypass Graft Without Pump Oxygenator", Annals Thorac. Surg. Vol. 19, No. 1, (January 1975) pgs. 1-9, immobilized the area of a bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass", Annals Thorac. Surg. Vol. 55, (February 1993) pgs. 486-489 also reported immobilizing the area of a bypass graft with stabilization sutures.

Suction stabilization systems, such as the Medtronic Octopus® Tissue Stabilizer and the Medtronic Starfish® and Urchin® Heart Positioners (available from Medtronic, Inc., Minneapolis, Minn. USA) use suction to grip and immobilize the surface of the heart. Additionally, the system allows the surgeon to manipulate the surgical site into better view by rotating and supporting the heart. See, also, e.g., U.S. Pat. Nos. 5,836,311; 5,927,284 and 6,015,378, and co-assigned U.S. patent application Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806. The Octopus® stabilizer and Starfish® and Urchin® positioners facilitate moving or repositioning the heart to achieve better access to areas which would otherwise be difficult to access, such as the posterior or backside of the heart.

The recently developed, beating heart procedures also disclosed in U.S. Pat. No. 6,394,948, for example, eliminate the need for any form of CPB, the extensive surgical procedures necessary to connect the patient to a CPB machine, and to stop the heart. These beating heart procedures can be performed on a heart exposed in a full or limited thoracotomy or accessed percutaneously.

In some percutaneous procedures, the epicardium of the beating or stopped heart is exposed to view typically by use of grasping and cutting instruments inserted through one port to cut through the pericardium surrounding the heart while the area is viewed through the thoracoscope or endoscope inserted through another port. The thoracoscopic approach typically requires the placement of a chest tube and admission to the hospital for the initial 1-2 post-operative days.

Therefore, much effort has been expended to develop medical devices and techniques to access the pericardial space employing such minimally invasive percutaneous procedures. One difficulty has been that normally the pericardial space is so small or thin that it is difficult to penetrate the pericardium using miniaturized instruments capable of being introduced through a port to the site without also puncturing the underling epicardium and thereby, damaging the myocardium or a coronary vessel. Proliferative adhesions occur between the pericardium and the epicardium in diseased hearts and hamper access to the pericardial space employing such minimally invasive percutaneous procedures. The simple percutaneous approach can be used to penetrate the pericardium to drain a large pericardial effusion, i.e., an accumulation of too much fluid in the pericardial space that widens the pericardial space. A spinal needle (18-20 gauge) and stylet occluding the needle lumen are advanced incrementally in a superior/posterior fashion through a small (2-4 mm) cutaneous incision between the xyphoid and costal cartilage. Periodically, the stylet is removed, and fluid aspiration is attempted through the needle lumen. The advancement is halted when fluid is successfully aspirated, and the pericardial effusion is then relieved.

Methods and apparatus for accessing the pericardial space for the insertion of implantable defibrillation leads are disclosed in U.S. Pat. Nos. 5,071,428 and 6,156,009, wherein a forceps device is used to grip the pericardium and pull it outward to form a "tent". In the '428 patent, a scissors or scalpel is introduced to cut the pericardium (pericardiotomy) under direct vision through a sub-xyphoid surgical incision. The forceps device disclosed in the '009 patent incorporates a mechanism for introducing electrical leads or guidewires through the outwardly displaced pericardium. It is difficult to introduce and use the forceps through the narrow lumen of a port or sleeve, particularly if the pericardial fluid is under pressure that makes the pericardium taut like an inflated balloon.

Further methods and apparatus for accessing the pericardial space for the insertion of devices or drugs are disclosed in U.S. Pat. No. 6,423,051, wherein an access tube having a device access lumen is provided with a plurality of hooks in the tube distal end that can be used to hook into the pericardium to enable the lifting and "tenting" of the pericardium. A cutting instrument or sharpened tip guidewire or the like can be advanced through the device access lumen to perforate the pericardium.

Other methods and apparatus that are introduced through percutaneously placed ports or directly through small trans-thoracic incisions for accessing the pericardial space employ suction devices to grip the pericardium or epicardium as disclosed, for example, in U.S. Pat. Nos. 4,991,578, 5,336,252, 5,827,216, 5,868,770, 5,972,013, 6,080,175, and 6,231,518 and the above-referenced '948 patent. The suction devices are configured like a catheter or tube having a single suction tool lumen and typically having a further instrument delivery lumen. The suction tool lumen terminates in a single suction tool lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction tool lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic.

For these reasons, it would be desirable to provide additional and improved methods and apparatus for the minimally invasive access to a patient's pericardial space. The methods and devices should be suitable for a wide variety of minimally invasive approaches to the pericardium, including at least intercostal/transthoracic and subxiphoid approaches, and the like. The methods and devices should further provide for secure and stable capture of the pericardium and permit the opening of a large space or volume between the pericardium and epicardium. Such access methods and apparatus should be useful for a wide variety of procedures to be performed in the pericardial space, including fluid withdrawal, drug delivery, cell delivery, diagnostic and therapeutic electrophysiology procedures, pacemaker lead implantation, defibrillator lead placement, transmyocardial revascularization, transmyocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like. At least some of these objectives will be met by the invention described herein.

Heart disease, including myocardial infarction, is a leading cause of death and impaired activity in human beings, particularly in the western world, most particularly among males. Heart disease can in turn degrade other physiological systems. Each year over 1.1 million Americans have a myocardial infarction, usually as a result of a heart attack. These myocardial infarctions result in an immediate depression in ventricular function and many of these infarctions are very likely to expand, provoking a cascading sequence of myocellular events known as negative or ventricular remodeling. In many cases, this progressive myocardial infarct expansion and negative remodeling leads to deterioration in ventricular function and heart failure.

A stenosed or blocked coronary artery is one example of heart disease. A totally blocked, or substantially blocked coronary artery can cause immediate, intermediate term, and long-term problems. In the immediate term, myocardial cells can be starved of oxygen resulting in cell death. In the intermediate term, the cell death can "cascade", leading to cell death in adjacent cells. In the long term, the myocardial cell death, which creates weakened, non-contracting infarct regions of the heart, can lead to heart failure.

A myocardial infarction (MI) can occur when a coronary artery becomes occluded and can no longer supply blood to the myocardial tissue, thereby resulting in myocardial cell death. When a myocardial infarction occurs, the myocardial tissue that is no longer receiving adequate blood flow dies and is replaced with scar tissue. Within seconds of a myocardial infarction, the under-perfused myocardial cells no longer contract, leading to abnormal wall motion, high wall stresses within and surrounding the infarct, and depressed ventricular function. The infarct expansion and negative remodeling are caused by these high stresses at the junction between the infarcted tissue and the normal myocardium. These high stresses eventually kill or severely depress function in the still viable myocardial cells. This results in an expansion of injury and dysfunctional tissue including and beyond the original myocardial infarct region.

According to the American Heart Association, in the year 2000 approximately 1,100,000 new myocardial infarctions occurred in the United States. For 650,000 patients this was their first myocardial infarction, while for the other 450,000 patients this was a recurrent event. Two hundred-twenty thousand people suffering MI die before reaching the hospital. Within one year of the myocardial infarction, 25% of men and 38% of women die. Within 6 years, 22% of Men and 46% of women develop chronic heart failure, of which 67% are disabled.

The consequences of MI are often severe and disabling. In addition to immediate hemodynamic effects, the infarcted tissue and the myocardium or cardiac tissue undergo three major processes: Infarct Expansion, Infarct Extension, and Negative remodeling.

Infarct expansion is a fixed, permanent, disproportionate regional thinning and dilatation of the infarct zone. Infarct expansion occurs early after a myocardial infarction. The mechanism is slippage of the tissue layers.

Infarct extension is additional myocardial necrosis following myocardial infarction. Infarct extension results in an increase in total mass of infarcted tissue. Infarct extension occurs days after a myocardial infarction. The mechanism for infarct extension appears to be an imbalance in the blood supply to the peri-infarct tissue versus the increased oxygen demands on the tissue.

When a myocardial infarction occurs, the myocardial tissue that is no longer receiving adequate blood flow dies and is replaced with scar tissue. This infarcted tissue cannot contract during systole, and may actually undergo lengthening in systole and leads to an immediate depression in ventricular function. This abnormal motion of the infarcted tissue can cause delayed conduction of electrical activity to the still surviving peri-infarct tissue and also places extra mechanical stress on the peri-infarct tissue. These factors individually and in combination contribute to the eventual myocardial dysfunction observed in the myocardial tissue remote from the site of the infarction.

The processes associated with infarct expansion and negative remodeling are believed to be the result of high stresses exerted at the junction between the infarcted tissue and the normal myocardium (i.e., the peri-infarct region). In the absence of intervention, these high stresses will eventually kill or severely depress function in the adjacent myocardial cells. As a result, the peri-infarct region will therefore grow outwardly from the original infarct site over time. This resulting wave of dysfunctional tissue spreading out from the original myocardial infarct region greatly exacerbates the nature of the disease and can often progress into advanced stages of congestive heart failure (CHF).

Negative remodeling is usually the progressive enlargement of the ventricle accompanied by a depression of ventricular function. Myocyte function in the myocardium remote from the initial myocardial infarction becomes depressed. Negative remodeling occurs weeks to years after myocardial infarction. Such negative remodeling usually occurs on the left side of the heart. Where negative remodeling does occur on the right side of the heart, it can generally be linked to negative remodeling (or some other negative event) on the left side of the heart. There are many potential mechanisms for negative remodeling, but it is generally believed that the high stress on peri-infarct tissue plays an important role. Due to altered geometry, wall stresses are much higher than normal in the myocardial tissue surrounding the infarction.

The treatments for myocardial infarction that are used currently, and that have been used in the past are varied. Immediately after a myocardial infarction, preventing and treating ventricular fibrillation and stabilizing the hemodynamics are well-established therapies.

Newer approaches include more aggressive efforts to restore patency to occluded vessels. This is accomplished through thrombolytic therapy or angioplasty and stents. Reopening the occluded artery within hours of initial occlusion can decrease tissue death, and thereby decrease the total magnitude of infarct expansion, extension, and negative remodeling. The immediate effects of a blocked coronary artery can be addressed through percutaneous coronary transluminal angioplasty (PCTA). PCTA can be used to dilate an occluded coronary artery, often in conjunction with stenting, to provide perfusing blood flow to cardiac cells downstream of the blockage. Alternatively, a coronary artery bypass graft (CABG) procedure may be used to bypass a blocked coronary artery.

More intermediate term damage can be addressed through the systemic or local delivery of agents to reduce or treat the cells affected by the initial injury. The longer-term problems, for example, heart failure resulting from infarct cardiac tissue, can be addressed by the systemic or local delivery of medical agents to the cardiac tissue. Some treatments include pharmaceuticals such as ACE inhibitors, beta blockers, diuretics, and $Ca.^{++}$ channel antagonists. These agents have multiple effects, but share in the ability to reduce aortic pressure, and thereby cause a slight decease in wall stress. These agents have been shown to slow the negative remodeling. However, drug compliance is far from optimal.

The direct delivery of agents to cardiac tissue is often preferred over the systemic delivery of such agents for several reasons. One reason is the substantial expense and small amount of the medical agents available, for example, agents used for gene therapy. Another reason is the substantially greater concentration of such agents that can be delivered directly into cardiac tissue, compared with the dilute concentrations possible through systemic delivery. Yet another reason is the undesirability or impossibility of systemically delivering agents to the heart tissue requiring treatment.

One mode of delivery for medical agents to myocardial tissue has been an epicardial, direct injection into myocardial tissue during an open chest procedure. Open chest procedures are inherently traumatic procedures with associated risks. The risks are often justified when the alternatives are a substantially high probability of death. In many cases, however, an open chest procedure is not believed justifiable only for the injection of medical agents into the myocardium.

Another approach taken to deliver medical agents into the myocardium has been an intravascular approach. Catheters may be advanced through the vasculature and into the heart to inject materials into myocardial tissue from within the heart. This approach may not allow all areas of the heart to be easily reached however. The size and type of instruments that can be advanced, for example, from a femoral artery approach, are also limited.

One relatively new therapy for treating infarcted cardiac tissue includes the injection of cells that are capable of maturing into actively contracting cardiac muscle cells. Examples of such cells include myocytes, mesenchymal stem cells, and pluripotent cells. Delivery of such cells into the myocardium is believed to be beneficial, particularly to prevent heart failure. Current intravascular delivery devices are less than optimal, being limited in the cardiac regions they can reach and the amount and types of materials they can deliver. Open chest procedures allow access to a larger range of cardiac tissue and also allow the delivery of greater varieties and amounts of agents, for example, cells. An open chest procedure may not be justifiable, however, only for the injection of such cells. In particular, patients having suffered a recent heart attack may be very poor candidates for such a procedure.

Despite improvements in therapy, the total number and incidence of heart failure continues to rise with over 400,000 new cases each year. Approximately 85% of these new cases are due to ischemic cardiomyopathy.

At present, there are no available procedures that provide both mechanical stabilization and biological therapy of ischemic myocardium to address myocardial extension, and negative remodeling. Such treatments would be advantageous over previously used treatments.

For this reason, it would be desirable to have a medical or biological agent that could be injected into myocardial tissue to provide mechanical stabilization and/or biological therapy of ischemic myocardium to address myocardial extension and negative remodeling.

It would further be desirable to have a delivery device and method for injecting medical or biological agents into myocardial tissue. In particular, devices and methods enabling a minimally invasive delivery of one or more agents into myocardial tissue would be most advantageous.

It would further be desirable to have improved devices that can be used to inject cells into myocardial tissue. In particular, devices enabling a minimally invasive cell delivery into myocardial tissue would be most advantageous.

It would further be desirable to have an organ positioning system and method, which is capable of positioning, manipulating, stabilizing and/or holding an organ and/or tissue while controllably providing one or more agents to the positioned organ and/or tissue during a medical procedure.

SUMMARY OF THE INVENTION

The present invention provides a device for injecting medical agents into tissue, with a preferred medical agent being cells, for example, that can form contracting cardiac muscle cells. The device can be used to inject bone marrow cells, stem cells, pluripotent cells, and other cardiocyte precursor cells. The device can be used to inject these cells into infarct zones of cardiac tissue to prevent or postpone heart failure in heart disease patients. The devices and methods according to the present invention can be used to inject medical agents or substances into any soft tissue, including, but not limited to, heart, kidney, liver, tumor, and muscle tissue.

One device includes an elongate shaft having a distal region coupled to a plurality of hollow needles having sharp distal ends, with the needles operably coupled to the elongate shaft distal region such that the elongate shaft distal region is substantially perpendicular to the needle axes. The device can further include means for driving the needles along the needle axes in the direction of the needle sharp distal ends and means for discharging the fluid from the needle discharge ports. The device can further include a needle trigger operably coupled to the needle driving means for initiating the needle driving means and a discharge trigger operably coupled to the fluid discharge means for initiating fluid discharge from the needles. In one device, the means for driving the needles along the needle axes includes a first body having the needles fixedly attached thereto and a second body having the needles slidably disposed therethrough. In some devices, the first and second bodies each include a substantially planar portion substantially perpendicular to the needle axes. The means for driving the needles can include means for driving the first body toward the second body.

Some devices include a first body inclined portion disposed at an angle to the elongate shaft distal region longitudinal axis. The device can further include a third body longitudinally slidably coupled to the second body and being inclinably slidably coupled to the first body along the first body inclined portion. Longitudinally translating the third body relative to the second body can thus move the first body relative to the second body.

One device includes an elongate shaft having a distal region and an injection head coupled to the shaft distal region. The head can have a plurality of needles for injecting the substance into the tissue, where the needles are oriented substantially perpendicular to the elongate shaft distal region longitudinal axis. The device can include a needle driver for driving the plurality of needles past the injection head tissue-contacting surface and into the tissue. The device preferably includes means for transferring a longitudinal force directed along the shaft to a transverse force at the injection head. The means for transferring force can include two substantially planar members, where the first planar member has the plurality of needles fixedly and transversely attached thereto, and where the second planar member has the plurality of needles transversely and slidably disposed therethrough.

In some devices, the means for transferring force includes the first planar member being transversely slidably coupled to the second planar member, where the first planar member has at least one inclined portion disposed at an angle to the plane of the first planar member. A drive member can be slidably coupled to the second planar member to bear against the first planar member inclined portion. An elongate drive shaft can be slidably disposed along the elongate shaft and coupled to the drive member, such that moving the drive shaft longitudinally urges the drive member to bear against the inclined portion, urging the first planar member toward the second planar member and the plurality of needles away from the second planar member.

Another device includes a first and a second body coupled to each other through a pantograph mechanism having two opposing sides, where the pantograph includes a proximal arm pair and a distal arm pair on each side. The arm pairs can include a first member pivotally joined at one end to the first body, and a second member pivotally joined at one end to the second body. The first and second members each have second ends pivotally coupled to each other at a central joint, in a preferred embodiment. Moving the proximal and distal arm pair central joints closer together urges the first and second bodies apart, and moving the proximal and distal arm pair central joints closer together urges the first and second bodies together. In some devices, the central joint of each proximal and distal arm pair are joined to the corresponding joint on the opposite side, through a rod or other mechanism.

In still another device, the first body has a plurality of hollow needles attached thereto and a first plurality of magnets secured thereto. The second body has a plurality of needles slidably received therethrough. A third body can be slidably disposed on the second body and have a second plurality of magnets thereon, where the first and second plurality of magnets are disposed and have polarities oriented such that the slidable third body has a first position in which the first and third body are magnetically attracted to each other and a second position in which the first and third body are magnetically repulsed from each other. In this way, sliding the third member can pull the first body toward the second body and also push the first body away from the second body, depending on the degree of sliding. In one device, the third body has longitudinally adjacent magnetic pairs having opposite polarities, such that sliding the third member into the first position brings magnets having opposite facing polarities opposite each other, and sliding the third member into a second position brings magnets having the same facing polarities opposite each other.

In yet another device, the first body has a plurality of hollow needles attached thereto and a second body has the needles slidably received therethrough. The device can include a rack fixedly coupled to the second body and a pinion rotatably coupled to the first body and having teeth engaging the rack. Rotating the pinion in a first direction thus urges the first and second bodies closer together, and rotating the pinion in a second direction urges the first and second bodies further apart.

In yet another device, the first body has a plurality of hollow needles attached thereto and the second body has the plurality of needles slidably received therethrough. The first and second bodies can have a first expandable member disposed therebetween, such that expanding the first expandable member urges the first and second bodies apart and retracts the needles toward the second body. The expandable member can be a fluid inflatable member. In some devices, the first inflatable member is coupled to the first and second bodies and is deflatable, such that withdrawing fluid from the first inflatable member urges the first and second bodies closer together. Some devices further include a second expandable member disposed on the first body away from the second body and on a major surface facing away from the second body, such that disposing the second body against the tissue and disposing the second expandable member against a body part urges the first body toward the tissue.

In some devices, the plurality of needles attached to the first body may have a substantially different length as among the needles, to form a phased depth array of needles. The phased array of needles can distribute the initially higher force required to puncture the outer tissue temporally over the needle insertion process. In addition, the phased array of needles can allow the delivery one or more medical agents or substances at different depths within the tissue simultaneously.

One device includes an elongate shaft having a distal region coupled to a plurality of hollow needles having sharp distal ends, with the needles operably coupled to the elongate shaft distal region such that the elongate shaft distal region is substantially parallel to the needle axes. The device can further include means for driving the needles along the needle axes in the direction of the needle sharp distal ends and means for discharging the fluid from the needle discharge ports. The device can further include a needle trigger operably coupled to the needle driving means for initiating the needle driving means and a discharge trigger operably coupled to the fluid discharge means for initiating fluid discharge from the needles. In one device, the means for driving the needles along the needle axes includes a first body having the needles fixedly attached thereto and a second body having the needles slidably disposed therethrough. In some devices, the first and second bodies each include a substantially planar portion substantially perpendicular to the needle axes. The means for driving the needles can include means for driving the first body toward the second body.

One device includes an elongate shaft having a distal region and an injection head coupled to the shaft distal region. The head can have a plurality of needles for injecting the substance into the tissue, where the needles are oriented substantially parallel to the elongate shaft distal region longitudinal axis. The device can include a needle driver for driving the plurality of needles past the injection head tissue-contacting surface and into the tissue.

One device includes an injection head having a suction member for grasping tissue to be injected by one or more needles.

One device includes a suction member for grasping tissue and a lumen sized and shaped to accommodate a needle and syringe barrel.

The present invention also provides a method for injecting platelet gel into ischemic tissue of a heart of a patient, wherein the method comprises identifying ischemic tissue of the heart and injecting platelet plasma and thrombin into the ischemic tissue, wherein the platelet plasma and the thrombin combine to form a platelet gel.

DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 29 is a schematic illustration of the application of suction through the suction ports of the suction pad to form a pericardial bleb;

FIG. 30 is a schematic illustration of the advancement of a cutting instrument through the working lumen of the suction tool and through the pericardium while suction continues to be applied through the suction ports of the suction pad to maintain the pericardial bleb;

FIG. 34 is a schematic illustration of a modification of the suction tool providing for the capability of deflecting the suction pad to steer it to a particular pericardial or epicardial site and to orient the suction cavity to the pericardium or epicardium to form a respective pericardial or myocardial bleb;

FIGS. 35A and 35B are schematic illustrations of a first alternate shape of the suction tool distal end to facilitate advancement through and widening of the incision in the pericardium as depicted in FIG. 31;

FIGS. 36A and 36B are schematic illustrations of a second alternate shape of the suction tool distal end to facilitate advancement through and widening of the incision in the pericardium as depicted in FIG. 31;

FIGS. 37A and 37B are schematic illustrations of a first alternate shape of the suction tool distal end to facilitate advancement through and widening of the incision in the pericardium as depicted in FIG. 31;

FIG. 41 is a plan view of a further variation of the distal suction pad of a suction tool of the present invention;

FIG. 42 is a perspective view of the distal suction pad of FIG. 41;

FIG. 56B is a side view of one embodiment of a device in accordance with the present invention;

FIG. 70 is a depiction of a heart with a region of infracted/ischemic myocardium;

Figure 1:
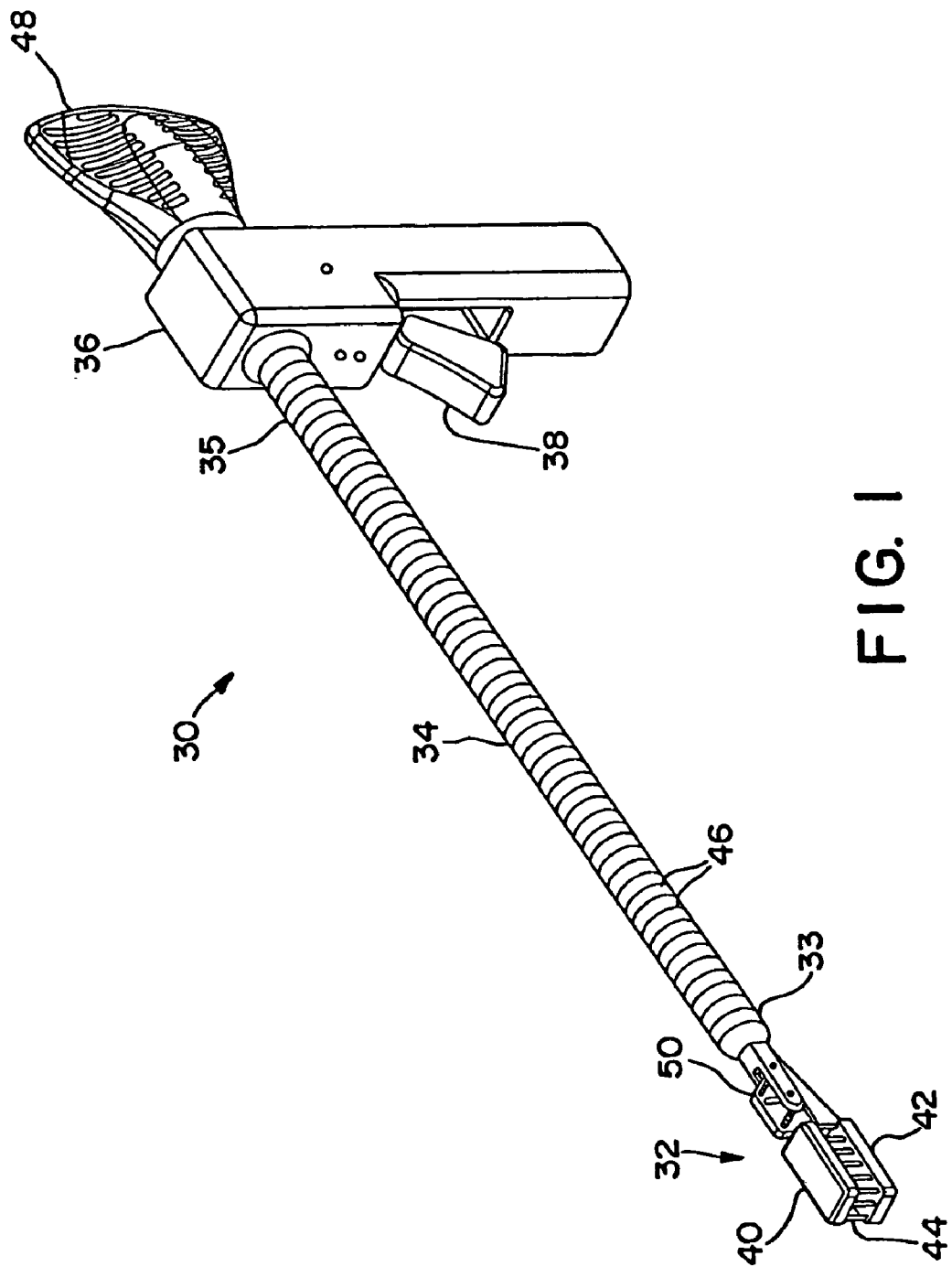
FIG. 1 is a perspective view of an interstitial injection device having a proximal handle, an elongate shaft, a distal injection head, and a mechanism for converting energy received through the elongate shaft to a transverse force to drive injecting needles from the distal injection head into tissue.

The drawing Figures are not necessarily to scale.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described below are merely for illustrative purposes, and are not intended to limit the scope of the invention as defined in the claims that follow.

Figure 2:
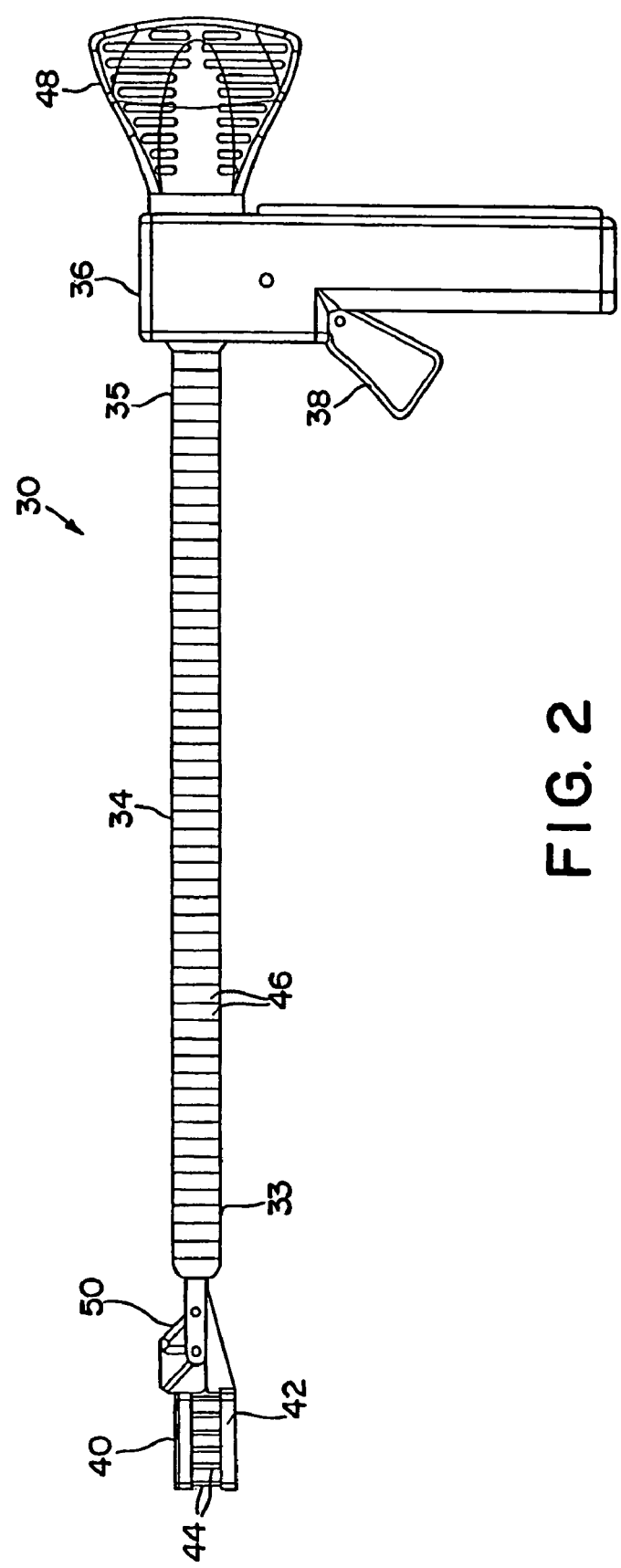
FIG. 2 is a side view of the interstitial injection device of FIG. 1.

FIGS. 1 and 2 illustrate an interstitial injection device 30 having a distal injection head 32, an elongate shaft 34, and a proximal handle 36. Elongate shaft 34 includes generally a distal region 33 and a proximal region 35. Proximal handle 36 includes a trigger mechanism 38 for initiating the needle insertion and/or fluid injection. Distal injection head 32 may include a first body 40, a second body 42, and numerous injecting needles 44. In one embodiment, injecting needles 44 are fixedly attached to first body 40 and are slidably received through second body 42. Urging first body 40 towards second body 42 thus drives injecting needles 44 transversely through second body 42 and into the target tissue. Drawing first body 40 and second body 42 apart retracts injecting needles 44 from the tissue. In preferred embodiments, the depth of needle penetration can be controllably varied. In this way, the needle penetration depth can be varied to match the thickness of tissue, e.g., tissue of a heart chamber wall. In some embodiments, the first body is referred to as a "needle plate" and the second body may be referred to as a "vacuum plate" or "suction member", as the second body can include vacuum suction pods for securing the device to tissue. Injection device 30 includes a mechanism 50 for translating energy that can be provided along elongate shaft 34 into transverse motion to urge needles 44 transversely into the tissue.

As used herein, with respect to the injection devices, the term "transversely" refers to a direction substantially orthogonal to a plane that includes the longitudinal axis of the elongate shaft distal portion. In one embodiment of the present application, a plane of injection may be defined as being orthogonal to the needles that are to extend into the tissue. Many embodiments of the invention include a needle driver that translates force parallel to the injection plane into a needle driving force. Thus, in many of the embodiments illustrated, the second body distal portion or vacuum plate extends substantially along or parallel to the injection plane. Similarly, as used in the present application, a surface may be defined as "inclined" with respect to the injection plane and may often be found to be inclined with respect to a plane extending through the second body distal portion or second body vacuum plate.

The elongate shaft provided can vary from embodiment to embodiment, with one ball-and-socket embodiment being illustrated in FIGS. 1 and 2. In this embodiment, several ball-and-socket elements 46 are nested within each other. Injection device 30 includes a proximal, rotable and threaded member 48 for increasing and decreasing tension on an elongate cable disposed through elongate shaft 34. Tightening rotable member 48 causes elongate shaft 34 to rigidly maintain its present position, while loosening rotable member 48 allows elongate member 34 to be formed into the desired shape. Other elongate handles are also within the scope of the present invention. Some elongate shafts include flexible elongate members that can be introduced using endoscopic methods through endoscopic device ports. Other elongate shafts are malleable shafts that can be bent into a desired shape that is then retained, absent a large application of further force. Some elongate shafts are flexible, and are introduced using endoscopes and other endoscopic instruments such as an endoscopic grasper or hemostat. Some flexible shafts have insufficient strength in compression to be advanced without being further stiffened with an enclosing guide tube or endoscope, or an enclosed stiffening stylet. Still other elongate shafts include pull wires for steering the shaft distal region from the proximal region. Pull wire technology is well known to those skilled in the art.

Figure 3:
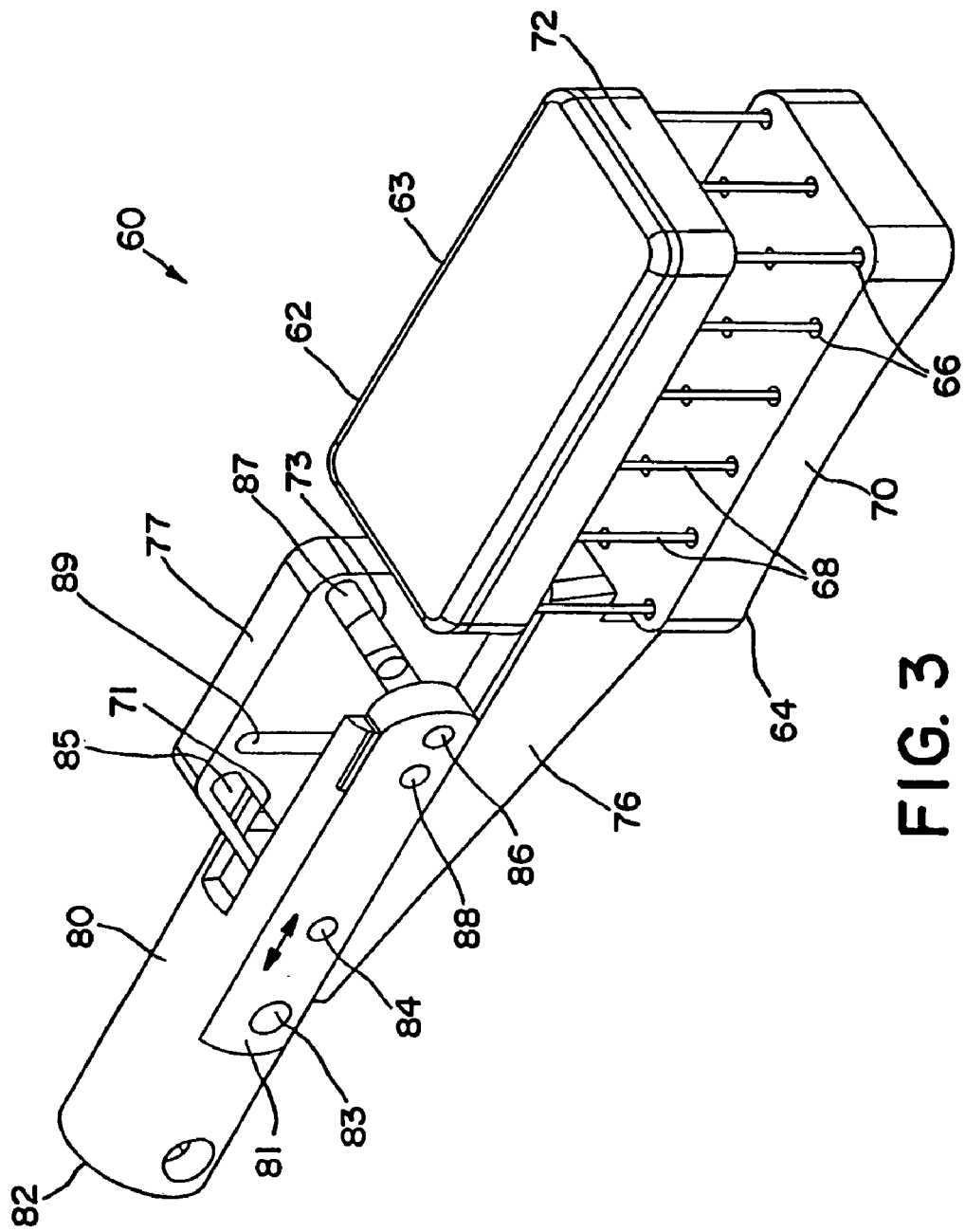
FIG. 3 is a perspective view of a distal injection head having a mechanism for translating a longitudinal motion to a transverse, needle driving motion through use of drive pins disposed through inclined slots.

FIG. 3 illustrates one example of a distal injection head 60 having a mechanical slide mechanism for translating longitudinal motion along the elongate shaft axis and perpendicular to the needles, to a transverse motion for driving needles into tissue. The mechanical slide mechanism may also be referred to as a cam mechanism. Mechanical slide distal injection head 60 includes generally a first body 62 and a second body 64, that can be maintained in a spaced-apart relationship to each other, and opened and closed through the mechanism described below. First body 62 includes numerous injecting needles 68 fixedly attached to first body 62. Needles 68 are slidably received through holes 66 in second body 64. First body 62 includes a distal portion 63 terminating in a distal end 72, and a proximal portion 77 that can slide transversely relative to second body 64. Injection head 60 further includes a drive member on yoke 81. Drive yoke 81 can slide longitudinally to drive first body 62 transversely.

Second body 64 includes a distal portion 70, an intermediate portion 76, and a proximal portion 80. Proximal portion 80 includes a proximal end 82 that can include a cavity for receiving part of the elongate shaft. Second body proximal portion 80 may also be referred to as a clevis. In some embodiments, second body 64 distal portion 70, intermediate portion 76, and proximal portion 80 are all rigidly joined together to move as a single piece. Injection head 60 further includes a drive yoke 81 longitudinally slidably disposed within second body proximal portion 80. Drive yoke 81 can include an internal blind cavity 83 to assist in coupling drive yoke 81 to a drive cable slidably disposed within an elongate shaft coupled to proximal end 82. Second body proximal portion 80 can be coupled to a rigid, outer sheath portion of the elongate shaft while drive yoke 81 is coupled to an elongate drive shaft or cable slidably disposed within the elongate shaft.

First body proximal portion 77 may be seen to include a proximal inclined drive slot 85, a distal inclined drive slot 87, and an intermediate guide slot 89 that is disposed transversely to the longitudinal axis of the elongate shaft coupled to first body proximal portion 80. Drive yoke 81 may be seen to include a proximal drive pin 84 slidably disposed within proximal inclined drive slot 85, an intermediate guide pin 88 extending through transverse guide slot 89, and a distal drive pin 86 extending through distal inclined drive slot 87. Inclined drive slots 85 and 87 may also be referred to as angled slots, having inclined or angled cam surfaces 71 and 73, respectively. Distal injection head 60 is shown in the open position, having drive yoke 81 in the proximal position and first body proximal portion 77 in the upward most position. Forcing a drive cable through the elongate shaft can force drive yoke 81 distally, causing pins 84 and 86 to bear against inclined surfaces 71 and 73 in inclined slots 85 and 87. This distal movement of pins 84 and 86 over inclined surfaces 71 and 73 urges first body proximal portion 77 downward, with slot 89 moving transversely downward over guide pin 88. As first body distal portion 63 is rigidly secured to first body proximal portion 77, first body distal portion 63 is urged toward second body distal portion 74, driving needles 68 through holes 66 and into the target tissue.

With the needles inserted into the tissue, agents can be injected into the tissue by the application of pressure through injection lumens (not shown in FIG. 3). First body distal portion 63 and second body distal portion 70 can be moved apart to retract the needles by proximally retracting drive yoke 81 to the position shown in FIG. 3.

Figure 4:
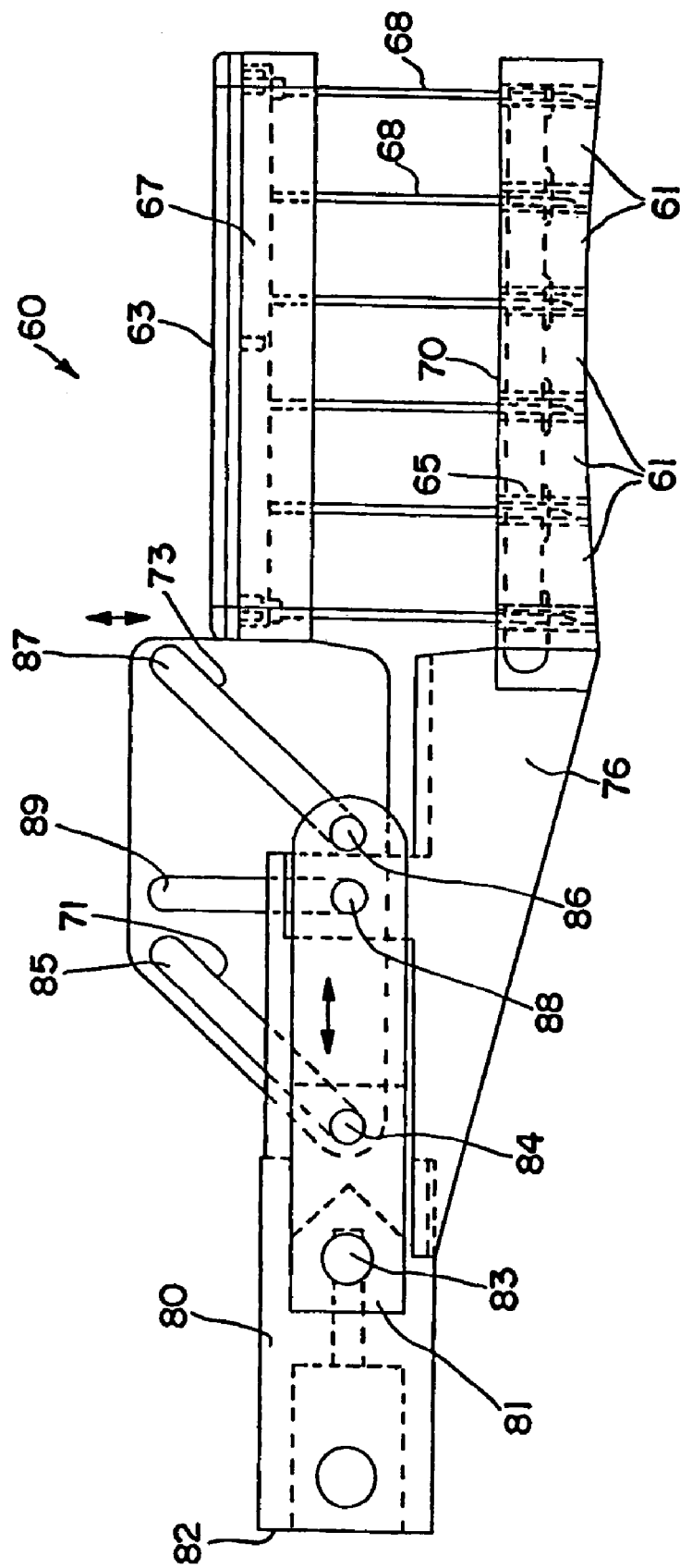
FIG. 4 is a side view of the injection head of FIG. 3.

FIG. 4 shows distal injection head 60 from the side. Second body distal portion 70 may be seen to include a vacuum lumen 65 coupled to several vacuum pods 61 that are in communication with vacuum lumen 65 and open at the bottom of second body distal portion 74. A vacuum line (not shown in FIG. 4) can be coupled to vacuum lumen 65 to reversibly adhere distal injection head 60 to the target tissue. In one example of use, distal injection head 60 can be urged against the epicardial surface of a heart, and vacuum applied to vacuum lumen 65 and vacuum pods 61 to adhere second body distal portion 70 to the heart. Vacuum pods are well known to those skilled in the art, and are currently provided on Medtronic products such as the Octopus® and Starfish®. A fluid manifold 67 may be seen coupled to needles 68 for supplying the needles with injectable material. Fluid manifold 67 can be coupled to a fluid supply tube or lumen extending along the length of the elongate shaft. In some embodiments, fluid manifold 67 serves as a reservoir, holding most or all of the material to be injected. Injection pressure can be provided by a fluid source coupled to the reservoir.

Figure 5:
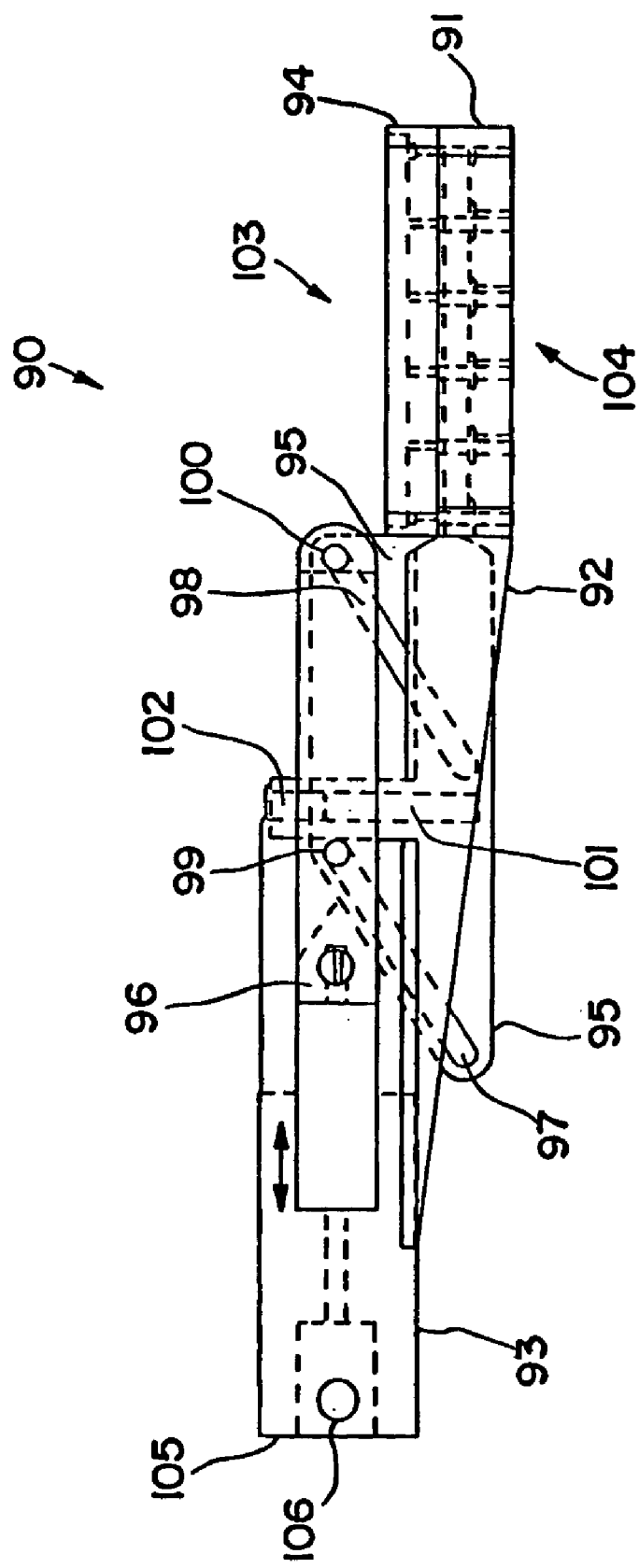
FIG. 5 is a side view of an injection head having a tongue-in-groove guide similar to that of FIGS. 3 and 4, shown in the closed, driving position.

FIG. 5 illustrates another mechanical slide mechanism for translating longitudinal movement along the elongate shaft to a transverse needle-driving movement at the injection head. Distal injection head 90 is similar in some respects to distal injection head 60 illustrated in FIGS. 3 and 4. Distal injection head 90 includes a proximal-most portion 105 for securing to an elongate shaft and a lumen 106 within for receiving a drive cable for attachment to a drive yoke 96. Distal injection head 90 includes generally a first body 103, and a second body 104 including several needles (not illustrated in FIG. 5) fixedly attached to first body 103 and slidably received through second body 104. First body 103 includes a distal portion or needle plate 94 secured to a proximal portion 95. First body proximal portion 95 includes inclined or angled drive slots 97 and 98 having inclined surfaces as described with respect to FIGS. 3 and 4. First body proximal portion 95 also has a groove guide 102 formed into each outward face, with only one face being illustrated in FIG. 5.

Distal injection head second body 104 includes a distal portion or vacuum plate 91 secured to an intermediate portion 92, which is in turn secured to a proximal portion 93. Second body vacuum plate 91, intermediate portion 92 and proximal portion 93, are all preferably rigidly secured to each other. Intermediate portion 92 preferably includes matching opposite portions on either side of first body proximal portion 95. Intermediate portion 92 includes a tongue 101 extending inwardly from each side of intermediate portion 92 into groove guides 102 in first body proximal portion 95. Tongue 101 is thus slidably and transversely received within groove 102. Intermediate portion 92 can form side-by-side jaws opposed to an inner jaw formed by first body proximal portion 95.

Drive yoke 96 may be seen slidably disposed within second body proximal portion 93. Drive yoke 96 includes drive pins 99 and 100 secured to drive yoke 96 and extending through inclined slots 97 and 98 of first body proximal portion 95, respectively. Drive yoke 96 is shown in the far, distal position, having forced drive pins 99 and 100 distally through inclined slots 97 and 98 to force first body proximal portion 95 downward to force needle plate 94 against vacuum plate 91. Second body intermediate portion 92 has had groove guide 102 of first body intermediate portion 95 slid downward over tongue 101 of second body intermediate portion 92. Proximally retracting drive yoke 96 relative to second body proximal portion 93 can force drive pins 99 and 100 to the far proximal ends of inclined slots 97 and 98, to force needle plate 94 away from vacuum plate 91.

Figure 6:
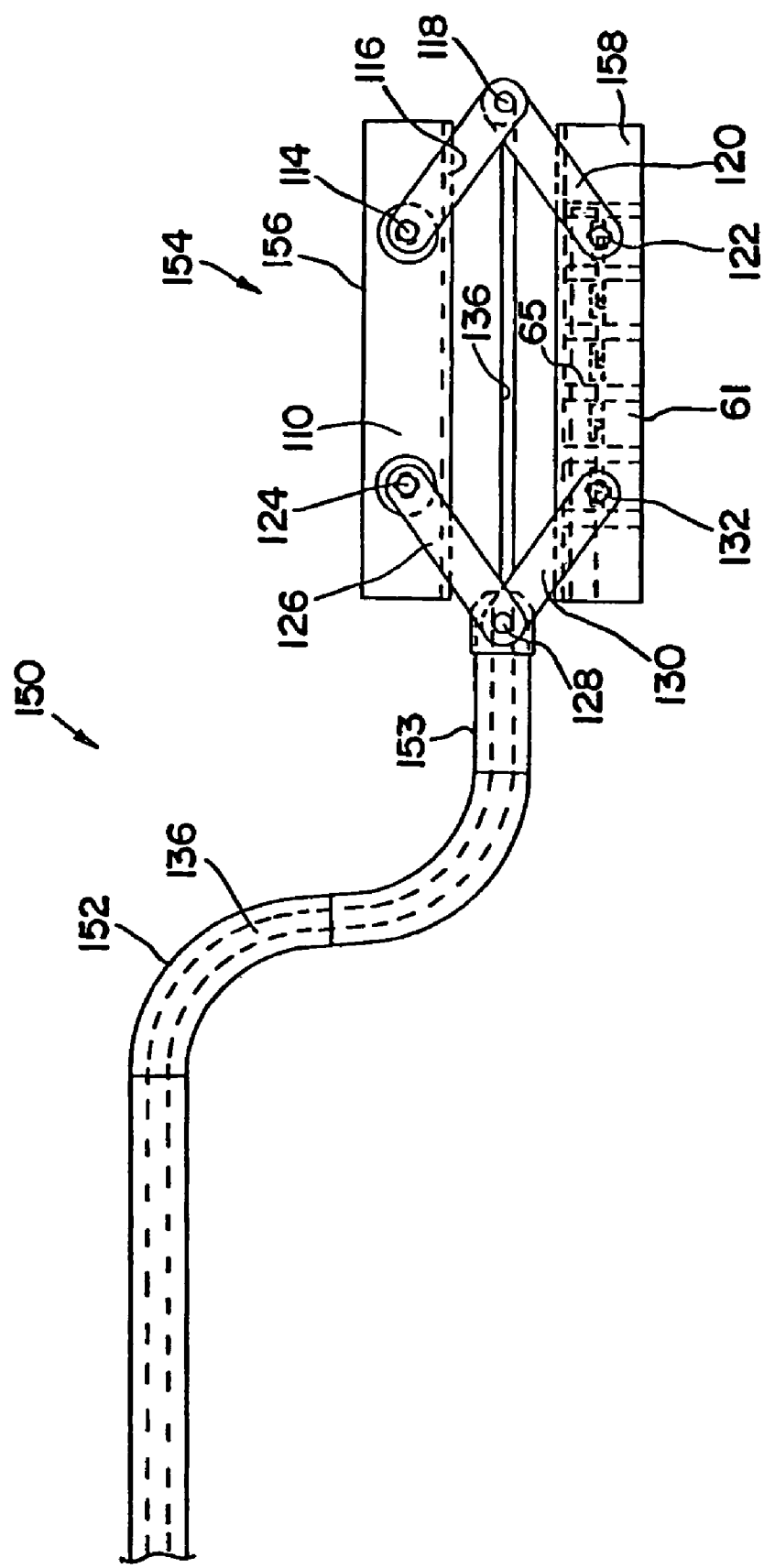
FIG. 6 is a side view of another distal injection head employing a four-link mechanism pantograph, attached to an elongate flexible sheath.

FIG. 6 illustrates an injection device 150 having an elongate, flexible sheath 152 and a distal injection head 154 utilizing a four-link pantograph mechanism. Flexible sheath 152 includes a distal portion 153 secured to distal injection head 154 and further includes a drive cable or rod 136 slidably disposed therethrough. Sheath 152 can also include a fluid injection lumen and a vacuum lumen within, or in separate tubes alongside.

Distal injection head 154 includes a first body 156 mounted in a spaced-apart relation to a second body 158. As previously described with respect to other embodiments, first body 156 can have several injecting needles fixedly attached to first body 156 and slidably received through holes in second body 158. Second body 158 may be seen to have vacuum pods 61 and a vacuum lumen 65, as previously described with respect to FIG. 3. First body 156 can have a fluid manifold within.

A first side 110 of distal injection head 154 is visible in FIG. 6, with a second, opposite side 112 (not visible in FIG. 6) located on the opposite side. Device 154 includes a distal arm pair including a first or upper distal arm 116 pivotally coupled to first body 156 at 114 and a second or lower arm 120 pivotally coupled to second body 158 at 122. First arm 116 is pivotally coupled to second arm 120 at a central distal joint 118. Device 154 also includes a proximal arm pair including a first or upper proximal arm 126 pivotally coupled to first body 158 at 124 and a second or lower arm 130 pivotally coupled to second body 158 at 132. First arm 126 is pivotally coupled to second arm 130 at a central proximal joint 128. Elongate, flexible sheath 152 includes drive cable or rod 136 slidably extending through sheath 152 and extending distally past proximal joint 128 to be coupled to distal joint 118. A corresponding set of four linkage arms may also be found on the opposite side of first body 156 and second body 158 (not visible in FIG. 6).

Inspection of FIG. 6 shows that distally extending drive cable or rod 136 acts to push proximal joint 128 and distal joint 118 further apart, thereby bringing first body 156 closer to second body 158, thereby urging the injecting needles through second body 158 and into the tissue. Similarly, retracting drive cable or rod 136 into flexible sheath 152 acts to bring proximal joint 128 and distal joint 118 closer together, thereby forcing first body 156 and second body 158 further apart, acting to retract the injecting needles.

In some embodiments, drive rod or cable 136 is externally helically threaded and is received through corresponding, receiving threads near distal joint 118 and/or proximal joint 128. In this embodiment, rotating drive cable or rod 136 can act to bring joints 128 and 118 either closer together or further apart, acting to advance needles into tissue or retract the needles from tissue, as previously described.

Figure 7:
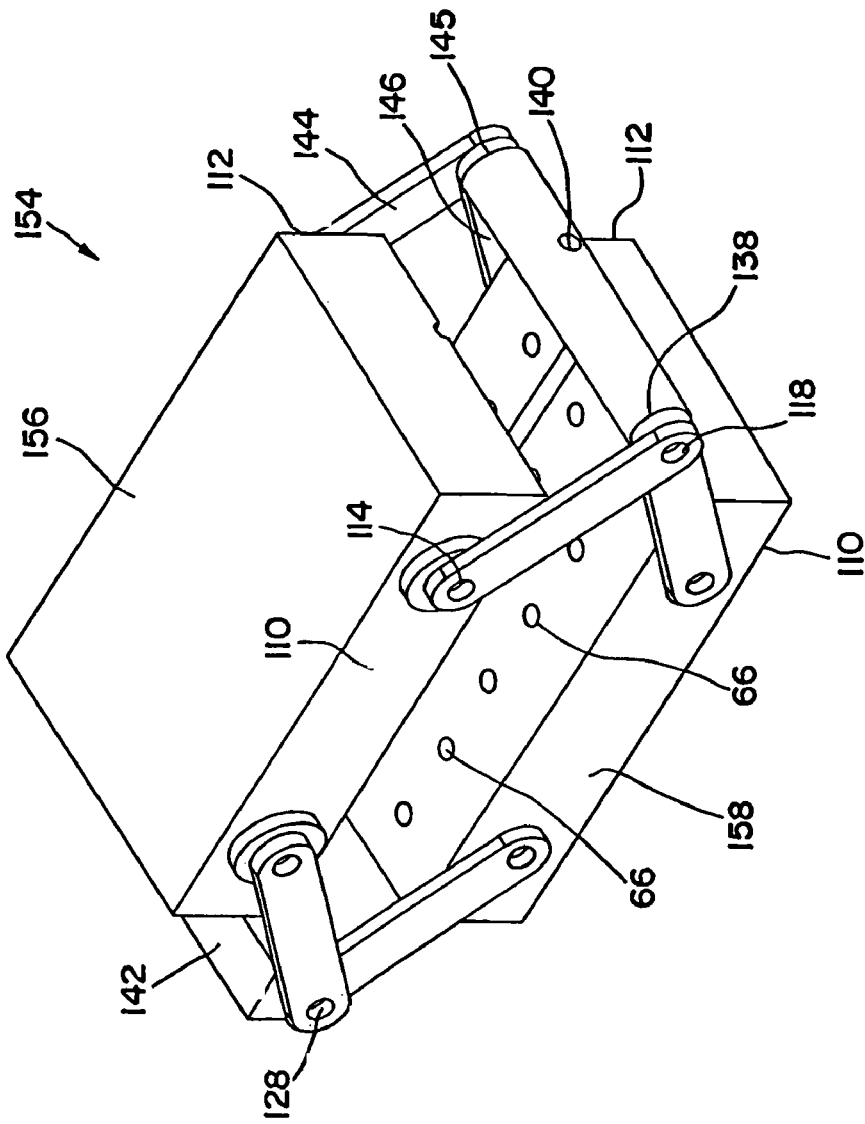
FIG. 7 is a perspective view of the distal injection head of FIG. 6.

FIG. 7 illustrates distal injection head 154 in greater detail. Distal central joint 118 may be seen to include a distal joint rod 138 that includes an aperture 140 for receiving drive cable or rod 136 therethrough. Proximal central joint 128 may also be seen to have a corresponding proximal joint rod 142. Distal injection head 154 also has a second, opposite side 112 carrying a second side, upper, distal linkage arm 144 and a second side, lower distal linkage arm 146, coupled to each other through distal, second side central joint 145. Joints such as 114 in first side 110 are coupled entirely through first body 156 to the second side 112 in some embodiments. In other embodiments, a rod or screw extends from joint 114 only partially into first body 156.

Figure 8:
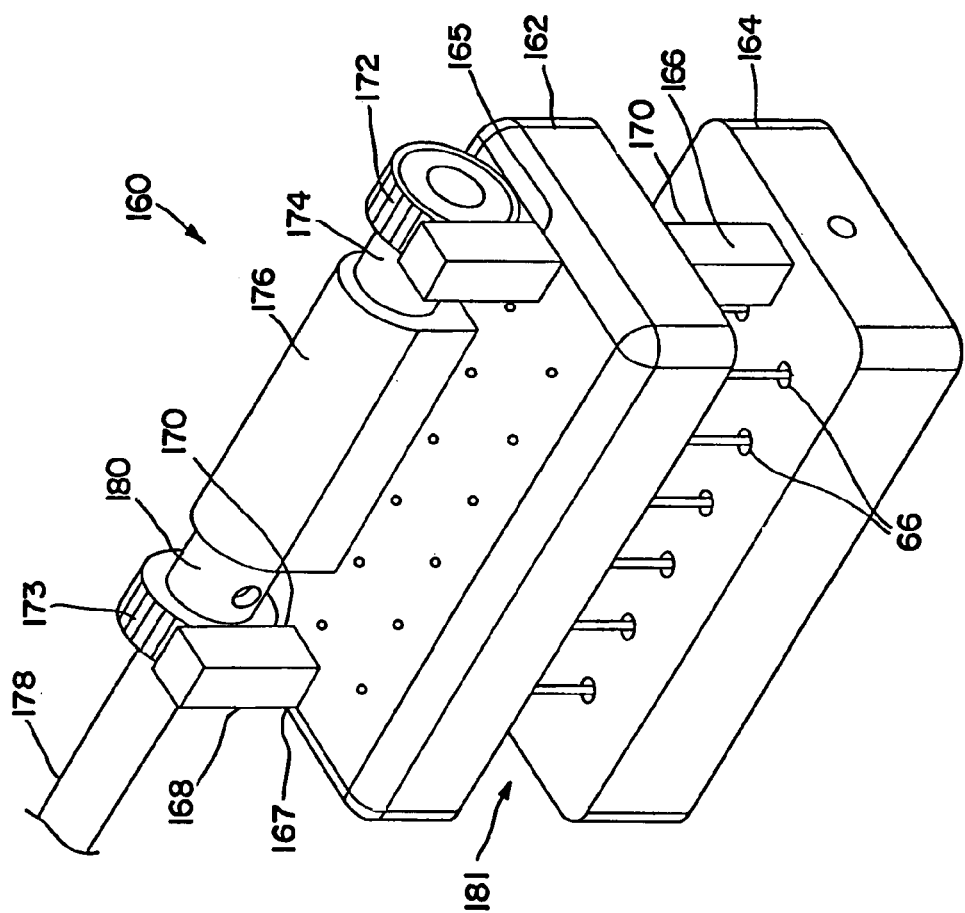
FIG. 8 is a fragmentary, perspective view of another distal injection head employing a rack and pinion mechanism.

FIG. 8 illustrates still another distal injection head 160, including a first body 162 slidably disposed in a spaced apart relationship to a second body 164. First body 162 has several needles forming a phased depth needle array 181 that is slidably disposed through holes 66 formed in second body 164. Phase needle array 181 is described below. Second body 164 has a distal guidepost 166 fixedly attached and slidably disposed through a distal opening 165 formed in first body 162. Similarly, second body 164 has a proximal guidepost 168 fixedly attached and slidably disposed through a proximal guide hole 167 in first body 162. Both distal guidepost 166 and proximal guidepost 168 carry a rack or set of teeth 170. A bushing 176 is fixedly attached to first body 162.

Distal injection head 160 further includes a rotable shaft 178 coupled to a proximal gear 185 including a tooth bearing portion 173 and a more distal bushing portion 180. Intermediate sleeve or bushing 176 has rotable shaft 178 rotatably disposed within. Shaft 178 continues distally to couple to a distal gear 187 including a proximal, bushing portion 174 and a tooth bearing portion 172. Teeth portions 173 and 172 engage teeth 170 on guideposts 166 and 168.

Inspection of FIG. 8 shows that rotating shaft 178 in a first direction will force first body 162 closer to second body 164, thereby driving needle array 181 into the target tissue. Similarly, rotating shaft 178 in the opposite direction will carry first body 162 away from second body 164, retracting the needle array.

Figure 9:
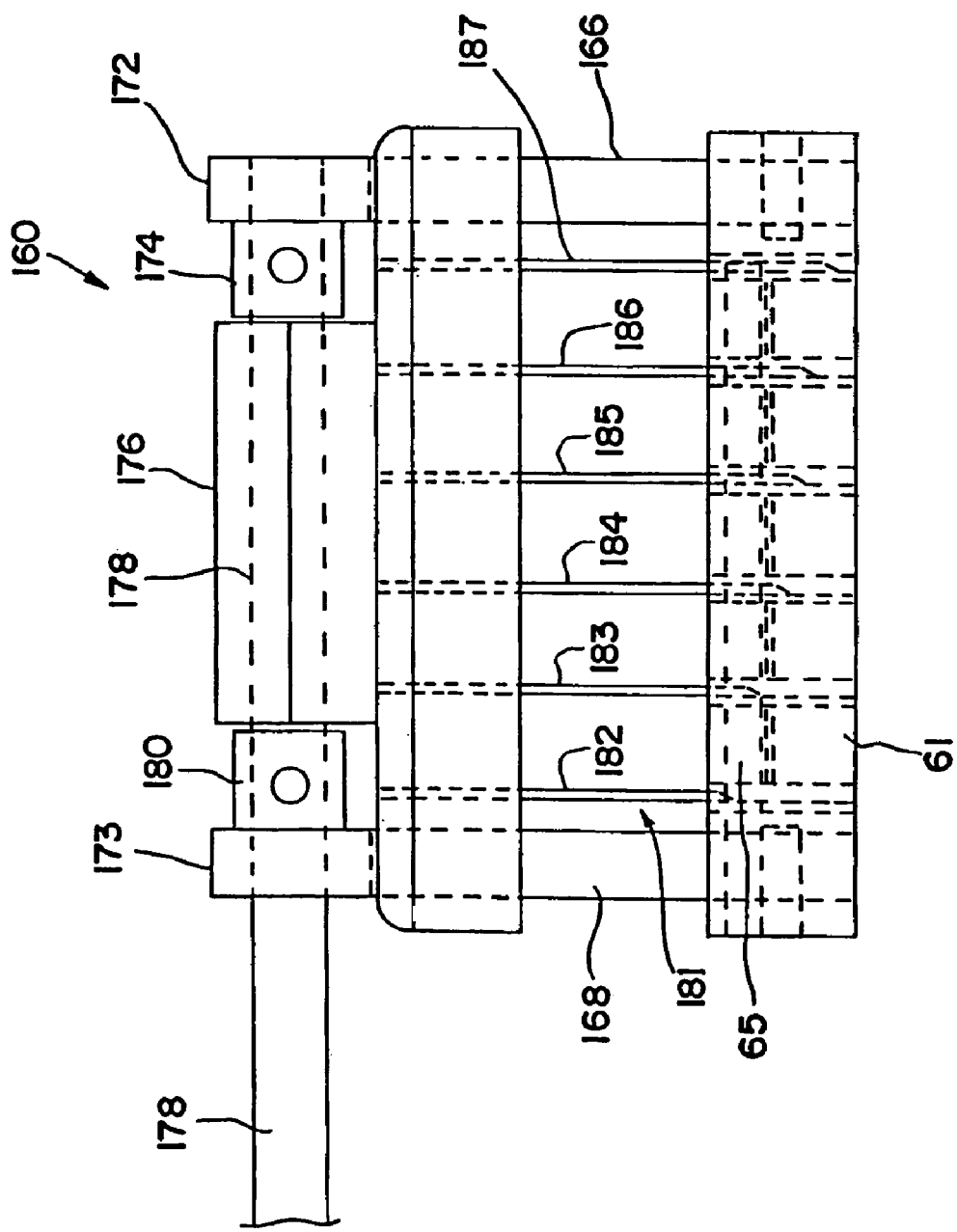
FIG. 9 is a fragmentary, side view of the distal injection head of FIG. 8, illustrating a phased array of needle depths.

FIG. 9 illustrates distal injection head 160, further showing vacuum pods 61 and vacuum lumen 65, as previously described with respect to other embodiments. Phased depth needle array 181 is illustrated in FIG. 9, including a series of needles, having varying lengths. In the example illustrated in FIG. 9, needles 182, 183, 184, 185, 186 and 187 each have a length greater than the previous, more proximal needle. This arrangement is for purposes of illustration only, with other arrangements, orders and depth pattern of needles all within the scope of the invention. Providing a phased depth array of needles allows tissue to be penetrated with less force. The force required to initially penetrate tissue, in particular, epicardial tissue, is generally greater than the force required to continually penetrate deeper into the tissue. The phased depth array of needles 181 provides an arrangement where this greater force requirement is felt first by needle 187, then 186, then 185, and so forth. This arrangement does not require that the initial, greater resistance encountered by a single needle penetrating outer tissue be encountered by all the needles at the same time. In addition, the phased needle array can allow the delivery of one or more medical agents or substances at different depths within the tissue simultaneously. The phased needle array may be used in any embodiment illustrated in the present application.

Figure 10:
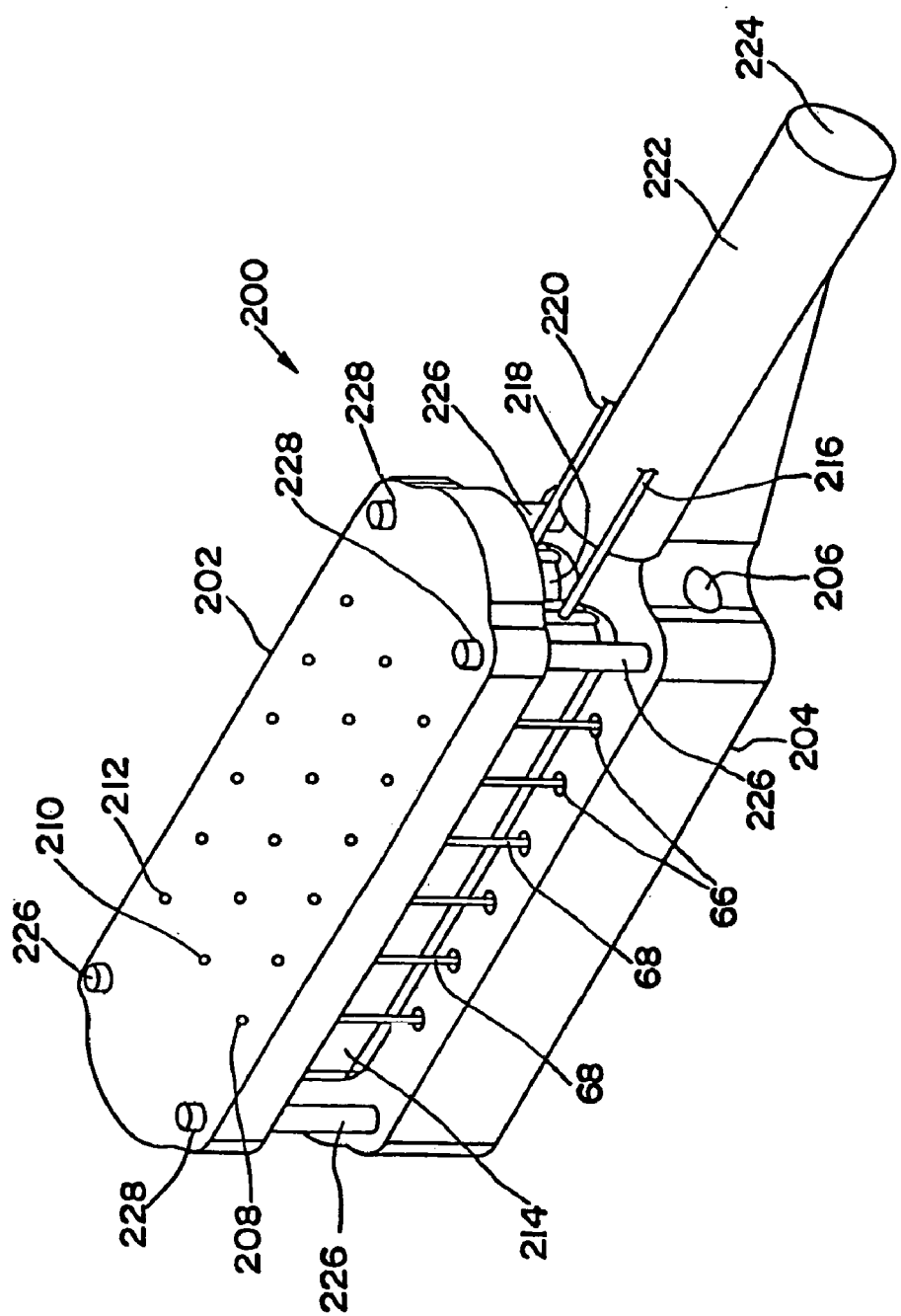
FIG. 10 is a perspective view of a distal injection head employing inflatable balloons to open and close the head.

FIG. 10 illustrates still another distal injection head 200, including a first body 202 and a second body 204. First body 202 can have a series of needles 68 fixedly attached, and oriented in a first longitudinal row 208, an intermediate longitudinal row 210, and an opposite side longitudinal row 212. A first inflatable and deflatable envelope, balloon, or bellows 214 may be seen disposed between needle rows 208 and 210. First inflatable envelope 214 can be coupled to an inflation and deflation tube 216. Similarly, a second inflation and deflation tube 220 may be seen supplying a second inflatable and deflatable envelope, balloon, or bellows 218 that is disposed between needle row 210 and 212.

Inflatable envelopes 214 and 218, and other inflatable envelopes in the present application can be cylindrical, round, or pancake shaped. The envelopes can be made of many polymeric materials, including polyurethane, latex, PVC, silicone, and polyamide. Distal inflation head 200 includes a proximal, mounting stub 222, including a proximal aperture 224. Distal injection head 200 further includes an aperture or port 206 that can be used for supplying vacuum to the vacuum pods, previously described. Inflation and deflation tubes 216 and 220 can continue along the length of the elongate shaft or be carried within the elongate shaft for much of its length, either as separate tubes or integral lumens, depending on the embodiment. Similarly, vacuum aperture or port 206 can be coupled along the length of the shaft through a separate vacuum tube or have the vacuum carried within a lumen within the elongate shaft itself. Second body 204 has four guideposts 226 fixedly attached to second body 204. Guideposts 226 are slidably received within receiving apertures 228 formed in first body 202.

In use, distal injection head 200 can be advanced to the tissue site of interest, and disposed against the tissue. In some embodiments, a vacuum is applied through vacuum pods, as previously described. A vacuum can then be applied to envelopes 214 and 226, acting to pull first body 202 toward second body 204, and drive needles 68 through second body 204 and into the tissue.

Inflation pressure can be supplied through tubes 216 and 220 to envelopes 214 and 226, urging first body 202 away from second body 204, thereby retracting needles 68 from the tissue. In some embodiments, a gas, for example, carbon dioxide or nitrogen or air is injected through tubes 216 and 220 to inflate inflatable envelopes 214. In other embodiments, liquid, for example, saline, is supplied to tubes 216 and 220 to operate distal injection head 200. In some embodiments, the depth of needle penetration can be controllably and variably set by adjusting the inflation pressure.

Figure 11:
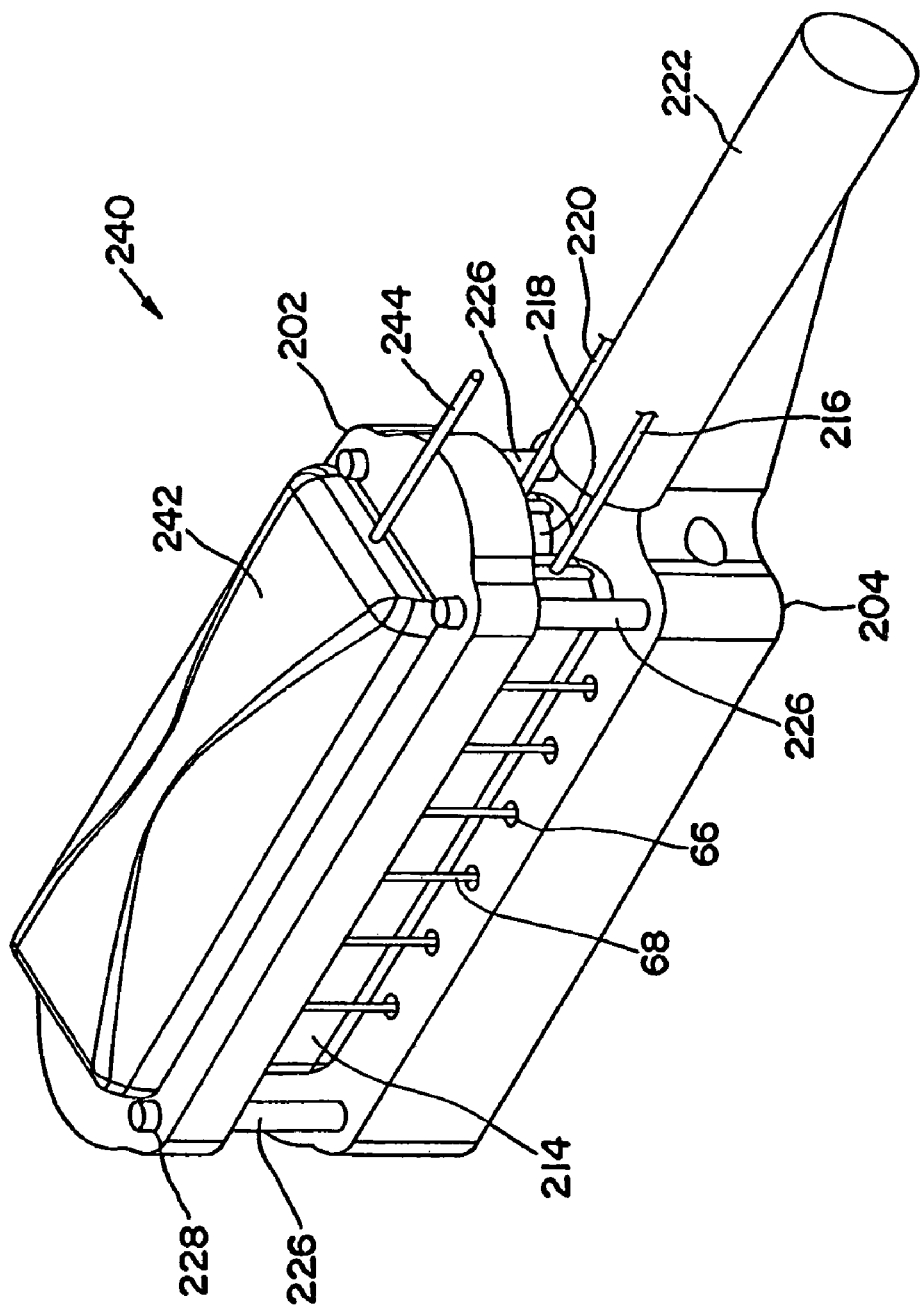
FIG. 11 is a perspective view of yet another distal injection head employing inflatable balloons for withdrawing needles and another inflatable balloon for transversely driving needles into tissue and/or stabilizing the head.

FIG. 11 illustrates another distal injection head 240, similar in many respects to injection head 200 illustrated in FIG. 10. Injection head 240 includes first body 202, second body 204, proximal hub 222, needles 68, needle receiving holes 66, first inflatable envelope 214, second inflatable envelope 218 and guide posts 226, all as previously described with respect to injection device 200 of FIG. 10. Distal injection device 240 further includes another inflatable envelope, balloon, or bellows 242 fixedly attached to the top of first body 202 and supplied by another inflation and deflation tube 244. Inflatable envelope 242 is thus located on the body opposite the body disposed against the tissue, and on the opposite side or major surface of that body. Inflatable envelope 242 may be used to force distal injection head 240 against the target tissue. In one use, inflatable envelope 242 is inflated to fill the pericardial space and press against the inside of the pericardial sac to stabilize the position of distal injection head 240 against the epicardial surface. In some methods, inflatable envelope 242 is used in conjunction with vacuum pods to stabilize the position of the distal injection head against the epicardial surface. In other methods, inflatable envelope 242 is used to replace the vacuum pods. In still other methods, inflatable envelope 242 is used to provide some or all of the transverse driving force to drive needles 68 into the target tissue.

Figure 12:
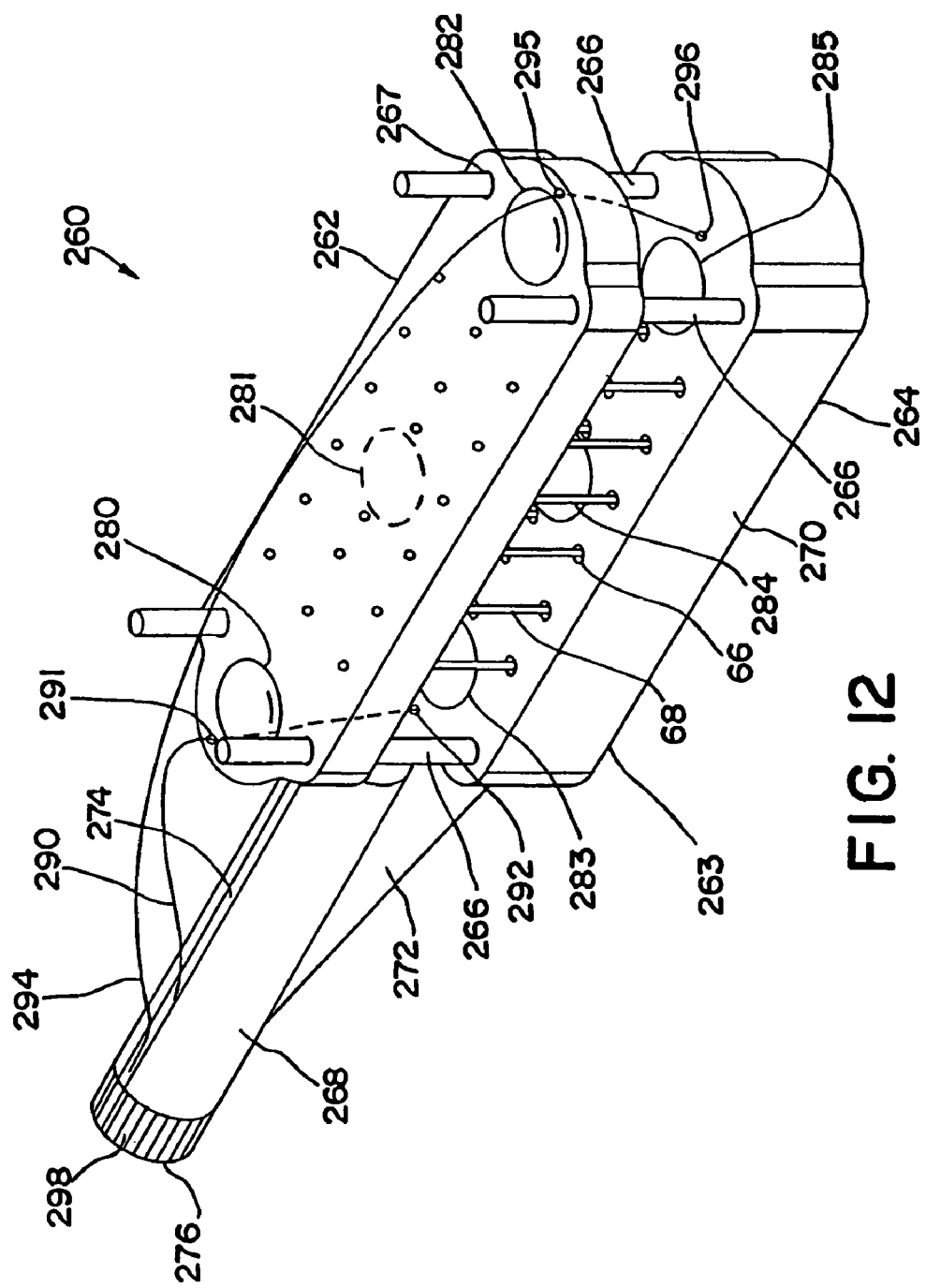
FIG. 12 is a perspective view of still another distal injection head employing drawstrings to drive needles into tissue and magnets to bias the needles away from the tissue.

FIG. 12 illustrates another distal injection head 260 including a first body 262 and a second body 263. Second body 263 includes a distal portion 264 that can serve as a vacuum plate in some embodiments, an intermediate portion 272 that can act as a strut or brace, and a proximal portion 268 for coupling to an elongate shaft. Second body proximal portion 268 may be seen to include a longitudinal slit 274 along its length and terminate proximately in a proximal aperture or port 276. Second body 263 has attached guideposts 266 that are slidably received within guide holes 267 in first body 262.

First body 262 may be seen to include three magnets 280, 281, and 282. Second body distal portion 270 also includes three magnets 283, 284, and 285. The magnets may be oriented such that each of the opposing pairs of magnets repel each other. Thus, magnet 280 may have the positive pole oriented downward and corresponding second body magnet 283 may have the positive pole oriented upward, and so forth. The pairs formed by magnets 280 and 283, 281 and 284, and 282 and 285 can act to magnetically bias first body 262 away from second body 264. This magnetic repulsive force may be used in conjunction with other embodiments described elsewhere in the present application.

Distal injection head 260 may also be seen to include a first drawstring or wire 290 extending outward from slot 274, extending through a receiving hole 291 in first body 262, and terminating at a hole or junction point 292 in second body distal portion 264. Similarly, a second pullstring, wire, or tether 294 may be seen also extending from slot 274, extending through a distal receiving hole 295 in first body 264 and terminating in a receiving hole or connection point 296 in second body distal portion 264. A proximal collar 298 may be seen disposed about longitudinal slot 274, limiting the transverse travel of tethers 294 and 290 from longitudinal slot 274.

In use, tethers 290 and 294 may be proximally retracted through longitudinal slot 274 and collar 298. As tethers 290 and 294 are slidably received through holes 291 and 295, respectively, retracting the tethers acts to force first body 262 toward second body distal portion 264. This acts to drive needles 68 through receiving holes 66 and into the target tissue. When the tethers are relaxed, the biasing force of the magnet pairs acts to retract the needles from the target tissue. In some embodiments, electromagnets are used in place of some or all of the magnets, with the wires or electrodes extending the length of the elongate shaft to provide energy to the electromagnets. In the electromagnetic embodiments, the polarity of the magnets can be reversed electronically, to both extend the needles and retract the needles.

Figure 13:
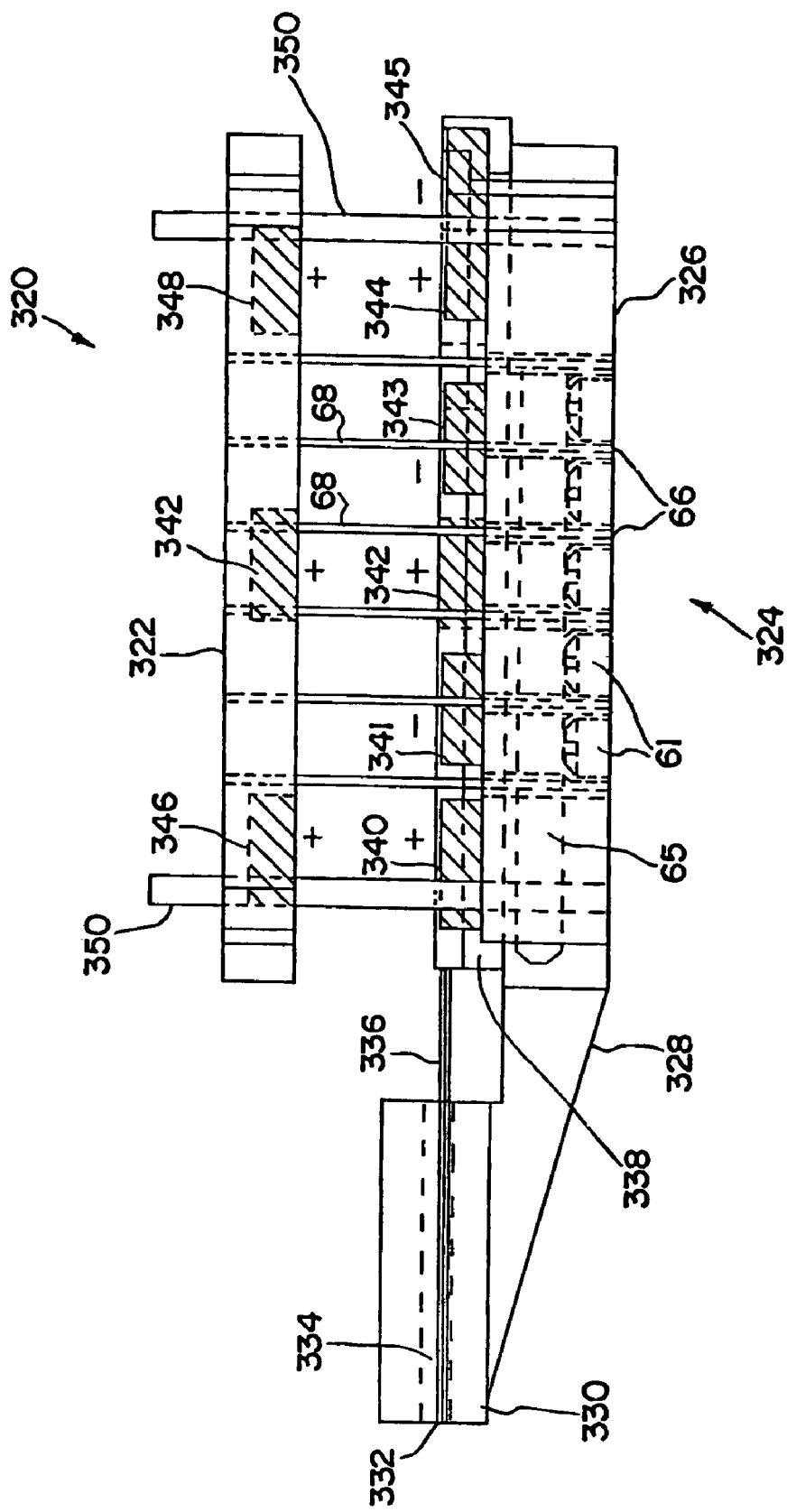
FIG. 13 is a side view of another distal injection device employing alternating polarity magnet pairs slideably disposed opposite other magnets to translate longitudinal motion into transverse, needle-driving motion.
Figure 14:
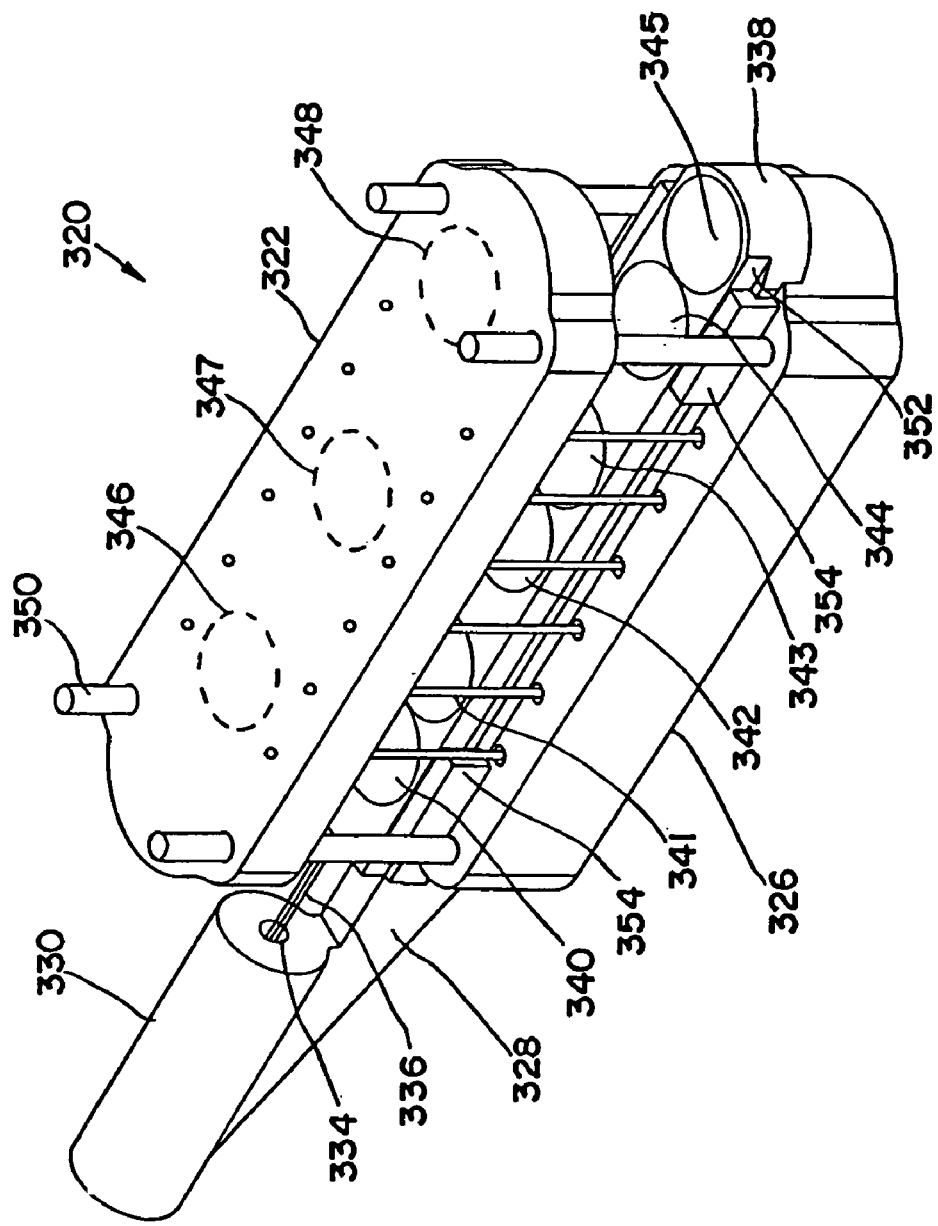
FIG. 14 is a perspective view of the distal injection head of FIG. 13.

FIGS. 13 and 14 illustrate another distal injection head 320, also employing magnets. While distal injection device 260 of FIG. 12 employed magnets acting in repulsion to bias the first and second bodies apart, distal injection head 320 employs magnets to drive the first and second bodies both apart and together. Distal injection device 320 includes a first body 322, and a second body 324 including a second body distal portion 326, an intermediate strut or brace portion 328, and a proximal tube portion 330. Proximal tube 330 may be seen to include a lumen 334 therethrough, terminating in a proximal port 332. Second body distal portion 326 can act as a vacuum plate in some embodiments. In the embodiment illustrated, second body distal portion 326 includes vacuum pods 61 and vacuum lumen 65, as previously discussed. Second body 324 includes guideposts 350 fixedly secured to second body distal portion 326. Guideposts 350 are slidably received through first body 322.

First body 322 may be seen to include three magnets, 346, 347, and 348 disposed therein. In the example illustrated, each of the three magnets is oriented to have the positive pole facing downward, toward second body 324. Distal injection head 320 also includes a longitudinally slideable third member 338 secured to a shaft 336 that is slidably received through lumen 334. In FIG. 14, longitudinally slideable member 338 may be seen to have a lip 352 and a corresponding guide 354 secured to second body distal portion 326. Longitudinally slideable member 338 is slidably secured to second body distal portion 326, and is shown in a far, distal position. Slideable member 338 may be seen to include three pairs of alternating polarity magnets disposed beneath magnets 346, 347, and 348. In the example illustrated, three magnets, 340, 342, and 344 are shown having the positive pole facing upward, and repulsing the positive pole of magnets 346, 347, and 348. Longitudinally slideable member 338 also carries three magnets 341, 343, and 345, having the negative pole facing upwards. The positive and negative polarities of the upward facing magnets are longitudinally offset and alternating in the example illustrated.

Inspection of FIG. 13 shows that proximally retracting shaft 336 through lumen 334 will proximally retract longitudinally slideable member 338, thereby carrying negative polarity magnets 341, 343, and 345 beneath magnets 346, 347, and 348, respectively. This will act to bring the opposite polarity magnet faces closer to each other and will act to drive first body 322 downward against second body distal portion 326. Similarly, distally advancing shaft 336 and longitudinally slideable member 338 acts to bring the same polarity magnet poles opposite each other, acting to drive first body 332 away from second body distal portion 326. These attracting and repulsing forces act to drive needles 68 into tissue, and retract the needles from the tissue, respectively. The use of rare earth magnets can provide a substantial amount of driving and repulsing force in a small volume.

Figure 15A:
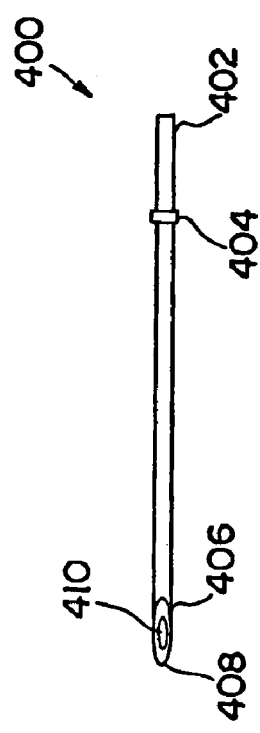
FIGS. 15A and 15B illustrate a single orifice needle that can be used in conjunction with the distal injection heads.
Figure 15B:
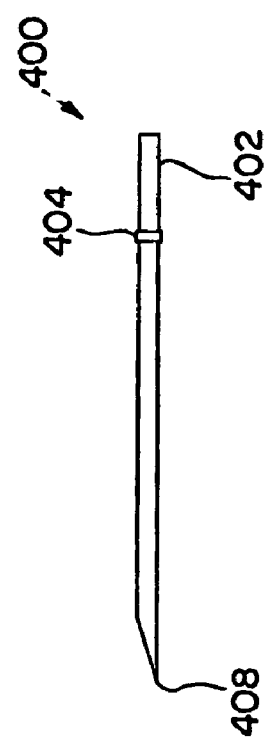

FIGS. 15A and 15B illustrate one needle 400 that can be used in conjunction with the present invention. Needle 400 includes generally a proximal region 402, a shoulder 404, a beveled, distal region 406, a discharge orifice 410, and a sharp end at 408. Needles used in conjunction with the present invention are preferably smaller in size than about a 24-gauge needle, preferably smaller than a 25-gauge needle, and most preferably about a 27-gauge needle for cardiac applications. Applicants believe that needles of a substantially small size, for example, about 27 gauge, allow for penetrating well into the myocardium, while not presenting any problem with bleeding. In one embodiment, the needle is about 0.5 inches in length, having about 0.40 inch between shoulder 404 and sharp distal end 408. Collar 404 can be about 0.010 inch in length in some embodiments. Needle 400 can have an outer diameter of about 0.016 inch, and an inner, lumen diameter of about 0.008 inch. As illustrated in FIGS. 15A and 15B, needle 400 has only a single, distal injection orifice.

Figure 16A:
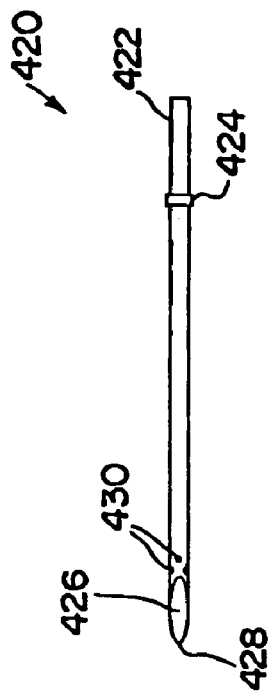
FIGS. 16A and 16B illustrate another needle having eight side holes that can be used in conjunction with the distal injection heads.
Figure 16B:
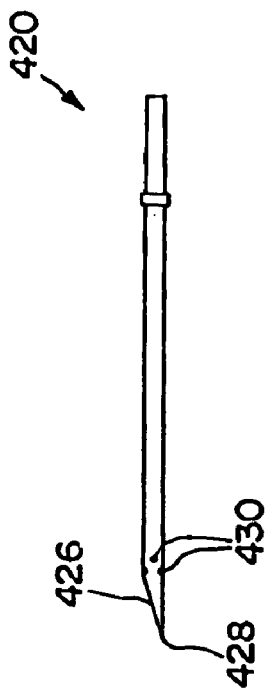

FIGS. 16A and 16B illustrate another needle 420 having eight side holes 430 formed in a distal region of the needle. Needle 420 includes generally a proximal region 422, a shoulder 424, a closed distal region 426, and a sharp distal tip 428. Needle 420 may be seen to have numerous side holes 430 formed in the distal region. In one embodiment, four side holes are formed in the needle. In another embodiment, eight side holes are provided through the needle sidewall. In one embodiment, the side holes have an inside diameter of about 0.0005 inch, and are located between about 0.065 inch and about 0.075 inch from distal tip 428. Side holes 430 allow for injection of material at different depths in the tissue to be treated. In one example, material can be injected at several depths of the myocardium simultaneously. In one embodiment, one set of side holes are located about 90 degrees apart, with a second set of side holes longitudinally offset, and radially offset by about 45 degrees from the first set of four side holes. Needles can be formed from stainless steel or other materials well known to those skilled in the art. The side holes can be formed by methods well known to those skilled in the art, such as laser drilling/cutting, wire EDM, traditional EDM, micro drilling, or water jet cutting. The dimensions of needle 420 can be as described with respect to needle 400 of FIGS. 15A and 15B.

Figure 17:
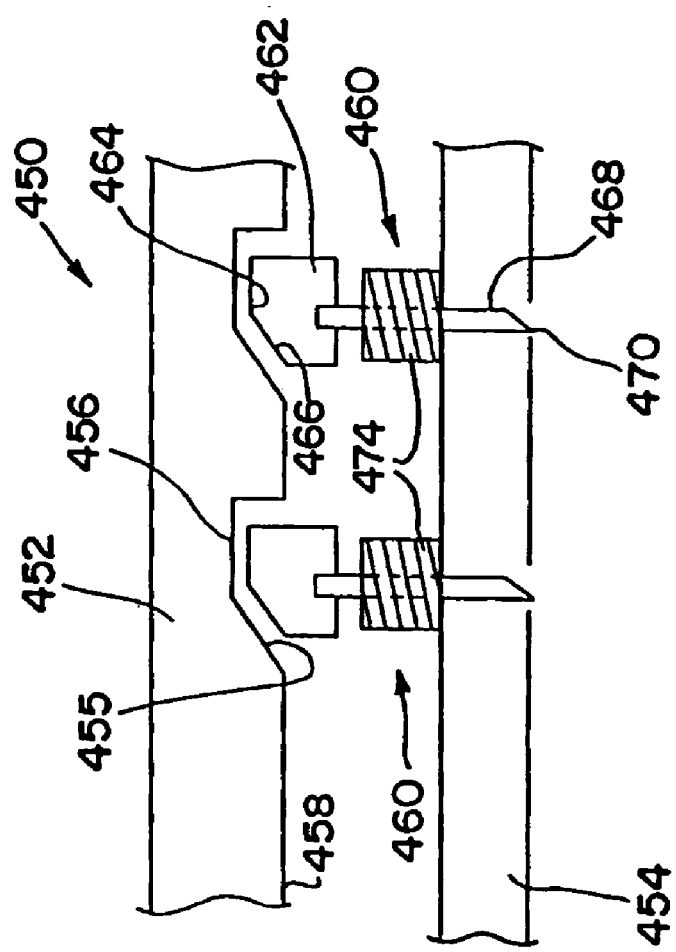
FIG. 17 is a fragmentary, side view of needles that can be individually transversely driven by a cam mechanism.

FIG. 17 illustrates a mechanism that can be used in conjunction with other embodiments previously illustrated. FIG. 17 includes a portion of a distal injection head 450 having a first body 452 disposed in a spaced apart relationship to a second body 454. As previously discussed with respect to other embodiments, second body 454 can be disposed against the tissue to be injected, and first body 452 used to drive needles into the tissue.

First body 452 has inclined cam surfaces 455 that lie at an angle relative to the longitudinal plane of first body 452. First body 452 also includes substantially level, planar high portions 456 that are not substantially inclined with respect to the plane of first body 452 or the plane of second body 454.

First body 452 may also be seen to have a second set of lower non-inclined regions 458 that are not inclined with respect to the injection plane. Thus, extending from distal to proximal, the underside of first body 452 includes a non-inclined portion 456, an inclined portion 455 extending downward, followed by a non-inclined portion 458. Spring-loaded needles 460 may also be seen in FIG. 17. Spring-loaded needles 460 include generally a cam follower head 462, including a non-inclined portion 464 and an inclined portion 466. Spring-loaded needles 460 further include a shaft 468 terminating in a sharp, distal point 470 and having a compression spring 474 disposed about needle shaft 468, between second body 454 and cam follower head 462. Inspection of FIG. 17 shows that distally advancing first body 452 will cause first body inclined portion 455 to bear against spring-loaded needle cam follower head inclined portion 466, acting to drive needle distal tip 470 downward. As the needles are biased by compression springs 474, proximally retracting first body 452 will allow needles 468 to retract from the tissue.

Figure 18:
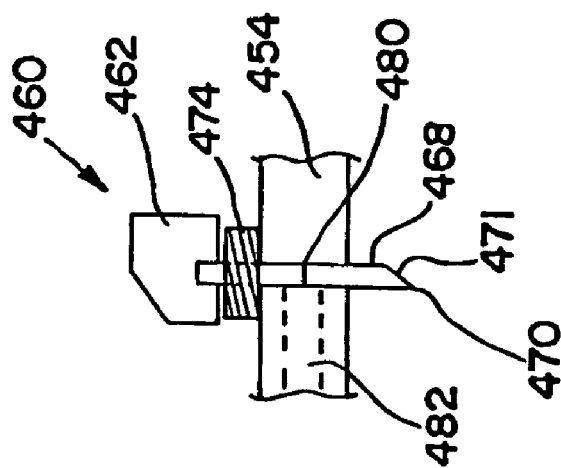
FIG. 18 is a transverse, cross-sectional view of one cam driven needle of FIG. 17, having a side hole for admitting fluid into the needle.

FIG. 18 illustrates second body 454 and spring-loaded needle 460 in greater detail. Spring-loaded needle 460 is shown in the extended, injecting position. Needle shaft 468 may be seen to include a side hole or entry orifice 480 through the sidewall of the needle and an injection orifice 471. Second body 454 may be seen to have a fluid, injection manifold or lumen 482 disposed through second body 454. When spring-loaded needle 460 is in the depressed configuration, fluid may be injected through fluid supply lumen 482, through needle entry orifice 480, and then out needle distal orifice 471. The fluid supply system illustrated in FIG. 18 may be used in conjunction with any of the embodiments illustrated in the present application. Specifically, a fluid supply lumen or channel may be provided in the second body distal portion or second body vacuum plate in any of the embodiments illustrated in the present application. Fluid may also be supplied in a more conventional manner, being supplied by a manifold supplying the proximal ends of the needles from within the first body, or needle plate in any of the embodiments illustrated in the present application.

Figure 19:
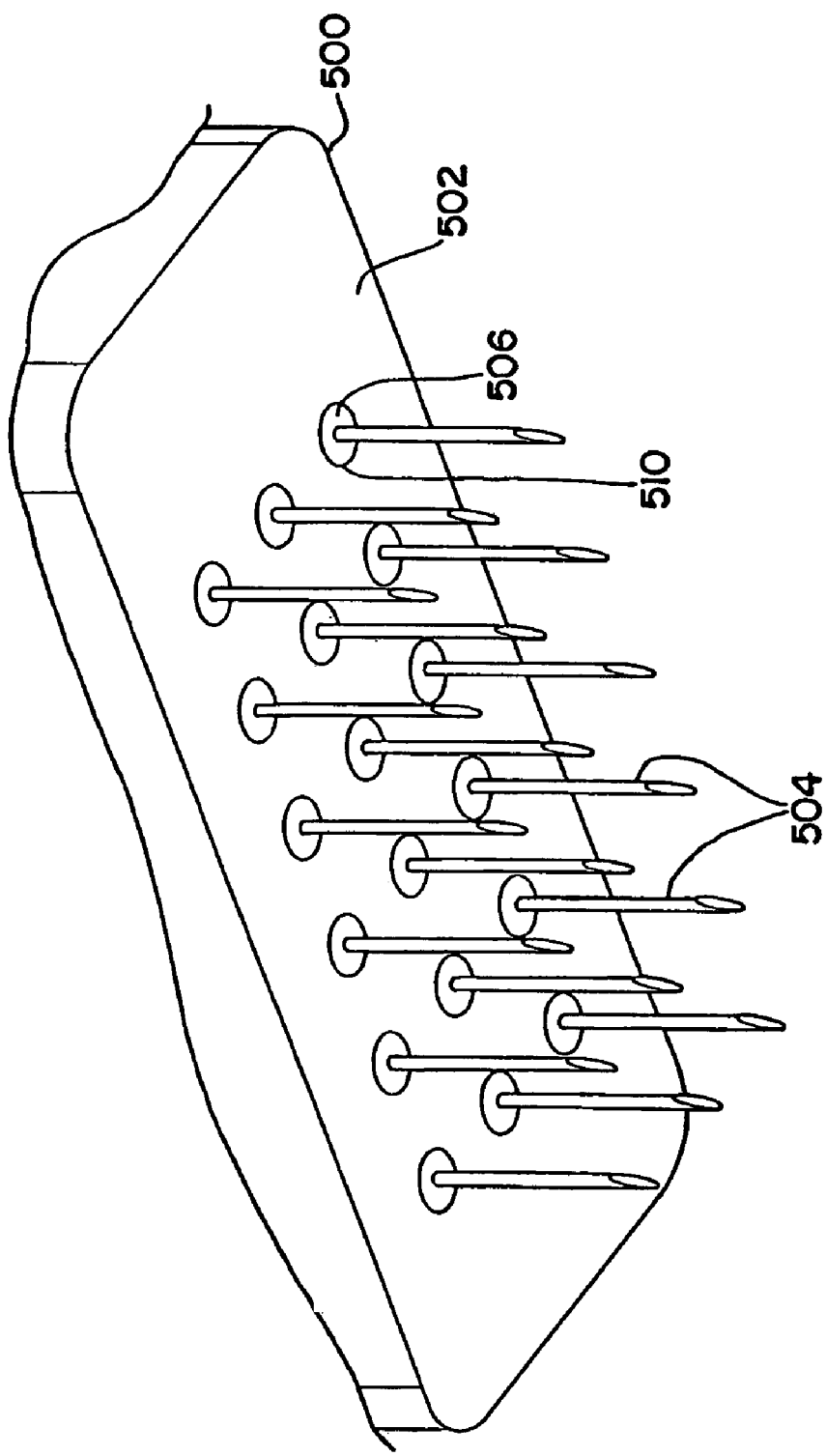
FIG. 19 is a fragmentary perspective view of a second body, tissue-contacting surface having several needles secured to needle holders that are removably secured in the second body.

FIG. 19 illustrates a first body 500 having a surface 502, which includes several holes 510 having needle holders 506 secured within. Needle holders 506 have needles 504 secured within the holders. The needle holders can be removably secured to first body 500 to allow adding and removing needles to the body. Needles, together with the needle holders, can be added or removed to vary the number, pattern, and depth of needles to be used for a particular procedure. In some devices, the needles may be removed and the injection head re-used with different needles in another procedure. Unused openings in surface 502 can be plugged with blanks or solid screws.

Figure 20:
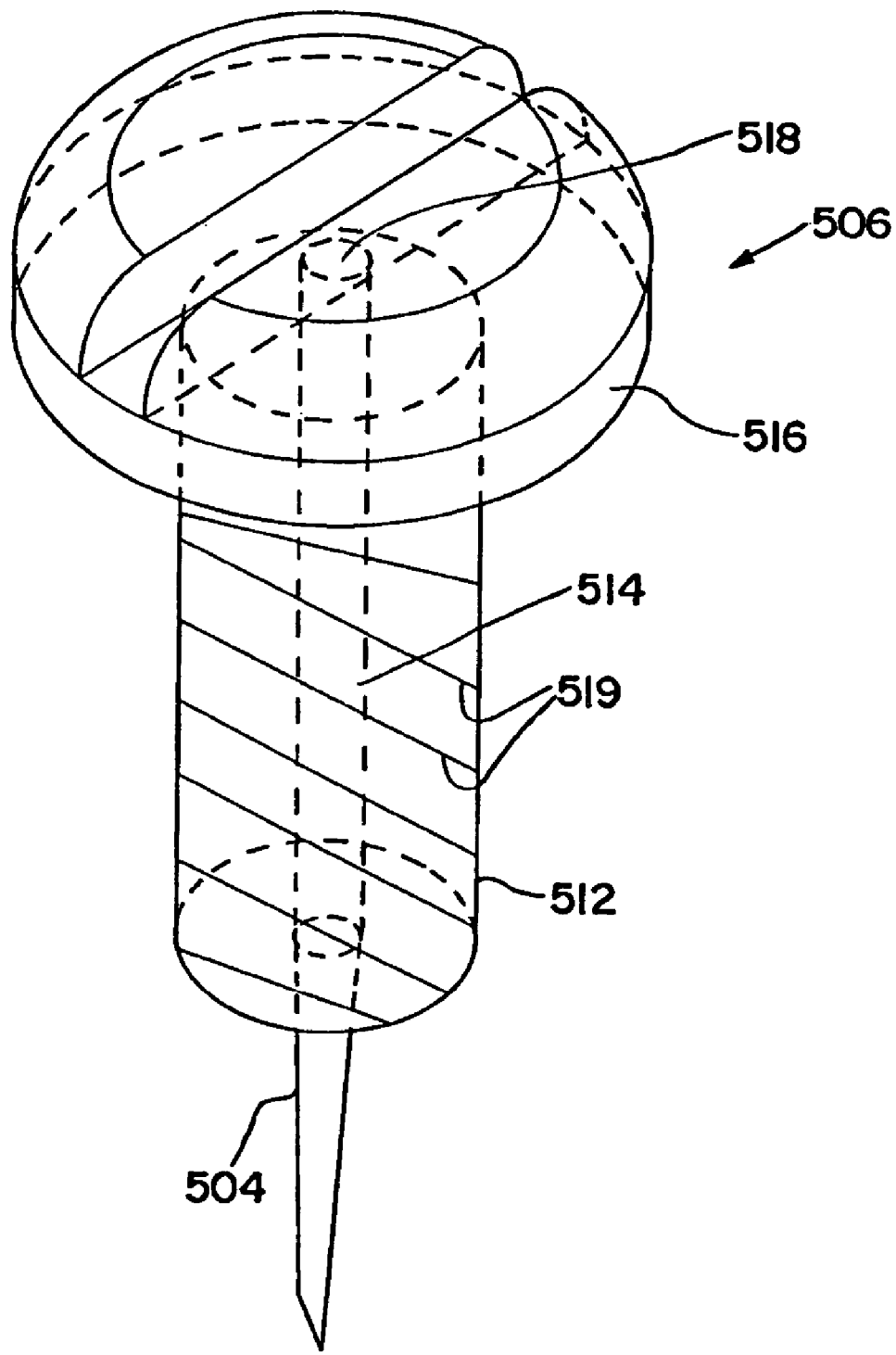
FIG. 20 is a perspective, cut-away view of one threaded screw holder of FIG. 19, having a central longitudinal bore within.

FIG. 20 illustrates needle holder 506 in greater detail. Needle holder 506 includes a cylindrical body 512 having a slotted head 516. A bore 514 extends from a top port 518 through the length of screw holder 506, and has needle 504 fixedly secured within. In the embodiment illustrated, needle holder 506 is threaded at 519, to allow the needle holder to be screwed into the top portion of first body 500 while providing fluid entry to hollow needle 504 through top port 518.

Needle holder 506 can be made by taking a #4 screw having 40 threads per inch, forming bore 514 with electron discharge machining (EDM) or laser welding, then inserting hollow needle 504 into the bore. Needle 504 can be secured to needle holder 506 using epoxy, sliver solder, or a laser weld.

Figure 21:
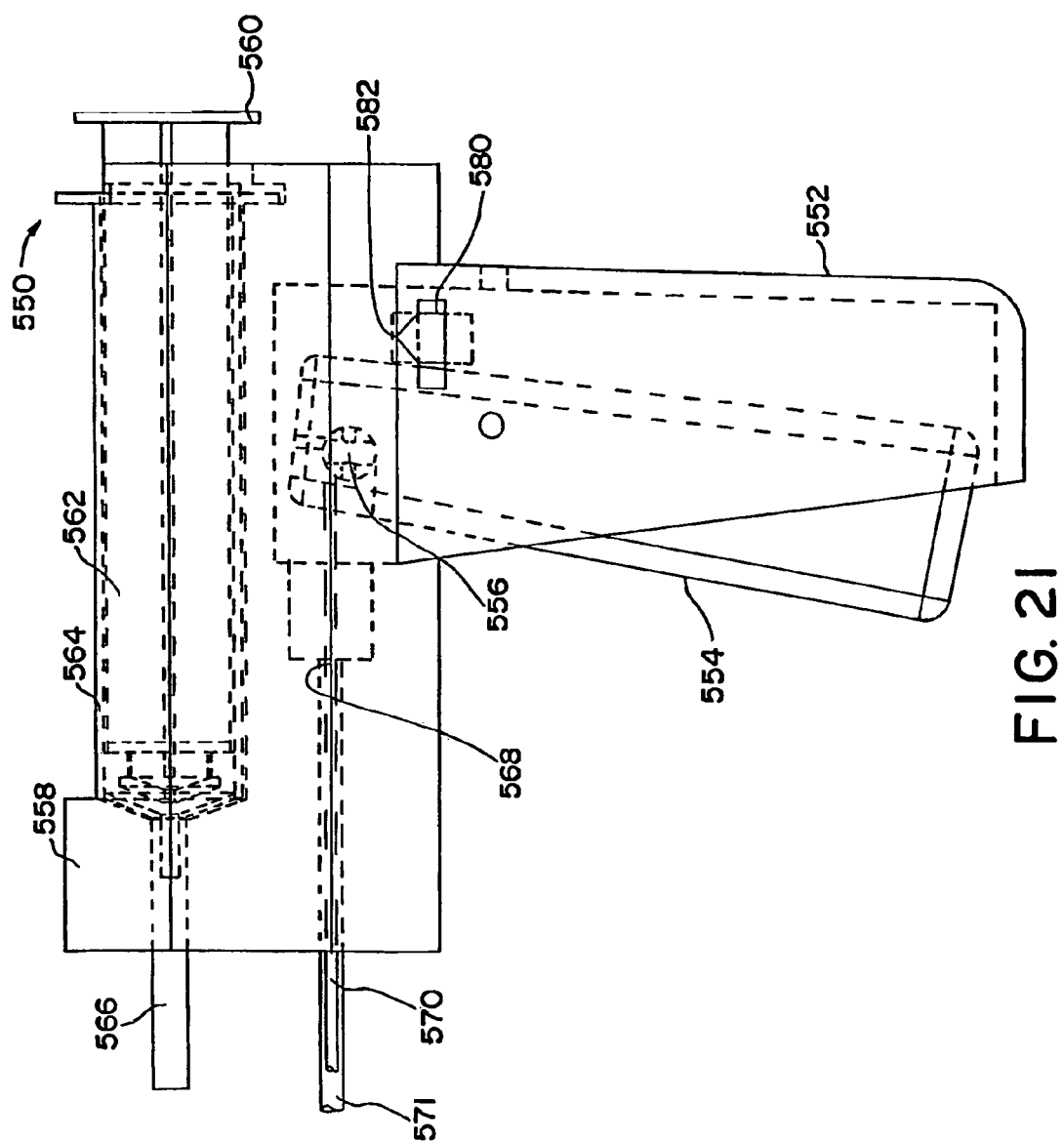
FIG. 21 is a side view of one proximal handle that can be used to supply energy along the elongate shaft and provide fluid for injection along the elongate shaft.

FIG. 21 illustrates a handle 550 that can be used in conjunction with many of the embodiments of the present invention. Handle 550 includes generally a stationary handle portion 552, an actuator lever 554 pivotally mounted about pivot point 556, and a housing or barrel 558. Handle 550 includes a drive cable 570 slideably disposed within a cable sheath 571. Drive cable 570 is coupled to actuator lever 554 at 568. Actuator lever 554, together with drive cable 570 and cable sheath 571 can provide the longitudinal motion and energy for actuating the transverse, needle driving motion described previously with respect to many embodiments of the present invention. A longitudinally slidable depth indicating member 580 may be seen, that can be distally biased and include a pointer 582. Handle 554 bears against depth indicator 580, such that pulling handle 554 extends drive cable 570 and drives the needles. Pulling handle 554 also allows biased depth indicator 580 and pointer 582 to slide forward, to provide a proximal indication of the degree of needle extension.

A syringe mechanism 560 may be seen to include a plunger 562 disposed within a bore or barrel 564. Plunger 562 is in fluid communication with a fluid tube 566. One syringe may be used to provide injectable material, for example biologic agents to be injected into the tissue. Some embodiments include a second syringe or other pressurized fluid mechanism for providing pressure and vacuum to inflate and deflate the envelopes, balloons, and bellows described previously in the present application.

Figure 22:
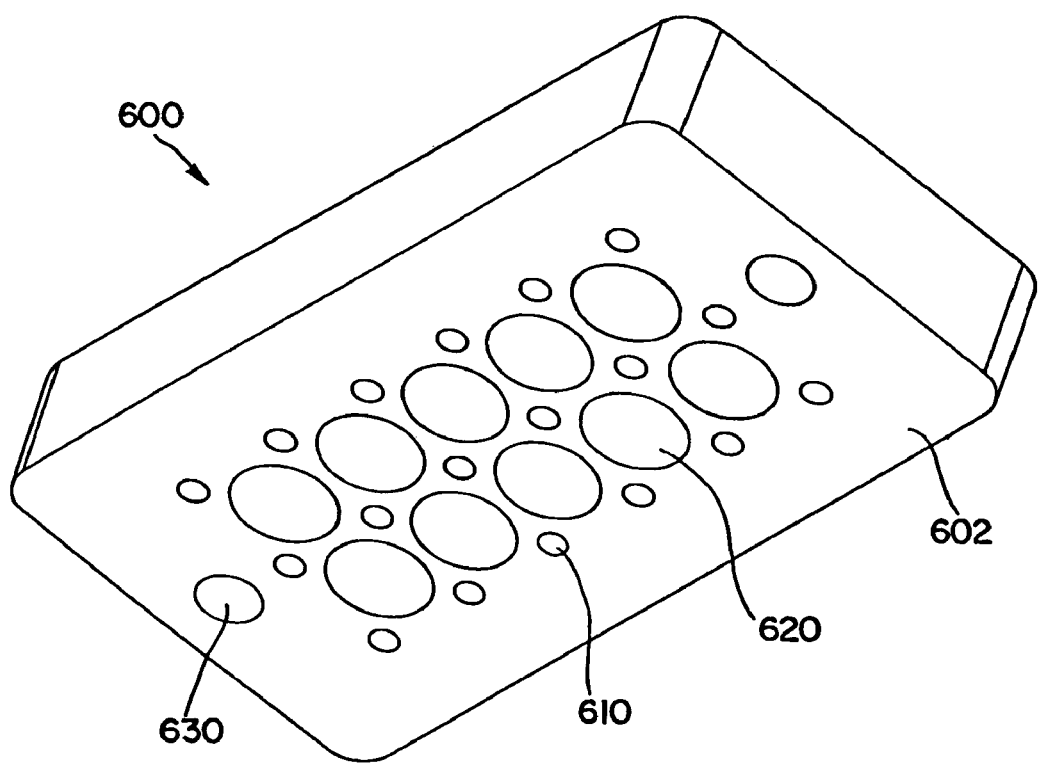
FIG. 22 is a bottom, perspective view of an interstitial injection device second body having needle receiving holes and a sensor.

FIG. 22 illustrates one embodiment of a second body 600 of a distal injection head. Second body 600 has a tissue-contacting surface 602 for contacting tissue. Tissue contacting surface 602 includes one or more holes 610 for slidably receiving one or more needles (not shown) and vacuum suction pods 620. The distal injection head may include one or more sensors, for example, located on the first body and/or the second body. The one or more sensors may be tissue depth sensors for determining the depth of tissue adjacent the distal injection head. The one or more depth sensors may be used to control the depth of needle penetration into the tissue. In this way, the needle penetration depth can be controlled, for example, according to the thickness of tissue, e.g., tissue of a heart chamber wall. In some embodiments (as shown in FIG. 22), one or more sensors 630 may be located on the tissue-contacting surface of second body 600.

The one or more sensors may comprise one or more sensing electrodes. The one or more sensing electrodes may be used to control the delivery of one or more medical agents. The one or more sensors may be used to determine when the distal injection head contacts tissue. For example, a pair of electrodes located on the tissue-contacting surface of the second body may be used to sense when the second body has made contact with tissue. An indicator may then be used to alert the physician that the distal injection head has made contact with tissue thereby allowing the physician to activate suction and/or inject the needles into the tissue. A variety of indicators, e.g., visual or audible, may be used to indicate to the physician that tissue contact has been made.

Figure 23:
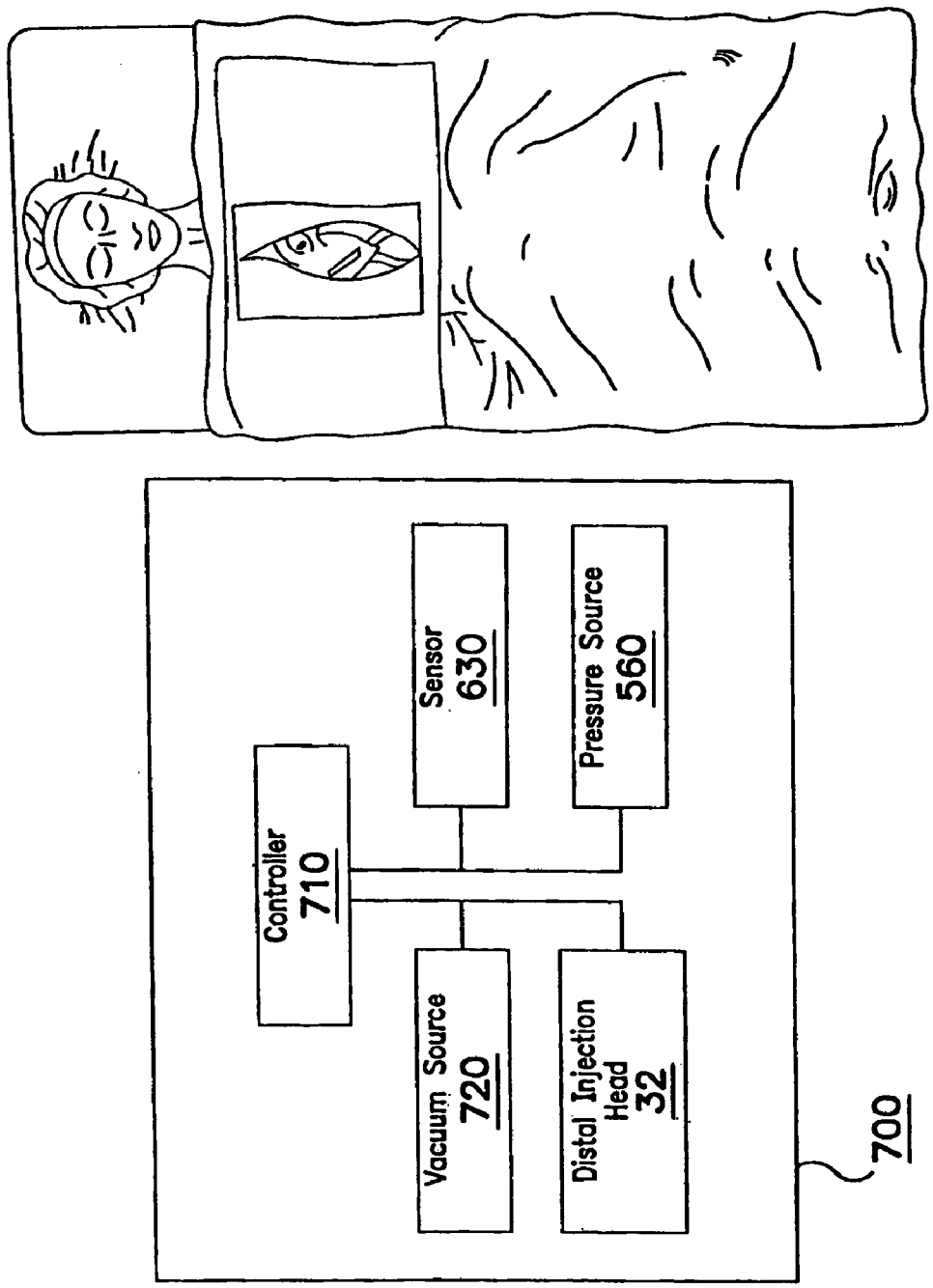
FIG. 23 is a schematic view of a system that can control an interstitial injection device.

FIG. 23 illustrates a system 700 according to the present invention. In one embodiment of the present invention, the one or more sensors may be used to control suction to vacuum suction pods 620. For example, a controller 710 may accept a trigger signal from sensors 630 and in-turn will activate suction to the device from vacuum source 720. Controller 710 may also accept a signal from a vacuum sensor or vacuum switch of vacuum source 720 and activate alarms if vacuum is not within a specific range.

In one embodiment of the present invention, controller 710 may be used to control one or more functions, elements or components of system 700. For example, controller 710 may control a vacuum source 720, distal injection head 32, e.g., injection of needles into tissue, and/or pressure source 560, e.g., injection of one or more medical agents into tissue. For example, controller 710 may accept a trigger signal from sensor 630 and in-turn will control a vacuum source, control delivery or injection of needles into the tissue and/or control delivery or injection of one or more medical agents into the tissue.

Controller 710 may incorporate any suitable processor. Controller 710 may be used to gather and process information from one or more sensors of the system. For example, controller 710 may be used to gather and process information from sensor 630. Controller 710 may incorporate one or more switches to facilitate regulation of the various components by the operator. The switches may be, for example, hand switches, foot switches, and/or a voice-activated switches comprising voice-recognition technologies. Controller 710 may have different modes, e.g., a standby mode, an automatic mode and/or a manual mode. Indicator lights may be used to indicate the mode of operation selected and if the system has malfunctioned. In one embodiment of the present invention, a system malfunction may trigger a flashing light and/or an audible alarm.

On power up, the controller 710 may perform one or more tests. For example, controller 710 may perform a self-test on its self and/or the sensors, switches, valves and/or devices connected to it. If controller 710 detects a malfunction, visual and/or audible alarms may be activated. Controller 710 may be designed to detect failures during operation and set off visual and/or audible alarms if so desired.

Controller 710 may be powered by AC power, e.g., 90 to 264 VAC, 50 or 60 Hz, or by a primary cell or rechargeable battery pack. It may be equipped with one or more fuses. Controller 710 may supply regulated voltage to one or more sensors, indicator lights, and/or audible alarms. Controller 710 may be designed to detect under/over voltage and shut off power to devices and sound an alarm.

Controller 710 may include an electronics enclosure that encloses one or more circuit boards and/or processors. The enclosure may have a front panel for one or more mounted switches, gauges, displays, and/or indicator lights, e.g., a power switch with indicator light. The enclosure may also include audio feedback system for sounding one or more alarms. The enclosure may include one or more entry points for a power cord and/or connectors for cables, e.g., cables from one or more sensors. The enclosure may be mountable onto a pole or be free standing. The enclosure may contain part or all of the power supply, e.g., a battery pack.

Controller 710 may be designed such that it will tolerate or disable itself in a safe mode if a sensor, electronic, and/or mechanical failure occurs. In addition, controller 710 may be designed to remain functional if, for example, the hospital electrical power or the hospital vacuum system fails. There are several modes in which the electrical power can fail, from a local failure in an individual operating room to a total hospital failure that disables the vacuum system.

In one embodiment of the present invention, the front panel or user interface of controller 710 may provide a place for the user to turn the power on and/or off, to provide the user the ability to select the operating mode, to provide the user the ability to control suction, to provide the user the ability to control needle insertion, and/or to provide the user the ability to mute any audible alarms. Controller 710 may accept inputs from a keypad located on the front panel and/or a reset button on a back panel. In addition, the user interface may provide a place for displaying one or more visual alarms. The circuitry of controller 710 may contain, for example, all of the necessary electronic components for processing signals from the system's sensors, e.g., contact sensors 620, controlling suction and/or power to the distal injection head, driving visual displays, visual alarms and/or audible alarms on the user interface, and/or handling the power supply and/or battery backup.

In one embodiment of the present invention, distinct visual and/or audible alerts inform the user, for example, that suction is on or off, the needles are deployed or retracted, that one or more medical agents are being delivered or have been delivered, and/or that the instrument is no longer operable.

In one embodiment of the present invention, the user interface may include one or more LCDs for displaying messages as well as one or more LEDs for visual warnings and/or alarms. Preferably, display information is visible, under normal indoor lighting conditions, from at least 10 feet away and audible alarms have a 2-minute mute capability with visual alert uninterrupted. Preferably, depending on the operating status, indicator lights will be off or flash. A flashing yellow light may be used to indicate a warning condition is occurring. A flashing red light may be used to indicate an alarm condition is occurring. The audible alarms may be monotone or varying frequency.

In one embodiment one or more tissue activated switches and/or sensors may be coupled to vacuum source 720 for turning on or modulating suction to the distal injection head. For example, when one or more sensors and/or switches determine distal injection head contacts tissue suction may be activated. The one or more sensors may be one or more electrical sensors, fiber optic sensors, chemical sensors, mechanical sensors and/or proximity sensors that measure conductance. The one or more switches may be one or more electrical, chemical and/or mechanical switches. For example, sensors 630 may be replaced with one or more small mechanically activated switches. When the mechanical switches are pushed against tissue they become activated thereby turning on suction to the distal injection head. In addition, sensors that can identify different tissue types may be used. For example, fatty tissue has different impedance than vessel wall tissue, therefore impedance sensors may be used to identify fatty tissue from vessel wall tissue. Sensors designed to sense difference in impedance may be used to change the amount of energy supplied to the distal injection head.

In one embodiment of the present invention, the delivery of medical agents from the distal injection head may be enhanced via iontophoresis. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules through tissue. For example, lidocaine hydrochloride may be applied to the heart via the distal injection head. Sensors 630 located on the tissue-contacting surface of second body 600 may comprise a positive electrode and a negative electrode. These electrodes may be used for iontophoresis. Current may be applied between the two electrodes, e.g., between the positive electrode and the negative electrode.

In one embodiment of the present invention, one or more electrodes located on the tissue-contacting surface of second body 600 may be used as stimulation electrodes, e.g., to pace the heart during delivery of one or more medical agents. For example, controller 710 may supply stimulation energy to the one or more electrodes for pacing cardiac tissue. One or more sensors 630 may be used to sense contractions of the heart, thereby allowing the delivery of medical agents to be timed with cardiac contractions. For example, it may be desirable to deliver one or more medical agents between contractions of the heart.

Cardiac contraction sensors may be any suitable sensor, e.g., an electrical sensor, a chemical sensor or a biosensor, for detecting one or more signals indicative of a cardiac contraction or heartbeat. In one embodiment, the cardiac contraction sensor may be coupled to controller 710.

In one embodiment, sensor 630 may be used to monitor the electrical activity of the heart by picking up and amplifying electrical signals from the heart and displaying a visual output and/or providing an audio output. For example, the output may be displayed on a display interface of controller 710. The surgeon may check this output to determine the optimal time to inject the needles and/or medical agents into the tissue.

A cardiac contraction sensor may be a sensor that detects cardiac depolarizations. The electrical signal generated by the sinus node of the heart causes the atria to contract to force blood into the ventricles. After a brief delay, the ventricles contract to force blood out through the body. The contraction of the ventricles is reflected by the passage of a depolarization wavefront through the heart muscle. If a depolarization is sensed, a beat is likely to occur. One such depolarization sensor is disclosed in U.S. Pat. No. 5,156,149 entitled "Sensor for Detecting Cardiac Depolarizations Particularly Adapted for use in a Cardiac Pacemaker", Oct. 2, 1992, to inventor Hudrlik. This patent is assigned to Medtronic, Inc. and is incorporated herein by reference.

A cardiac contraction sensor may be coupled to a cardiac stimulator or controller 710 which may act as a cardiac stimulator. A cardiac contraction sensor may be an apparatus that senses power levels of depolarizations in heart tissue. Such a sensor may be used to distinguish between normally conducted and ectopic heart beats while the heart is beating or may be used to sense an imminent heart beat while the heart is slowed or substantially stilled during a medical procedure. One apparatus that may serve as such a sensor is disclosed in U.S. Pat. No. 5,411,529 entitled "Waveform Discriminator for Cardiac Stimulation Devices", May 2, 1995, to inventor Hurdlik. This patent is assigned to Medtronic, Inc. and is incorporated herein by reference. Other suitable sensors may also serve as cardiac contraction sensor.

The devices according to the present invention can be used in several methods to deliver material to tissue. In one, mini-thoracotomy method, a patient is intubated with a double-lumen endobronchial tube that allows selective ventilation or deflation of the right and left lungs. The left lung is deflated, thereby helping to provide access to the surface of the heart. A left anterior thoracotomy or incision is created over an intercostal space, preferably the 4th intercostal space. An alternative intercostal space may be used depending on the patient's physiology, e.g., the 5th intercostal space. The thoracotomy should be as anterior and medial as possible without removing cartilage. A two-inch incision is preferable, however the size of the incision may vary depending on the patient. The ribs, adjacent the incision, may be spread, preferably two-inches or less, using a small rib retractor or spreader to allow adequate access into the chest. If desired, a retractor may be used to spread the ribs both horizontally and vertically. Next, the pericardium is opened directly under the incision. Dissection through fat may be required to reach the pericardium. The pericardium may be opened by a number of different techniques. In one embodiment of the present invention, the pericardium may be opened by tenting it with graspers and then cutting it with scissors. In an alternative embodiment of the present invention, a device as disclosed in either U.S. Pat. No. 5,931,810 or U.S. Pat. No. 6,156,009 both to Grabeck may be used to access the pericardial space. In addition, devices as disclosed in U.S. Pat. No. 5,972,013 to Schmidt, U.S. Pat. No. 5,827,216 to Igo, et al., U.S. Pat. No. 6,162,195 to Igo, et al., U.S. Pat. No. 4,991,578 to Cohen and U.S. Pat. No. 5,336,252 to Cohen may be used, for example, to access the pericardial space. These patents are incorporated herein by reference.

In one embodiment of the present invention, one or more devices may be used within the pericardial space for creating space and visualizing the surface of the heart. For example, a device comprising a rigid rod with a light may be used to push on the interior of the pericardium and to move the lung laterally if desired. Another device comprising a flat malleable spatula may be used to rotate the heart and expose the posterior lateral portion of the heart if desired. The spatula device may be bent or formed into whatever shape is required to move and rotate the heart.

In one embodiment of the present invention, a suction positioning device as described in U.S. Pat. No. 6,447,443 to Keogh et al., incorporated herein by reference, may be used to move the heart around and/or hold the pericardium out of the way. The positioning device may be used to engage the heart and to position the heart into a non-physiological orientation.

Upon gaining access to the epicardial surface of the heart, the injection head and shaft are inserted through the mini-thoracotomy. The distal injection head is then placed against the surface of the heart. Suction may be applied prior to the injection of needles into the tissue. Following delivery of one or more biologic agents or medical agents, the needles are retracted and suction, if used, may be turned off. The heart may be repositioned is desired, for example, with a suction positioning device. The distal injection head may then be repositioned for additional delivery of one or more medical agents or the head and shaft may be removed from the patient. All incision may then be closed using standard techniques. If the pleura is closed, a small tube for drainage may be left in place and removed the same day as surgery. If the pleura is open, a larger tube may be left in place for 24 hours.

In one, thoroscopic method, a patient is intubated with a double-lumen endobronchial tube that allows selective ventilation or deflation of the right and left lungs. The left lung is deflated, thereby helping to provide access to the surface of the heart. The patient is rotated approximately 30° with the left side up. The left arm is placed below and behind the patient so as not to interfere with tool manipulation during the delivery of one or more medical agents. While port positions depend to a large extent on heart size and position, in general a $7^{th}$ and $5^{th}$ space mid (to posterior) axillary port for tools and a $3^{rd}$ space anterior axillary port for the scope is preferable. A variety of endoscopes or thoracoscopes may be used including a 30 degree offset viewing scope or a straight ahead viewing scope. In general, short 10 to 12 mm ports are sufficient. A soft 20 mm port with an oval cross section sometimes allows for two tools in the port without compromising patient morbidity.

The pericardium may be opened by a number of different techniques. In one embodiment of the present invention, the pericardium may be opened by tenting it with graspers and then cutting it with scissors. In an alternative embodiment of the present invention, a device as disclosed in either U.S. Pat. No. 5,931,810 or U.S. Pat. No. 6,156,009 both to Grabeck may be used to access the pericardial space. In addition, devices as disclosed in U.S. Pat. No. 5,972,013 to Schmidt, U.S. Pat. No. 5,827,216 to Igo, et al., U.S. Pat. No. 6,162,195 to Igo, et al., U.S. Pat. No. 4,991,578 to Cohen and U.S. Pat. No. 5,336,252 to Cohen may be used, for example, to access the pericardial space. Upon gaining access to the epicardial surface of the heart, the injection head and shaft are inserted through an appropriate port. The distal injection head is then placed against the surface of the heart. Suction may be applied prior to the injection of needles into the tissue. Following delivery of one or more medical agents, the needles are retracted and suction, if used, is turned off. The distal injection head may then be repositioned for additional delivery of one or more medical agents or the head and shaft may be removed from the patient. All incisions may then be closed using standard techniques. Some methods may utilize insufflation, in which the incision or port is sealed about the device shaft and the interior of the thorax pressurized.

In one, sternotomy method, the device may be inserted through an incision made through the sternum. In yet another method, a xiphoid incision method, an incision is made below the sternum and the injection head is then inserted through the incision. The term "xiphoid incision" refers to a surgical incision proximate to, but not necessarily directly above, the xiphoid appendage. The xiphoid incision of the invention provides a surgical field and access site to the heart that extends through an opening beneath the sternum and preferably immediately beneath the lowest rib.

A vertical skin incision is made above the xiphoid process and the center of the xiphoid appendage is transected. Because the xiphoid appendage is cartilaginous, the appendage does not have to be removed and the sternum does not have to be transected. The total length of the xiphoid incision depends on length of xiphoid appendage, i.e., longer xiphoids are less likely to require any cutting into the sternum. The maximum incision is preferably approximately 6-7 cm from below the tip of the xiphoid appendage upwards towards the patient's head. The incision may be extended downward below the xiphoid appendage to the extent necessary to provide an adequate surgical field, but as noted above, the maximum length should not greatly exceed 6-7 cm. The incision may be strictly vertical or may be slightly curved, following the outline of the butt of either the right or left rib cage. In most cases, a curved incision will follow the lower left rib. An approximately 1 cm incision may be made in the pericardium to accommodate insertion of a surgical scope. The scope preferably has a flexible housing and at least a 16× magnification. Insertion of the scope through the pericardial incision allows the surgeon to inspect the epicardial surface of the heart thereby allowing the physician to plan the procedure depending on the clinical status of the individual patient. At this point, the surgeon can confirm that a xiphoid access is appropriate for the particular procedure to be performed.

A vertically offsetting retractor or access platform may be used to engage a portion of the rib cage capable of lifting at least one rib and preferably more than one rib and the sternum, see U.S. Pat. No. 6,199,556 to Benetti et al. This patent is incorporated herein by reference. The term "offsetting" herein is used to describe a manipulation of at least one rib that provides access to the thoracic cavity via the xiphoid incision, generally described herein as "xiphoid access." Typically, the vertical offsetting procedure comprises engaging the lowermost rib with an offsetting retractor or access platform and lifting at least a portion of the lowermost ribs. This may be accomplished by simultaneously applying force at one or more points about the chest and pelvis, and preferably includes at least a mechanical force applied vertically to orient at least a portion of the lower region of the sternum and rib cage relative to the remainder of the body below the rib cage. As noted, this orientation is most readily achieved by lifting one half of the lower edge of the rib cage, adjacent to the xiphoid appendage using a specially designed surgical retractor. Although retraction devices such as those described in U.S. Pat. No. 5,730,757 are preferred, other more conventional devices could be adapted, see for example U.S. Pat. Nos. 5,026,779, 4,726,358 and 4,852,552. These patents are incorporated herein by reference. Collectively, these devices can provide access to a beating heart via a xiphoid incision and comprise means for offset retraction of the lower rib cage.

Since the size of the incision is preferably minimized in a xiphoid procedure, an organ or tissue positioner may advantageously be used to retract or reposition tissue or internal organs at the site of the incision or inside the thoracic cavity near the site of the surgery. The positioner or retractor may be of any conventional mechanical design, or expandable by inflation on manipulation, and is preferably suitable for minimally invasive procedures. Moreover, a tissue or organ positioner may be affixed to the offsetting retractor during the procedure to maintain access to the surgical field.

Upon gaining access to the epicardial surface of the heart, the injection head and shaft are inserted through the xiphoid incision. The distal injection head is then placed against the surface of the heart. Suction may be applied prior to the injection of needles into the tissue. Following delivery of one or more medical agents, the needles are retracted and suction, if used, may be turned off. The distal injection head may then be repositioned for additional delivery of one or more medical agents or the head and shaft may be removed from the patient. All incisions may then be closed using standard techniques. A small incision may be made below the xiphoid appendage and a drainage tube may be inserted into the pericardium, if the pleura has not been opened, and into the pluera itself if it has been opened. Before finally closing the xyphoid incision, a scope may be used to check the position of the drainage tube, and to check the integrity of the pleura.

The elongate device shaft can be used to position the injection head over the epicardium as desired. In some methods, the device elongate shaft is flexible, and is introduced through a small incision, port or cannula. In some devices, the distal injection head has a thickness of no greater than about 15 millimeters, to allow for insertion between the ribs in an incision having a height of no greater than about 15 millimeters.

Cells suitable for implantation according to the present invention include a wide variety of cells, e.g., undifferentiated contractile cells. Typically, undifferentiated contractile cells differentiate to form muscle cells, however, they can be fibroblasts that have been converted to myoblasts ex vivo, or any of a wide variety of immunologically neutral cells that have been programmed to function as undifferentiated contractile cells. Cells of mesodermal origin that form contractile cells can be injected, and include skeletal muscle cells, heart muscle cells, and smooth muscle cells, as well precursor cells to the cells, such as pluripotent stem cells, embryonic stem cells, mesodermal stem cells, myoblast, fibroblasts, and cardiomyocytes. Suitable cells for use in the present invention can include umbilical cells, and skeletal muscle satellite cells. Suitable cells for implantation also include differentiated cardiac or skeletal cells, such as cardiomyocytes, myotubes and muscle fiber cells, and the like, whether they are autologous, allogeneic or xenogenic, genetically engineered or non-engineered. Mixtures of such cells can also be used. Autologous cells are particularly desirable. The cells are capable of repopulating the infarct zone of the myocardium or capable of establishing health tissue in damaged or diseased myocardial areas or aiding in the angiogenesis process.

Skeletal muscle satellite cells are particularly suitable for use in the present invention because they can differentiate to muscle cells that are capable of contracting in response to electrical stimulation. They are also particularly suitable for use in the present invention because they can be obtained from cell cultures derived from the biopsy samples of the same patient. Biopsy samples contain mature skeletal fibers along with reserve cells surrounding the mature fibers. Once placed in culture, reserve cells proliferate and their numbers quickly increase. These newly cultured cells can be injected back into the heart in and/or near the infarct zone. Once in the heart muscle, the skeletal myoblasts fuse to form multinucleated myotubes having contractile characteristics.

The undifferentiated and/or differentiated contractile cells can be delivered in combination with a delivery vehicle, such as liposomes or a polymeric matrix. Once the undifferentiated and/or differentiated cells form contractile tissue, their function can be further enhanced by metabolically altering them, for example, by inhibiting the formation of myostatin. This increases the number of muscle fibers.

In some methods, the cells are suspended in a liquid, and supplied to the distal injection head through a lumen in a tube. In other methods, the cells or other material is loaded into the needles in plug form, advanced to the target site, and ejected from the needles through the application of pressure to the needles. In one such method, cell material too viscous to flow through an elongate tube is loaded into the needles and discharged through the application of saline to the needles. In one method, a biopsy type sample is contained in the needles and injected under pressure to the target tissue.

Other therapeutic agents can be injected using devices and methods according to the present invention. Specific examples of therapeutic agents used in conjunction with the present invention include proteins, oligonucleotides, ribozymes, anti-sense genes, DNA compacting agents, gene/vector systems, nucleic acids (including recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers. Other pharmaceutically active materials include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidominc, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bc1-2 family factors and Akt kinase; and combinations thereof.

Examples of polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins useful in the present invention include, without limitation, angiogenic factors and other molecules competent to induce angiogenesis, including acidic and basic fibroblast growth factors, vascular endothelial growth factor, hif-1, epidermal growth factor, transforming growth factor .alpha. and .beta., platelet-derived endothelial growth factor, platelet-derived growth factor, tumor necrosis factor .alpha., hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and d the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Figure 24:
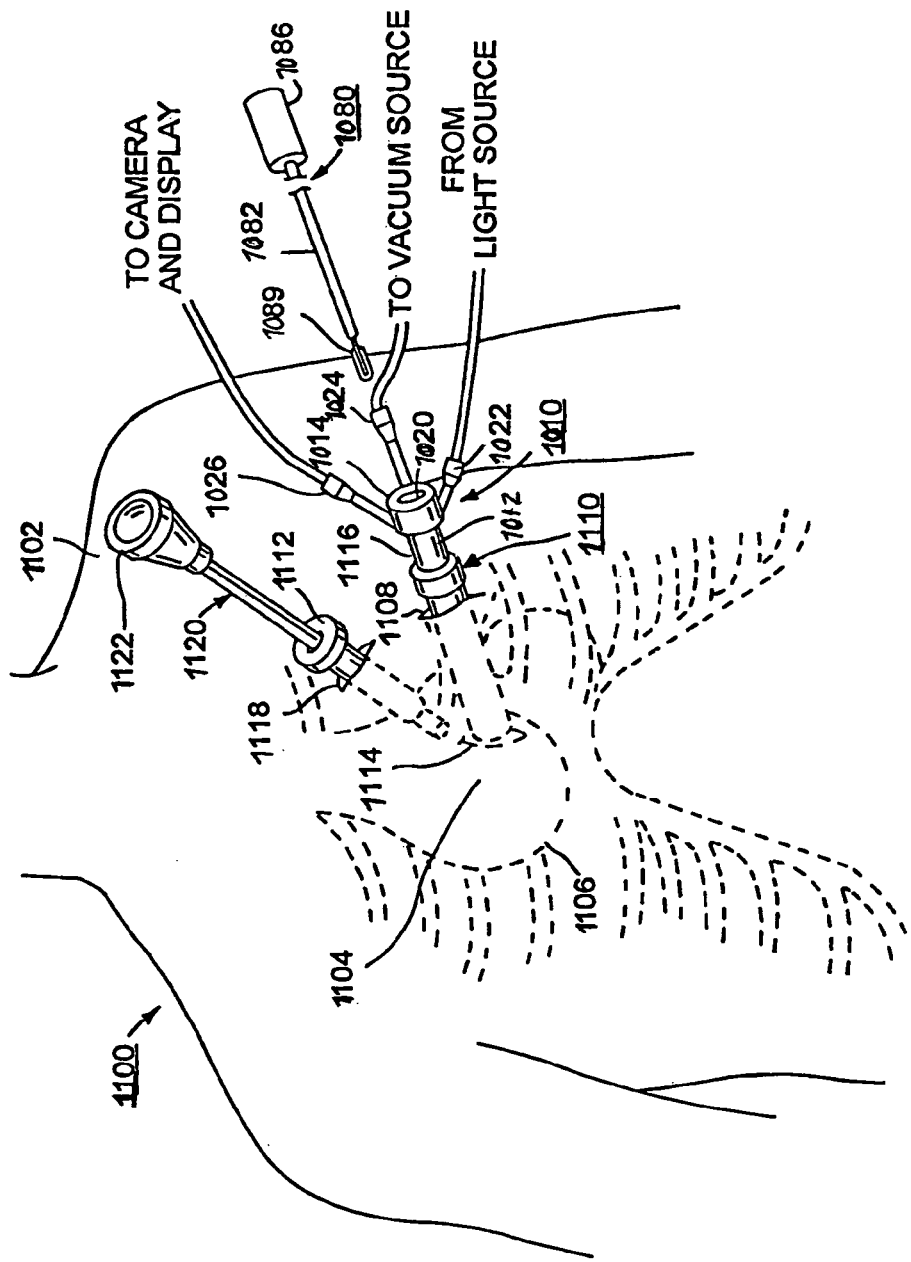
FIG. 24 is an illustration of the preparation of a patient for use of a suction tool of the present invention introduced through the sleeve lumen of a percutaneously placed tubular access sleeve.
Figure 25:
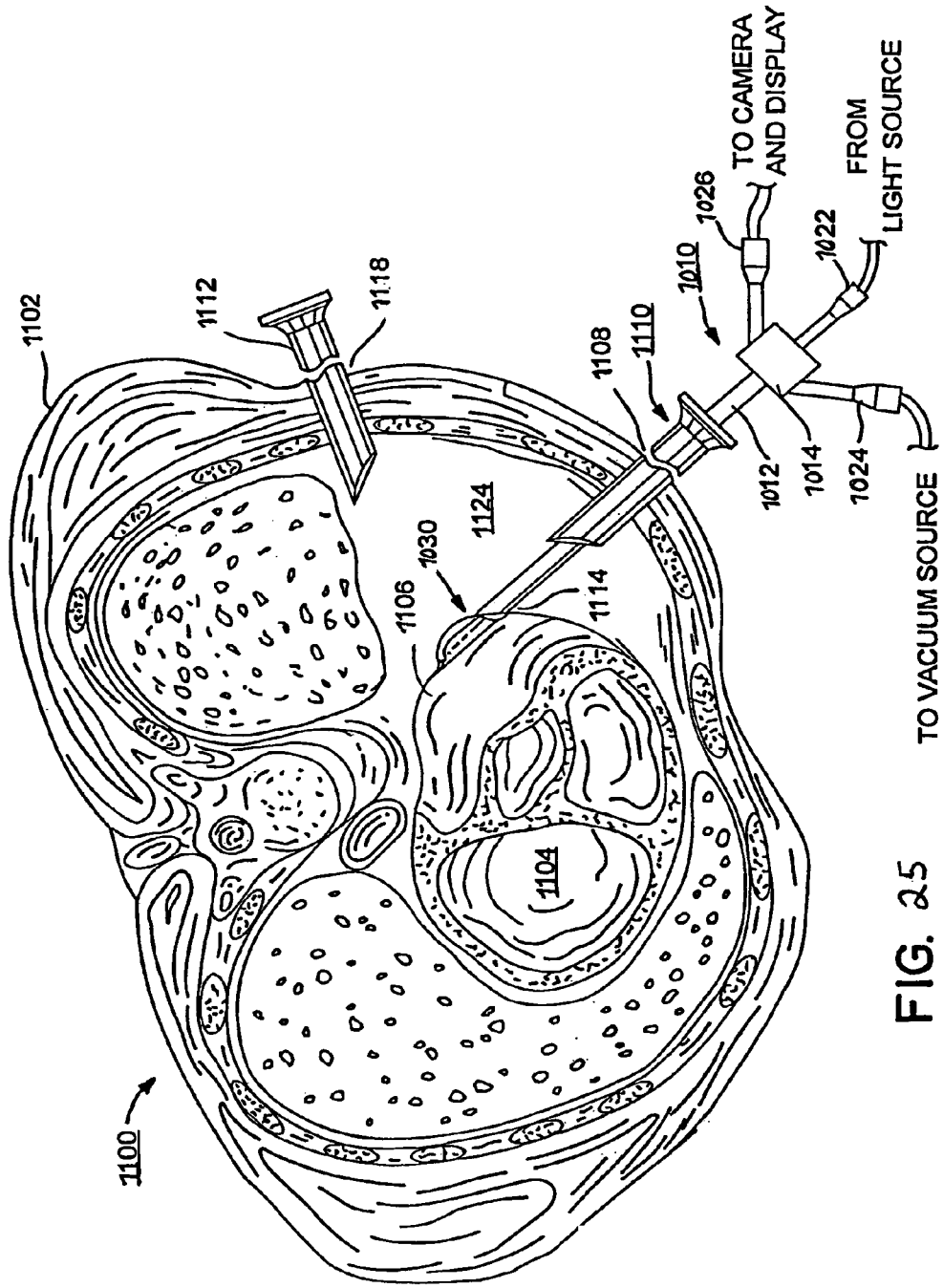
FIG. 25 is cross-section view of the patient's thorax depicting the advancement of the suction pad at the suction tool distal end against the heart.
Figure 26:
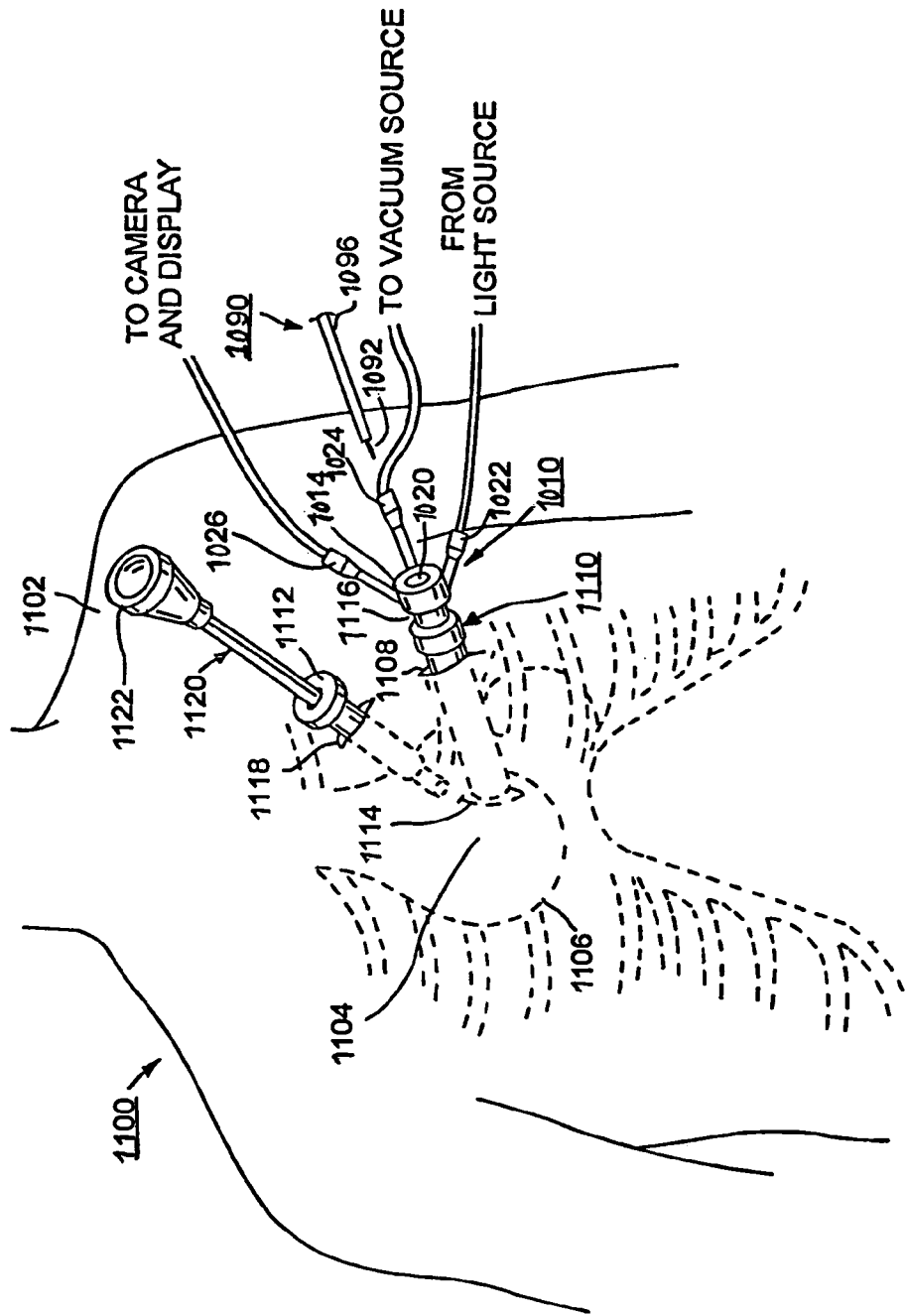
FIG. 26 is an illustration of the advancement of the suction tool within the sleeve lumen when the distal suction pad of the suction tool is advanced through an incision in the pericardium in preparation for advancement of a cell delivery device through the working lumen of the suction tool to enable the delivery of one or more biological agents and/or fluids into the myocardium.

FIGS. 24-26 illustrate the placement of instruments through the chest wall of a patient 1100 in one embodiment of the invention for observation and accessing the pericardial space through an incision in the pericardium 1106 exposing the pericardium of the heart 1104 to perform any of the ancillary procedures listed above. The patient 1100 is placed under general anesthesia, and the patient's left lung is deflated if necessary, using conventional techniques. The patient 1100 is placed in a lateral decubitus position on his right side, and small percutaneous incisions are to be made in the skin 1102 through the chest wall for the receipt of surgical instruments.

As used herein, the term "percutaneous" refers to any penetration through the skin of the patient, whether in the form of a small cut, incision, hole, cannula, tubular access sleeve or port or the like. A percutaneous penetration may be made in an interstitial space between the ribs of the patient 1100 or it may be made else where.

In one embodiment of the present invention, first and second passages 1108 and 1118 are made through the skin 1102 into the thoracic cavity. The passages 1108 and 1118 may be formed employing one-piece rods or trocars of prescribed diameters and lengths that are advanced through body tissue to form the passage and then removed so that other instruments can be advanced through the passage. The passage may also be formed employing two piece trocars that comprise a tubular outer sleeve, sometimes referred to as a port or cannula or at times as the tubular access sleeve itself, having a sleeve access lumen extending between lumen end openings at the sleeve proximal end and sleeve distal end, and an inner puncture core or rod that fits within the sleeve access lumen. The inner puncture rod typically has a tissue penetrating distal end that extends distally from the sleeve distal end when the inner puncture rod is fitted into the sleeve access lumen for use. The two-piece trocar can be assembled and advanced as a unit through body tissue, and the inner puncture rod then removed leaving the tubular access sleeve in place to maintain a fixed diameter passage through the tissue for use by other instruments.

In one of these ways, a tubular access sleeve 1110 is placed through first passage 1108 that is made as described above in the chest wall of patient 1100 between the patient's 2nd rib and 6th rib, for example. The selection of the exact location of the first passage 1108 is dependent upon a patient's particular anatomy. A further conventional tubular access sleeve 1112 is shown left in place in a second passage 1118 that is made as described above in the chest wall of patient 1100.

In one embodiment of the present invention, the patient's left lung is deflated to allow unobstructed observation of the pericardium 1106 employing a thoracoscope 1120 or other imaging device inserted through a sleeve lumen of tubular access sleeve 1112. The thoracoscope or other imaging device may have its own light source for illuminating the surgical field. Deflation of the patient's lung may be accomplished by use of a double lumen endotracheal tube that is inserted into the trachea, and independent ventilation of the right, left or both lungs can be selected. The left lung will collapse for visualization of the structures of the left hemisternum when ventilation of the left lung is halted and the left thoracic negative pressure is relieved through a lumen of the tubular access sleeve 1112 or a further access sleeve to atmospheric pressure. After deflation, the thoracic cavity may be suffused with a gas, e.g., carbon dioxide, introduced through a lumen of the tubular access sleeve 1112 or the further access sleeve to pressurize the cavity to keep it open and sterile. The pressurized gas keeps the deflated lung away from the left heart so that the left heart can be viewed and accessed and provides a working space for the manipulation of the tools of the present invention. It will be understood that the access sleeve lumens must be sealed with seals about instruments introduced through the lumens if pressurization is to be maintained.

A thoracoscope 1120 can then inserted into the lumen of the tubular access sleeve 1112 to permit wide angle observation of the thoracic cavity by a surgeon directly through an eyepiece 1122 or indirectly through incorporation of a miniaturized image capture device, e.g., a digital camera, at the distal end of the thoracoscope 1120 or optically coupled to the eyepiece 1122 that is in turn coupled to an external video monitor (not shown). The thoracoscope 1120 also incorporates a light source for illuminating the cavity with visible light so that the epicardial surface can be seen directly or indirectly. The depicted thoracoscope 1120 is used to directly visualize the thoracic cavity and obtain a left lateral view of the pericardial sac or pericardium 1106 over the heart 1104.

The elongated access sleeve 1110 provides an access sleeve lumen 1116 enabling introduction of suction tool 1010 to dispose the suction member or pad 1030 within the thoracic cavity. The tubular access sleeve 1110 and tool 1010 of the present invention are employed to access the pericardium 1106 and to grip its surface to tension it so that an incision can be made through the pericardium 1106. The accessed pericardial space 1124 and epicardium 1106 surrounding the heart 1104 are shown more specifically in the cross-section view of FIG. 25. A cutting instrument 1080, e.g., a knife, a needle, a stiff guidewire tip, an electrosurgical cutting tool, surgical scissors, or other piercing or cutting instrument 1080 is depicted in FIG. 24 poised to be inserted through the suction tool working lumen 1020 to perforate a bleb of pericardium 1106 within the suction cavity of the suction pad 1030 and then form a pericardial incision 1114 through the pericardial bleb exposing the pericardial space and exterior surface of the epicardium of the heart 1104. Exemplary cutting blades that can be employed in cutting instrument 1080 are disclosed herein.

The suction pad or member 1030, which includes a number of vacuum suction pods, is advanced through the incision formed through the pericardium and against the epicardium. In one use of the suction tool of the present invention, a myocardial bleb is formed by the applied suction so that one or more fluid and/or cell delivery needles may be advanced into the myocardium. An exemplary cell delivery tool 1090 having one or more distal cell delivery needles 1092 is depicted in FIG. 26 poised to be advanced through the working lumen 1020. The cell delivery tool can take any of the forms described herein. For example, the cell delivery tool or device may comprise one or more needles and a syringe. The tool body 1096 is sized and shaped to fit through the working lumen 1020. The one or more needles 1092 can comprise any of the needles described herein.

Figure 27:
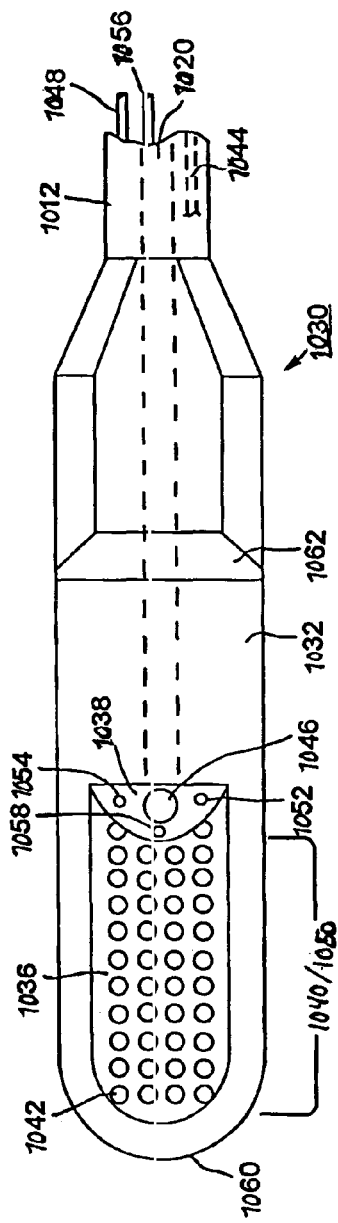
FIG. 27 is a plan view of the distal suction pad of a suction tool of the present invention.
Figure 28:
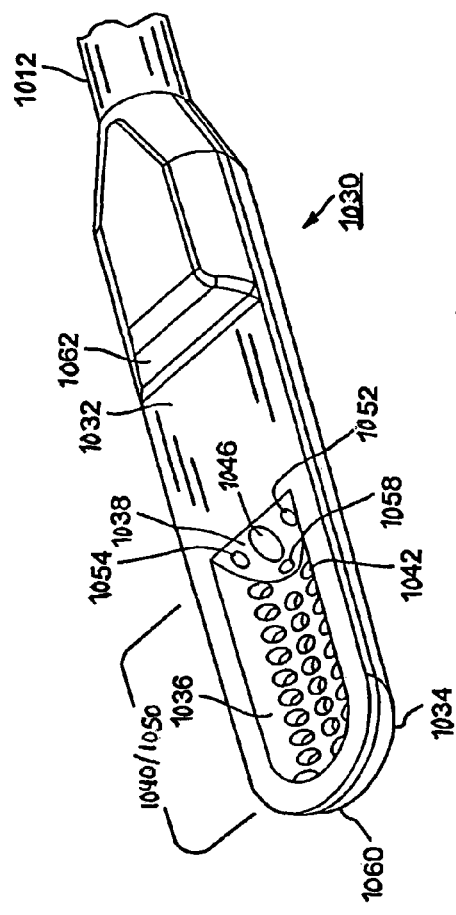
FIG. 28 is a perspective view of the distal suction pad of a suction tool of the present invention.

The suction tool 1010 may comprise a suction tool body 1012 extending between a proximal suction tool port assembly 1014 and a suction member 1030 depicted in greater detail in FIGS. 27 and 28. The suction tool body 1012 and the distal pad 1030 are sized to be inserted through an incision or the access sleeve lumen 1116 so that the suction member 1030 can first be introduced into the thoracic cavity and applied against the epicardium, then advanced through an incision made in the epicardium, and then applied against the myocardium.

In one embodiment of the present invention, the suction tool proximal assembly 1014 may comprise the proximal end opening of the suction tool working lumen 1020, an optical or electrical illumination connector 1022, a vacuum side port 1024, and an optical or electrical imaging connector 1026.

The vacuum side port 1024 may be adapted to be attached to a vacuum source at the surgical site to draw suction through one or more vacuum lumen extending through the suction tool proximal end assembly 1014, the suction tool body 1012 and then through a plurality of suction ports 1042 of suction port array 1040 depicted in FIGS. 27 and 28.

In accordance with one aspect of the present invention, the tissue sites, i.e., the pericardium, pericardial space and myocardium in this instance, adjacent to the suction pad are optionally illuminated and imaged through the suction tool 1010. The illumination of the sites can be accomplished by one or more miniaturized light emitters incorporated into the suction pad 1030 coupled to conductors extending through the tool body 1012 to an electrical illumination connector 1022 that is coupled to an external battery pack or the like. However, for safety, economic, and space reasons, it is preferred that light be conducted from an external light source to the suction pad 1030. As shown, suction tool 1010 may incorporate an optical illumination connector 1022 including one or more fiber-optic light pipes extending to one or more light emitting lens elements and/or light pipe ends, e.g., light pipe ends 1052 and 1054 depicted in FIGS. 27 and 28. The light pipe ends 1052 and 1054 can be polished or surface treated to enhance dispersion of light and light brightness.

The illuminated tissue site could be imaged by incorporating a miniaturized video camera digital imaging array and lens in the suction pad 1030 and powering the array and conducing image pixel data through conductors extending to an electrical imaging connector 1026 to be coupled to external video imaging and display apparatus. However, for safety, economic, and space reasons, it is preferred that an image of the illuminated site be optically conveyed from an external light source to the suction pad 1030. Again, it will be understood that the suction tool 1010 incorporates an optical imaging connector 1026 coupled with a fiber-optic light pipe extending to an imaging lens element or pipe end 1038 depicted in FIGS. 27 and 28. The light pipe end 1058 can be polished or shaped to function as a lens.

One preferred configuration of the non-conductive suction pad 1030 is depicted in FIGS. 27 and 28. The suction pad 1030 features a flat lower wall 1032, a convex upper wall 1034, a concave suction pad wall 1036 extending into the flat wall 1032 toward the convex upper wall 1034 and a proximal cavity wall 1038, whereby a suction cavity 1050 is created that a bleb of tissue can be drawn into. A suction port array 1040 comprises a plurality of suction ports 1042 through the concave suction pad wall 1036 from an interior manifold coupled with a suction lumen 1044 extending the length of the tool body 1012 to the suction side port 1024. The orientation of the suction cavity 1050 to the axis of the tool body 1012 allows the suction cavity to be advanced tangentially to the surface of the tissue that is approached to be drawn into the suction cavity 1050 as a tissue bleb.

The working lumen 1020 extends through the tool body 1012 and a proximal portion of the suction pad 1030 to a working lumen port 1046 in the proximal cavity wall 1038 defining the suction cavity 1050. Therefore, the various instruments such as cutting instrument 1080 and cell delivery needles 1092 referred to herein can be advanced tangentially into the tissue bleb.

It should be noted that the working lumen 1020 may also be the suction lumen 1044 in suction tools specifically designed to introduce medical instruments and devices, rather than fluids or materials, through the combined lumen. Suction would then be applied to the tissue bleb through the working lumen port 1046 as well as the array of suction ports.

Optionally, an illumination light pipe 1048 extends from the optical illumination connector 1022 through the length of the tool body 1012 and branches within the proximal portion of the suction pad 1030 to a pair of illumination light pipe ends 1052 and 1054 in proximal suction pad wall 1038. Similarly, optionally, an imaging light pipe 1056 extends from the optical imaging connector 1026 through the length of the tool body 1012 and the proximal portion of the suction pad 1030 to an imaging light pipe end 1058 in proximal cavity wall 1038. Therefore, the area within the concave suction wall 1036 and distal to the suction pad distal end 1062 can be illuminated and imaged remotely. It should be noted that the light pipes 1048 and 1056 can be extended past the suction cavity 1050 to terminate with the light pipe ends 1052, 1054 and 1058 arrayed near the suction pad distal end 1060. Or, the light pipes can extend simply to the more proximal suction pad wall 1062 and terminate with the light pipe ends 1052, 1054 and 1058 arrayed in the more proximal suction pad wall 1062.

In use, the suction pad 1030 is laterally extended out of the suction tool lumen 1020 so that a tangential approach can be made to the tissue, such as the pericardium 1106 as shown in FIG. 25. The area is optionally illuminated and imaged, as described above or by alternative techniques (e.g. separate illumination and imaging devices), and suction is applied to draw a pericardial bleb 1136 into the suction cavity 1050 as shown in FIG. 29. The pericardial space 1138 can then be tented away from the heart 1104.

In FIG. 30, the cutting instrument 1080 is advanced through the working lumen 1020 and the blade 1084 is advanced out of the working lumen port 1046 through a pericardial perforation and along the pericardium 1106 to form the pericardial incision 1114. The length of the pericardial incision 1114 generally corresponds to the length of the suction cavity 1050. The pericardial incision therefore has a perimeter that is larger than the perimeter of the cross section of the suction pad 1030, enabling the suction pad to be advanced through the pericardial incision 1114.

Advantageously, there is no suction applied through the suction tool working lumen 1020 that is necessary to maintain the attachment of the pericardium 1106 while it is being cut to form the pericardial incision 1114 to reach the pericardial space 1138. Due to their redundancy, the plurality of suction ports 1042 of the suction pads 1030 provide more robust fixation to the pericardium 1106 (or other outer tissue layer) than a single large area suction port. At least some of the suction ports 1042 readily engage the pericardial surface under low suction force to maintain the pericardial bleb 1136 and enable lifting of the pericardium 1106 or tracking movement of the pericardium 1106. Engagement of the surface of the pericardium 1106 by all of the suction ports 1042 is not necessary. Similarly, the loss of engagement of some of suction ports 1042 with the surface areas of the pericardium 1106 does not result in complete loss of engagement as is the case when an edge of a single large suction port releases from a tissue surface of an outer tissue layer or the pericardium.

Furthermore, the suction tool 1010 is versatile in that it can be used to simply access the pericardial space 1138. Various instruments, medical devices, drugs or materials can be advanced through the working lumen 1020, out of the working lumen port 1046, through the pericardial incision 1114, and into the pericardial space 1138 for temporary treatment of the heart 1104 or pericardial space 1138 or to complete a surgical procedure or for permanent implantation of medical devices against the epicardium 1140 or within the pericardial space or within the myocardium 1142 or within a coronary vein or artery.

Figure 31:
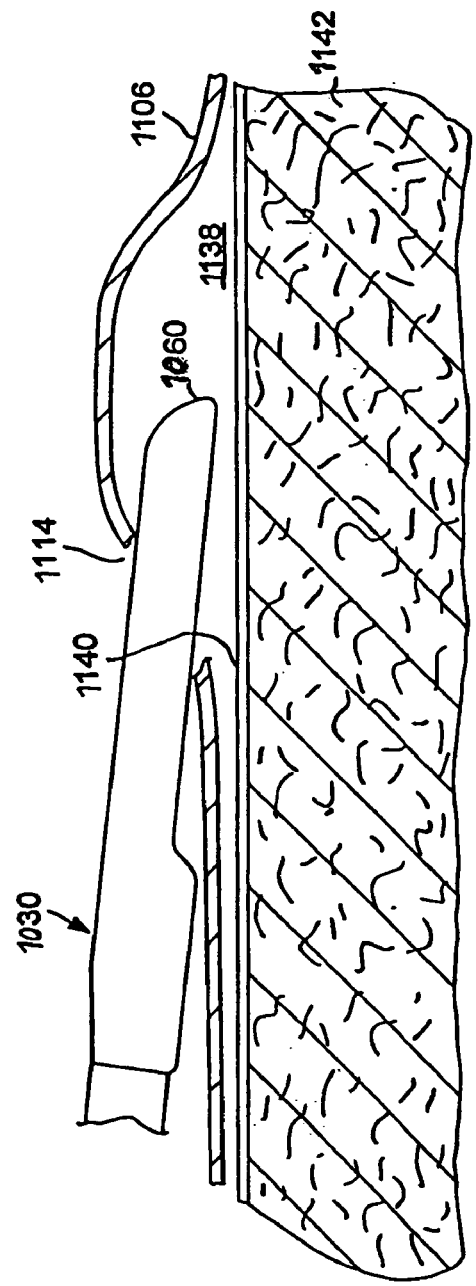
FIG. 31 is a schematic illustration of the advancement of the suction tool through the incision made through the pericardium.
Figure 32:
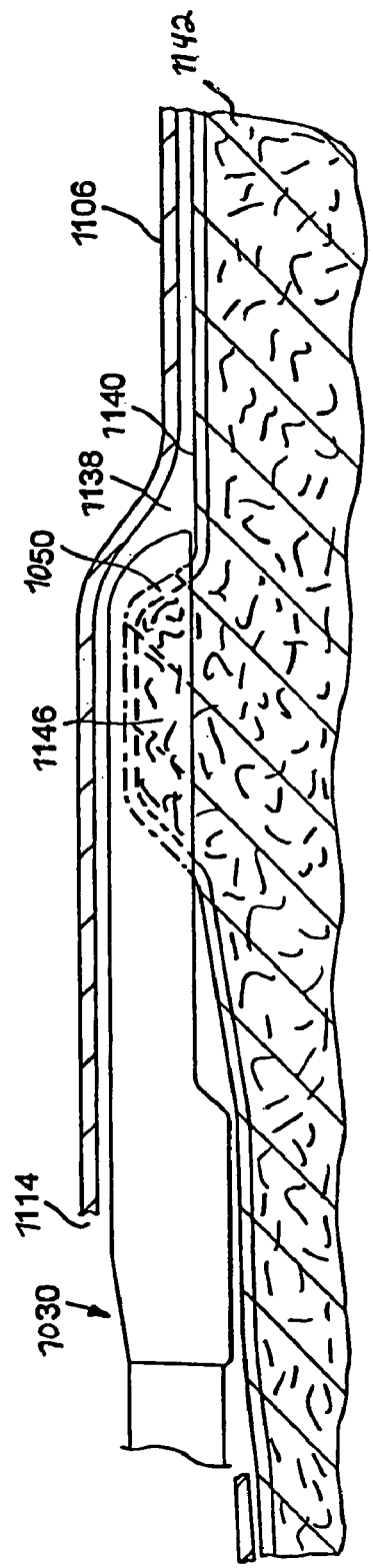
FIG. 32 is a schematic illustration of the application of suction through the suction ports of the suction pad against the epicardium to form a myocardial bleb.
Figure 33:
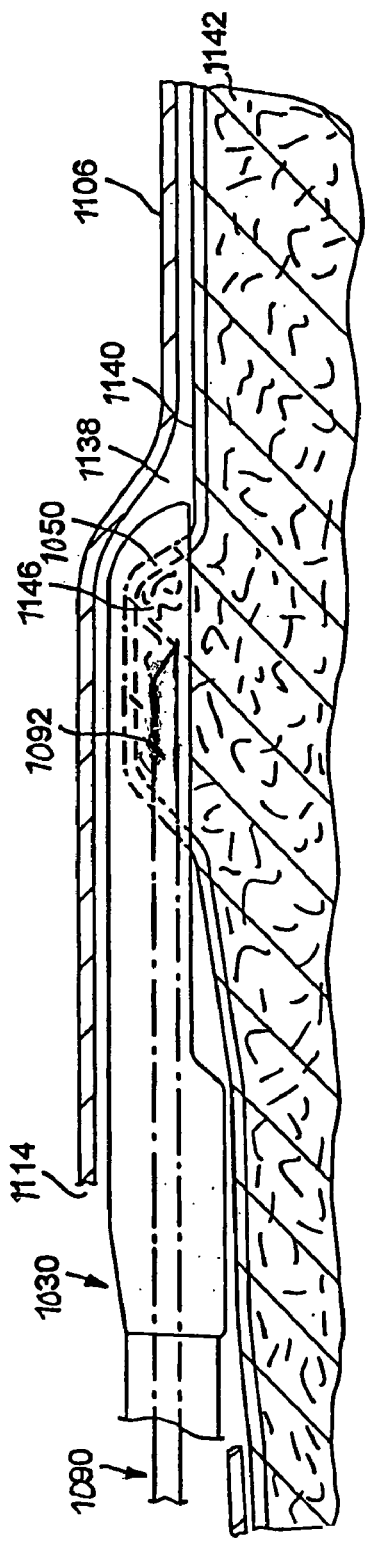
FIG. 33 is a schematic illustration of the advancement of one or more cell delivery needles of a cell delivery device through the working lumen of the suction tool and into the myocardium.

In one embodiment of the current invention, suction tool 1010 may be used to delivery one or more biological agents such as fluids and/or cells to the heart as illustrated in FIGS. 31-33. The cutting instrument 1080 is withdrawn from the working lumen 1020, and the pericardial bleb 1136 is released from the suction cavity 1050. The suction tool 1010 is manipulated to insert the suction pad distal end 1060 through a pericardial incision 1114 as shown in FIG. 31. The suction pad 1030 is inserted through the pericardial incision 1114 and advanced into the pericardial space 1138 with the suction cavity 1050 facing the epicardium 1140. Suction is then restored through the suction ports 1042, and a myocardial bleb 1146 is drawn into the suction cavity 50 as shown in FIG. 32.

The cell delivery tool 1090 is then advanced through the working lumen 1020 to dispose the one or more needles 1092 at the working lumen port into the suction cavity 1050. The one or more needles 1092 are then injected into and through the epicardium 1140 and into the myocardial bleb 1146. One or more biological agents may then be delivered into the myocardium. Following delivery, the suction tool 1010 may be withdrawn and the process of FIGS. 31-33 may be repeated until an acceptable amount of biological agents have been delivered into the myocardium.

In accordance with a still further aspect of the invention, the suction tool 1010 is equipped with a steering mechanism that the surgeon can manipulate at the suction tool proximal end assembly 1014 to steer the suction pad 1030 to a desired tissue site, e.g., a site of the pericardium or the epicardium illustrated in FIGS. 29-33. Such a capability is schematically depicted in FIG. 34. A deflection mechanism 1070 can be incorporated into the suction tool body 1012 that the user can manipulate to induce a bend in a distal segment 1072 of suction tool body 1012 to deflect the suction pad 1030 from position "A" to position "B", for example, generally defining a range of motion in a single plane. The deflection mechanism 1070 can be manipulated to steer the suction pad 1030 to a particular pericardial or epicardial site and to orient the suction cavity 1050 to the pericardium or epicardium to form a respective pericardial or myocardial bleb.

The deflection mechanism can take any of the forms known in the medical device art. A commonly employed approach to providing controllable deflection of the distal end segments of catheters, guidewires, and stylets employs a generally straight outer sheath or tube and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 4,815,478, 4,898,577, 4,940,062, 5,545,200 and 6,251,092. U.S. Pat. Nos. 4,815,478 and 4,940,062 disclose the use of push-pull wires extending through guidewire lumens for deflecting a guidewire distal end by manipulating a handle at the guidewire proximal end.

Thus, deflection mechanism 1070 can comprise a proximal handle at the suction tool proximal end assembly 1014 coupled to a pair of pull wires extending from handle controls to opposite sides of the suction pad 1030 to selectively induce bends in distal segment 1072 to move the suction pad between positions "A" and "B" and intermediate positions therebetween.

In accordance with a further aspect of the invention, the suction pad distal end 1060 is shaped to facilitate advancement of the suction pad through the tissue incision to facilitate advancement of the suction pad 1030 through and widening of the pericardial incision 1114 as depicted in FIG. 31. For example, shaped suction pad distal ends 1060', 1060", and 1060''' of respective suction pads 1030', 1030", 1030''' are depicted in FIGS. 35A-35B, 36A-36B, and 37A-37B, respectively. The depicted "shovel" or "snout" shapes of suction pad distal ends 1060', 1060", and 1060''' generally are shaped to provide a leading end or "leader" 1074', 1074", 1074''' that can be easily inserted into the tissue incision, particularly the pericardial incision 1114, followed by a "dilator" 1076', 1076", 1076''' to widen the pericardial incision 1114 as the respective suction pad 1030', 1030", 1030''' is inserted through it. The leader 1074' is a rounded tip, the leader 1074" is a pointed tip, and the leader 1074''' is ball-tip.

Figure 40:
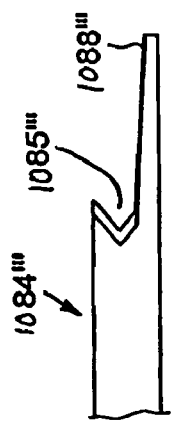
FIG. 40 is a schematic illustration of a still further shape of a cutting instrument blade of the cutting instrument advanced through the working lumen to form the incision through the pericardium as depicted in FIG. 30.
Figure 39:
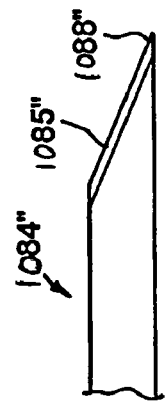
FIG. 39 is a schematic illustration of a further shape of a cutting instrument blade of the cutting instrument advanced through the working lumen to form the incision through the pericardium as depicted in FIG. 30.
Figure 38:
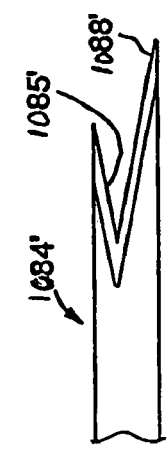
FIG. 38 is a schematic illustration of one shape of a cutting instrument blade of the cutting instrument advanced through the working lumen to form the incision through the pericardium as depicted in FIG. 30.

Returning to the cutting instrument, cutting blade 1084 of FIGS. 24 and 30 can be shaped in a variety of ways, e.g., the exemplary blades 1084', 1084" and 1084''' depicted in FIGS. 38-40 to facilitate making the tissue incision, particularly the pericardial incision 1114 through the pericardium 1106. Generally, like cutting blade 1084, the cutting blades 1084' and 1084" incorporate a sharpened perforation tip 1088' and 1088" and trailing cutting blade edges 1085' and 1085". The cutting blade 1084''' incorporates a blunt leading tip 1088'''. Trailing cutting blade edges 1085', 1085" and 1085''' make the tissue incision, through the tissue layer held against the convex upper wall 1036 by suction. In this way, the pericardial incision 1114 can be made through the pericardial bleb 1136 maintained by suction in the suction cavity 1050 as depicted in FIG. 30.

The cutting blade 1084' of FIG. 38 comprises the sharpened perforation tip 1088' and "V" shaped blade edge 1085'. The pericardium 1106 is punctured by the sharpened perforation tip 1088' and is slitted as it is trapped in the "V" shaped blade edge 1085' while the cutting blade 1084' is advanced through the elongated suction cavity 1050.

The cutting blade 1084" of FIG. 39 comprises a sharpened leading blade point 1085" and the elongated blade edge 1085" that is inverted from the blade edge orientation shown in cutting blade 1084. The cutting blade 1084" is advanced through the tissue, e.g., the pericardium 1106 to make a relatively limited tissue incision, e.g., a limited size pericardial incision 1114.

The cutting blade 1084''' of FIG. 40 can be used after such a limited tissue incision is made by use of a cutting instrument having a cutting blade 1084" of FIG. 39. The cutting blade 1084''' comprises the blunt leading blade point 1085''' and the trailing "V" shaped blade edge 1085'''. The blunt leading blade point 1085''' is advanced through the pericardial incision 1114, and the pericardium is slitted as it is trapped in the "V" shaped blade edge 1085''' while the cutting blade 1084''' is advanced through the elongated suction cavity 1050.

The suction tool 1010 as described above can be further modified to facilitate making and increasing the length of such tissue incisions, e.g. pericardial incision 1114, and to facilitate implantation of cardiac leads into or through the myocardial bleb 1146. In particular, an elongated, tapered, suction pad distal end 1060'''' is depicted in the suction pad 1030'''' of FIGS. 41 and 42 enclosing a distally extending slot or recess 1047. The distally extending slot or recess 1047 is axially aligned with the working lumen 1020 and the working lumen port 1046 as shown in FIGS. 41 and 42. Thus, the cutting instrument 1080 can be pushed distally so as to advance the cutting blades 1084, 1084', 1084", 1084''' all the way across the tissue bleb, e.g., pericardial bleb 1136 of FIG. 30, to lodge the cutting blade distal tip 1088, 1088', 1088", and 1088''' within the recess 1047. Then, the cutting tool can be withdrawn, and the suction pad 1030'''' can be advanced into the pericardial space, steered to a desired site of the epicardium under visualization, and deployed against the epicardium, as described above. Suction can be applied to draw the myocardial bleb 1146 into the suction cavity 1050.

The suction tool 1010 can be further modified to incorporate a pair of elongated electrodes attached to the suction pad lower wall extending alongside the suction cavity 1050. In use, suction is applied to form the pericardial bleb 1136, and ablation current can be applied to the electrodes that would create the peridardial incision 1114. The electrodes can also be used when the suction pad 1030 is applied to the epicardium 1140 to conduct a mapping and threshold determination to locate infarct sites for implantation of cells.

The tubular access sleeve 1010 can be circular or oval or have any other desirable cross-section shape. The tubular access sleeve 1010 can be straight, curved or formed with a bend or formed of a bendable material to be shaped by the user.

The access to the pericardial space in accordance with the present invention facilitates the performance of a number of ancillary procedures. For example, the procedures include introducing and locating the distal end of a catheter or guidewire or an electrode of a cardiac ablation catheter or a pacing lead or a cardioversion/defibrillation lead within the pericardial space and attached to the epicardium or myocardium. Other possible procedures include performing a coronary artery anastomosis in a thoracoscopic CABG procedure, replacing a defective heart valve, ablating aberrant electrical pathways in the atria to alleviate atrial tachyarrhythmias, introducing cells, drugs or anti-bacterial agents into the pericardial space, relieving pericardial fluid pressure or providing cardiac resynchronization therapy. Other procedures that can be performed in the pericardial space, include fluid withdrawal, drug delivery, cell delivery, diagnostic and therapeutic electrophysiology procedures, transmyocardial revascularization, transmyocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like.

Figure 43:
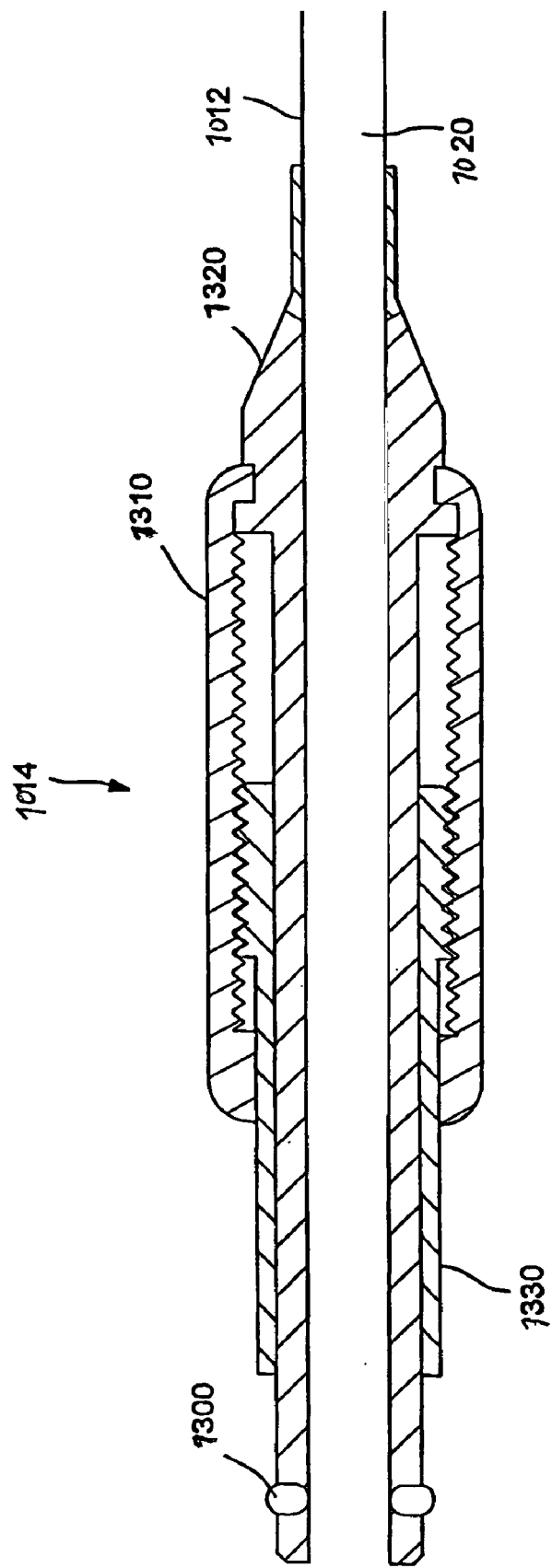
FIG. 43 is a schematic illustration of a portion of a suction tool.
Figure 44:
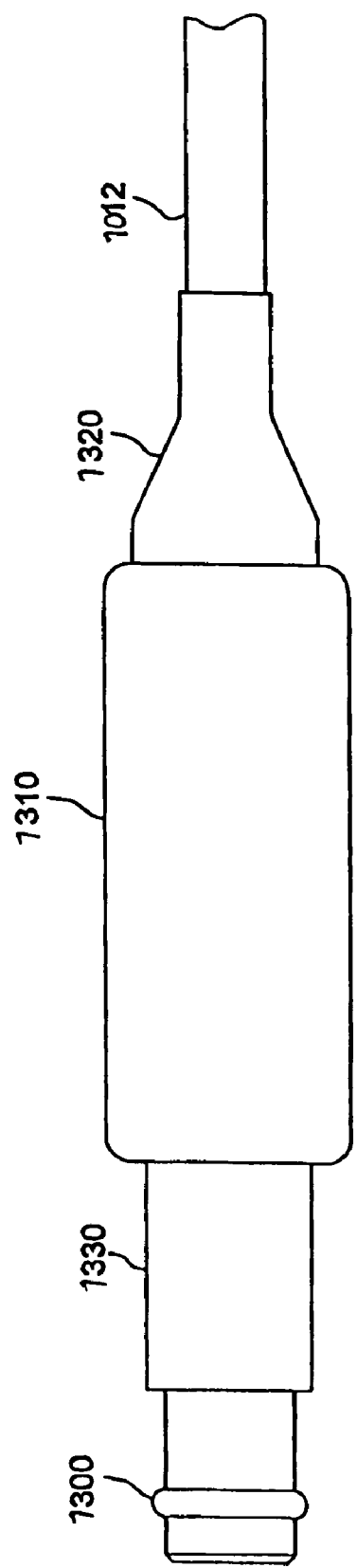
FIG. 44 is a schematic illustration of a portion of a suction tool.

Referring to FIGS. 43 and 44, one embodiment of suction tool 1010 includes an adjustable suction tool proximal end assembly 1014 mounted at the proximal end of suction tool body 1012. The suction tool proximal end assembly 1014 comprises the proximal end opening of the suction tool working lumen 1020, a vacuum seal O-ring 1300, a threaded collar 1310, a collar mounting component 1320, and a threaded tool stop 1330. Collar mounting component 1320 is rigidly coupled to suction tool body 1012 and is designed to hold collar 1310 in place while allowing collar 1310 to be rotated freely about suction tool body 1012. Rotation of collar 1310 causes tool stop 1330, a portion of which is threaded inside collar 1310, to move proximal or distal relative to suction tool body 1012. This adjustable "depth" control feature allows a surgeon to finely adjust the amount the distal end of a medical instrument or device, e.g., installation tool 1160, inserted into working lumen 1020, to advance out of the working lumen port 1046. For example, a surgeon can "dial in" a pre-selected amount the distal end of installation tool 1160 will protrude from working lumen port 1046. The surgeon can then remove and/or retract installation tool 1160 from port 1046. Suction tool 1010 may then be manipulated thereby positioning suction pad 1030 at a desired tissue site. Installation tool 1160 can then be advanced or inserted back into working lumen 1020 until handle 1210 of installation tool 1160 engages tool stop 1330 thereby pre-selecting the distance the distal end of installation tool 1160 protrudes from working lumen port 1046. This distance may be, for example, from about 0 to about 5 cm. This adjustable "depth" control feature can allow a surgeon to accommodate differences between patients. For example, a surgeon may change the depth based on a patient's heart wall thickness.

Figure 45:
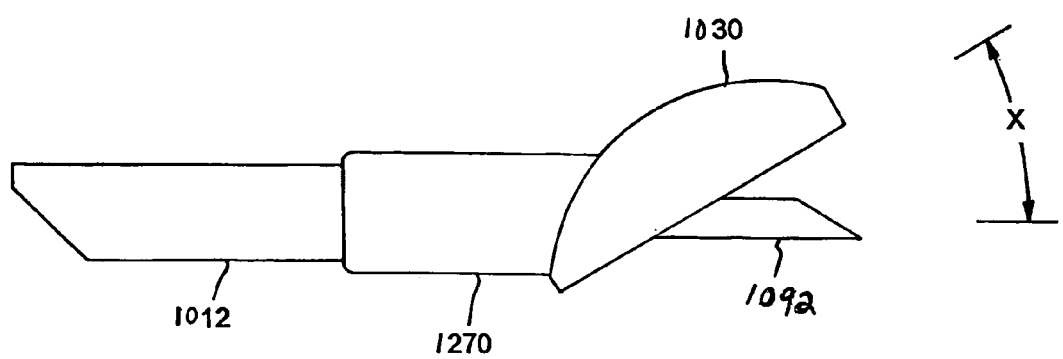
FIG. 45 is a schematic illustration of a portion of a suction tool.
Figure 46:
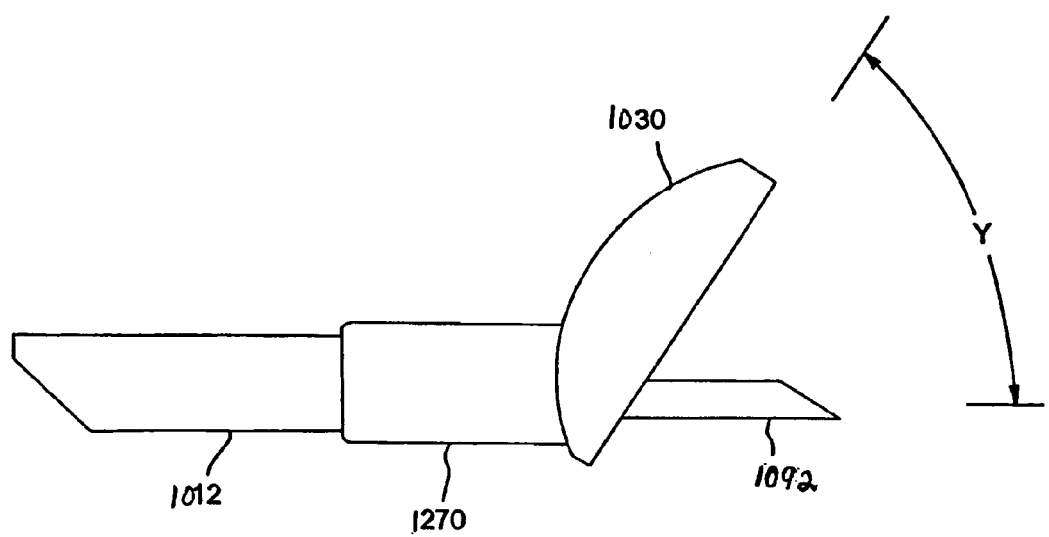
FIG. 46 is a schematic illustration of a portion of a suction tool.

Referring to FIGS. 45 and 46, suction tool 1010 may be equipped with a deflection mechanism 1270 that a surgeon can manipulate at the suction tool proximal end assembly 1014 to change the angle between suction pad 1030 and suction tool body 1012. A deflection mechanism 1270 may be incorporated into suction tool body 1012 or suction pad 1030. Deflection mechanism 1270 may be used to deflect suction pad 1030 from an angle "X" to an angle "Y", for example, generally defining a range of motion in a single plane. The deflection mechanism 1270 may be manipulated to change the angle of entry of a distal end of a tool advanced through working lumen 1020 of suction tool 1010 into tissue engaged by suction pad 1030. For example, the larger the angle, e.g., angle Y, between suction pad 1030 and suction tool body 1012, the more perpendicular the needles 1092 will penetrate tissue when advanced out of the working lumen port 1046, whereas the smaller the angle, e.g., angle X, between suction pad 1030 and suction tool body 1012, the more tangential the needles 1092 will penetrate tissue when advanced out of the working lumen port 1046. Therefore, deflection mechanism 1270 can allow a surgeon to select an appropriate angle of penetration of a tool advance out of working lumen port 1046 into tissue engaged by suction pad 1030.

The deflection mechanism 1270 can take any of the forms known in the medical device art. A commonly employed approach to providing controllable deflection of the distal end segments of catheters, guidewires, and stylets employs a generally straight outer sheath or tube and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 4,815,478, 4,898,577, 4,940,062, 5,545,200 and 6,251,092. U.S. Pat. Nos. 4,815,478 and 4,940,062 disclose the use of push-pull wires extending through guidewire lumens for deflecting a guidewire distal end by manipulating a handle at the guidewire proximal end. Thus, deflection mechanism 1270 can comprise a proximal handle at the suction tool proximal end assembly 14 coupled to a pair of pull wires extending from handle controls to suction pad 1030 to selectively move suction pad 1030 relative to working lumen 1020 of suction tool body 1012 between angle positions 0 degrees and 90 degrees and positions therebetween, e.g., "X" and "Y".

Deflection mechanism 1270 can allow suction tool 1010 to accommodate a variety of approach procedures including sternotomy, thoracotomy, and thoracoscopy procedures. For example, depending on the angle of approach the surgeon is taking relative to a targeted tissue site and depending on the particular procedure, e.g., lead delivery, ablation and/or cell delivery, the more or less angle the surgeon may want suction pad 1030 to be relative to working lumen 1020. It may be desirable to have a lead implanted tangentially to the surface of heart to reduce the strain at the surface of the heart on the lead. In the case of a cell delivery procedure, it may be more desirable to implant the cells more perpendicular to the surface of the tissue or organ thereby placing the cells more deeply into the targeted tissue.

An alternative embodiment of the present invention is to fix the angle between suction pad 1030 and working lumen 1020. In one embodiment, this angle is fixed at approximately 1030 degrees. In cases where the angle needs to be approximately 0 degrees, suction pad 1030 may be made to include a channel, slot or groove within the suction pad 1030 thereby allowing one or more needles to be directed out of suction pad 1030 at an angle greater than 0 degrees, for example 30 degrees relative to the surface of the heart.

Figure 47:
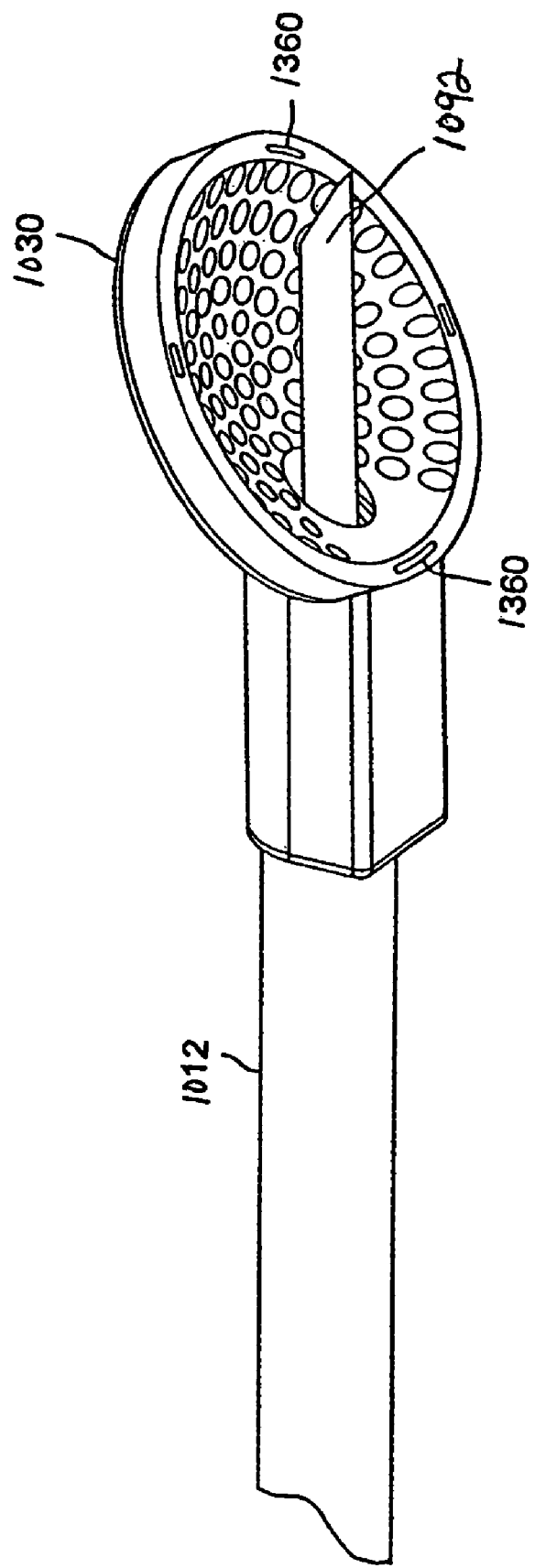
FIG. 47 is a schematic illustration of a portion of a suction tool and a portion of a cell delivery tool.

In one embodiment of the present invention, the device for injecting agents into tissue may incorporate one or more sensors for sensing or monitoring. For example, referring to FIG. 47, suction tool 1010 may be modified to incorporate one or more sensors 1360 for sensing or monitoring, e.g., temperature, vibration, voltage, amperage, wattage and/or impedance. A vibration sensor may be used to sense the vibration in tissue that occurs prior to a "steam pop." Water (from within and around the tissue) present at an ablation site may be heated to exceed 100° C., if this happens, the water will change phase, boil and may result in an audible "steam pop" within the tissue. This pop may damage and even rupture the tissue. Irrigation cooling of the site shifts the location of the "steam pop" even deeper within the tissue, resulting in even greater damage than a superficial pop. It has been observed that before a "steam pop", there is a mechanical vibration within the tissue (suspected to be caused by the phase transition of water, which may create microbubbles within the tissue).

Alternatively, the one or more sensors of suction tool 1010 may be any suitable blood gas sensor for measuring the concentration or saturation of a gas in the blood stream. For example, a sensor for measuring the concentration or saturation of oxygen or carbon dioxide in the blood and/or tissues may be employed.

Alternatively, the one or more sensors of suction tool 1010 may be any suitable sensor for measuring blood pressure or flow, for example a Doppler ultrasound sensor system, or a sensor for measuring hematocrit (HCT) levels.

Alternatively, the one or more sensors of suction tool 1010 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Alternatively, the one or more sensors of suction tool 1010 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

The one or more sensors of suction tool 1010 may be used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc.

The one or more sensors of suction tool 1010 may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors; vibration sensors, sound wave sensors; magnetic sensors; UV light sensors; visible light sensors; IR light sensors; radiation sensors; flow sensors; temperature sensors; or any other appropriate or suitable sensor. The one or more sensors of suction tool 1010 may be powered by any suitable power source. In addition, the one or more sensors of suction tool 1010 may be coupled to any appropriate output device, for example, a LCD or CRT monitor which receives and displays information regarding the one or more sensors.

A temperature sensor may incorporate one or more temperature-sensing elements such as, for example, thermocouples, thermisters, temperature-sensing liquid crystals, or temperature-sensing chemicals. A temperature sensor could be used, for example, to monitor tissue temperature generated by an ablation apparatus.

Ablation may be performed by heating the tissue to a suitable temperature. Alternatively, ablation may be performed by freezing the tissue to a suitable temperature. The change in tissue temperature may be sensed and/or monitored by one or more temperature sensors of suction tool 10. In one embodiment, the change in tissue temperature may be displayed on an output device. By software control, the user may choose to display the information in a number of ways. The output device may show the current temperature of each sensor. The output device may also lock and display the maximum temperature achieved at each sensor. The output device may also indicate when each sensor has reached an appropriate combination of temperature and time to ensure cell/tissue death.

The signals from one or more sensor may preferably be amplified by a suitable amplifier before reaching an output device. The amplifier may also be incorporated into an output device. Alternatively, the amplifier may be a separate device. The output device may incorporate one or more processors.

In one embodiment, a plurality of temperature sensors may be positioned around the perimeter of suction pad 1030. When sensed tissue reaches a certain temperature, the corresponding temperature sensor may send a signal. Preferably, the temperature sensor may send constant signals. For example, thermocouples may send a constant signal based on their voltage. As the temperature changes, the voltage of the thermocouples may change proportionately and the signal sent by the thermocouples may change proportionately.

Figure 48:
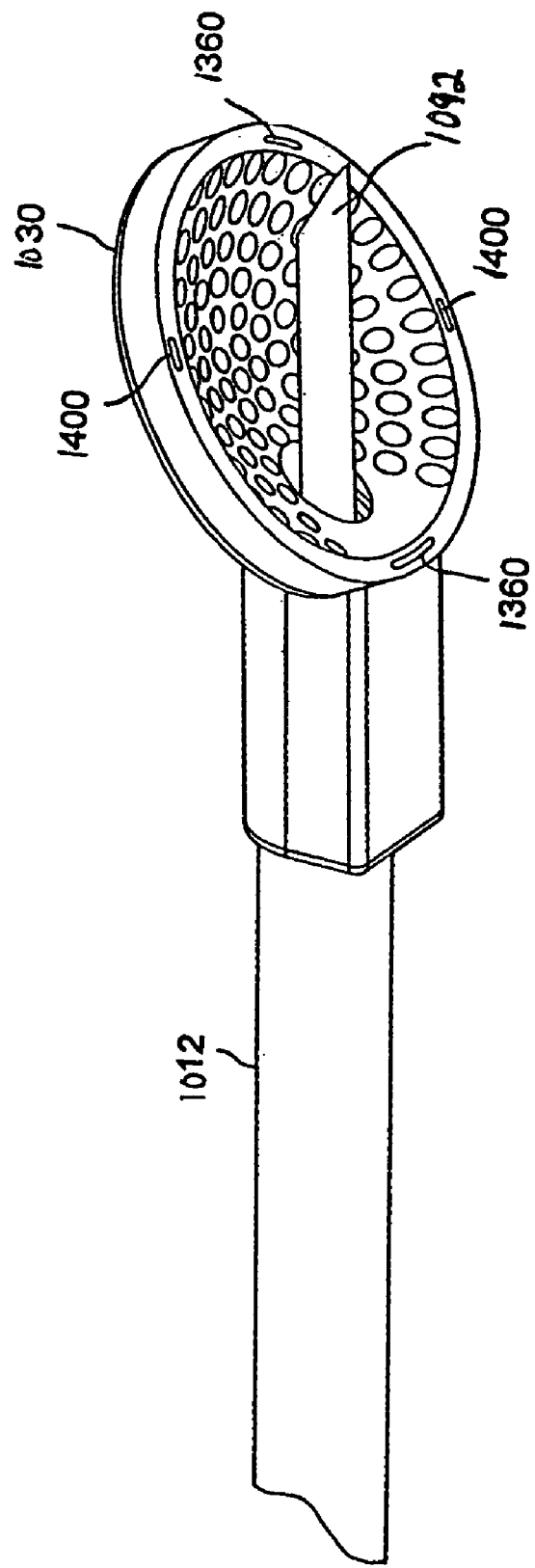
FIG. 48 is a schematic illustration of a portion of a suction tool and a portion of a cell delivery tool.
Figure 49:
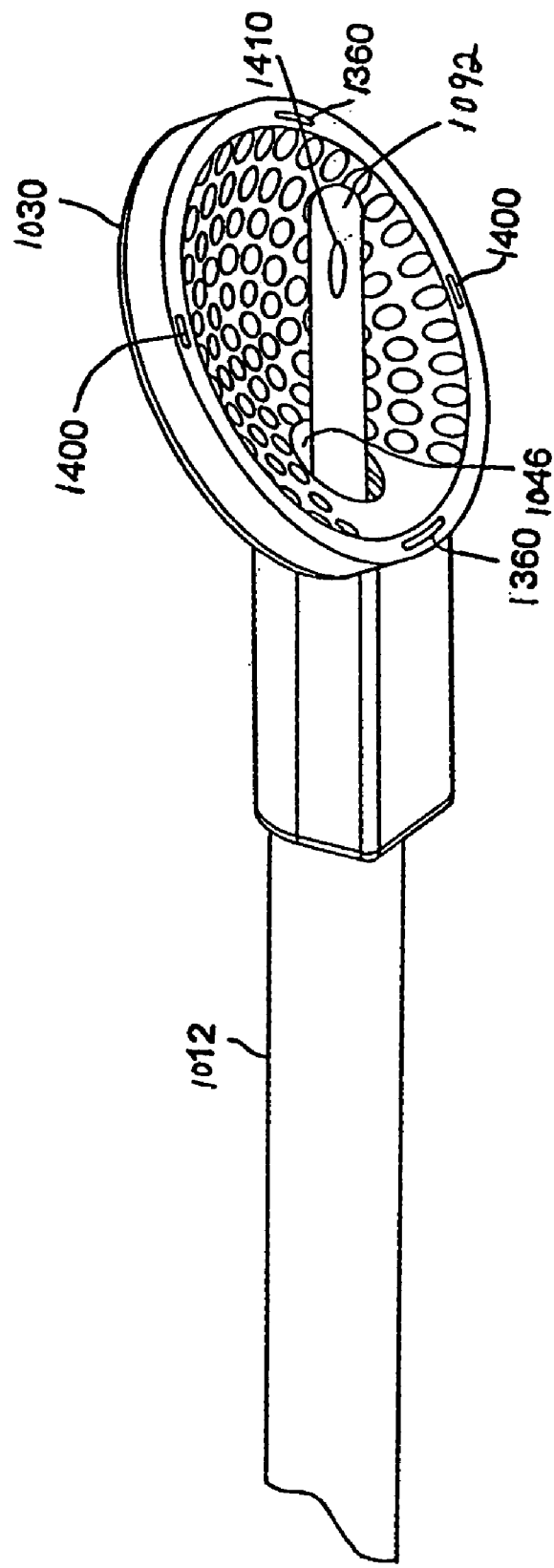
FIG. 49 is a schematic illustration of a portion of a suction tool and a portion of a cell delivery tool.

In one embodiment of the present invention, the device for injecting agents into tissue may comprise one or more energy transfer elements. For example, suction tool 1010 may comprise one or more energy transfer elements 1400 positioned on, along, within or adjacent a tissue contact surface of suction tool 1010 (see FIG. 48). Energy transfer elements may transfer tissue ablation energy to target tissue. For example, energy transfer elements may be conductive elements, which may supply RF energy, microwave energy or ultrasound energy to target tissue. Energy transfer elements may be, for example, laser elements for supplying laser light to target tissue or they may be cryo elements for cooling target tissue. Two or more energy transfer elements or conductive elements of suction tool 10 may be arranged in a biopolar arrangement, for example one element may be used as a positive electrode and one element may be used as a negative electrode. One or more energy transfer elements or conductive elements of suction tool 1010 may be arranged in a monopolar arrangement, for example, one element may be used as one electrode and an indifferent element or electrode is placed elsewhere on the patient's body such as the back, thigh or shoulder or another site other than the suction tool site. Alternatively, one or more energy transfer elements, e.g., an electrode, of suction tool 1010 may be used in combination with one or more needles 1092 advanced through working lumen 1020 and out working lumen port 1046 (see FIG. 49). Needles 1092 may comprise one or more holes 1410 located along the length of needles 1092 for delivering one or more biological agents and/or fluids. In one embodiment, needles 1092 may be used as energy transfer elements. Suction tool 1010 may include an indifferent (or non-ablating) electrode which may serve as the return plate for energy one or more energy transfer elements 1400. In one embodiment, an ablation tool may be advances through working lumen 1020 and out working lumen port 1046. Suitable ablation tools may include, for example, a catheter, an electrocautery device, an electrosurgical device or an ablation wire having one or more energy transfer elements. Ablation tool and its components are preferably made of a biocompatible material such as stainless steel, biocompatible epoxy or biocompatible plastic.

Energy transfer elements or conductive elements may comprise one or more conductive materials or blends including titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, conductive polymers or plastics, or conductive ceramics. Energy transfer elements or conductive elements may not be conductive but may serve as a conduit to deliver a conductive material such as a conductive fluid. Energy transfer elements or conductive elements may be porous. For example, energy transfer elements or conductive elements may comprise porous polymers, metals, or ceramics. Energy transfer elements or conductive elements may be coated with non-stick coatings such as PTFE or other types of coatings as discussed herein. Energy transfer elements or conductive elements may be flexible thereby allowing them to conform to the surface of target tissue. Energy transfer elements or conductive elements may be malleable thereby allowing a surgeon to shape them to conform to the surface of target tissue.

Energy transfer elements or conductive elements may comprise one or more metal conductors such as windings inside a polymer or a conductive mesh material. The energy transfer elements or conductive elements may comprise tubes for delivering fluids. The tubes may comprise holes or slots. A polymer tube may be placed inside a metal tube to control fluid deliver through energy transfer elements or conductive elements. One or more of the energy transfer elements or conductive elements may be used as stimulation electrodes, for example, nerve stimulation electrodes or cardiac stimulation electrodes.

Energy transfer elements or conductive elements may comprise needles designed to penetrate tissues such as fat and muscle. For example, energy transfer elements or conductive elements may be designed to penetrate fat on the heart thereby allowing the energy transfer elements or conductive elements to reach cardiac tissue. The needles may allow fluids such as conductive fluids, tissue ablation chemicals, drugs, and/or cells to pass through.

Figure 50:
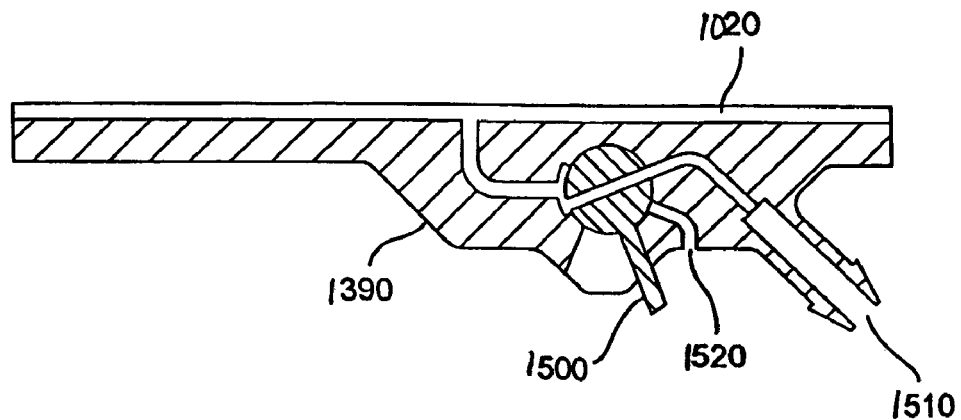
FIG. 50 is a schematic illustration of a portion of a suction tool.
Figure 51:
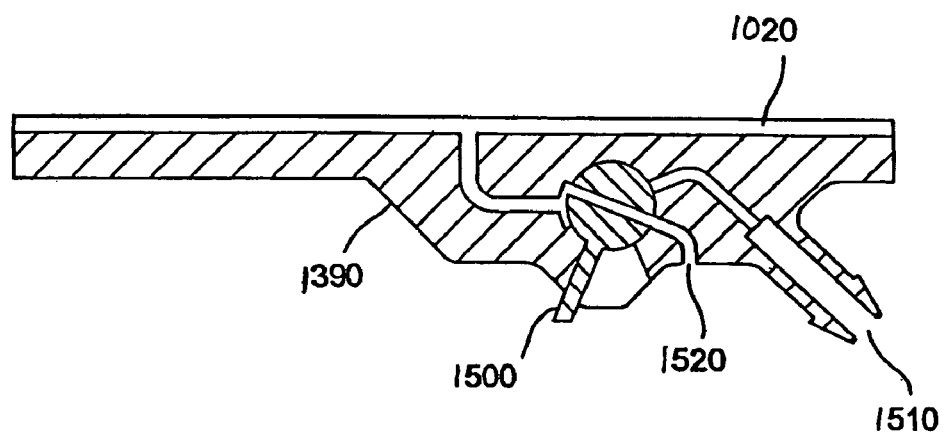
FIG. 51 is a schematic illustration of a portion of a suction tool.

In one embodiment of the present invention, the device for injecting agents into tissue may comprise one or more surgeon-controlled switches and/or valves. For example, a switch or valve may be incorporated in or on suction tool 1010 or any other location easily and quickly accessed by the surgeon for regulation of suction device 1010 by the surgeon. The switch or valve may be, for example, a hand switch or valve, a foot switch or valve, or a voice-activated switch or valve comprising voice-recognition technologies. For example, a vacuum valve may be incorporated into a proximal handle 1390 at the suction tool proximal end assembly 1014 for controlling the application of suction to suction pad 1030 (see FIGS. 50 and 51). As shown in FIG. 50, valve 1500 may be manipulated by a surgeon to provide suction from suction port 1510 thereby providing suction to working lumen 1020 of suction tool 1010. Alternatively, suction may be provided to suction lumen 1044 of suction tool 1010. As shown in FIG. 51, valve 1500 may be manipulated by a surgeon to release suction from suction pad 1030 and working lumen 1020 and/or suction lumen 1044 by venting to vent port 1520. In one embodiment of suction tool 1010, a switch for controlling the delivery of energy, e.g., from an RF generator, to one or more energy transfer elements may be incorporated into suction tool proximal end assembly 1014. In one embodiment of suction tool 1010, a switch for controlling one or more sensors may be incorporated into suction tool proximal end assembly 1014. A visual and/or audible signal used to alert a surgeon to the completion or resumption of a medical procedure, for example, an ablation procedure, may be incorporated into suction tool 1010. For example, a beeping tone or flashing light that increases in frequency as the medical procedure, e.g., an ablation procedure or cell delivery procedure, ends or begins may be used.

During a tissue ablation procedure, it is sometimes desirable to irrigate the ablation site with irrigation fluid, which may be, for example, any suitable fluid such as saline or another conductive fluid. The irrigating fluid may cool one or more energy transfer elements of suction tool 1010 and may allow for greater lesion depth. Furthermore, continuous fluid flow may keep the temperature below the threshold for blood coagulation, which may clog suction tool 1010 or an ablation device placed within suction tool 1010. Use of irrigating fluid may therefore reduce the need to remove a clogged ablation device for cleaning or replacement. The presence of an ionic fluid layer between an energy transfer element and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as lidocaine, $CA^{++}$ blockers, ionic contrast, or gene therapy agents may also be delivered before, with or after the delivery of the irrigating fluid. A standard fluid pump, for example, may be used to deliver fluids. The pump may be connected to central power source or may have its own source of power. Suction tool 1010 may include a means for delivering fluid to an ablation site from a fluid source. Such means may be, for example, fluid openings coupled to one or more fluid conduits or lumens.

A fluid source may be any suitable source of fluid. An fluid source may include a manual or electric pump, an infusion pump, a syringe pump, a syringe, a pressurized reservoir or bag, a squeeze bulb or other fluid moving means, device or system. For example, a pump may be connected to power source or it may have its own source of power. A fluid source may be powered by AC current, DC current, or it may be battery powered either by a disposable or re-chargeable battery. A fluid source may comprise one or more fluid regulators, e.g., to control fluid flow rate, valves, fluid reservoirs, conduits, lines, tubes and/or hoses. The conduits, lines, tubes, or hoses may be flexible or rigid. For example, a flexible line may be used to communicate fluid to suction tool 1010, thereby allowing suction tool 1010 to be easily manipulated by a surgeon. Fluid reservoirs, for example, may be an IV bag or bottle. It may be preferred that the fluid be sterile.

A fluid source may be incorporated into the device for injecting agents into tissue. For example, suction tool 1010 may include a fluid source thereby allowing the delivery of fluid or agents at a targeted site. A fluid source may be slaved to suction tool 1010, for example, to one or more sensors of suction tool 1010. A fluid source may be designed to automatically stop or start the delivery of fluid during a medical procedure. A fluid source and/or suction tool 1010 may be slaved to a robotic system or a robotic system may be slaved to a fluid source and/or suction tool 1010.

Fluid from a fluid source may include saline, e.g., normal, hypotonic or hypertonic saline, Ringer's solution, ionic contrast, blood, or other energy-conducting liquids. An ionic fluid may be used electrically couple one or more electrodes of a suction tool 1010 to the tissue to be ablated thereby lowering the impedance at the ablation site. An ionic fluid may create a larger effective electrode surface. A fluid may be used to cool the surface of the tissue thereby preventing the over heating or cooking of tissue which can cause popping, desiccation, and charring of tissue. A hypotonic fluid may be used to electrically insulate a region of tissue thereby preventing ablation of tissue by an electrical means.

Tissue and/or bodily fluids contacting components of suction tool 1010 are preferably made of one or more biocompatible materials. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make the delivery device of the present invention and/or one or more of its components may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, epoxies, human or animal protein or tissue such as bone, skin, teeth, collagen, laminin, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of the delivery device of the present invention and/or one or more of its components may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Suction may be provided by the standard suction available in the operating room. The suction source may be coupled to the delivery device of the present invention with a buffer flask. Alternatively, suction may be provided via a manual or electric pump, a syringe, a suction or squeeze bulb or other suction or vacuum producing means, device or system. The suction source may comprise one or more vacuum regulators, valves, e.g., vacuum releasing valves, conduits, lines, tubes and/or hoses. The conduits, lines, tubes, or hoses may be flexible or rigid. For example, a flexible suction line may be used to communicate suction to suction tool 1010, thereby allowing suction tool 1010 to be easily manipulated by a surgeon. Another method that would allow the surgeon to easily manipulate suction tool 1010 includes incorporation of a suction source into suction tool 1010. For example, a small battery operated vacuum pump may be incorporated into suction tool 10. A suction source may include a visual and/or audible signal used to alert a surgeon to any change in suction. For example, a beeping tone or flashing light may be used to alert the surgeon when suction is present.

One or more portions of the delivery device of the present invention may be malleable, flexible, bendable and/or moveable. For example, suction tool 1010 may comprise one or more hinges or joints (not shown) for maneuvering and placing suction pad 1030 against tissue. The hinges or joints of suction tool 1010 may be actuated, for example, from handle located at the proximal suction tool port assembly 1014. Suction tool body 1012 may be malleable or shapeable. One or more hinges or joints may be used to move suction pad 30 relative to suction tool body 1012 and/or working lumen 1020.

An output device (not shown) coupled to the delivery device of the present invention may be used to control, for example, a suction source, a power source or generator, a cell delivery source, and/or a fluid delivery source. For example, a signal of a first intensity from a sensor of suction tool 1010 may indicate that the power level from a power source should be lowered; a signal of a different intensity may indicate that the power source should be turned off. Preferably, an output device may be configured so that it may automatically raise or lower the power from a power source appropriately. Alternatively, the control of a power source, for example, based on output from output device may be manual.

An output device coupled to the delivery device of the present invention may also be a visual display that indicates to the user the status of a medical procedure. Such a display may be, for example, an indicator on a LCD or CRT monitor. By software control, the surgeon may choose to display the information in a number of ways. The monitor may show the current reading of each sensor, for example. The monitor may also lock and display the maximum reading achieved at each sensor. For example, a monitor may indicate when an appropriate combination of temperature and time has been reached to ensure cell death during an ablation procedure. One such appropriate combination may be 60° C. for 5 seconds. Another combination may be 55° C. for 20 seconds. Information may be displayed to the user in any other suitable manner, such as for example, displaying a virtual representation of an ablation lesion on the monitor.

Alternatively, the monitor may display the voltage corresponding to the signal emitted from a sensor. This signal corresponds in turn to the intensity of the temperature at the tissue site. Therefore a voltage level of 2 would indicate that the tissue was hotter than when the voltage level was 1. In this example, a user may monitor the voltage level and, if it exceeded a certain value, may turn off or adjust a power source.

An indicator, such as an LED light, may be permanently or removably incorporated into suction tool 1010. The indicator may receive a signal from one or more sensors indicating that the tissue had reached an appropriate temperature, for example. In response, the indicator may turn on, change color, grow brighter or change in any suitable manner to indicate that the flow of power from a power source should be modified or halted. The indicator may be located anywhere that would be visible to the user.

Alternatively, an output device may be an audio device that indicates to the user the status of a medical procedure. Such an audio device may be, for example, a speaker that broadcasts a sound (for example, a beep) that increases in intensity, frequency or tone as a characteristic of the procedure has changed, for example, the temperature measured by a sensor. The user may adjust, for example, turn down or turn off a power source when the sound emitted reaches a given volume or level. In another embodiment, the audio device may also give an audible signal (such as the message "turn off power source") when the temperature, for example, sensed by one or more sensors reaches a certain level. Such an audio device may be incorporated in suction tool 10 or the audio device may be a separate device coupled to suction tool 10.

The delivery device of the present invention may be permanently or removably attached to a source of energy such as electrical, radiofrequency (RF), laser, thermal, microwave or ultrasound or any other appropriate type of energy that may be used during a medical procedure including the use of suction tool 1010. The energy source may be powered by AC current, DC current or it may be battery powered either by a disposable or re-chargeable battery. The energy source may incorporate a controller or any suitable processor. For example, the processor may gather and/or process sensed information from one or more sensors. The controller may store and/or process such information before, during and/or after a medical procedure. For example, the patient's tissue temperature may be sensed, stored and processed prior to and during an ablation procedure.

The information stored and/or processed may be used to adjust power levels and delivery times. For example, an energy source may incorporate one or more switches or be coupled to one or more switches of suction tool 1010 to facilitate regulation of the various system components by the surgeon. An energy source may be coupled to an output device or an output device may be incorporated into the energy source. The energy source may incorporate a cardiac stimulator and/or cardiac monitor. For example, electrodes used to stimulate or monitor the heart may be incorporated into suction tool 1010. An energy source coupled to suction tool 10 may comprise a surgeon-controlled switch for cardiac stimulation or monitoring. A visual and/or audible signal used to alert a surgeon to the completion or resumption of ablation, suction, sensing, monitoring, stimulation and/or delivery of irrigation fluid, drugs and/or cells may be incorporated into an energy source and/or suction tool 1010. For example, a beeping tone or flashing light that increases in frequency as the ablation period ends or begins may be used.

Delivery of suction, energy, cells, and/or fluids may be slaved to one or more sensors of suction tool 1010, for example. In addition, the delivery of energy may be designed to automatically stop if a sensor measures a predetermined sensor value, e.g., a particular temperature value. In one embodiment of the invention, if a sensor of the present invention indicates that tissue has reached a particular temperature, the delivery of energy is stopped automatically, thereby preventing charring of the tissue.

One or more of a variety of diagnostic agents, therapeutic agents, pharmacological agents and/or drugs may be delivered or administered to the patient during a medical procedure performed according to the present invention, prior to a medical procedure performed according to the present invention, intermittently during a medical procedure performed according to the present invention, continuously during a medical procedure performed according to the present invention and/or following a medical procedure performed according to the present invention. For example, one or more of a variety of pharmacological agents or drugs, as discussed below, may be delivered before, during or after an ablation procedure, as discussed earlier.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, suction tool 1010 may incorporate a delivery device for delivering one or more diagnostic agents, therapeutic agents, pharmacological agents and/or drugs. Alternatively, a delivery device may be advanced through working lumen 1020 and out port 1046 of suction tool 1010. For example, a delivery device such as a needle or catheter may be inserted into working lumen 1020. A delivery catheter may include an expandable member, e.g., a low-pressure balloon, and a shaft having a distal portion, wherein the expandable member is disposed along the distal portion. A delivery catheter may comprise one or more lumens. A delivery catheter or needle may be advanced through working lumen 1020 and out port 1046 and into tissue and/or a blood vessel, e.g., an artery such as a femoral, radial, subclavian or coronary artery. Suction tool 1010 can be guided into a desired position using various guidance techniques, e.g., flouroscopic guidance and/or a guiding catheter or guide wire placed through working lumen 1020 or a guide lumen (not shown). Drugs may be delivered with suction tool 1010 via iontophoresis. In general, the delivery of ionized drugs may be enhanced via a small current applied across two electrodes, for example, one or more electrodes located on suction pad 1030. Positive ions may be introduced into the tissues from the positive pole, or negative ions from the negative pole. The use of iontophoresis may markedly facilitate the transport of certain ionized drug molecules. For example, lidocaine hydrochloride may be applied to the heart using iontophoresis. A positive electrode could be located on suction pad 30 while the negative electrode could contact the heart or other body part at some desired distance point to complete the circuit. One or more of the iontophoresis electrodes may also be used as nerve stimulation electrodes or as cardiac stimulation electrodes.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered. Biological agents may be found in nature (naturally occurring) or may be chemically synthesized. Cells and/or cell components, e.g., mammalian cells, may be delivered. Blood and/or blood components, e.g., platelet rich plasma or autologous platelet gel, may be delivered. One or more tissue sealants, glues or adhesives may be delivered.

A delivery device may be incorporated into suction tool 1010, thereby delivering biological agents at or adjacent the suction tool site, or the delivery device may be placed or used at a location differing from the location of suction tool 1010. For example, a delivery device may be placed in contact with the inside surface of a patient's heart while suction tool 1010 is placed or used on the outside surface of the patient's heart.

The delivery device may be slaved to an output device. For example, a delivery device may be designed to automatically stop or start the delivery of drugs or agents during the placement of a lead. The delivery device may be slaved to a robotic system or a robotic system may be slaved to the delivery device.

The delivery device may comprise a surgeon-controlled switch. For example, a switch may be incorporated in or on the delivery device, suction tool 1010, or any other location easily and quickly accessed by the surgeon. The switch may be, for example, a hand switch, a foot switch, or a voice-activated switch comprising voice-recognition technologies.

The delivery device may include a visual and/or audible signal used to alert a surgeon to any change in the delivery of agents. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta- adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites. Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof. The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine.

Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors. Suction tool 10 can be modified to incorporate one or more fluid lumens and/or conduits for providing one or more fluids, e.g., irrigation fluid to an ablation site.

Tissues and organs of a patient, such as the heart, lung, liver, stomach, intestine, spleen, brain, spine, bone, muscle, and tumor, may be treated using the present invention.

Figure 52:
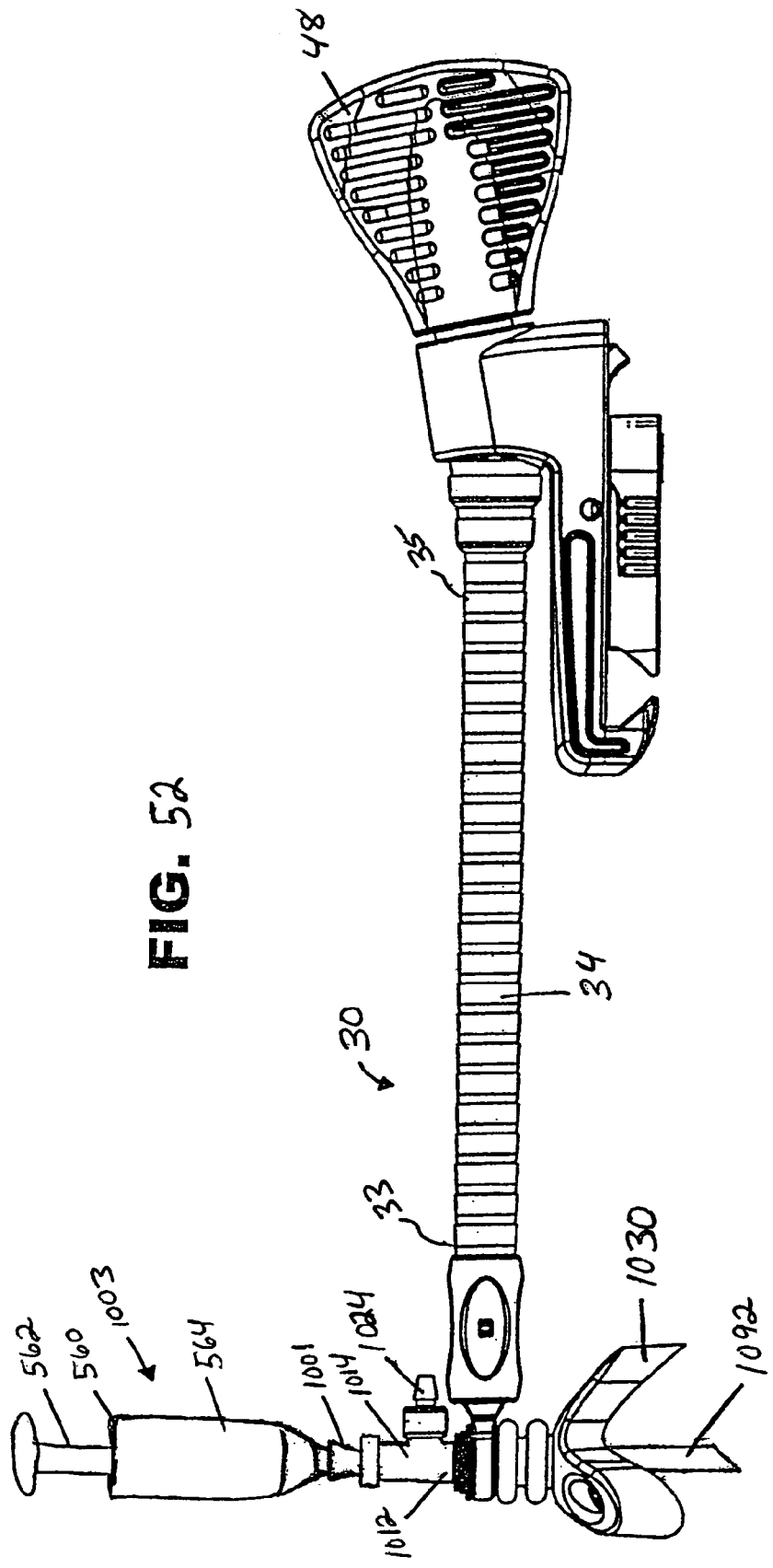
FIG. 52 is a side view of one embodiment of a device in accordance with the present invention.
Figure 53:
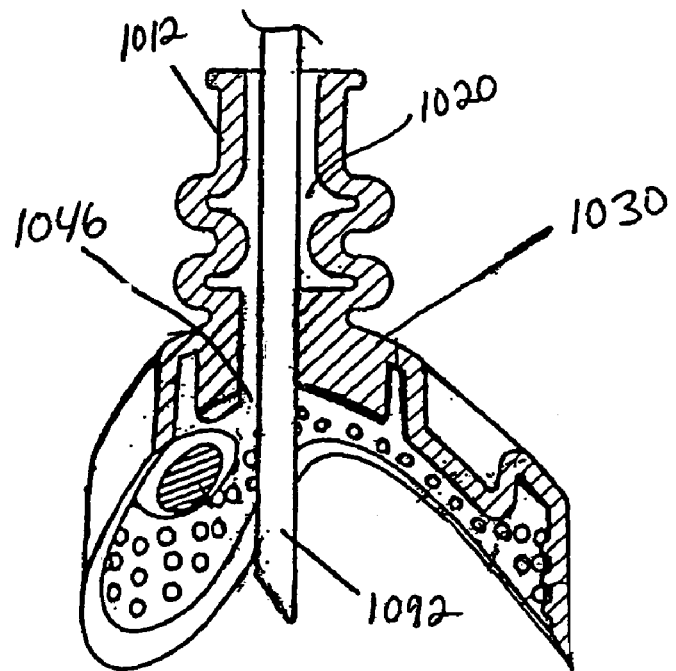
FIG. 53 is a cross-sectional view of one embodiment of a portion of a device in accordance with the present invention.
Figure 54:
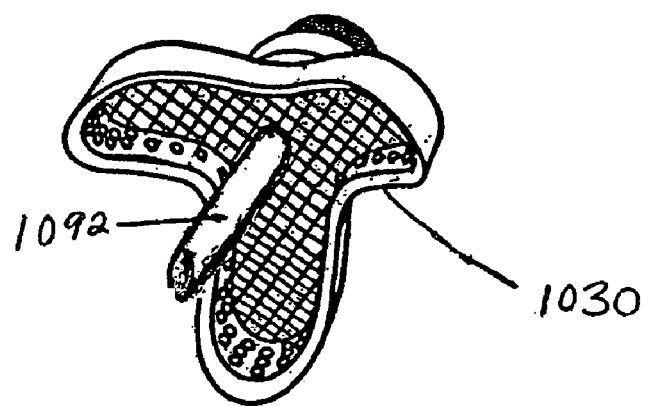
FIG. 54 is a bottom view of one embodiment of a portion of a device in accordance with the present invention.

An alternative embodiment of injection device 30 is shown in FIG. 52-54. In this embodiment, injection device 30 comprises a suction pad 1030 and an elongate shaft 34 coupled to suction pad 1030. Elongate shaft 34 includes generally a distal region 33 and a proximal region 35. Injection device 30 includes a proximal, rotatable and threaded member 48 for increasing and decreasing tension on an elongate cable disposed through elongate shaft 34. Tightening rotatable member 48 causes elongate shaft 34 to rigidly maintain its present position, while loosening rotatable member 48 allows elongate member 34 to be formed into the desired shape. Injection device 30 also includes a fluid and/or cell delivery element 1092 which may be advanced through the working lumen 1020. Alternatively, delivery element 1092 may be fixed to suction pad 1030 as shown in FIG. 54. If delivery element 1092 is to be advanced through working lumen 1020, it may be part of a cell delivery tool, which can take any of the forms described herein. As shown in FIG. 52, cell delivery tool 1003 may include a needle 1092 and a syringe 560. Syringe 560 may include a plunger 562 disposed within a barrel 564. Cell delivery tool 1003 which may be docked into cell delivery tool port or fitting 1001 located at the proximal opening of working lumen 1020. Needle 1092 may be passed through working lumen 1020 as shown in FIG. 53. Needle 1092 may comprise any of the needles described herein. The suction tool 1010 may comprise a suction tool body 1012 extending between a proximal suction tool port assembly 1014 and a suction pad 1030. In this embodiment, injection device 30 may also serve as a tissue-engaging device capable of stabilizing an area of tissue and/or positioning an area of tissue or an organ such as the heart.

Figure 55:
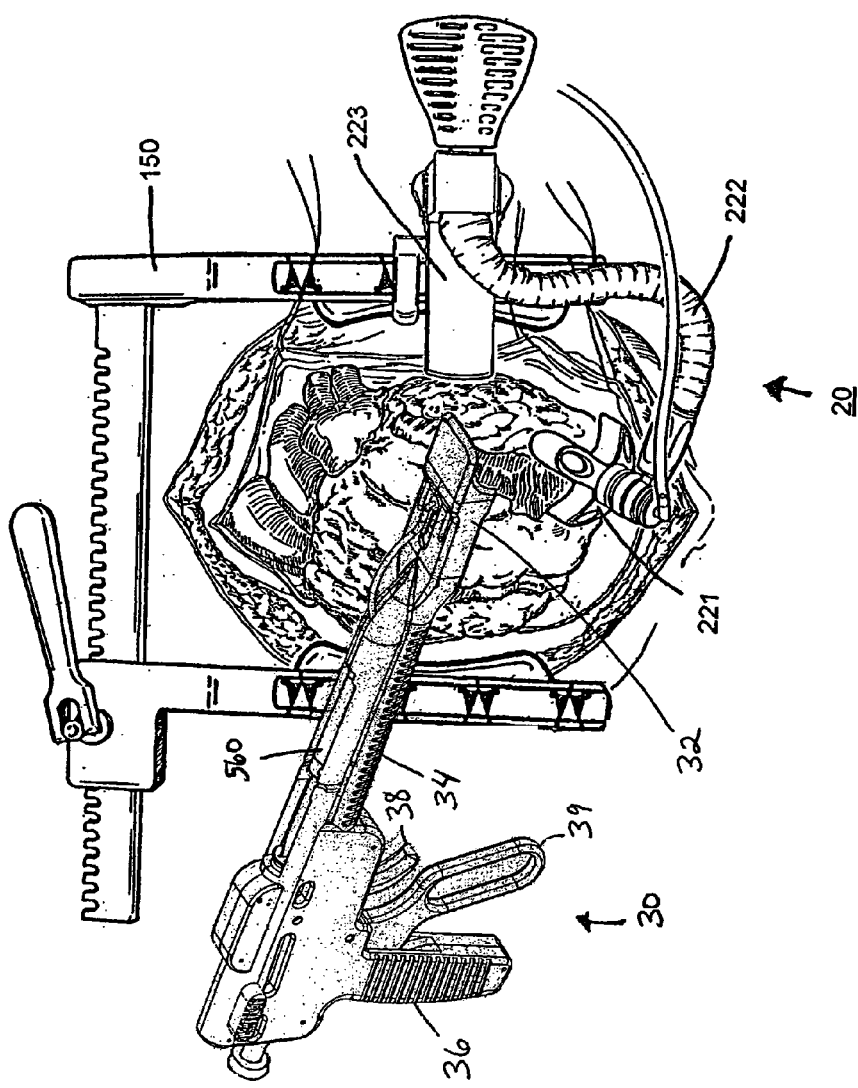
FIG. 55 is an illustration of one embodiment of multiple devices in use in accordance with the present invention.
Figure 56A:
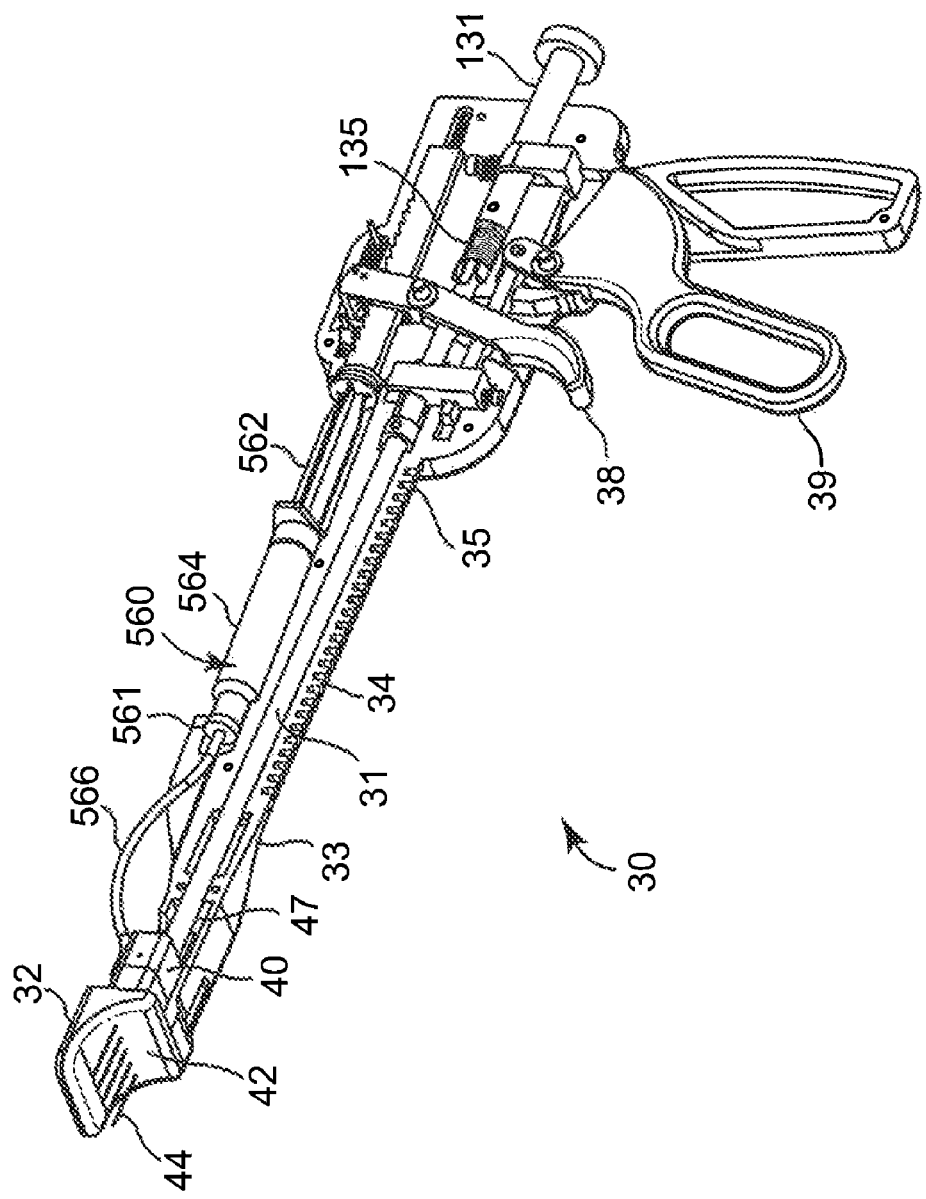
FIG. 56A is a cross-sectional view of one embodiment of a device in accordance with the present invention.
Figure 57A:
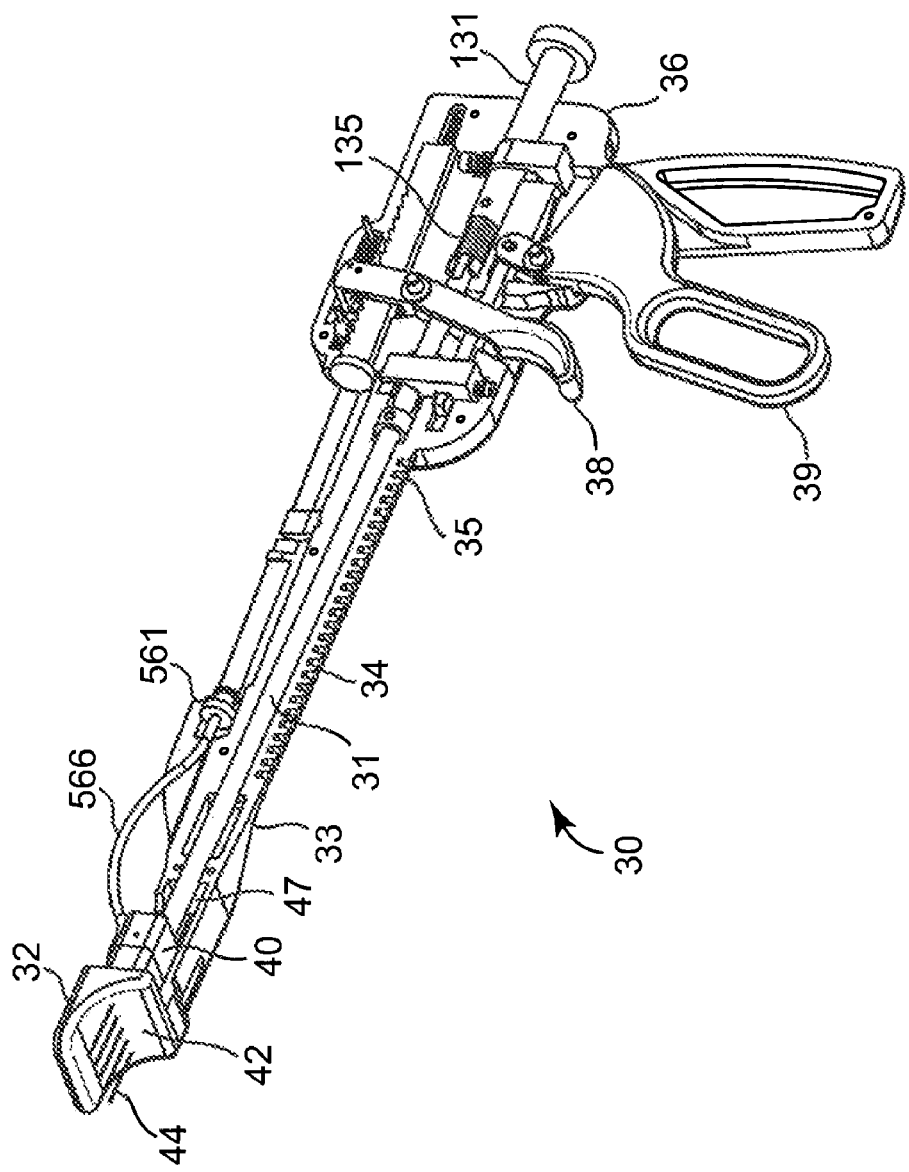
FIG. 57A is a cross-sectional view of one embodiment of a device in accordance with the present invention.
Figure 57B:
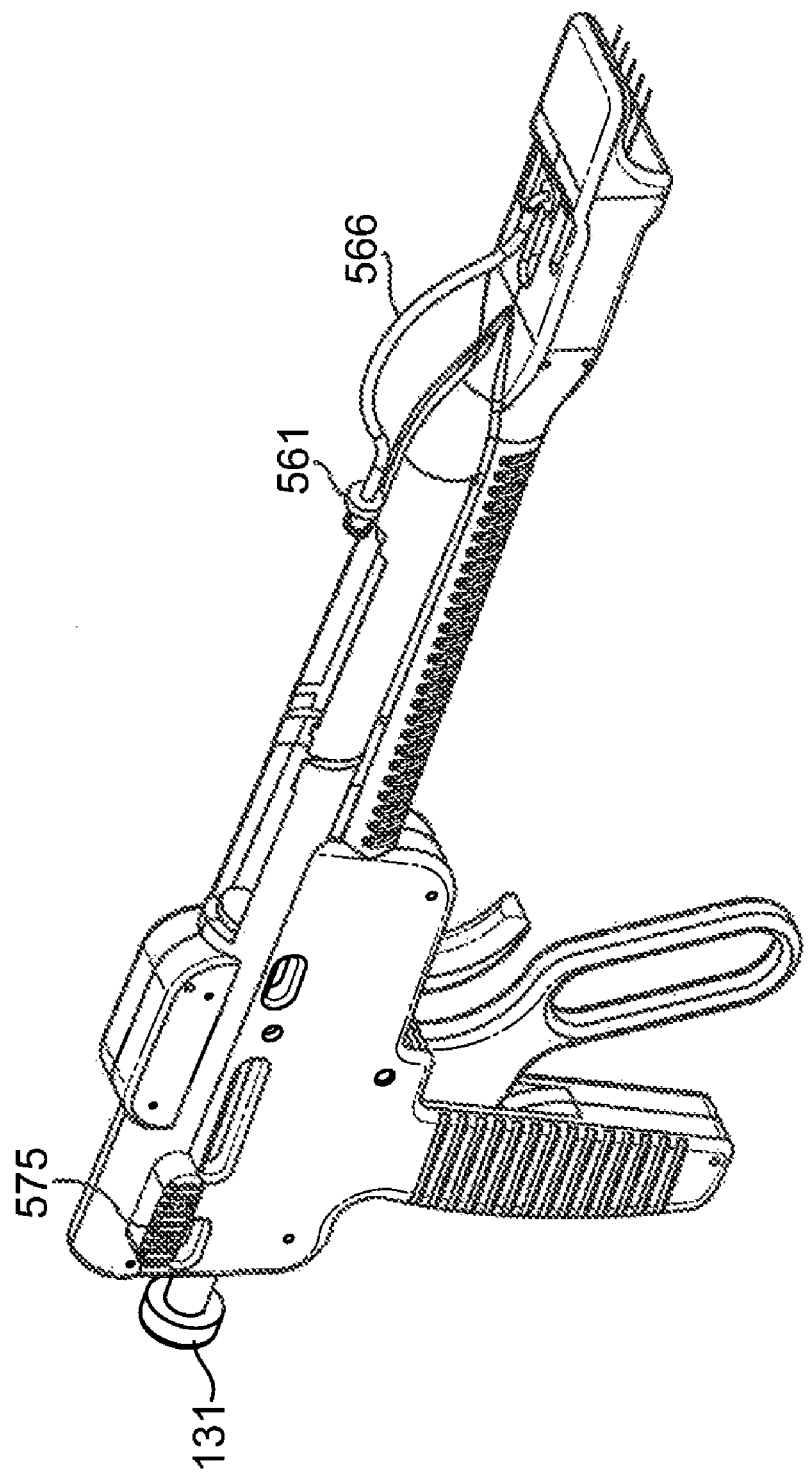
FIG. 57B is a side view of one embodiment of a device in accordance with the present invention.

In one embodiment of the present invention, a tissue-engaging device 20 may be fixed in position relative to a patient. For example, the maneuvering or support apparatus of device 20 may be designed to attach to or lock onto one or more stable objects such as an operating table, a retractor, an endoscopic port and/or a support arm of another tissue-engaging apparatus. A retractor may be, for example, a sternal retractor or a rib retractor. An endoscopic port may be, for example, a cannula, such as a trocar cannula placed in a patient's chest. A portion of a patient's skeletal system may also be considered a stable object. FIG. 55 shows an open-chest procedure wherein a tissue-engaging device 20 is locked onto a sternal retractor 150 fixed to a patient's chest. Tissue engaging device is shown comprising a tissue-engaging head 221, an articulating support arm 222 and a mounting clamp 223. In FIG. 55, tissue-engaging device 20 is shown supporting a patient's heart while it is engaged or attached to the apex of the patient's heart. The patient's heart may be beating or stopped. Also in FIG. 55, an alternative injection device 30 is shown in position for injecting one or more medical or biological agents into the myocardium of the heart. In this embodiment, injection device 30 is shown to include a removable syringe 560, which includes a plunger 562 disposed within a barrel 564 as shown in FIGS. 56A and 56B. Syringe 560 is shown fluidly coupled to a fluid tube 566. The proximal end of fluid tube 566 includes a syringe port 561. The distal end of fluid tube 566 is fluidly coupled to needles 44. FIGS. 57A and 57B show the injection device 30 with syringe 560 removed. In the current embodiment, injection device 30 includes a distal injection head 32, an elongate shaft 34, and a proximal handle 36. Proximal handle 36 includes a discharge trigger mechanism 38 coupled to a discharge mechanism for controlling the injection of one or more medical or biologic agents, such as cells. Injection device 30 is also shown to include a needle trigger mechanism 39 coupled to a needle movement mechanism for controlling needle movement, e.g., needle insertion and retraction. Elongate shaft 34 includes generally a distal region 33 and a proximal region 35. Distal injection head 32, which is coupled to the distal region of the elongate shaft 34, may include a first body 40, a second body 42, and numerous injecting needles 44. In one embodiment, injecting needles 44 are fixedly attached to first body 40 and are slidably received through second body 42. Urging first body 40 towards second body 42 thus drives injecting needles 44 transversely through second body 42 and into the target tissue. Drawing first body 40 and second body 42 apart retracts injecting needles 44 from the tissue. In some embodiments, the depth of needle penetration can be controllably varied.

As described above, the elongate shaft provided can vary from embodiment to embodiment, with a rigid embodiment being illustrated in FIGS. 55-57B. Needle movement mechanism includes a push rod 31, wherein the distal end of push rod 31 is fixedly coupled to first body 40. Push rod 31 is slidably contained within elongate shaft 34. Movement of push rod 31 in a proximal direction draws first body 40 apart from second body 42, thereby causing the retraction of injection needles 44. Movement of push rod 31 in a distal direction moves first body 40 towards second body 42, thereby driving injecting needles 44 transversely through second body 42 and into the target tissue. The proximal end region of push rod 31 is coupled to needle trigger mechanism 39 so that movement of trigger mechanism 39 translates into movement of push rod 31. For example, movement of trigger mechanism 39 by a surgeon towards handle 36 causes injecting needles 44 to move transversely through second body 42 and into the target tissue. Needle movement mechanism may include one or more injection spring elements 133 to help drive injecting needles 44 into tissue. Needle movement mechanism may also include one or more retraction spring elements 135 to help retract injecting needles 44. Needle movement mechanism may include a needle loading element 131. In one embodiment, needle loading element 131 is configured to be moved by a surgeon in a distal direction until it locks into position wherein it puts a load on injection spring element 133. In one embodiment, needle trigger mechanism 39 may be moved into first and second positions.

Figure 58A:
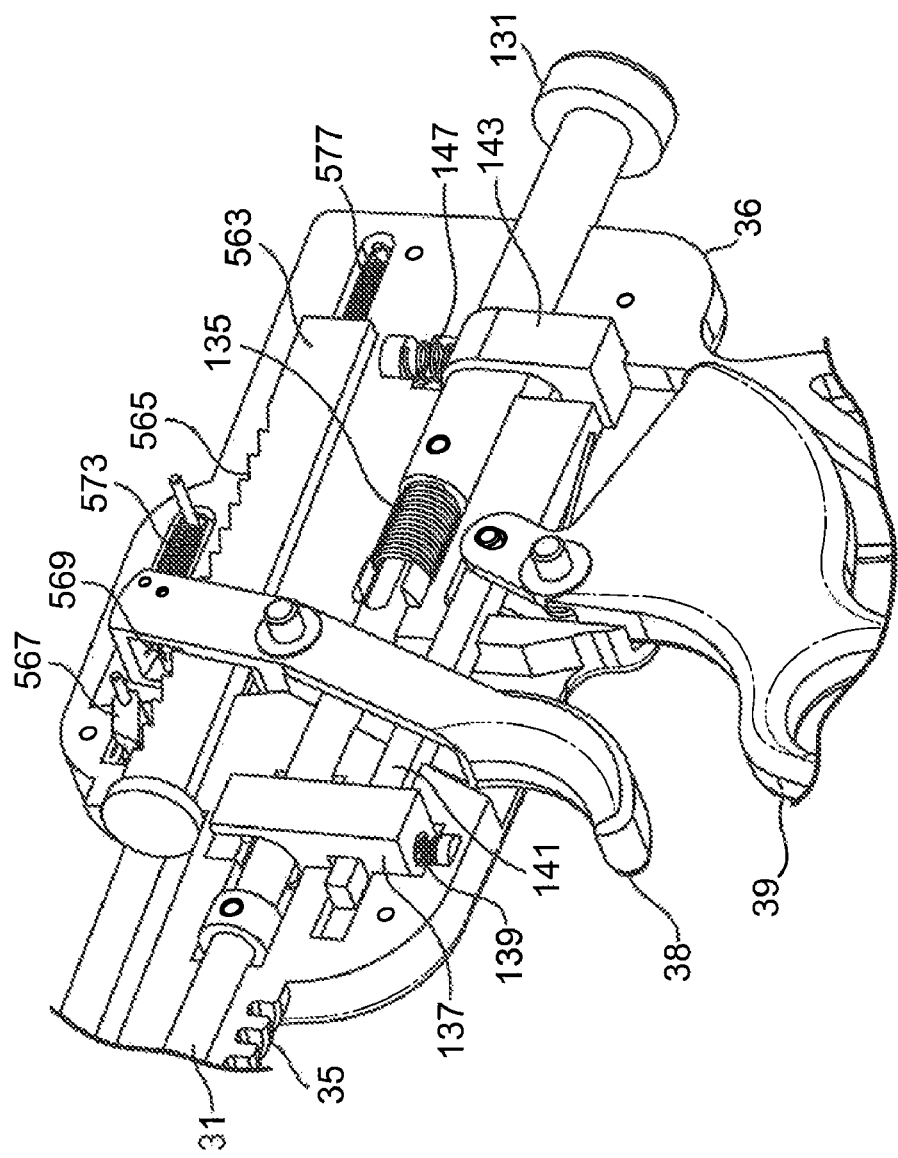
FIGS. 58A and 58B are cross-sectional views of one embodiment of a portion of a device in accordance with the present invention.
Figure 58B:
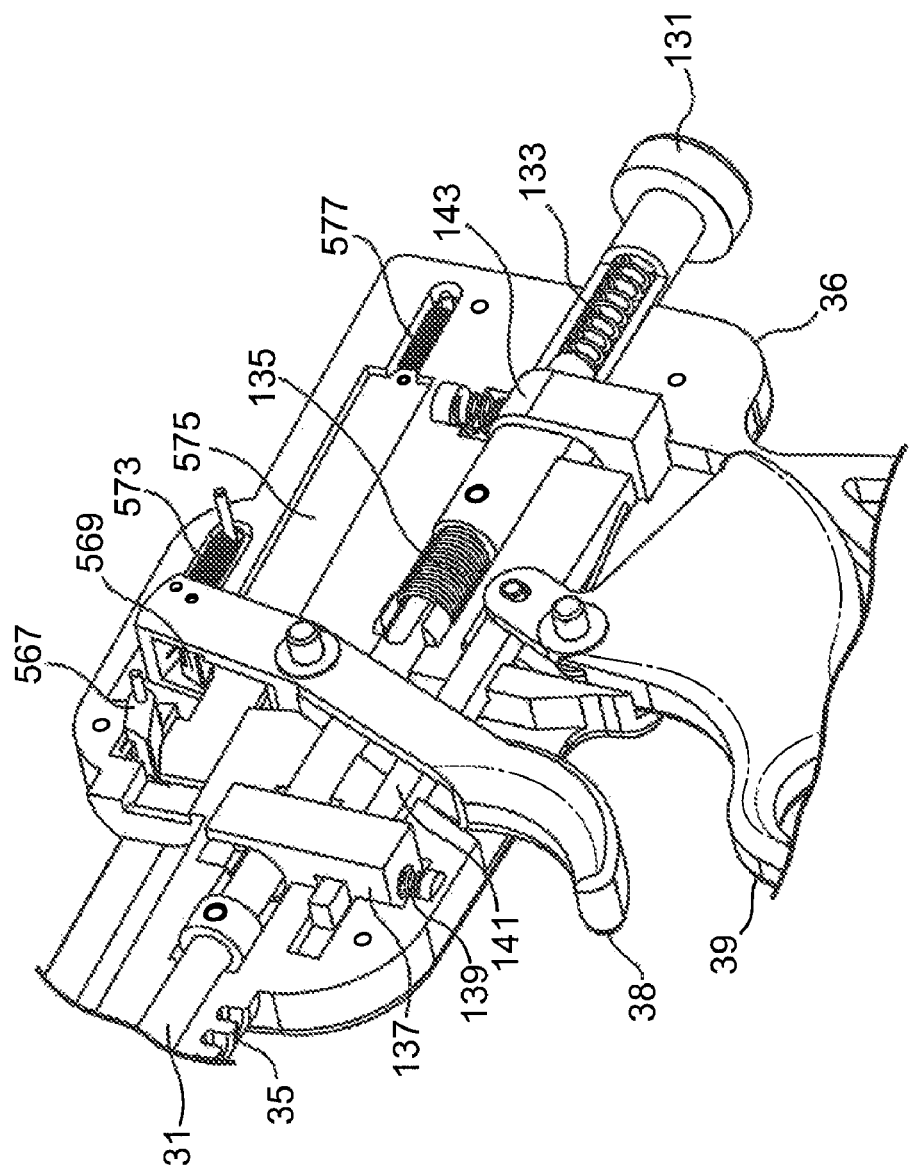

The first position of needle trigger mechanism 39 causes the release of a needle injection locking mechanism, which comprises a needle injection locking element 137 and a needle injection locking spring 139. Needle trigger mechanism 39 is movably coupled to needle injection locking element 137 via element 141 (as shown in FIGS. 58A and 58B). Movement of needle trigger mechanism 39 into a first position causes the release of the needle injection locking mechanism thereby allowing injection spring element 133 to exert a force that moves push rod 31 in a distal direction.

The second position of needle trigger mechanism 39 causes the release of a needle retraction locking mechanism, which comprises a needle retraction locking element 143 and a needle retraction locking spring 147. Movement of needle trigger mechanism 39 into a second position causes the release of the needle retraction locking mechanism thereby allowing retraction spring element 143 to exert a force that moves push rod 31 in a proximal direction. Movement of needle trigger mechanism 39 into a second position also releases needle loading element 131, thus allowing element 131 to move back into a preloading position wherein a surgeon may again move needle loading element 131 back into a loaded position if desired.

In one embodiment of the present invention, discharge trigger mechanism 38 is movably coupled to a discharge mechanism for controlling the injection of one or more medical or biologic agents. The discharge mechanism may comprise multiple ratcheting elements such as plunger push element 563. Movement of plunger push element 563 in a distal direction pushes or moves plunger 562 further into barrel 564. Pushing or moving plunger 562 into barrel 564 causes the discharge of the contents of syringe mechanism 560 through fluid tube 566 and out through injecting needles 44. Plunger push element 563 has a plurality of notches 565 along one edge (as shown in FIG. 58A). Ratcheting elements 567 and 569 are spring loaded so as to drop into notches 565, thereby preventing movement of plunger push element 565 in a proximal direction. Ratcheting elements 567 and 569 thus allow push plunger element 565 to be moved incrementally in a distal direction via discharge trigger mechanism 38. Movement of discharge trigger mechanism 38 advances plunger push element 563 one notch at a time, thus allowing a predetermined metering of the discharge of the contents of syringe mechanism 560. The discharge mechanism may also include discharge spring element 573 to move trigger mechanism 38 back into a starting position following movement of trigger mechanism 38 by a surgeon. The discharge mechanism may also include a release element 575 (as shown in FIG. 58B). Movement of release element 575 by a surgeon in a distal direction moves ratcheting elements 567 and 569 out of notches 565, thereby allowing plunger push element 563 to be moved in a proximal direction. Discharge spring element 577 moves release element 575 back into a starting position following movement of element 575 by a surgeon.

Figure 59:
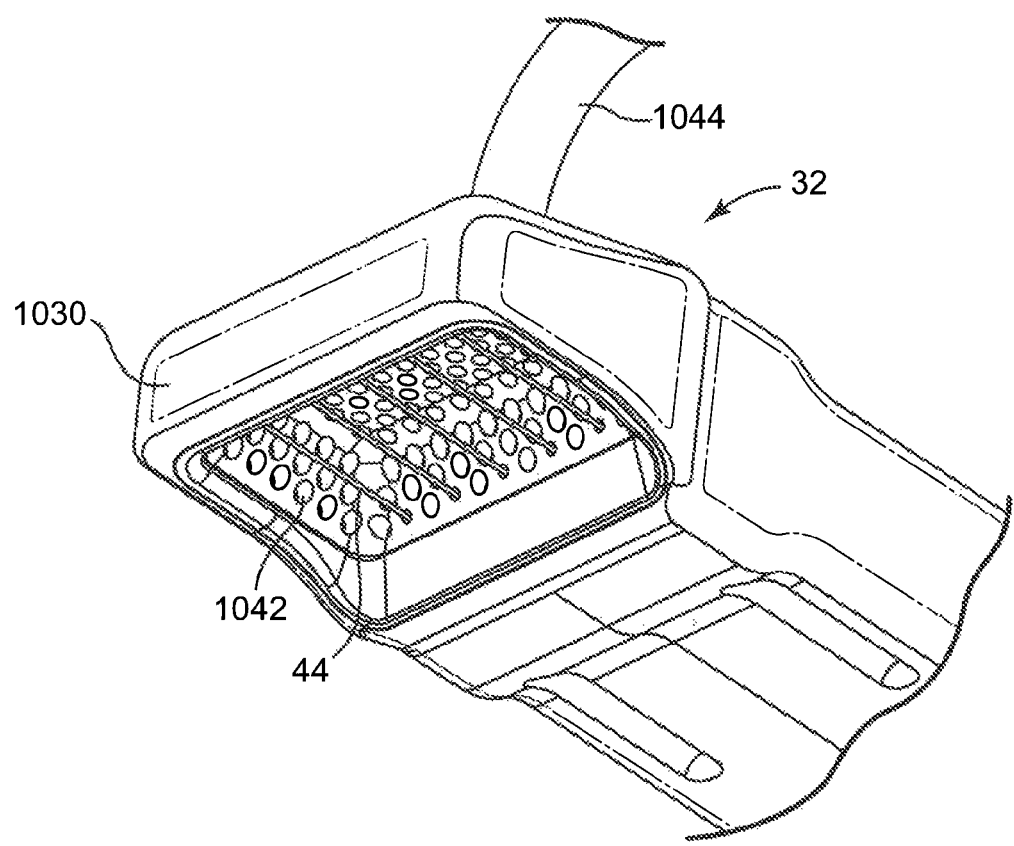
FIG. 59 is a view of one embodiment of a portion of a device in accordance with the present invention.
Figure 60:
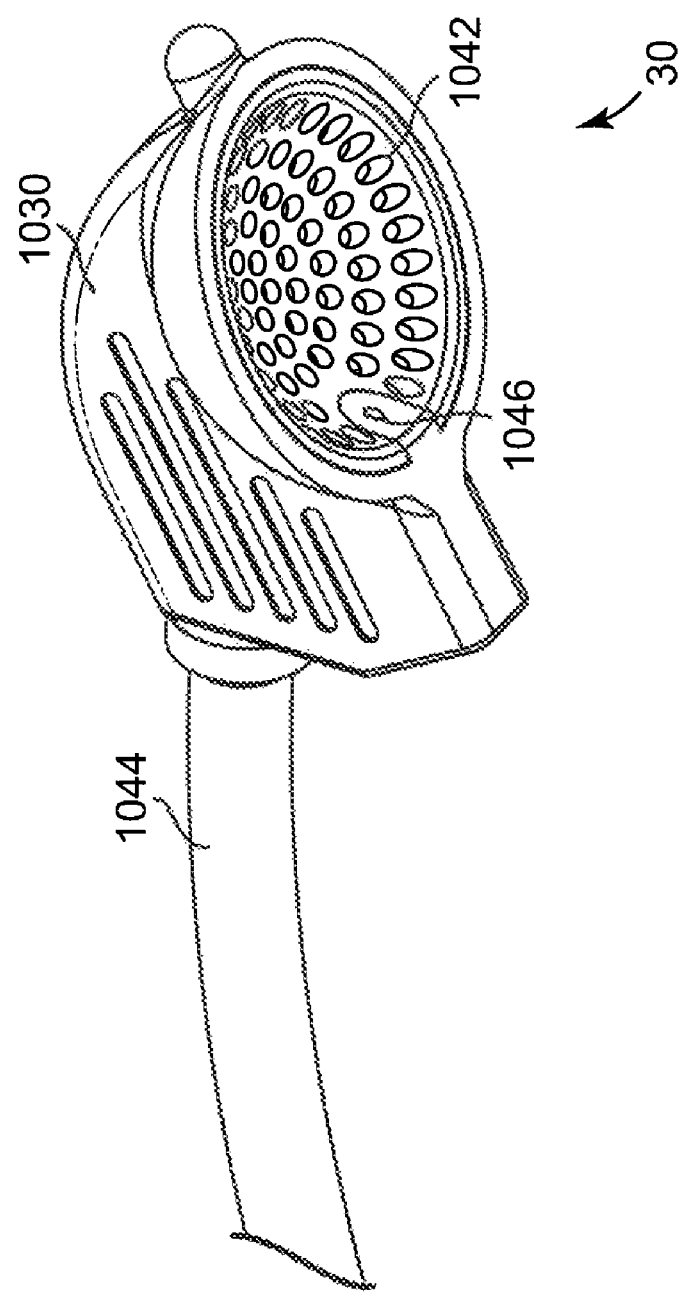
FIG. 60 is a view of one embodiment of a device in accordance with the present invention.

In one embodiment of the present invention, interstitial injection device 30 may comprise a distal injection head 32 having suction capabilities, see FIG. 59. Distal injection head 32 may comprise suction pad 1030 having a plurality of suction ports 1042 coupled to a suction lumen 1044. Suction lumen 1044 may be adapted to be attached to a vacuum source at the surgical site.

Figure 61:
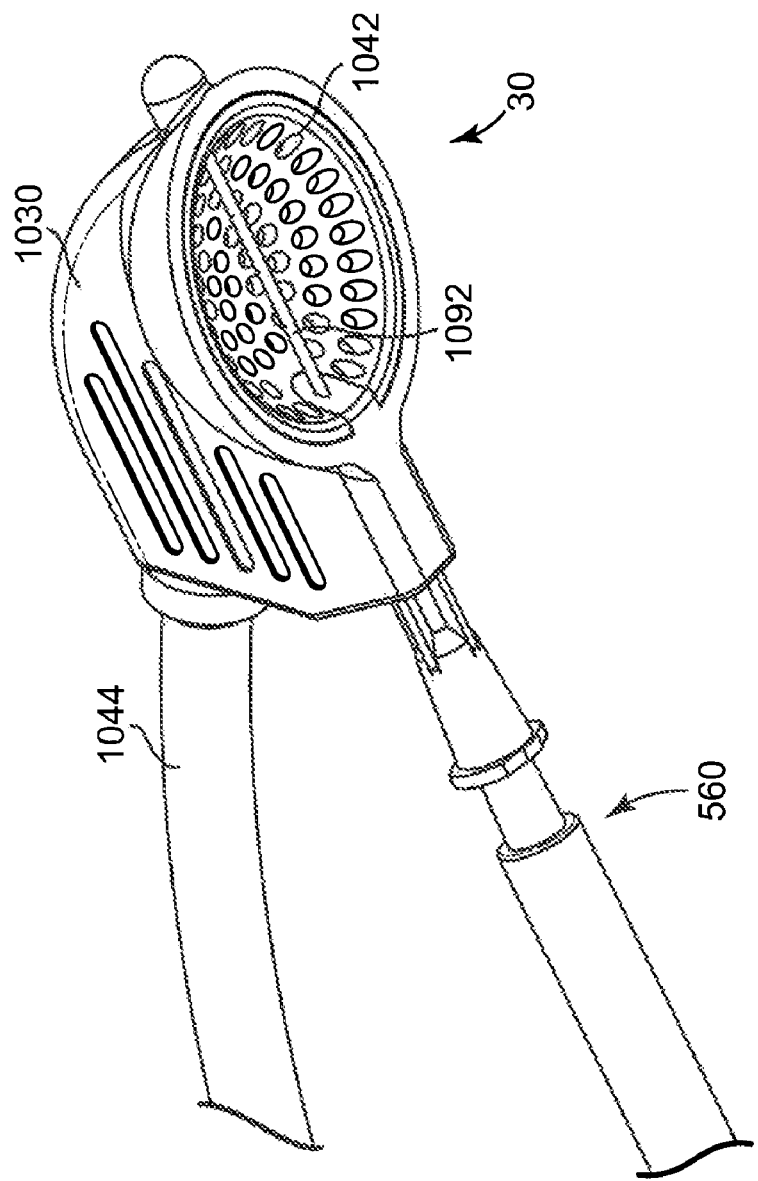
FIG. 61 is a view of one embodiment of a device in accordance with the present invention.

In one embodiment of the present invention, suction tool 1010 may comprise a suction pad 1030 having a plurality of suction ports 1042 coupled to a suction lumen 1044. Needle 1092 of syringe mechanism 560 may be advanced through working lumen port 1046 as shown in FIG. 61.

Figure 62:
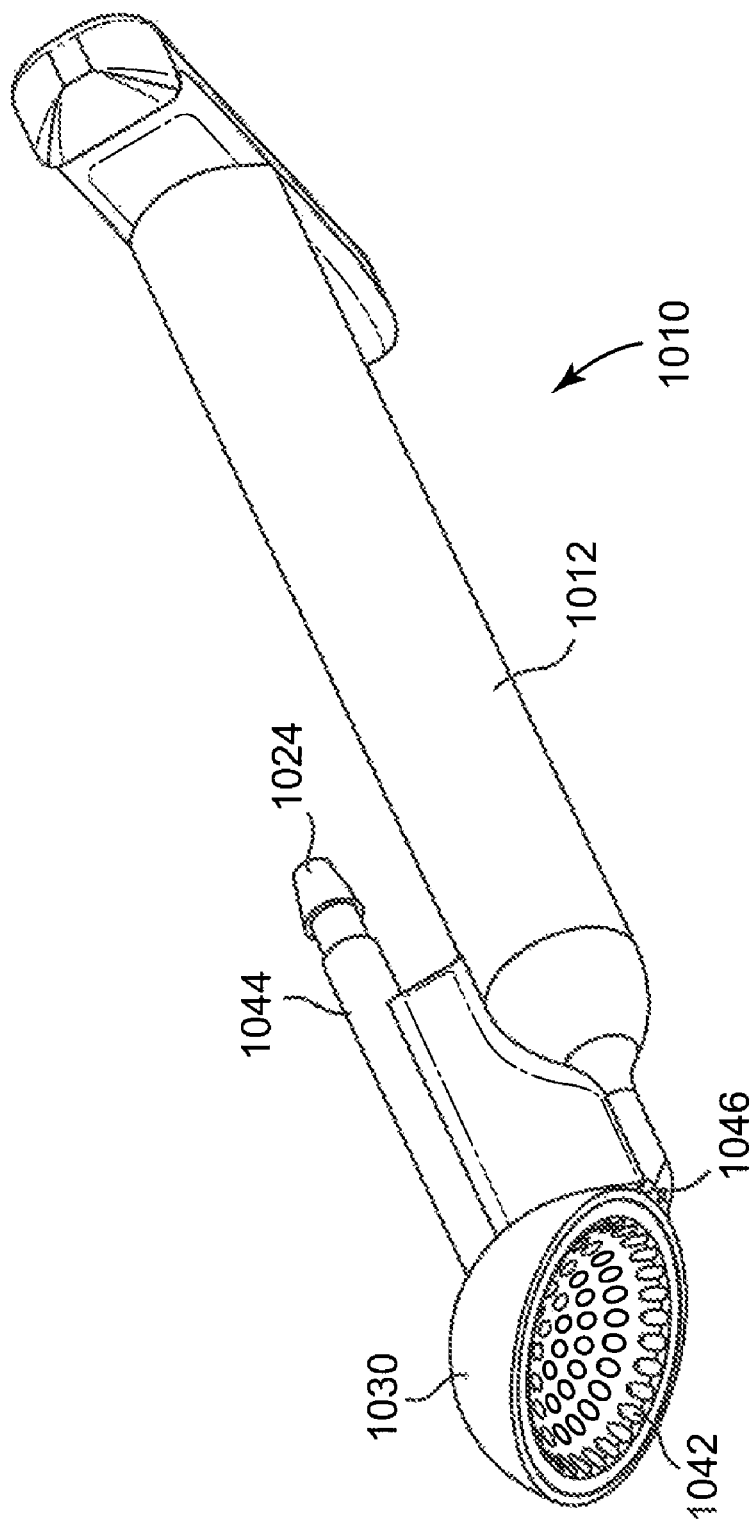
FIG. 62 is a view of one embodiment of a device in accordance with the present invention.
Figure 63:
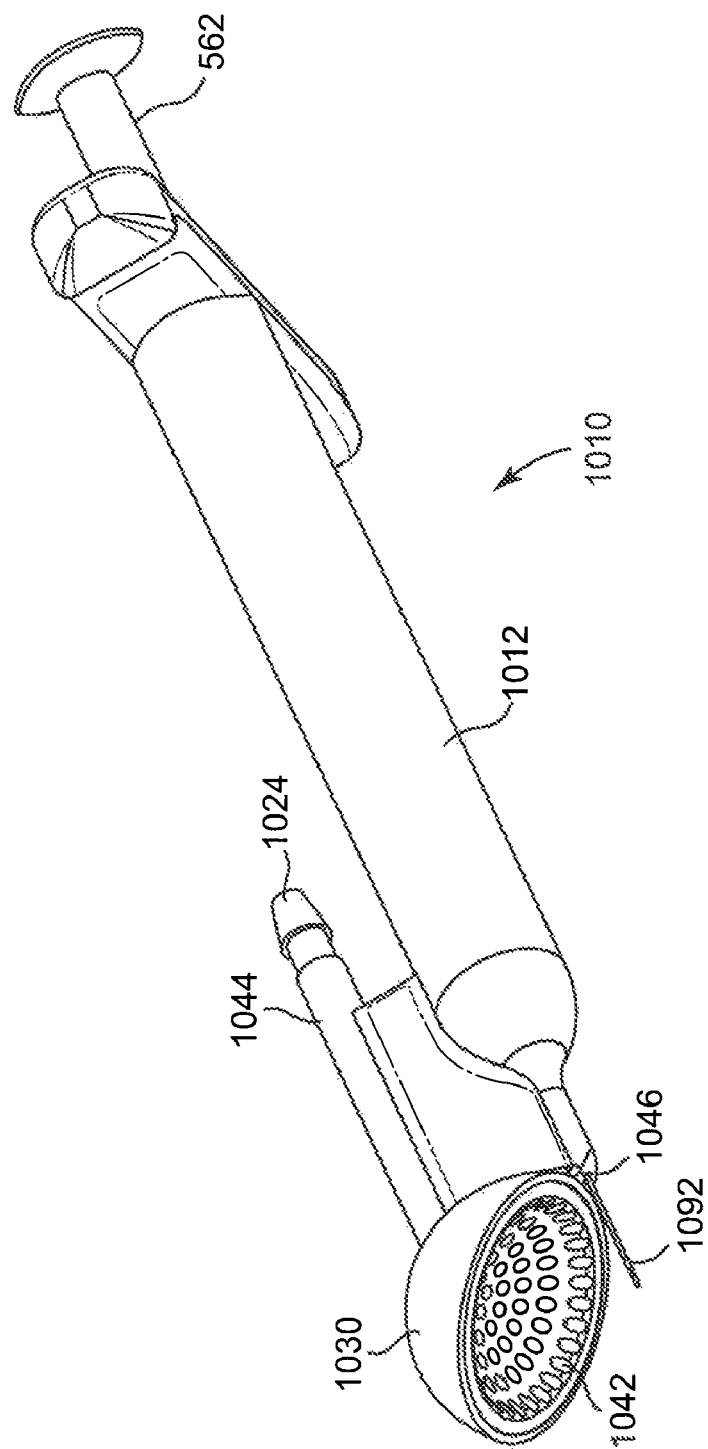
FIG. 63 is a view of one embodiment of a device in accordance with the present invention.
Figure 64:
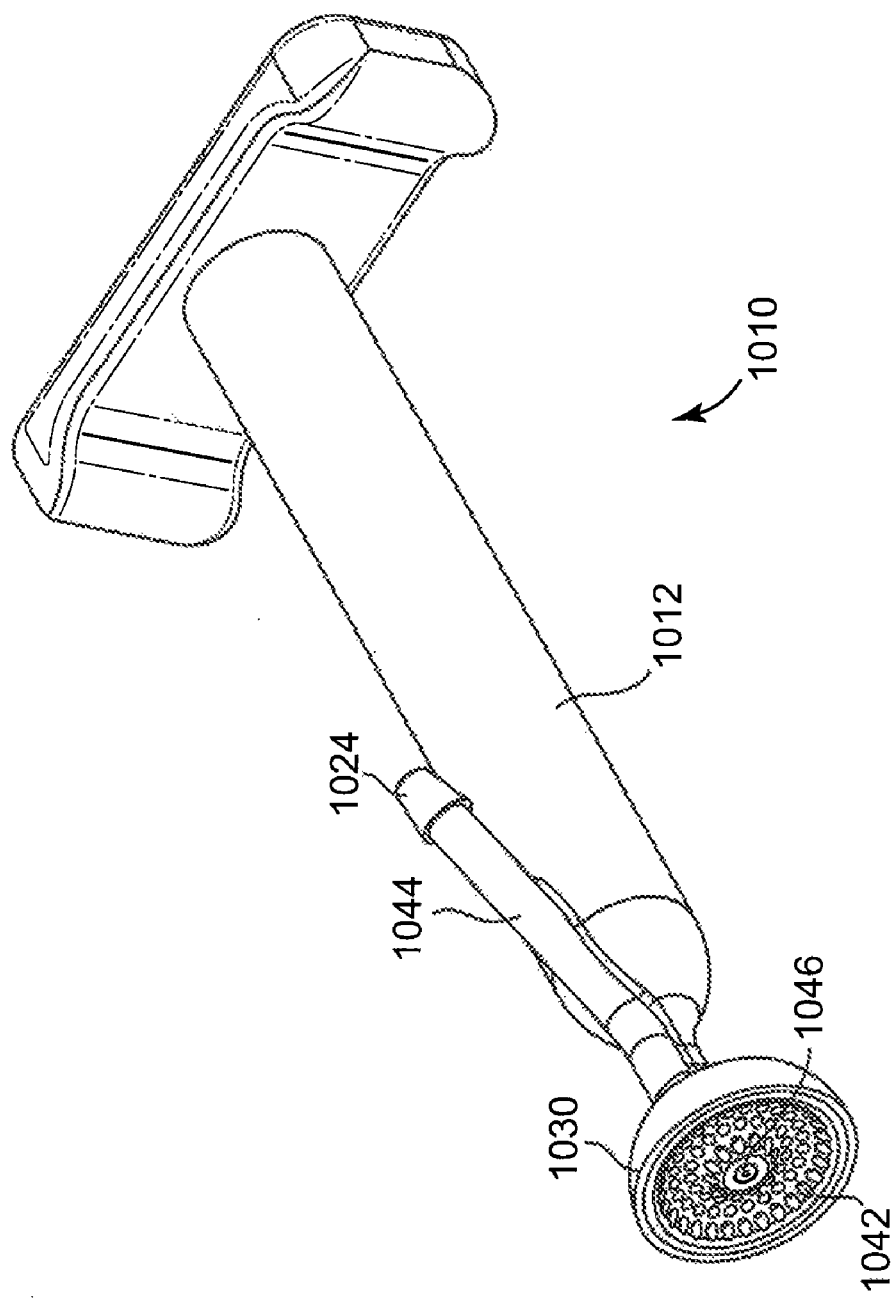
FIG. 64 is a view of one embodiment of a device in accordance with the present invention.
Figure 65:
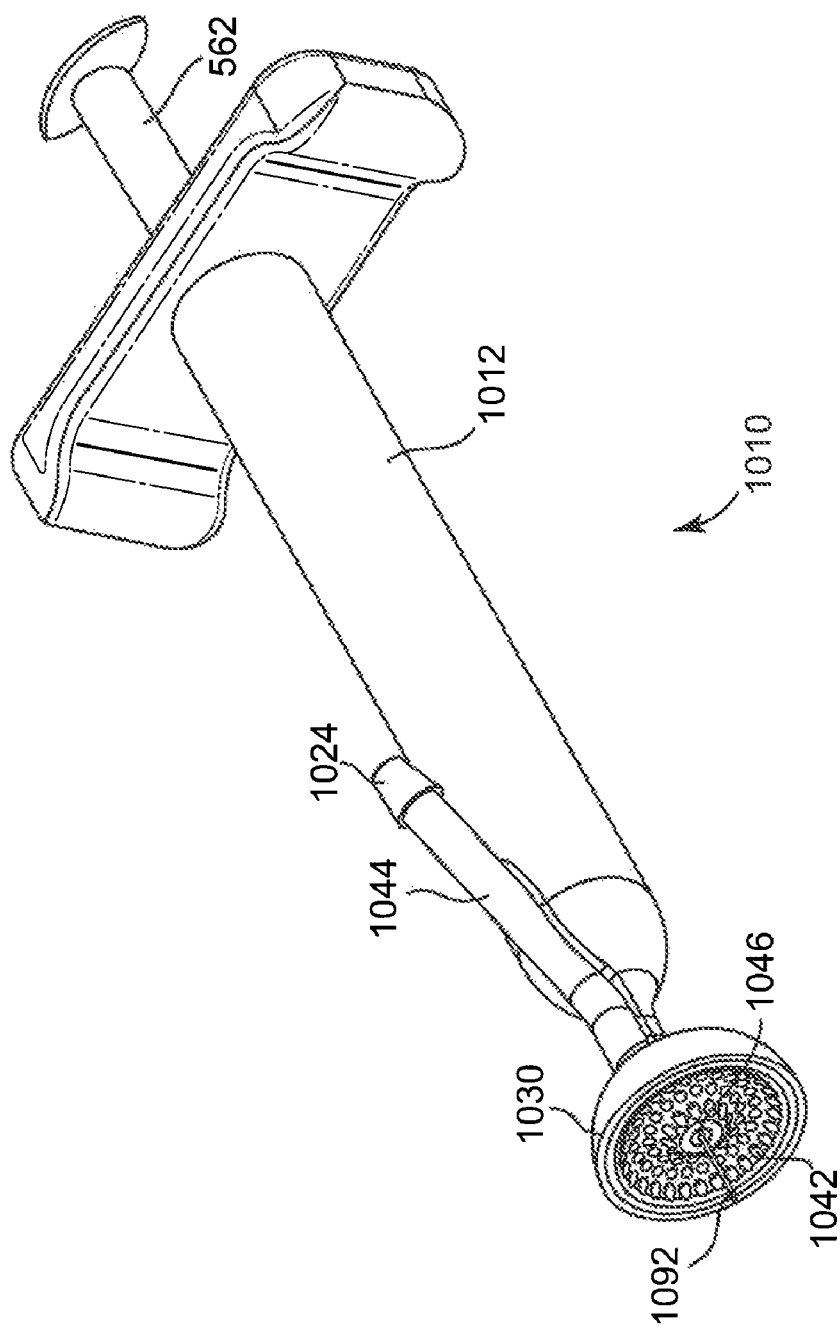
FIG. 65 is a view of one embodiment of a device in accordance with the present invention.

In one embodiment of the present invention, suction tool 1010 may comprise a suction pad 1030 having a plurality of suction ports 1042 coupled to a suction lumen 1044 and a suction port 1024, see FIGS. 62-65. In this embodiment, suction lumen 1044 is separate from tool body 1012. Needle 1092 of syringe mechanism 560 may be advanced through working lumen 1020 of tool body 1012 and out through working lumen port 1046, as shown in FIGS. 63 and 65. Working lumen 1020 of tool body 1012 in this embodiment is sized and shaped to accept needle 1092 and barrel 564 of syringe 560. In FIGS. 62 and 63, working lumen port 1046 is shown positioned adjacent suction pad 1030. Alternatively, as shown in FIGS. 64 and 65, working lumen port 1046 is positioned within suction pad 1030.

In one embodiment of the present invention, a nerve stimulator may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced, thereby maintaining a normal cardiac output. Vagal stimulation, alone or in combination with electrical pacing, may be used selectively and intermittently to allow a surgeon to perform injection of one or more agents into a temporarily stopped heart. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to Hill and Junkman and in U.S. patent application Ser. No. 09/670,441 filed Sep. 26, 2000, Ser. No. 09/669,960 filed Sep. 26, 2000, Ser. No. 09/670,370 filed Sep. 26, 2000, Ser. No. 09/669,961 filed Sep. 26, 2000, Ser. No. 09/669,355 filed Sep. 26, 2000 and Ser. No. 09/670,369 filed Sep. 26, 2000. These patents and patent applications are assigned to Medtronic, Inc. and are incorporated herein by reference.

Figure 66:
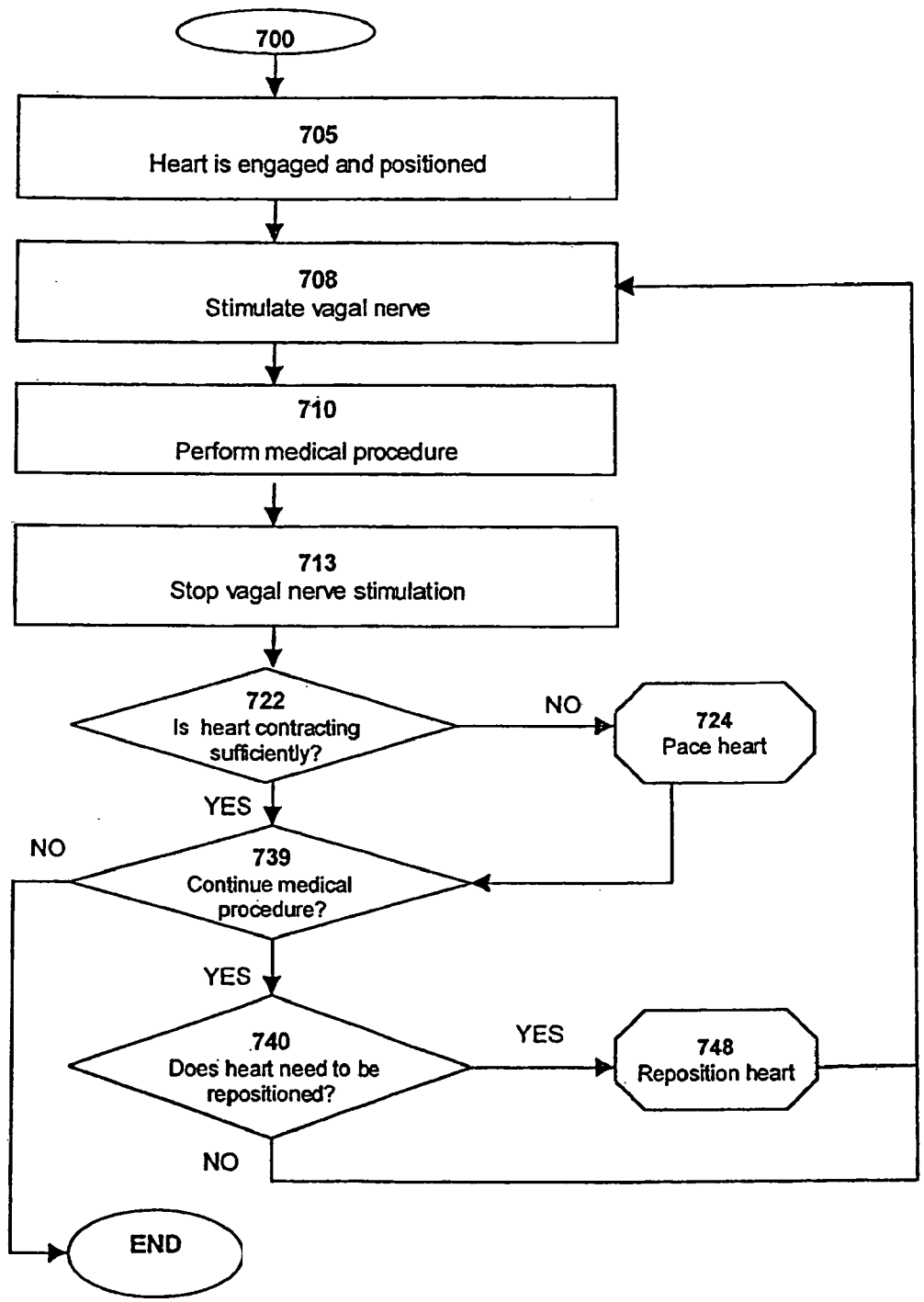
FIG. 66 is a flow diagram of one embodiment of the present invention.

FIG. 66 shows a flow diagram of one embodiment of the present invention. The patient is prepared for a medical procedure at 700. Once the patient is prepared, the heart may be engaged and positioned using a tissue-engaging device 20, as shown in FIG. 55 (Block 705). Once the heart is positioned in a desired orientation, a nerve that controls the beating of the heart is stimulated to slow down or stop the contractions of the heart (Block 708). Such a nerve may be for example a vagal nerve. During this time, one or more of a variety of pharmacological agents or drugs may be delivered to the patient. These drugs may produce reversible asystole of a heart while maintaining the ability of the heart to be electrically paced. Other drugs may be administered for a variety of functions and purposes as described above. Drugs may be administered at the beginning of the procedure, intermittently during the procedure, continuously during the procedure or following the procedure.

Typically, vagal nerve stimulation prevents the heart from contracting. This non-contraction must then be followed by periods without vagal nerve stimulation during which the heart is allowed to contract, and blood flow is restored throughout the body. Following initial slowing or stopping of the heart, a medical procedure comprising the delivery of one or more biologic or medical agents, such as cells, may be delivered via a delivery device of the present invention to the stopped or slowed heart (Block 710). Following a brief interval of nerve stimulation while the medical procedure is performed, nerve stimulation is ceased (Block 713) and the heart is allowed to contract. A cardiac stimulator or pacemaker may be used to cause the heart to contract or the heart may be free to beat on its own (Blocks 722 and 724). In one embodiment of the present invention, tissue-engaging device 20 includes one or more electrodes, which may be used for pacing, coupled to an energy source. A processor may control both cardiac and nerve stimulation. For example, a processor may automatically proceed to block 713 to cease nerve stimulation. In addition, processor 70 may automatically begin cardiac stimulation. If the medical procedure needs to continue or a new medical procedure is to be performed, the heart may be repositioned if necessary or desired at Block 748.

Figure 67:
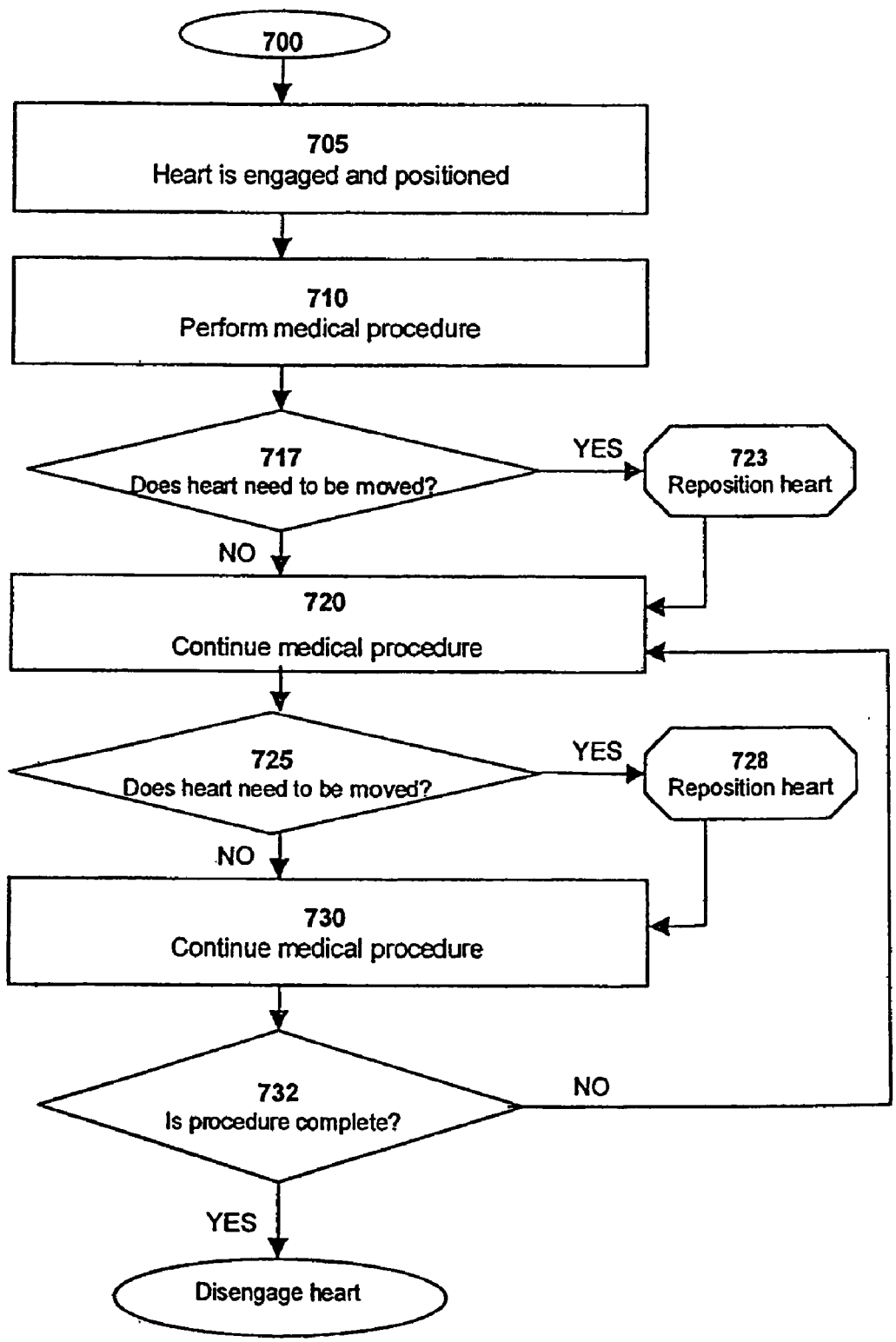
FIG. 67 is a flow diagram of one embodiment of the present invention.

FIG. 67 shows a flow diagram of one embodiment of the present invention. The patient is prepared for a medical procedure at 700. At this point, a beating or stopped heart may be engaged and positioned by tissue-engaging device 20, for example, to provide access to the posterior or backside of the heart (Block 705). The tissue-engaging device may be inserted into a patient through a percutaneous opening. For example, device 20 may be positioned through a sternotomy or thoracotomy or through a xiphoid incision as described above. As seen in FIG. 67, heart positioning may occur throughout the entire procedure in a continuous or intermittent manner. At Block 710, a medical procedure comprising the delivery of one or more biologic or medical agents, such as cells, delivered via a delivery device of the present invention is begun. At Block 717, it is determined if the heart needs to be repositioned. For example, upon completion of one or more injections of cells in cardiac tissue at a first location, the heart may be repositioned to provide better access for an additional one or more injections of cells in cardiac tissue at a second location. Again at Block 725, it is determined if the heart needs to be repositioned. For example, upon completion of a second series of injections, the heart may again be repositioned to provide access for a third series of injections. During the medical procedure fluids may be delivered to tissue-engaging device 20 from a fluid source. A processor may control the delivery of fluids from the fluid source. A processor may control the delivery of agents from a delivery device of the present invention.

It is known that infarcted tissue does not regenerate naturally in humans. Therefore, if a person has a heart attack the resultant infarcted tissue won't regenerate and the heart generally becomes weaker as a result. If the weaker heart, in turn, cannot keep up with the necessary cardiac output, heart failure will often ensue. Currently, methods for treating heart failure include administration of various pharmacological agents, use of left ventricular assist devices, and use of cardiac wraps or reinforcement devices. A promising technique for cardiac regeneration is cell transplantation.

One method for improving cell retention and cell survival in a cell transplantation technique is the use of a platelet gel, e.g., an autologous platelet gel, to provide a better "growth" medium for the cells. In addition, autologous platelet gel can "hold" the cells in place by forming a clot. Other methods for improving cell retention in a cell transplantation technique is to use a thermo-sensitive gel that firms up at body temperature or a viscous medium such as polyethylene glycol that could hold the cells in place at the injection or transplantation site.

There are potentially a number of reasons why injected cells in cardiac tissue may not survive long after injection. One reason may be that the beating heart is constantly being perfused and an injectate may be washed out of the extracellular space. Another reason may be that cells injected into ischemic tissue will not have the proper nutrients to survive. A third reason why fewer cells may be found chronically after cell injection, is that the cells may not be distributed well enough around the injection site. For example, the distribution of cells around an injection needle may be fairly discreet. Therefore, there is a need for methods that aid in more broadly distributing cells around an injection site.

The use of a fibrin or platelet gel, e.g., an autologous platelet gel (APG), may provide for improved cell retention, dispersion and/or survival. For example, APG can provide a very rich growth medium for the cells. In fact, APG has been shown to enhance cell survival in vitro. Therefore, cells injected with APG may find themselves in a richer milieu then if injected simply into infarcted tissue. APG can also help hold the cells in place until they have had a chance to integrate into the existing extracellular matrix. Just as a natural blood clot degrades with time, the platelet gel will also degrade with time, serving as an ideal biodegradable matrix. APG may prevent injected cells from being "washed out" soon after injection.

In general, platelet gel is formed by activating plasma that contains platelets, e.g., platelet rich plasma (PRP) or platelet poor plasma (PPP), with a clot promoting activator or agent, e.g., thrombin. For example, platelet gel may be formed by mixing platelet rich plasma with thrombin. The thrombin initiates the clotting cascade and creates a platelet gel. The addition of thrombin to platelet rich plasma and platelet poor plasma is further disclosed in U.S. Pat. No. 6,444,228, the disclosure of which is incorporated herein by reference. Since it would be difficult to pass a clot through a needle, it is preferable to inject the platelet gel with the cells before it forms a clot. Therefore, methods for causing the plasma and platelets to clot within the tissue are desirable. Mixing a clotting agent or activator, e.g., thrombin, with the plasma and platelets immediately prior to administration can be desirable. For example, thrombin and PRP may be mixed at the very tips of two separate injection needles lying adjacent each other wherein thrombin is delivered via one needle and PRP is delivered via the second needle. In this case, the PRP may permeate tissue at the injection site prior to clotting. Alternatively, thrombin may be injected into tissue through one or more needles and the PRP injected through a different needle or needles. In one embodiment, the needles may be interlaced so that the thrombin and the plasma and platelets are injected simultaneously in close proximity. For example, a device may be designed to comprise alternating PRP and thrombin needles spaced 2 mm apart such that mixing will occur within the tissue around the injection site. In one embodiment, delivery devices of the present invention may include two or more syringes 560 for the delivery of multiple agents such as cells, PRP and thrombin to an injection site. For example, a first syringe 560 may be used to deliver PRP and cells to a first set of needles 44 while a second syringe 560 may be used to deliver thrombin to a second set of needles 44. In one embodiment, the first and second sets of needles are interlaced with each other in a needle array. In one embodiment, the first and second sets of needles alternate with each other along a row. In an alternative embodiment, two or more syringes 560 with needles 1092 may be used sequentially. For example, cells and PRP may be delivered with a first syringe to an injection site followed by a second syringe used to deliver thrombin to the same injection site.

In one embodiment, plasma, e.g. PRP, may be injected into tissue without the addition of any exogenous clotting agent or agents, since there are initiators within the extracellular matrix to cause the plasma to clot. Therefore, cells may be injected in combination with plasma into target tissue with or without the addition of an activating agent, for example, via a cell delivery device of the present invention. In an alternative embodiment, a clotting protein, e.g. fibrinogen, may be injected into tissue in combination with cells. The fibrinogen and cells may be injected into tissue with or without the addition of a clotting agent, for example, thrombin.

It can be desirable in a cell transplantation therapy to distribute the cells as widely as possible around the injection site. It can also be desirable to have the cells be uniformly distributed around the injection site. One method for enhancing distribution of an injectate around an injection site is to use needles having holes in the side vs. using needles having holes in the end. Multiple side holes can provide a wider distribution of injectate around the injection site. Side holes also provide access to the tissue from a multitude of places rather than just from the end of the needle, therefore requiring less travel of the injectate for wider distribution. A potential benefit of side holes in the needles is that if the needle tip accidentally penetrates through the heart wall and into a cardiac chamber, the cells may still be injected into cardiac tissue as opposed to being all injected into the blood stream within the cardiac chamber. Another method for enhancing distribution of an injectate around an injection site is to increase the number of needles used at the injection site. If desired, the multi-needle injection device of the present invention, allows for multiple needles to be placed close to each other in order to provide a uniform distribution over a larger area as compared to the use of a single needle device. The combination of side holes on the needles of a multi-needle device may provide a broad distribution of cells around an injection site.

In one embodiment of the present invention, suction may be used to improve the distribution of cells around the injection site. The use of suction can create a negative pressure in the interstitial space. This negative pressure within the interstitial space can help the injectate to travel farther and more freely, since the injectate is traveling into a negative pressure gradient. The applicants have discovered that an injectate such as cells will distribute more broadly around a needle injection site when suction has been provided than when no suction has been provided. Cells have been seen to distribute throughout an area under suction even when only one end hole needle is used at the center of the area under suction. For this reason, the combination suction and side holes on the needles of a multi-needle device may provide a very thorough and broad distribution of cells around an injection site. Furthermore, the combination of suction with side holes on the needles as well as the injection of platelet rich plasma and thrombin may provide a broad distribution of cells with a nutritious milieu and an enhanced retention of the cells at the injection site. For example, device 1010 as shown in FIGS. 62 and 63 may be used in the following procedure. Device 1010 is placed on a target area of tissue, for example, cardiac tissue. Suction is applied to secure the device to the tissue and to create a negative pressure in the interstitial space. A first syringe 560 is placed within tool body 1012 so that needle 1092 is passed through port 1046 and into tissue. The contents of the first syringe 560, e.g., PRP and cells, are injected into the tissue. Syringe 560 is then removed from tool body 1012. A second syringe 560 is then placed within tool body 1012 and a second needle 1092 is passed through port 1046 and into tissue at the same location as the first needle. The contents of the second syringe 560, e.g., thrombin, is then injected into the tissue. The second syringe is then removed from tool body 1012. Suction is then ceased and the delivery device is then removed from the tissue. The technique may then be repeated on a different area of tissue if desired.

To avoid injecting a needle to deeply into an area of tissue, the needle may be aligned essentially parallel to the tissue to be injected. For example, certain areas of the myocardium are relatively thin. Therefore, to avoid having the needle(s) penetrate through the myocardium and into a cardiac chamber where the injectate can be washed away by the blood stream, the needle(s) may be delivered relatively parallel to the surface of the heart. As shown earlier, an injection device could be designed so that a suction member pulls up a certain depth of myocardium and then allows the needle to be injected into this bleb of myocardium at a fixed depth, thereby allowing good distribution of cells due to use of suction yet the needle would not penetrate the cardiac chamber and the cells or injectate would not be lost to the bloodstream.

In one embodiment, following the injection of cells within cardiac tissue a pacemaker lead, e.g., an epicardial pacing lead, may be placed or implanted at the injection site as disclosed earlier. For example suction tool 1010 may be used to deliver cells to an infarct area of tissue of the heart. Following cell delivery, suction tool 1010 may then be used to deliver and implant an epicardial pacing lead at the injection site or adjacent the area of tissue implanted with cells. The pacing lead may then be coupled to a pacing device to provide electrical stimulation to the area of the newly implanted cells.

Figure 68:
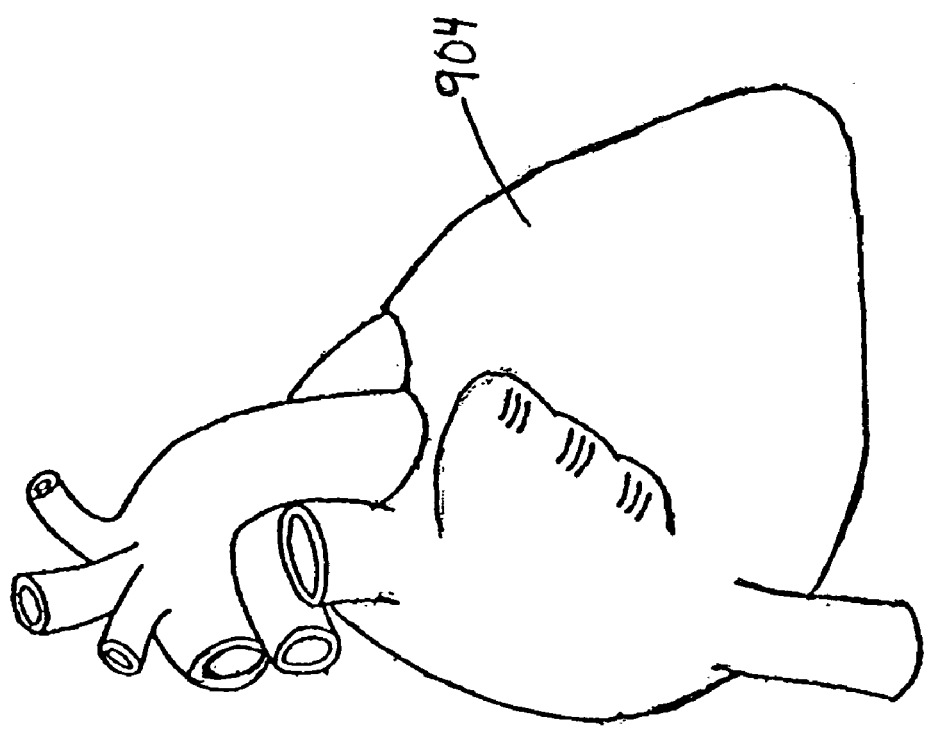
FIG. 68 is a depiction of a normal heart.
Figure 69:
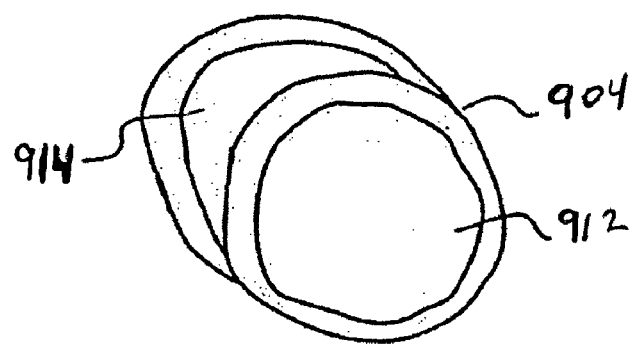
FIG. 69 is a cross-sectional depiction of a normal heart.
Figure 71:
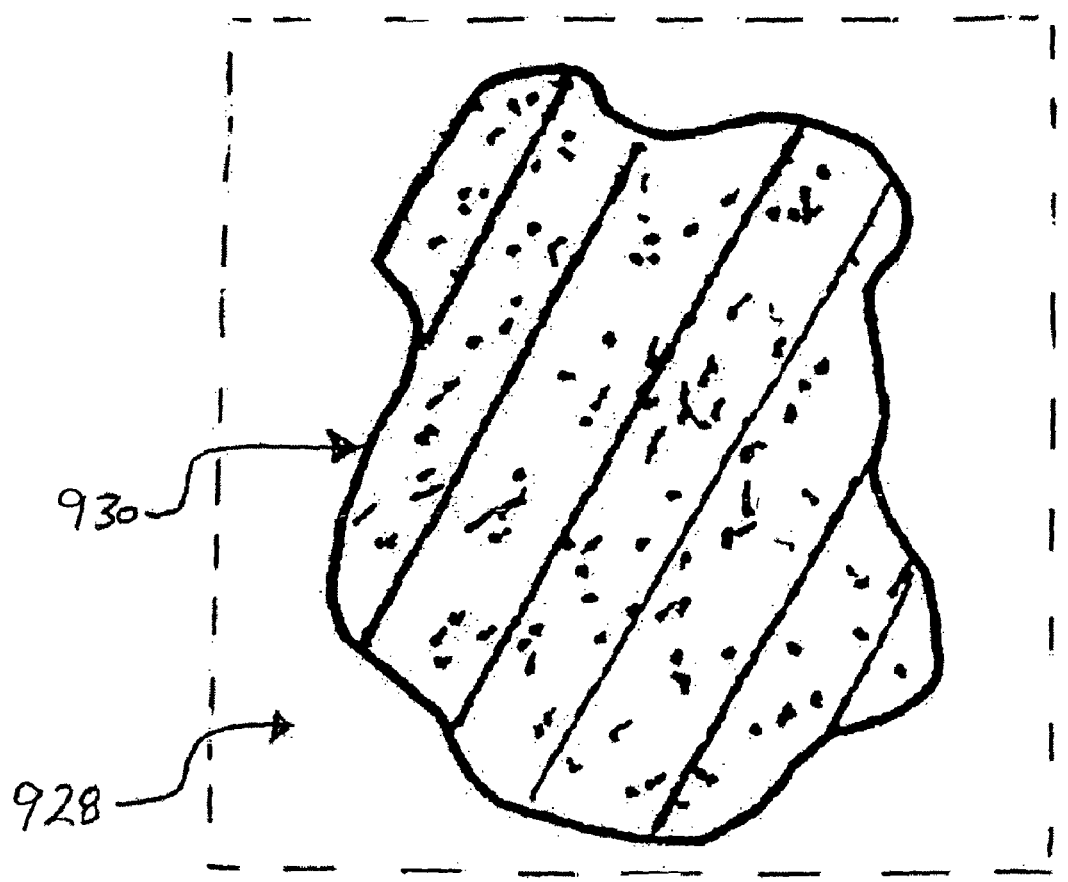
FIG. 71 is an enlarged view of the infracted/ischemic myocardium depicted in FIG. 70.

Referring to FIGS. 68 and 69, there can be seen depictions of a heart 904. The cross-sectional view in FIG. 69 shows the right ventricle 914 and the left ventricle 912 of heart 904 that has not undergone negative remodeling. FIG. 70 depicts a heart 904 having an ischemic region 930 that is surrounded by non-ischemic myocardium 928. FIG. 71 is an enlarged view of the ischemic region 930 surrounded by the non-ischemic region 928. After an MI, the ischemic tissue can undergo negative remodeling. When a myocardial infarction occurs, the myocardial tissue that is no longer receiving adequate blood flow generally dies and is replaced with scar tissue. This leads to negative remodeling in which the walls thin, dilate, and fail.

Figure 72:
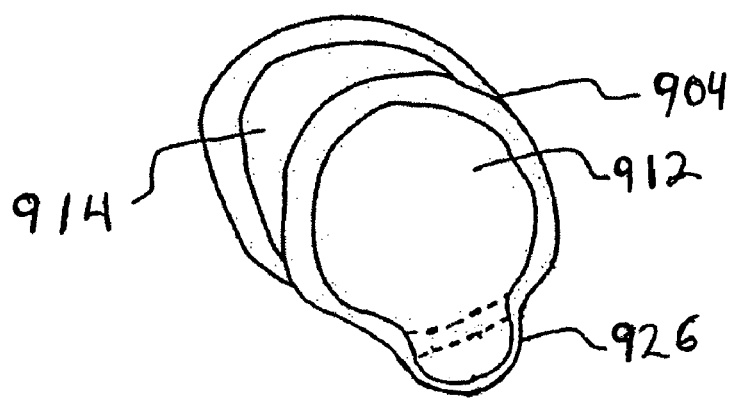
FIG. 72 is a cross-sectional depiction of a heart showing a region of infracted/ischemic myocardium on the wall of the left ventricle.

Negative remodeling is usually the progressive enlargement of the ventricle accompanied by a depression of ventricular function, and it can occur weeks to years after myocardial infarction. There are a variety of potential mechanisms for negative remodeling, but it is generally believed that the high stress on peri-infarct tissue plays an important role. Due to altered geometry, wall stresses are much higher than normal in the myocardial tissue surrounding the infarction. FIG. 72 is a cross sectional view of the heart shown in FIG. 70 showing an area 926 of a left ventricle 912 that has undergone negative remodeling. As depicted in FIG. 72, the heart walls tend to be thinner in the expanded area 926.

As described further below, the current invention attempts to address negative remodeling by injecting one or more agents or substances into the myocardium to provide mechanical reinforcement by preventing the heart wall from thinning, and thus prevent or reduce negative remodeling. The injected substance may occupy a portion of the interstitial space between the cells of an area of the myocardium and provide mechanical reinforcement.

The injected substance can include one or more agents or substances described herein, or any substance suitable for providing the desired mechanical reinforcement. The injectate may be a substance or include a substance that can provide some level of biological therapy as well as the desired mechanical reinforcement. One such substance that may provide both mechanical reinforcement and biological therapy is platelet gel. Another substance that may be injected according to one embodiment of the invention is Matrigel. Matrigel may be injected in combination with platelet gel or without platelet gel.

The injection of platelet gel may provide many features and promoters of healthy healing of cardiac tissue that may be beneficial in preventing ventricular remodeling after MI.

These feature may include the structural reinforcement that the "gel" may provide. Platelet gel (alone or augmented by additives described elsewhere in this disclosure) may provide a biocompatible reinforcement to the area of tissue the platelet gel is delivered. The presence of platelet gel within the injured cardiac tissue may resist or prevent dilatation of the tissue and may permit a more healthy distribution of forces as the injured ventricle adjusts to sub-optimal forces post-MI. Additionally, platelet gel may provide many biologically active agents which can facilitate healthy healing of tissue and potentially local regeneration of tissue. A number of agents may be found in platelet gel including cytokines (including IL-1β, IL-6, TNF-α), chemokines (including ENA-78 (CXCL5), IL-8 (CXCL8), MCP-3 (CCL7), MIP-1α (CCL3), NAP-2 (CXCL7), PF4 (CXCL4), RANTES (CCL5)), inflammatory mediators (including PGE2), and growth factors (including Angiopoitin-1, bFGF, EGF, HGF, IGF-I, IGF-II, PDGF M and BB, TGF-β 1, 2, and 3, and VEGF). Multiple agents found in platelet gel can have an effect in regards to facilitating wound healing. For example, one or more agents found in platelet gel can play a role in the recruitment of circulating cells to the injured site. One or more agents found in platelet gel may play a role in the stimulation of local angiogenesis. It is believed that the various agents found in platelet gel can promote more healthy remodeling of injured tissue.

Before any substance is injected into a heart having a region of ischemic tissue, the location and extent of the ischemic region may first be identified. Multiple technologies and approaches may be used by a physician to identify and assess normal, ischemic-non-viable, and ischemic-viable myocardial tissue. These include, but are not limited to, visual inspection during open chest surgical procedures, localized blood flow determinations, local electrical and mechanical activity, nuclear cardiology, echocardiography, echocardiographic stress test, coronary angiography, MRI, CT scans, and ventriculography.

To aide the physician in delivering injectate specifically to the target tissue, real-time determinations of one or more features of the tissue to be injected and/or surrounding tissue may be made prior to injection. For example, real-time recording of electrical activity (e.g. EKG, pH, metabolites (e.g., lactic acid, CO2, or other metabolites) and/or local indicators of myocardial viability or activity can help guide the injection process.

Once the location, size and shape of the ischemic region are identified, the physician can access the myocardium and begin injecting the myocardium with the desried substance or substances. If platelet gel is selected as the injectate, it can comprise multiple components. In several embodiments of the present invention, platelet gel may comprise plasma, e.g., PRP or PPP, and thrombin. These embodiments can use combinations of autologous or non-autologous PRP or PPP and autologous or non-autologous thrombin. For example, the platelet gel of one embodiment may be made using autologous PRP and bovine thrombin, while the platelet gel of another embodiment may be made using autologous PRP and autologous thrombin. Other embodiments of the present invention may include injecting the myocardium with plasma, e.g., PRP or PPP, alone.

The injected substances of various embodiments of the present invention may include additives, such as fibrinogen, fibrin and/or collagen to increase the mechanical strength of the myocardium. One embodiment of the present invention includes the injection of elastin to increase the elasticity of the myocardium. One embodiment of the present invention includes the delivery or injection of fibrin glue, e.g., comprising the components fibrinogen and thrombin, into the myocardium. This embodiment may use combinations of autologous or non-autologous fibrinogen and autologous or non-autologous thrombin.

The injectates of the present invention may be fortified with or comprised wholly of a biocompatible substance that solidifies and/or cross-links in-situ to render a mechanically supportive structure following injection into the myocardium. Other embodiments of the injectate of the present invention may include one or more synthetic and/or naturally-occurring components and/or one or more non-degradable and/or biodegradable materials to provide strength and mechanical reinforcement, for example. Some embodiments of the injectate of the present invention may include chemical crosslinkers, monomers, polymers and/or proteins. For example, some embodiments of the injectate of the present invention may include cyanoacrylate and/or silk-elastin protein polymers.

The invention may be practiced using substances containing synthetic biodegradable materials that provide strength and mechanical reinforcement for a specified time interval after delivery, and then resorb. Such materials may include genetically-engineered and/or modified compounds such as collagen or fibrin. Naturally-occurring materials, such as cartilage, bone or bone components, gelatin, collagen, glycosaminoglycans, starches, polysaccharides, or any other material that can provide strength and mechanical reinforcement for a specified time interval after delivery or injection, and then resorb may be used according to one embodiment of the present invention. One or more components of the injectates of the present invention may be derived from humans and/or animals and/or they may be derived from various recombinant techniques.

In one embodiment, additives or modifications may be added to the injectate that prolong the injectates survival in tissue, e.g., the myocardium, following injection into tissue. One embodiment includes the addition of fibrinogen to the platelet gel composition. One embodiment includes the modification of one or more components within the platelet gel so as to make the modified components more resistant to breakdown, e.g., endogenous breakdown, thus sustaining the platelet gel durability within the tissue, e.g., the myocardium, so as to provide mechanical reinforcement, for example, for a longer period of time.

Other embodiments of the invention may include a combination of any of a variety of compounds that have the ability to create the desired local effect of edema, thickening of tissue, mechanical reinforcement, and/or any other effect that prevents remodeling. Such compounds may include hydrogels for mechanical reinforcement and/or ground suture material for producing local edema and mechanical reinforcement. These materials may be added to PRP or PRP plus thrombin, or these materials may be used alone without the addition of PRP or PRP plus thrombin.

To help provide mechanical reinforcement, biodegradable micro-particles roughly 50-100 μm in size may be added to the injectate, e.g., platelet gel. Micro-particles small enough for needle injection but too large to fit into capillaries and venules, may be added to the injectate. In one embodiment, the micro-particles are impregnated with a drug or agent, e.g., a biological agent, that can elute, e.g., as the micro-particles degrade. In one embodiment, micro-particles alone may be injected into the coronary sinus to provide mechanical reinforcement. In one embodiment, micro-particles having a glass transition temp (Tg)>=37° C. may be used. In one embodiment, a substance, e.g, micro-particles, that gels following insertion or injection into the target tissue may be used. Gelation may occur immediately following injection or it may occur over minutes, hours and/or days following injection. In one embodiment, injected micro-particles may provide "mass" and volume to the injection area for immediate mechanical reinforcement, but over time may fuse into a single member or entity.

Some embodiments of the injectate may include one or more chemicals, e.g., polymers and/or chemical crosslinkers, that can chemically bind to one or more chemical constituents, e.g., proteins, located within the tissue. For example, one or more proteins that can chemically bind to the surface of one or more cell types contained in the tissue may be used according to one embodiment. In one embodiment, polymers that can covalently bind to primary amine groups ($-NH_3$) of proteins contained within the injectated tissue may be used. For example, one or more components of the injectate may be anchored to one or more cell types and/or the extracellular matrix. Several embodiments of the injectate may include pro-inflammatory molecules, such as histamine, cytokines, and/or chemokines. At least one embodiment of the injectate of the current invention includes one or more biological growth factors. A contrast agent may be used in the injectate of some embodiments for visual confirmation of injection success. Examples of such contrast agents include but are not limited to X-ray contrast (e.g. IsoVue), MRI contrast (e.g. gadolinium), and ultrasound contrast (echogenic or echo-opaque compounds).

In one embodiment of the invention, the injectate is a platelet gel comprising PRP and thrombin in a ratio of about 10:1, respectively. In another embodiment, the injectate is a platelet gel comprising PRP and thrombin in a ratio of about 11:1, respectively. In at least one embodiment, no thrombin is included in the injectate and PRP is injected into the myocardium alone. Other embodiments of the invention may include one or more injectates having multiple components in desired ratios necessary to achieve the desired effect or effects.

In one embodiment, PRP and thrombin are injected separately into the same area of tissue so that the PRP and thrombin mix and react within the myocardium and thereby form a platelet gel while in the myocardium. Several embodiments of the invention can provide accelerated gel or reaction times. Gel times in these embodiments may be accelerated by applying heat to the injection site (e.g., via a heat delivery catheter or other heat delivery device), increasing the thrombin concentration, or combining the PRP and/or PPP and thrombin in a mixing chamber prior to injection and then injecting the combine mixture into the myocardium after the mixture has begun to polymerize. These same techniques may be applied to other multi component injectates, wherein the components gel, crosslink and/or polymerize after being mixed together.

In one embodiment, a physician may perform one or more epicardial injections (e.g, via open chest surgery, thoracoscopic surgery, or sub-xiphoid access surgery), or the physician may perform one or more endocardial or transvascular injections (e.g., via a percutaneous approach). Regardless of the method used to access a beating or temporarily stopped heart having a region of ischemic myocardium, the injection devices used in some embodiments would be capable of injecting multiple components separately into the myocardium. One embodiment of the current invention enables the repeated injection of one or more components by one or more delivery devices as disclosed herein. One embodiment of the current invention enables one or more components to be mixed prior to injection by one or more delivery devices as disclosed herein. A proximal one-hand trigger delivery device that enables the predictable delivery of a determinable (e.g. dial-in) dose of a single- or multiple-constituent injectate in a determinable ratio may be used according to one embodiment. One embodiment of the current invention utilizes one or more delivery devices having multi-lumen needles. One embodiment uses delivery devices having two or more lumen needles. Needle lumens may be in a coaxial configuration or a side-by-side configuration.

At least one embodiment of the invention includes two or more side-by-side syringes for one-handed injection of an injectate having multiple components. The injectate components may be delivered in a prescribed ratio. This prescribed ratio may be pre-set (and fixed) or dialable (and dynamic). One embodiment of the invention utilizes separate gears or levers (with gear-ratios or lever-ratios that are settable) to enable delivery of multiple compounds in different ratios without generating a pressure gradient between syringes, for example. Other multi-component injection devices of the current invention include one or more lumens of varying diameters to allow for delivery of a predetermined ratio of each component. Some multi-component delivery devices of the current invention include lumens of different lengths, such that one component is released more distally than another. Still other devices incorporate one or more mixing chambers in the device. At least one embodiment of the delivery devices of the current invention include single lumen needles that are used for serial delivery of multiple components, e.g., one component after another.

Figure 73:
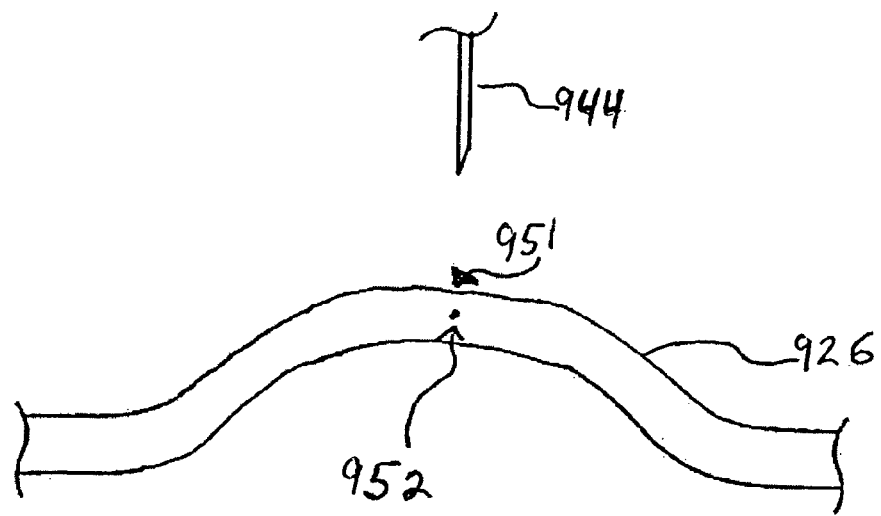
FIG. 73 depicts a delivery device of the current invention delivering an injectate to an ischemic myocardium.

Referring now to FIG. 73, there can be seen a portion of a delivery device according to one embodiment of the current invention wherein a delivery needle 44 of the delivery device is approaching at an angle approximately perpendicular to a target tissue area 926, e.g., a remodeled portion of myocardium. The needle will puncture the tissue at a point 951 directly above the desired delivery location 952 within the tissue. The device may include one or more means, as described herein, for example, to ensure that the delivery needle achieves the desired penetration depth into the tissue.

Figure 74:
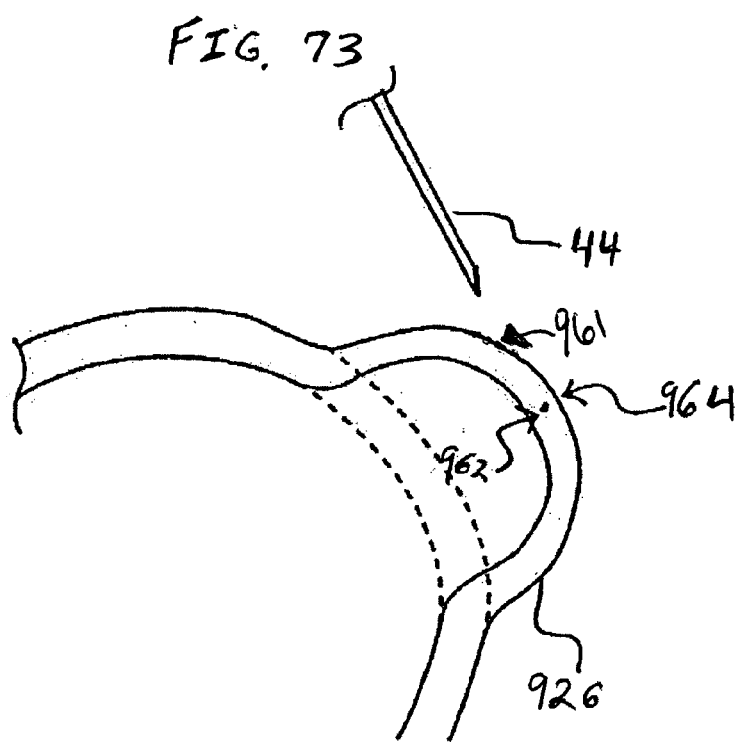
FIG. 74 depicts an alternate embodiment of a delivery device of the current invention delivering an injectate to an ischemic myocardium.

Referring now to FIG. 74 shows a portion of a delivery device according to one embodiment of the current invention wherein a delivery needle 44 of the delivery device is approaching at an angle approximately tangentally to the desired injection point within the target tissue area 926, e.g., a remodeled portion of the myocardium. The needle will puncture the tissue at a point 961 located a desired distance tangentally from the desired delivery location 962 within the tissue. In one embodiment, a tissue stabilizer device, as described herein, for example, may be applied to the surface of the tissue, at a location 964 near the injection site, to stabilize the tissue. For example, a tissue stabilizer may be used to stabilize a tissue area of a beating heart. The delivery device may include one or more means as described herein to ensure that the needle achieves, but does not exceed, the desired penetration into the tissue.

At least one embodiment of the invention uses a "Smart-Needle" to detect distance from the needle tip to the ventricular blood compartment or endocardial surface, so that the needle tip is maintained in the myocardium. Such a needle can rely on imaging around or ahead of the needle tip by imaging modalities such as ultrasound. In one embodiment, a pressure-sensor positioned on the needle, e.g., at the tip, may be used to alert the operator when the tip experiences ventricular chamber pressures rather than the desired intra-myocardial pressures, thereby indicating the needle has been advanced too far. A fail-safe system may be used that disables further injections until the needle tip is repositioned back into the myocardium where pressures are detected in the desired range. While pressure sensing was described above, other properties that distinguish myocardium from ventricular space (e.g. oxygen saturation) are also contemplated by this invention.

Examples of several transvascular delivery devices that may be used according to at least one embodiment of the current invention are shown in FIGS. 75A-75D. The depicted devices are similar to devices depicted in U.S. Pat. No. 6,283, 951, which is owned by the assignee of the current application, and the contents of which are incorporated herein by reference. Either of these devices could be placed in a vessel neighboring the target injection site, and used to deliver injectate to the myocardium by piercing through the vessel wall and navigating to the desired location with the needle-tip or microcatheter-tip. The distal needle may contain a semi-rigid microcatheter. The catheter tip or needle itself may contain a local imaging system (e.g. intravascular ultrasound system).

Figure 75A:
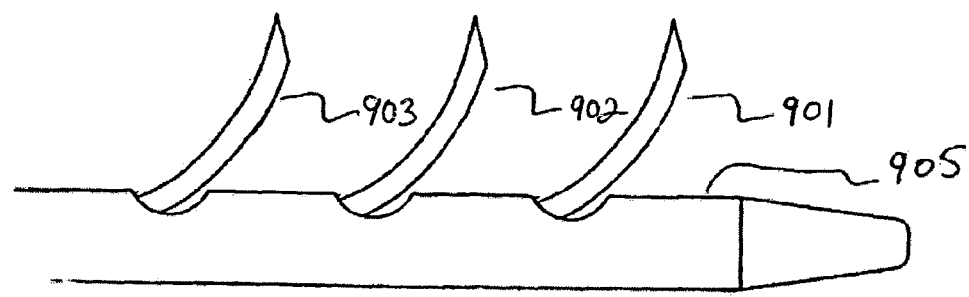
FIGS. 75A-75D depict several embodiments of delivery devices that can be used to deliver an injectate to an ischemic myocardium according to the current invention.

As shown in FIG. 75A, the distal end of a delivery device may include a plurality of needle assemblies, for example, needles 901, 902, 903, to be deployed in a predetermined arrangement along the periphery of delivery device 905, for example. In one embodiment, the needle assemblies may be arranged in one or more rows, as shown in FIG. 75A. In one embodiment, it may be desirable to access an extended remote tissue region, for example, extending substantially parallel to a vessel, within the myocardium. With a multiple needle transvascular catheter system, a single delivery device may be positioned within a vessel and oriented so that the array of needles may be sequentially or simultaneously deployed to inject a substance into the extended tissue region, thereby providing a selected trajectory pattern.

Figure 75B:
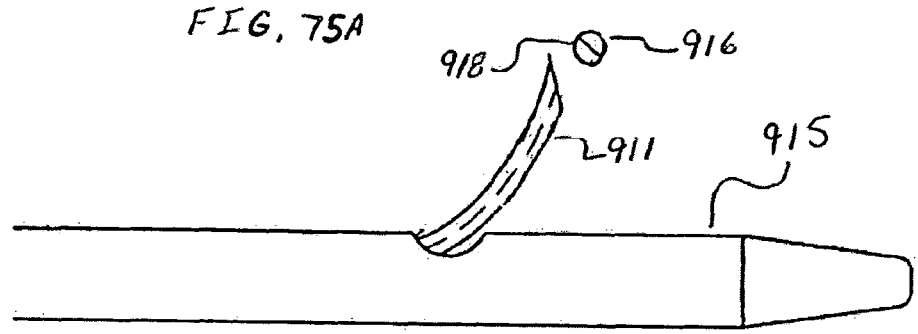

As shown in FIG. 75B, the distal end of a delivery device 915 may include one or more needles having a plurality of lumens that extend between a multiple line manifold on the proximal end (not shown) to adjacent outlet ports, for example, outlet ports 916, 918. A multi-lumen needle assembly may allow components of a substance to be independently injected, thereby allowing the components to react with one another following injection within the selected tissue region, as described herein. For example, a dual lumen needle assembly may allow two components of a substance to be independently injected, which may then react with one another once within the selected tissue region, as described herein.

Figure 75C:
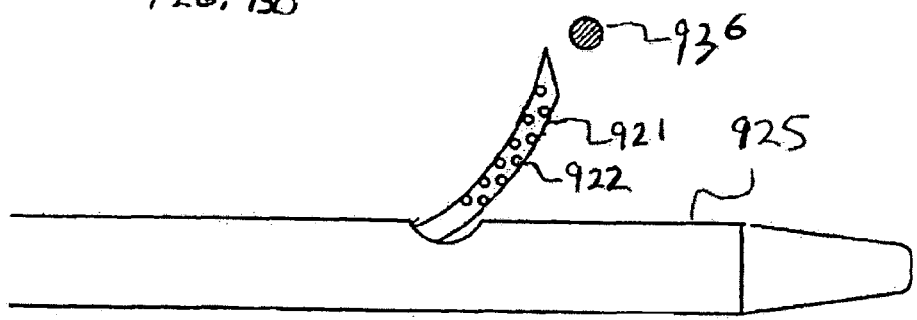

As shown in FIG. 75C, the distal end of a delivery device 925 may include one or more needles 921 having a closed distal tip 936 and one or more side openings 922 for delivering an injectate substantially laterally from the distal tip 936 into the tissue.

Figure 75D:
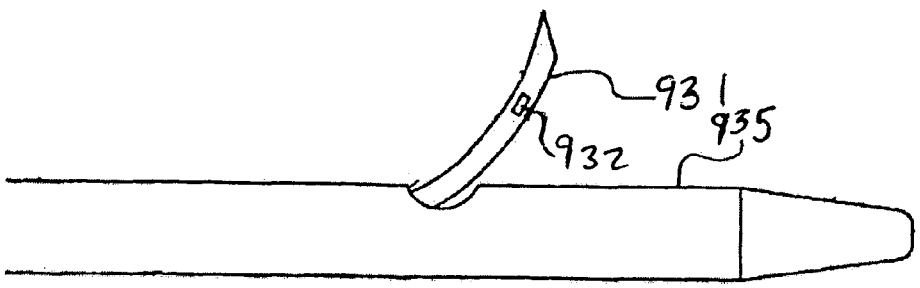

As shown in FIG. 75D, the distal end of a delivery device 935 may include one or more needles 931 having one or more feedback elements or sensors as described herein, for example. The one or more feedback elements or sensors may be used to help guide the delivery device into a desired position for delivering an injectate. For example, an EKG electrode may be included on the distal tip or otherwise delivered within the selected tissue region, thereby allowing electrical events within the heart to be monitored during delivery of the injectate. During treatment, for example, the injectate may be delivered into a tissue region until a desired condition is met. Also, local EKG monitoring may be used to help target and guide injection or injections into or near electrically silent or quiet areas of myocardium.

If the method of delivery comprises a minimally invasive or percutaneous access technique, the physician may need some sort of real-time visualization or navigation equipment to ensure site-specific injections. Thus, at least one embodiment of the invention uses MNav technologies to superimpose pre-op MRI or CT images onto fluoro images of a delivery catheter to track it in real-time to target tisasue sites. In one embodiment of the invention, the physician may use a contrast agent and/or navigation technologies to track the needle-tip during injection as it relates to a virtual 3-D environment. This technique enables one to target injections and mark previous injections to ensure proper spacing of future injections.

In one embodiment, the delivery devices include one or more needles having a sufficiently small gauge diameter such that needle track or tracks in the tissue are substantially self-sealing to prevent escape of the injectate upon removal of the needle or needles.

Figure 76:
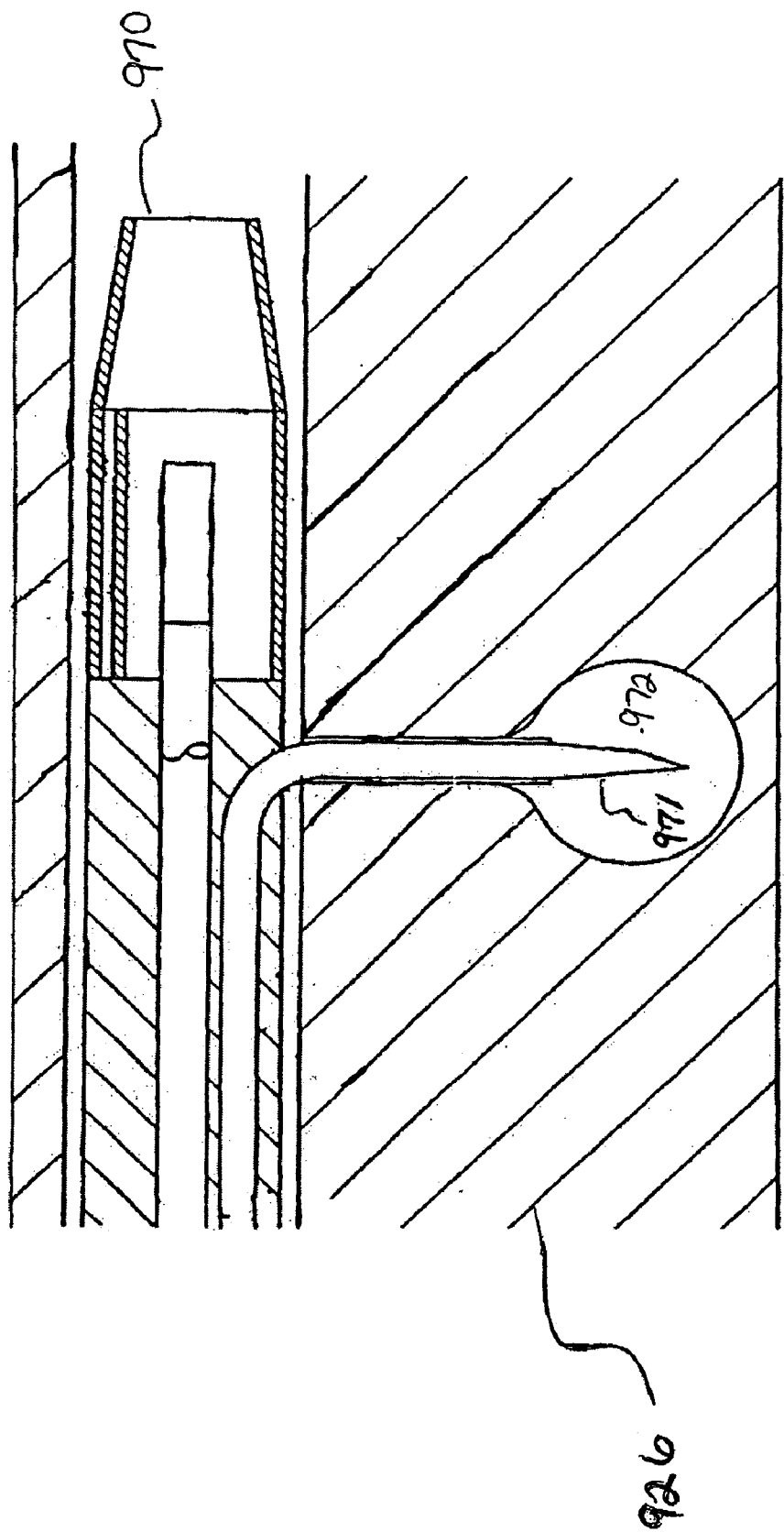
FIG. 76 depicts a percutaneous, transluminal delivery device delivering an injectate according to the current invention.

Turning now to FIG. 76, another embodiment of a transvascular catheter system 970 in accordance with the present invention is partially shown. Catheter system 970 may be used to create an injectate reservoir 972 within the an area of tissue 926, e.g., the myocardium, to provide sustained delivery. Catheter 970 may be introduced endovascularly into a blood vessel until the distal portion is adjacent the desired injection location. The needle assembly 971 may be oriented and deployed to puncture the wall of the vessel and enter the the tissue area 926. The injectate may then be injected into the tissue and, thereby, form reservoir 972.

Regardless of the delivery device, a physician practicing the current invention may need to make multiple injections using a single delivery assembly. Thus, at least one embodiment of the delivery devices of the current invention includes a device having at least one reusable needle. Some embodiments of the invention may include delivery devices having an automated dosing system, e.g., a syringe advancing system. The automated dosing system may allow each dose to be pre-determined and/or dialed in (can be variable or fixed), e.g. a screw-type setting system. One embodiment of the current invention may include a proximal handle wherein each time a portion of the proximal handle is pushed, a pre-determined dose is delivered at a pre-determined or manually-controllable rate.

When practicing the current invention, a physician may need to stabilize a beating heart for injection. Embodiments of the current invention achieve this stabilization by pharmacologic and/or electrophysiologic means. Regardless of the method used, the goal of some embodiments of the current invention is to temporarily place a heart in controlled intermittent asystole. In at least one preferred embodiment of the invention, a heart is stabilized using pharmacologic asystole and/or vagal stimulation asystole. In other embodiments, a heart is stabilized using electrophysiologic over-drive pacing or other algorithms that render the heart fairly static. These include reversible initiation of asystole, fibrillation, or a prolonged refractory state.

In other embodiments of the invention, areas of a beating heart may be stabilized mechanically. In one embodiment of the invention, a tissue stabilizer device may be used to temporarily stabilize the immediate area of the injection site during an epicardial injection procedure. In another embodiment of the invention, the immediate area of the injection site is temporarily stabilized using a tissue stabilizing member or device that is part of the injection device. Other embodiments of the invention use other mechanical means such as sleeves and compressors that are held against the injection region to stabilize the injection area.

In various embodiments of the invention, platelet gel may be injected epicardially, endocardially, and/or transvascularly. Regardless of the delivery device or method, a physician practicing the current invention may have the need for precise local placement and depth-control for each injection. To achieve depth control, the delivery device of at least one embodiment of the invention includes a stopper fixed (or adjustably fixed) on the needle shaft, at a desired distance from the distal tip of the needle, to prevent penetration of the needle tip into tissue beyond a specified depth. Some embodiments of the invention use the method of injecting one or more needles into tissue at a tangent to the tissue surface to control the depth of the injection. In at least one embodiment of the invention the needle can be positioned to inject at an angle approximately perpendicular (90 degrees) to the tissue, tangential (0 degrees) to the tissue, or any desired angle (0-90 degrees) in between. In at least one embodiment, suction may be used to facilitate controlled positioning and entry of the injector.

In one embodiment of the present invention, the delivery of injectate from the delivery device into tissue may be enhanced via the application of an electric current, for example via iontophoresis. In general, the delivery of ionized agents into tissue may be enhanced via a small current applied across two electrodes. Positive ions may be introduced into the tissue from the positive pole, or negative ions from the negative pole. The use of iontophoresis may markedly facilitate the transport of certain ionized agents through tissue.

In one embodiment, one or more needles of the delivery device may act as the positive and/or negative poles. For example, a grounding electrode may be used in combination with a needle electrode via a monopolar arrangement to delivery an ionized injectate iontophoretically to the target tissue. In one embodiment, an injectate may be first dispersed from the needle into tissue, following injection, the injectate may be iontophoretically driven deeper into the tissue via the application of an electric current. In one embodiment, a delivery device having multiple needles may comprise both the positive and negative poles via a bipolar arrangement. Further, in one embodiment, multiple needle electrodes may be used simultaneously or sequentially to inject a substance and/or deliver an electric current.

Significant motion of the heart during the cardiac cycle poses a challenge when attempting to deliver injectate to an area of the heart, e.g., the myocardium, in a temporally and spatially controlled fashion. One method to predictably deliver injectate into such a moving target tissue is to time injections specifically for delivery during a select portion of the cardiac cycle, e.g. via "cardiac gating" or cardiac synchronization. In one embodiment of the present invention, one or more electrodes may be used as stimulation electrodes, e.g., to pace the heart during delivery of injectate. In this way, the cardiac cycle is made to be predictable and injection can be timed and synchronized to it. In fact, the beat-to-beat period can be artificially lengthened so as to permit complete injection during a specific (and relatively) stationary phase of the cardiac cycle.

Figure 77:
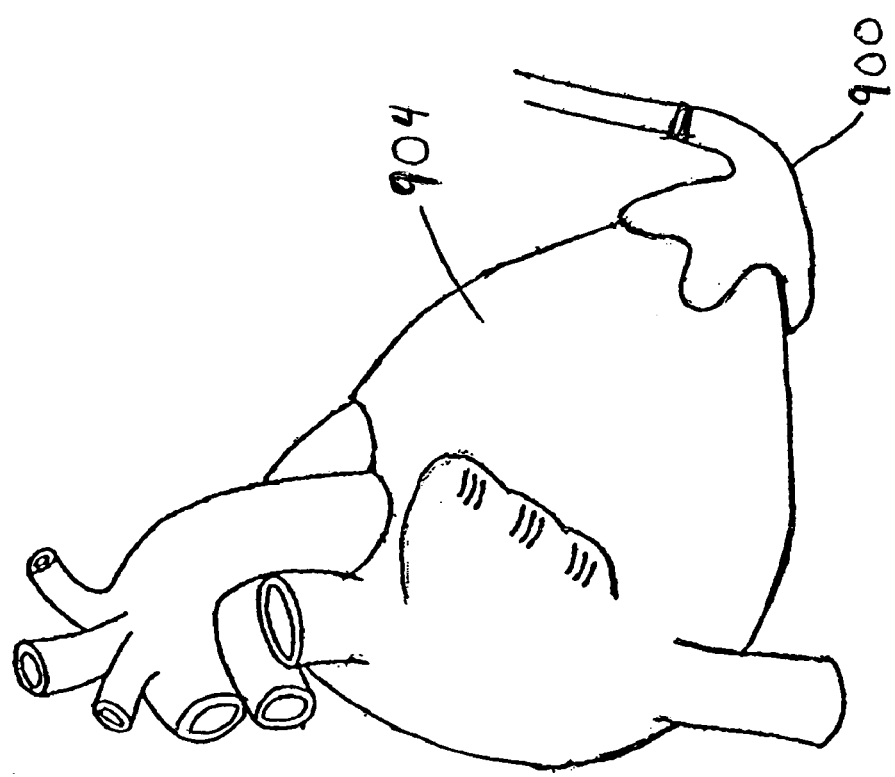
FIG. 77 depicts a positioning device positioning a heart into a non-physiological orientation.

As shown in FIG. 77, a heart positioner 904 may be used by a surgeon to manipulate the injection site into better view by rotating and supporting the heart 904. In one embodiment, the use of a positioning device can facilitate moving or repositioning the heart to achieve better access to areas which would otherwise be difficult to access, such as the posterior or backside of the heart. In one embodiment, one or more positioning devices may be used to position an organ, e.g., a heart, into a non-physiological orientation.

While the volume of substance injected may vary based on the size of the heart and the extent of mechanical reinforcement needed, in at least one embodiment of the invention, 50 ul of platelet gel is injected into the myocardium per injection site. In another embodiment, 200 ul to 1000 ul of the injectate is delivered per injection site. In at least one other embodiment, the volume of substance injected per injection site can vary between 100 ul and 10000 ul. In one embodiment of the invention the clinician adjusts the injection volume, the number and spacing of injection sites, and the total volume of injectate per heart to optimize clinical benefit while minimizing clinical risk.

The total injection volume per heart may be dosed based on the size of the heart, the size of the ischemic region of myocardium and the desired extent of mechanical reinforcement of the tissue. In at least one embodiment, the total volume of substance injected into the myocardium is as much as can be accommodated by the tissue in a reasonable number of injection sites. In another embodiment, the total volume of substance injected is less than 6000 ul.

The number of injection sites per heart will be based on the size and shape of the ischemic region, the desired location of the injections, and the distance separating the injection sites. In at least one embodiment, the number of injection sites can range from 5-25. The distance separating injection sites will vary based on the desired volume of platelet gel to be injected per injection site, the desired total volume to be injected, and the condition of the ischemic myocardium. In at least one embodiment, the distance between injection sites is approximately 2 cm and in at least one other embodiment, the distance between injection sites is 1 cm. In still another embodiment, the separation distance between injection sites can range between about 50 mm and about 2 cm.

The location of the injection can vary based on the size and shape of the ischemic region of myocardium, and the desired extent of mechanical reinforcement of the tissue. In at least one embodiment of the invention, the injectate is injected only into the ischemic myocardium, while in other embodiments the peri-infarct zone around the ischemic region is injected, and, in at least one embodiment of the invention, the injectate is injected into only the healthy tissue that borders an ischemic region. In other embodiments, the injectate may be delivered to any combination of the regions of ischemic myocardium, myocardium in the peri-infarct zone, and healthy myocardium.

The timing of injections relative to an MI will be based on the severity of the MI, the extent of the injury, the condition of the patient, and the progression of any negative remodeling. In at least one embodiment, the injectate is delivered 1-8 hr following ischemia-reperfusion (e.g., in the cath lab setting immediately following re-perfusion). In another embodiment the substance is injected three to four days after ischemic insult (e.g., after clinical stabilization of the patient, which would make it safe for the patient to undergo a separate procedure). In at least one embodiment, the injectate is delivered more than one week after the injury. Other times for injecting substances into the myocardium are also contemplated, including prior to any ischemic insult, and immediately upon finding an area of ischemic myocardium (for older injuries).

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A method to treat negative remodeling comprising:
providing an injection device fluidly coupled to a source of platelet plasma and a source of thrombin, wherein the device includes a first needle for separately injecting platelet plasma into tissue and a second needle for separately injecting thrombin into tissue;
advancing the first and second needles of the injection device through an opening in a patient to the patient's heart;
identifying the location, size and shape of ischemic tissue in the heart by the use of one or more sensors;
driving the first and second needles of the injection device into the ischemic tissue; and
injecting the platelet plasma and the thrombin separately into the ischemic tissue, wherein
the platelet plasma and the thrombin combine within the ischemic tissue to form a platelet gel to provide mechanical reinforcement to the heart.

2. The method as in claim 1, wherein the opening is an intercostal opening.

3. The method as in claim 1, wherein the opening is a xiphoid opening below the sternum.

4. The method as in claim 1, wherein the opening is a sternotomy.

5. The method as in claim 1, wherein the opening is a percutaneous opening.

6. A method as in claim 1, wherein the platelet plasma is autologous.

7. A method as in claim 1, wherein the platelet plasma is non-autologous.

8. A method as in claim 1, wherein the thrombin is autologous.

9. A method as in claim 1, wherein the thrombin is non-autologous.

10. A method as in claim 1, wherein the platelet plasma is platelet rich plasma.

11. A method as in claim 1, wherein the platelet plasma is platelet poor plasma.

12. A method as in claim 1, wherein the injecting occurs between contractions of the heart.

13. A method as in claim 1, wherein the heart is temporarily stopped using vagal nerve stimulation.

14. A method as in claim 1, further comprising:
providing a positioning device;
engaging the heart with the positioning device; and
positioning the heart into a non-physiological orientation.

15. A method as in claim 14, wherein the injecting occurs following the positioning of the heart in a non-physiological orientation step.

16. A method as in claim 1, wherein the injecting step occurs following a myocardial infarction.

17. A method as in claim 1, wherein the first and second needles each include a sharp distal end and at least one discharge port.

18. A method as in claim 17, wherein the injection device further includes:
a suction member for grasping an area of tissue;
an elongate shaft having a longitudinal axis, a proximal region and a distal region, the distal region coupled to the suction member and operably coupled to the first and second needles; and
a mechanism for driving the sharp distal ends of the first and second needles into the area of tissue grasped by the suction member.

19. A method as in claim 18, wherein the injection device includes a mechanism for controllably varying the needle penetration depth of the first and second needles into the tissue.

20. A method as in claim 18, wherein the suction member includes one or more sensors.

21. A method as in claim 17, wherein the first and second needles each include a distal discharge port.

22. A method as in claim 17, wherein the first and second needles each include a discharge port proximal the sharp distal end of the first and second needles.

23. A method as in claim 1, wherein the platelet plasma and the thrombin are injected multiple times into the ischemic tissue.

24. A method as in claim 23, wherein each injection of the platelet plasma and the thrombin into the ischemic tissue is at a different location.

* * * * *